United States Patent [19]

Randall et al.

[11] Patent Number: 5,703,231
[45] Date of Patent: Dec. 30, 1997

[54] PROCESS FOR MAKING ANTIMICROBIAL COMPOUNDS

[75] Inventors: Jared Lynn Randall, Oxford; Jane Ellen Godlewski, South Plymouth, both of N.Y.

[73] Assignee: The Procter & Gamble Company, Mason, Ohio

[21] Appl. No.: 749,046

[22] Filed: Nov. 14, 1996

Related U.S. Application Data

[63] Continuation of Ser. No. 284,960, Aug. 2, 1994, abandoned.

[51] Int. Cl.$^6$ ............... C07D 215/56; C07D 237/28; C07D 471/04; C07D 487/04
[52] U.S. Cl. ............ 540/200; 540/205; 540/214; 540/224; 540/300; 540/301; 540/302; 540/305; 540/310; 540/347; 540/348; 544/58.6; 544/101; 544/235; 544/236; 544/256; 544/279; 544/362; 544/363; 546/79; 546/80; 546/83; 546/90; 546/101; 546/123; 546/156
[58] Field of Search .................. 540/200, 205, 540/214, 224, 300, 301, 302, 305, 310, 347, 348; 544/58.6, 101, 235, 236, 256, 279, 362, 363; 546/79, 80, 83, 90, 101, 123, 156

[56] References Cited

U.S. PATENT DOCUMENTS

| | | | |
|---|---|---|---|
| 4,379,923 | 4/1983 | Bruynes et al. | 544/26 |
| 4,383,946 | 5/1983 | Christensen et al. | 260/245.2 |
| 4,546,176 | 10/1985 | Machida et al. | 544/21 |
| 4,684,648 | 8/1987 | Tone et al. | 514/249 |
| 4,755,513 | 7/1988 | Tone et al. | 514/254 D |
| 4,833,270 | 5/1989 | Bitha et al. | 562/493 |
| 4,841,042 | 6/1989 | Häbich et al. | 540/200 |
| 4,868,295 | 9/1989 | Jaenicke et al. | 540/227 |
| 4,886,810 | 12/1989 | Matsumoto et al. | 514/312 |
| 5,221,741 | 6/1993 | Cecchetti et al. | 544/36 |
| 5,281,703 | 1/1994 | White et al. | 540/302 |

FOREIGN PATENT DOCUMENTS

| | | | |
|---|---|---|---|
| 0 181 521 A1 | 5/1986 | European Pat. Off. | C07D 215/56 |
| 0 300 311 | 1/1989 | European Pat. Off. | C07D 215/56 |
| 0 342 849 | 11/1989 | European Pat. Off. | C07C 63/70 |
| 0 376 870 | 4/1990 | European Pat. Off. | C07D 215/56 |
| 0 366 641 | 5/1990 | European Pat. Off. | C07D 499/88 |
| 0366 193 | 5/1990 | European Pat. Off. | C07D 499/88 |
| 0 451 764 A1 | 10/1991 | European Pat. Off. | C07D 519/00 |
| 0 470 578 A1 | 2/1992 | European Pat. Off. | C07D 471/06 |
| 0 522 277 A1 | 1/1993 | European Pat. Off. | C07D 513/06 |
| 279-886-A | 6/1990 | Germany | C07D 501/20 |
| 62-215591 A2 | 9/1987 | Japan | C07D 498/06 |
| 89/06649 | 7/1989 | WIPO | C07D 215/56 |
| WO 94/10163 | 3/1994 | WIPO | C07D 401/04 |

OTHER PUBLICATIONS

Chemical Abstract 99:139962c, Mitsui Petrochemical Ind. Ltd for JP 58-85,887 (May 23, 1983).
Chem. Abstract 114:82118d, Palamo-Nicolau et al. for EP 376,870 (Jul. 4, 1990).

Chu, D. T. W., I. M. Lico, A. K. Claiborne and H. Faubl, "An Alternative Synthesis of Temafloxacin, a Potent Antibacterial Agent", Can. J. Chem., vol. 70, No. 5, pp. 1323–1327 (May 1992).
Cecchetti, V. A. Fravolini and F. Schiafella, "One–Pot Synthesis of Rufloxacin", Synth. Commun., vol. 21, No. 22, pp. 2301–2308 (Dec. 1991).
Egawa, H. T. Miyamoto and J. Matsumoto, "A New Synthesis of 7H–Pyrido[1,2,3–de][1,4]benzoxazine Derivatives Including an Antibacterial Agent, Ofloxacin", Chem. Pharm. Bull., vol. 34, No. 10, pp. 4098–4102 (Oct. 1986).
Remuzon, P., D. Bouzard, P. Di Cesare, M. Essiz, J. P. Jacquet, J. R. Kiechel, B. Ledoussal, R. E. Kessler and J. Fung–Tomc, "Fluoronaphthyridines and Quinolones as Antibacterial Agents". 3. Synthesis and Structure–Activity Relationships of New 1–(1,1–Dimethyl–2–fluoroethyl), 1–[1–Methyl–1–(fluoromethyl)–2–fluoroethyl], and 1–[1, 1–Difluoromethyl)–2–fluoroethyl]Substiuted Derivatives, J. Med. Chem., vol. 34, No. 1, pp. 29–37 (Jan. 1991).

*Primary Examiner*—Philip I. Datlow
*Attorney, Agent, or Firm*—Mary P. McMahon; David L. Suter; Jacobus C. Rasser

[57] ABSTRACT

The present invention provides a process for making a compound having a structure according to Formula (I)

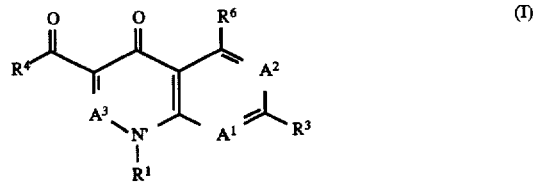

wherein $A^1$, $A^2$ and $A^3$ are independently carbon or nitrogen and $R^1$, $R^3$, $R^4$ and $R^6$ are known quinolone substituents; and wherein one of $R^1$, $R^3$ or $R^6$ may be a lactam-containing moiety;

or a protected form, salt, pharmaceutically-acceptable salt, biohydrolyzable ester, or solvate thereof;

the process comprising reacting one or more organosilicon compounds with a compound having a structure according to Formula (II)

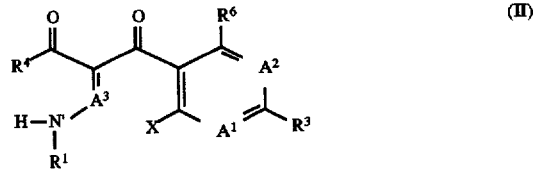

wherein $A^1$, $A^2$ and $A^3$, $R^1$, $R^3$, $R^4$ and $R^6$ as described above; wherein one of $R^1$, $R^3$ or $R^6$ may be a lactam-containing moiety; and X is a leaving group;
or a protected form, salt, biohydrolyzable ester, or solvate thereof.

The compounds prepared according to the processes of the invention are themselves useful as antimicrobials, or they may be used as intermediates for making other quinolone-containing antimicrobials.

25 Claims, No Drawings

PROCESS FOR MAKING ANTIMICROBIAL COMPOUNDS

This is a continuation of application Ser. No. 08/284,960, filed on Aug. 2, 1994 now abandoned.

BACKGROUND OF THE INVENTION

This invention relates to processes for making antimicrobial compounds. The invention also relates to processes for making intermediate compounds which can be further reacted to obtain antimicrobial compounds. In particular, the processes of this invention are useful for making compounds which contain a quinolone or related heterocyclic moiety.

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring (antibiotic), synthetic, or semi-synthetic compounds. They may be classified (for example) as the aminoglycosides, ansamacrolides, beta-lactams (including penicillins and cephalosporins), lincosaminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981), both incorporated by reference herein.

The pharmaceutical literature is replete with attempts to develop improved antimicrobials (i.e., compounds that have a broader scope of activity, greater potency, improved pharmacology, and/or less susceptibility to resistance development). One group of antimicrobials that has been developed for clinical use is the quinolones. These compounds include, for example, nalidixic acid, difloxacin, enoxacin, fleroxacin, norfloxacin, lomefloxacin, ofloxacin, ciprofloxacin, and pefloxacin. See, C. Marchbanks and M. Dudley, "New Fluoroquinolones", 7 *Hospital Therapy* 18 (1988); P. Shah, "Quinolones", 31 *Prog. Drug Res.* 243 (1987); *Quinolones—Their Future in Clinical Practice*, (A. Percival, editor, Royal Society of Medical Services, 1986); and M. Parry, "Pharmacology and Clinical Uses of Quinolone Antibiotics", 116 *Medical Times* 39 (1988).

Recently, a new class of highly potent, broad spectrum antimicrobials was discovered, combining beta-lactam moieties with quinolone moieties. These compounds have been referred to as "Lactam-quinolones" and "Quinolonyl Lactam Antimicrobials" ("QLAs"). Such compounds are described in European Patent Publication 366,189, White and Demuth, published May 2, 1990; European Patent Publication 366, 193, Demuth and White, published May 2, 1990; European Patent Publication 366,640, Demuth and White, published May 2, 1990; European Patent Publication 366,641, White and Demuth, published May 2, 1990. Other such compounds are described in Australian Patent Publication 87/75009, Albrecht et al., published Jan. 7, 1988; Australian Patent Publication 88/27554, published Jun. 6, 1989; European Patent Publication 335,297, Albrecht et al., published Oct. 4, 1989; and Albrecht et al., "Dual Action Cephalosporins; Cephalosporin 3'-Quinolone Carbamates", 34 *J. Medicinal Chemistry* 2857 (1991).

Manufacture of quinolone-containing compounds generally involves the use of a strong base (e.g., sodium hydride, potassium carbonate), polar solvents and high temperatures to affect cyclization of a quinolone precursor. The use of these cyclization conditions can result in low yields, due in-part to degradation, particularly with compounds that contain sensitive or labile functional groups.

It has now been discovered that processes which utilize organosilicon compounds are useful in making quinolones and quinolone-containing lactams. These processes allow for synthesis of such compounds under reaction conditions that eliminate the use of strong bases, polar solvents and high temperatures. Sensitive functional groups in the reaction substrate and product tolerate these mild reaction conditions. These processes may allow for improved yields and product purity and provide additional synthetic flexibility for the preparation of these classes of molecules.

SUMMARY OF THE INVENTION

The present invention provides a process for making a compound having a structure according to Formula (I)

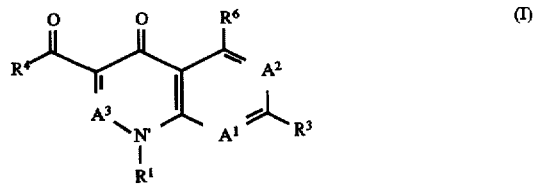

wherein (A)(1) $A^1$ is N or $C(R^7)$; where
   (a) $R^7$ is hydrogen, hydroxy, alkoxy, nitro, cyano, halogen, alkyl, or $-N(R^8)(R^9)$, and
   (b) $R^8$ and $R^9$ are, independently, $R^{8a}$; where $R^{8a}$ is hydrogen, alkyl, alkenyl, a carbocyclic ring, or a heterocyclic ring; or $R^8$ and $R^9$ together comprise a heterocyclic ring including the nitrogen to which they are bonded;

(2) $A^2$ is N or $C(R^2)$; where $R^2$ is hydrogen or halogen;

(3) $A^3$ is N or $C(R^5)$; where $R^5$ is hydrogen;

(4) $R^1$ is hydrogen, alkyl, a carbocyclic ring, a heterocyclic ring, alkoxy, hydroxy, alkenyl, arylalkyl, $-N(R^8)(R^9)$, or a lactam-containing moiety;

(5) $R^3$ is hydrogen, halogen, alkyl, a carbocyclic ring, a heterocyclic ring, or a tactam-containing moiety;

(6) $R^4$ is hydroxy; and (7) $R^6$ is hydrogen, halogen, nitro, hydrazino, alkoxyamino, $-N(R^8)(R^9)$, or a lactam-containing moiety;

except that if one of $R^1$, $R^3$, or $R^6$ is a lactam-containing moiety, then the other two are not a lactam-containing moiety;

(B) and (1) when $A^2$ is $C(R^2)$, $R^2$ and $R^3$ may together comprise $-O-(CH_2)_n-O-$, where n is from 1 to 4;

(2) when $A^3$ is $C(R^5)$, $R^4$ and $R^5$ may together comprise a heterocyclic ring including the carbon atoms to which $R^4$ and $R^5$ are bonded and the carbon atoms of Formula (I) to which said carbon atoms are bonded; and (3) when $A^1$ is $C(R^7)$, $R^3$ and $R^7$ may together comprise a heterocyclic ring including $A^1$ and the carbon atom to which $R^3$ is bonded;

or a protected form, salt, pharmaceutically-acceptable salt, biohydrolyzable ester, or solvate thereof, the process comprising reacting one or more organosilicon compounds with a compound having a structure according to Formula (II),

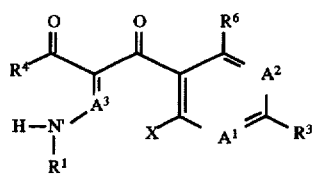

(II)

wherein (A)(1) A¹ is N or C(R⁷); where
(a) R⁷ is hydrogen, hydroxy, alkoxy, nitro, cyano, halogen, alkyl, or —N(R⁵)(R⁸), and
(b) R⁸ and R⁹ are, independently, R⁸ᵃ; where R⁸ᵃ is hydrogen, alkyl, alkenyl, a carbocyclic ring, or a heterocyclic ring; or R⁸ and R⁹ together comprise a heterocyclic ring including the nitrogen to which they are bonded;

(2) A² is N or C(R²); where R² is hydrogen or halogen;

(3) A³ is N or C(R⁵); where R⁵ is hydrogen;

(4) R¹ is hydrogen, alkyl, heteroalkyl, a carbocyclic ring, a heterocyclic ring, alkoxy, hydroxy, alkenyl, arylalkyl, —N(R⁸)(R⁹), or a lactam-containing moiety;

(5) R³ is hydrogen, halogen, alkyl, a carbocyclic ring, a heterocyclic ring, or a lactam-containing moiety;

(6) R⁴ is hydroxy;

(7) R⁶ is hydrogen, halogen, nitro, hydrazino, alkoxyamino, —N(R⁸)(R⁹), or a lactam-containing moiety; and (8) X is a leaving group; except that if one of R¹, R³, or R⁶ is a lactam-containing moiety, then the other two are not a lactam-containing moiety;

(B) and (1) when A² is C(R²), R² and R³ may together comprise —O—(CH₂)ₙ—O—, where n is from 1 to 4;

(2) when A³ is C(R⁵), R⁴ and R⁵ may together comprise a heterocyclic ring including the carbon atoms to which R⁴ and R⁵ are bonded and the carbon atoms of Formula (II) to which said carbon atoms are bonded; and (3) when A¹ is C(R⁷), R³ and R⁷ may together comprise a heterocyclic ring including A¹ and the carbon atom to which R³ is bonded;

or a protected form, salt, biohydrolyzable ester, or solvate thereof.

DESCRIPTION OF THE INVENTION

The present invention encompasses processes for the manufacture of quinolone-containing compounds. These quinolone-containing compounds are useful for treating infectious disorders in humans or other animals. When the compounds made according to these processes are used for treating such disorders, they must be pharmaceutically-acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio. Such pharmaceutically-acceptable forms include salts, biohydrolyzable esters and solvates.

The quinolone-containing compounds prepared according to the processes of the present invention may also be used as intermediates for preparation of other quinolone-containing compounds. That is, the compounds prepared may be further reacted, using known chemistry, to yield other active analogs. (See Examples 13, 14 and 16 below, which illustrate the preparation of such "intermediates".)

Compounds Prepared Using the Present Process

The compounds made by the processes of this invention encompass any of a variety of quinolone-containing compounds, and related heterocyclic moieties.

These compounds have a structure according to Formula (I):

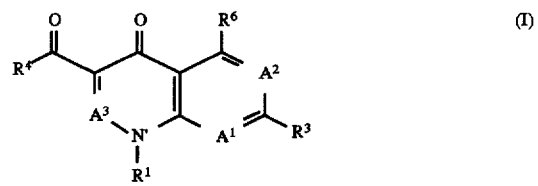

(I)

wherein (A)(1) A¹ is N or C(R⁷); where
(a) R⁷ is hydrogen, hydroxy, alkoxy, nitro, cyano, halogen, alkyl, or —N(R⁸)(R⁹) (preferably hydrogen or halogen), and
(b) R⁸ and R⁹ are, independently, R⁸ᵃ; where R⁸ᵃ is hydrogen, alkyl, alkenyl, a carbocyclic ring, or a heterocyclic ring; or R⁸ and R⁹ together comprise a heterocyclic ring including the nitrogen to which they are bonded;

(2) A² is N or (preferably) C(R²); where R² is hydrogen or (preferably) halogen;

(3) A³ is N or (preferably) C(R⁵); where R⁵ is hydrogen;

(4) R¹ is hydrogen, alkyl, a carbocyclic ring, a heterocyclic ring, alkoxy, hydroxy, alkenyl, arylalkyl, —N(R⁸)(R⁹), or a lactam-containing moiety (preferably alkyl or carbocyclic ring);

(5) R³ is hydrogen, halogen, alkyl, a carbocyclic ring, a heterocyclic ring, or a lactam-containing moiety (preferably a heterocyclic ring or a lactam-containing moiety);

(6) R⁴ is hydroxy; and (7) R⁶ is hydrogen, halogen, nitro, hydrazino, alkoxyamino, —N(R⁸)(R⁹), or a lactam-containing moiety (preferably hydrogen or a lactam-containing moiety; most preferably hydrogen);

except that if one of R¹, R³, or R⁶ is a lactam-containing moiety, then the other two are not a lactam-containing moiety;

(B) and (1) when A² is C(R²), R² and R³ may together comprise —O—(CH₂)ₙ—O—, where n is from 1 to 4;

(2) when A³ is C(R⁵), R⁴ and R⁵ may together comprise a heterocyclic ring including the carbon atoms to which R⁴ and R⁵ are bonded and the carbon atoms of Formula (I) to which said carbon atoms are bonded; and (3) when A¹ is C(R⁷), R³ and R⁷ may together comprise a heterocyclic ring including A¹ and the carbon atom to which R³ is bonded;

or a protected form, salt, pharmaceutically-acceptable salt, biohydrolyzable ester, or solvate thereof.

Where the compounds synthesized using the present methods are used as intermediates, they may contain various functional groups (e.g., alcohols, amines, carboxylic acids, etc.) that may be present in a protected form, utilizing protecting groups (e.g., esters, carbonates, ethers, silyl ethers, amides, carbamates, etc.) introduced by methods well known in the art. The art is also replete with methodology to remove these protecting groups. Where the compounds synthesized are used as antimicrobials, they may be in acid form, or as a pharmaceutically-acceptable salt, biohydrolyzable ester, or solvate thereof.

Definitions and Usage of Terms:

The following is a list of definitions for terms used herein.

"Acyl" or "carbonyl" is a radical formed by removal of the hydroxy from a carboxylic acid (i.e., R—C(=O)—). Preferred acyl groups include (for example) acetyl, formyl, and propionyl.

"Acyloxy" is an oxygen radical having an acyl substituent (i.e., —O-acyl); for example,—O—C(=O)-alkyl.

"Acylamino" is an amino radical having an acyl substituent (i.e., —N-acyl); for example, —NH—C(=O)—R. "Alkylacylamino" is where R is alkyl. "Arylacylamino" is where R is aryl. "Heteroalkylacylamino" is where R is heteroalkyl. "Heteroarylacylamino" is where R is heteroaryl.

"Alkyl" is an unsubstituted or substituted saturated hydrocarbon chain radical having from 1 to 8 carbon atoms, preferably from 1 to 4 carbon atoms. Preferred alkyl groups include (for example) methyl, ethyl, propyl, isopropyl, and butyl.

"Alkylamino" is an amino radical having one or two alkyl substituents (i.e., —N-alkyl).

"Alkenyl" is an unsubstituted or substituted hydrocarbon chain radical having from 2 to 8 carbon atoms, preferably from 2 to 4 carbon atoms, and having at least one olefinic double bond.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Aryl" is an aromatic carbocyclic ring radical. Preferred aryl groups include (for example) phenyl, tolyl, xylyl, cumenyl and naphthyl.

"Arylalkyl" is an alkyl radical substituted with an aryl group. Preferred arylalkyl groups include benzyl and phenylethyl.

"Arylamino" is an amine radical substituted with an aryl group (i.e., —NH-aryl).

"Aryloxy" is an oxygen radical having an aryl substituent (i.e., —O-aryl).

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Cycloalkyl" is a saturated carbocyclic ring radical. Preferred cycloalkyl groups include (for example) cyclopropyl, cyclobutyl and cyclohexyl.

"Halo", "halogen", or "halide" is a chloro, bromo, fluoro or iodo atom radical. Chloro and fluoro are preferred halides.

"Heteroatom" is a nitrogen, sulfur or oxygen atom. Groups containing one or more heteroatoms may contain different heteroatoms.

"Heteroalkyl" is an unsubstituted or substituted saturated chain radical having from 3 to 8 members comprising carbon atoms and one or two heteroatoms.

"Heteroalkenyl" is an unsubstituted or substituted chain radical having from 2 to 8 carbon atoms, preferably from 2 to 6 carbon atoms, having at least one olefinic double bond, and having one or two heteroatoms.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic rings contain from 3 to 9 atoms, preferably 4 to 8 atoms, more preferably from 5 to 8 atoms, most preferably from 4 to 6 atoms. Polycyclic rings contain from 7 to 17 atoms, preferably from 7 to 13 atoms.

"Heterocycloalkyl" is a saturated heterocyclic ring radical. Preferred heterocycloalkyl groups include (for example) piperazine, morpholine, and pyrrolidine.

"Heteroaryl" is an aromatic heterocyclic ring radical. Preferred heteroaryl groups include (for example) thienyl, furyl, pyrrolyl, pyridinyl, pyrazinyl, thiazolyl, pyrimidinyl, quinolinyl, and tetrazolyl.

"Heteroarylalkyl" is an alkyl radical substituted with an heteroaryl group.

Also, as referred to herein, a "lower" hydrocarbon moiety (e.g., "lower" alkyl) is a hydrocarbon chain comprised of from 1 to 6, preferably from 1 to 4, carbon atoms.

An "organosilicon" compound is any silicon-containing compound that is commonly utilized in silylation reactions, that is, reactions which substitute a hydrogen atom bound to a heteroatom (e.g., —OH, =NH, —SH, etc.) with a silyl group, usually a trialkylsilyl group, including reactions of a tautomer of a heteroatom system to form a silyl derivative (e.g., silyl enol ethers), forming a silicon-heteroatom bond. Many such compounds are well known in the art, as described in the following articles, all incorporated by reference herein: E. Plueddemann, "Silylating Agents", in: Kirk-Othmer, 3d ed., Vol. 20, "Encyclopedia of Chemical Technology" (1982); I. Fleming, "Organic Silicon Chemistry", in: Vol. 3, "Comprehensive Organic Chemistry" (D. Jones, editor, 1979); B. Cooper, "Silylation in Organic Synthesis", *Proc. Biochem.* 9 (1980); W. Weber, "Silicon Reagents for Organic Synthesis (1983); B. Cooper, "Silylation as a Protective Method in Organic Synthesis, *Chem. Ind.* 794 (1978); J. Rasmussen, "O-Silylated Enolates—Versatile Intermediates for Organic Synthesis" 91 *Synthesis* (1977). Such organosilicon compounds include chlorotrimethylsilane, N,O-bis(trimethylsilyl)acetamide, N,O-bis(trimethylsilyl)trifluoroacetamide, bis (trimethylsilyl)urea, hexamethyldisilazane, N-methyl-N-trimethylsilyltrifluoroacetamide, 1-trimethylsilylimidazole, trimethylsilyl trifluoromethanesulfonate, tert-butyldimethylchlorosilane, 1-(tert-butyldimethylsilyl)-imidazole, N-tert-butyldimethyl-N-methyltrifluoroacetamide, tert-butyldimethylsilyl trifluoromethanesulfonate, tert-butyldiphenylchlorosilane, tert-butyl-methoxyphenylbromosilane, dimethylphenylchlorosilane, triethylchlorosilane, triethylsilyl trifluoromethanesulfonate, and triphenylchlorosilane.

A "pharmaceutically-acceptable salt" or a "salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium). Preferred anionic salts include the halides (such as chloride salts).

A "protected form", as referred to herein, is a derivative of the described compound wherein certain functional groups contained in the structures (such as carboxyl, hydroxyl, and amino groups) are blocked in order to prevent undesired competing side reactions and, occasionally, to improve the solubility of the compound. Suitable protecting groups for carboxyl substituents include, for example, esters. Protecting groups for hydroxyl substituents include, for example, ethers, esters, and carbonates; and protecting groups for amino substituents include, for example, carbamates and amides. If various protecting groups are employed, then appropriate methods for introducing and removing the protecting groups, that will not decompose the quinolone or related heterocyclic compound, may be required to efficiently obtain antibacterially active products or intermediates thereof. Appropriate protecting groups for these processes are well known in the art. For hydroxyl groups, suitable derivatives include, for example, alkyl ethers [such as allyl, tert-butyl, and 2-(trimethylsilyl)ethoxymethyl], silyl ethers (such as trimethylsilyl, tert-butyldimethylsilyl, tert-butyldiphenylsilyl), esters (such as acetate and trifluoroacetate) and carbonates (such as allyl and vinyl). For amines, suitable carbamates include, for example, tert-butyl and 2-trimethylsilyl, and suitable amides include, for example, trifluoroacetamide. For carboxylic acids, suitable esters include, for example, allyl, p-methoxybenzyl, p-nitrobenzyl, diphenylmethyl, 2,2,2-trichloroethyl, 2-trimethylsilylethyl, 2-methylthioethyl, trimethylsilyl, t-butyldiphenylsilyl, t-butyl, and tributylstannyl esters. Such protecting groups and methods for their introduction and removal are described in T. W. Greene et al., *Protective Groups in Organic Synthesis*, 2d edition, J. Wiley and Sons (1991), incorporated by reference herein.

A "biohydrolyzable ester" is an ester of a quinolone that does not essentially interfere with the antimicrobial activity of the compounds, or that are readily metabolized by a human or lower animal subject to yield an antimicrobially-active quinolone. Such esters include those that do not interfere with the biological activity of quinolone antimicrobials. Many such esters are known in the art, as described in World Patent Publication 87/05297, Johnston et al., published Sep. 11, 1987, (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and alkyl acylamino alkyl esters (such as acetamidomethyl esters).

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyacyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryl oxy, aryl alkyl, and combinations thereof.

Also, as used in defining the structure of the compounds of this invention, a particular radical may be defined for use as a substituent in multiple locations. For example, the $R^8$ substituent is defined as a potential substituent of $R^7$, but is also incorporated into the definition of other substituents (such as $R^1$, and $R^6$). As used herein, such a radical is independently selected each time it is used (e.g., $R^8$ need not be alkyl in all occurrences in defining a given compound of this invention).

Groups $A^1$, $A^2$, $A^3$, $R^1$, $R^3$, $R^4$ and $R^6$ form any of a variety of quinolone, naphthyridine, lactam-quinolone, or related heterocyclic moieties known in the art to have antimicrobial activity. Such moieties are well known in the art, as described in the following articles, all incorporated by reference herein: L. Mitscher, et al., in "Quinolone Antimicrobial Agents", 2d ed., Chap. 2, pp 3–51 (D. C. Hooper and J. S. Wolfson, editors, 1993); J. Wolfson et al., "The Fluoroquinolones: Structures, Mechanisms of Action and Resistance, and Spectra of Activity In Vitro", 28 *Antimicrobial Agents and Chemotherapy* 581 (1985); T. Rosen et al., 31 *J. Med Chem.* 1586 (1988); T. Rosen et al., 31 *J. Med. Chem.* 1598 (1988); G. Klopman et al., 31 *Antimicrob. Agents Chemother.* 1831 (1987); 31:1831–1840; J. P. Sanchez et al., 31 *J. Med. Chem.* 983 (1988); J. M. Domagalia et al., 31 *J. Med. Chem.* 991 (1988); M. P. Wentland et al., in 20 *Ann. Rep. Med. Chem.* 145 (D. M. Bailey, editor, 1986); J. B. Cornett et al., in 21 *Ann. Rep. Med. Chem.* 139 (D. M. Bailey, editor, 1986); P. B. Fernandes et al., in 22 *Ann. Rep. Med. Chem,* 117 (D. M. Bailey, editor, 1987); R. Albrecht, 21 *Prog. Drug Research* 9 (1977); P. B. Fernandes et al., in 23 *Ann. Rep. Med. Chem.* (R. C. Allen, editor, 1987); European Patent Publication 366,189, White and Demuth, published May 2, 1990; European Patent Publication 366,193, Demuth and White, published May 2, 1990; European Patent Publication 366,640, Demuth and White, published May 2, 1990; European Patent Publication 366,641, White and Demuth, published May 2, 1990. Other such compounds are described in Australian Patent Publication 87/75009, Albrecht et al., published Jan. 7, 1988; Australian Patent Publication 88/27554, published Jun. 6, 1989; European Patent Publication 335,297, Albrecht et al., published Oct. 4, 1989; and Albrecht et al., "Dual Action Cephalosporins; Cephalosporin 3'-Quinolone Carbamates", 34 *J. Medicinal Chemistry* 2857 (1991).

Preferred quinolone moieties include those where $A^1$ is $C(R^7)$, $A^2$ is $C(R^2)$, and $A^3$ is $C(R^5)$ (i.e., quinolones); $A^1$ is nitrogen, $A^2$ is $C(R^2)$, and $A^3$ is $C(R^5)$ (i.e., naphthyridines); $A^1$ is $C(R^7)$, $A^2$ is $C(R^2)$, and $A^3$ is nitrogen (i.e., cinnoline acid derivatives); and where $A^1$ is nitrogen, $A^2$ is nitrogen, and $A^3$ is $C(R^5)$ (i.e., pyridopyrimidine derivatives). More preferred quinolone moieties are those where $A^1$ is $C(R^7)$, $A^2$ is $C(R^2)$, and $A^3$ is $C(R^5)$ (i.e., quinolones); and where $A^1$ is nitrogen, $A^2$ is $C(R^2)$, and $A^3$ is $C(R^5)$ (i.e., naphthyridines). Particularly preferred quinolone moieties are where $A^1$ is $C(R^7)$, $A^2$ is $C(R^2)$, and $A^3$ is $C(R^5)$ (i.e., quinolones).

$R^1$ is preferably alkyl, aryl, cycloalkyl and alkylamino. More preferably, $R^1$ is ethyl, 2-fluoroethyl, 2-hydroxyethyl, t-butyl, 4-fluorophenyl, 2,4-difluorophenyl, methylamino and cyclopropyl. Cyclopropyl is a particularly preferred $R^1$ group.

$R^2$ is preferably chlorine or fluorine. Fluorine is a particularly preferred $R^2$ group.

Preferred $R^3$ groups include nitrogen-containing heterocyclic rings. Particularly preferred are nitrogen-containing heterocyclic rings having from 5 to 8 members. The heterocyclic ring may contain additional heteroatoms, such as oxygen, sulfur, or nitrogen, preferably nitrogen. Such heterocyclic groups are described in U.S. Pat. No. 4,599,334, Petersen et al., issued Jul. 8, 1986; and U.S. Pat. No. 4,670,444, Grohe et al., issued Jun. 2, 1987 (both incorporated by reference herein). Preferred $R^3$ groups include unsubstituted or substituted pyridine, piperidine, morpholine, diazabicyclo[3.1.1]heptane, diazabicyclo [2.2.1]heptane, diazabicyclo-[3.2.1]octane, diazabicyclo [2.2.2]octane, thiazolidine, imidazolidine, pyrrole and thiamorpholine, as well as the following particularly preferred $R^3$ groups include piperazine, 3-methylpiperazine, 3-aminopyrrolidine, 3-aminomethylpyrrolidine, 3-(1- amino-ethyl)pyrrolidine N,N-dimethylaminomethylpyrrolidine, N-methylaminomethylpyrrolidine, N-ethylaminomethylpyrrolidine, pyridine, N-methylpiperazine and 3,5-dimethylpiperazine.

Preferred quinolones include those having a 6-fluoroquinolone moiety or an 8-halo-6-fluoroquinolone moiety, of formula:

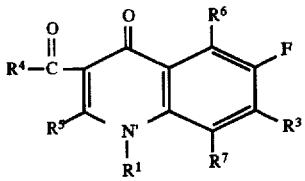

wherein, referring to formula (I), $A^2$ is $C(R^2)$ and $R^2$ is F; $A^3$ is $C(R^5)$; and $A^1$ is $C(R^7)$ where $R^7$ is hydrogen, fluorine or chlorine.

Also preferred are quinolones having a 1,8-naphthyridine moiety, of formula:

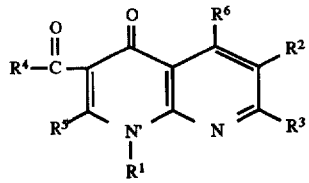

wherein, referring to formula (I), $A^1$ is N; $A^2$ is $C(R^2)$ and $A^3$ is $C(R^5)$.

Also preferred are quinolones having a pyridobenoxazine or pyridobenzthiazine moiety, of formula:

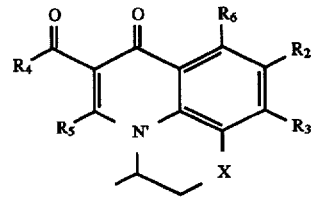

wherein, referring to formula (I), $A^1$ is $C(R^7)$; $A^2$ is $C(R^2)$; $A^3$ is $C(R^5)$; and $R^7$ and $R^1$ together comprise a linking moiety between N' and $A^1$ to form a 6-membered heterocyclic ring where X (in this formula) is oxygen or sulfur. These compounds are prepared by an additional reaction step subsequent to the reaction step of the present invention. Specifically, after the quinolone (i.e., two fused rings) is formed using the processes of the present invention, the third fused ring (i.e., between N' and $A^1$) is formed by methods known in the art. (See, for example, Bouzard et al., "Utilisation du Fluorure de Tetrabutylammonium comme Agent de Cyclisation dans la Synthese D'Antibacteriens Derives D'Acide Pyridone4-Carboxylique-3", 29 *Tet. Lett.* 1931-1934 (1988)). This additional step is illustrated hereinbelow in Example 12.

Also preferred are quinolones having an isothiazoloquinolinedione or isoxazoloquinolinedione moiety, of formula:

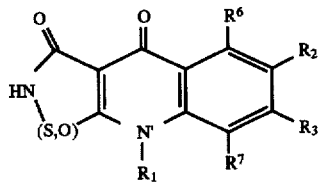

wherein, referring to formula (I), wherein $A^1$ is $C(R^7)$; $A^2$ is $C(R^2)$; $A^3$ is $C(R^5)$; and $R^4$ and $R^5$ together comprise a moiety forming a 5-membered, substituted, heterocyclic ring comprising a ring sulfur or oxygen atom.

Also preferred are lactam-quinolones. Such compounds are those of Formula (I) where one of $R^1$, $R^3$, or $R^6$ is a lactam-containing moiety. Such compounds are disclosed in European Patent Publication 366,189, White and Demuth, published May 2, 1990 and World Patent Publication 91/16327, published Oct. 31, 1991, both of which are incorporated by reference herein. Lactam-quinolones are those compounds of Formula (I) where:

(A)(1) $R^1$ is $R^{34}$—L—B; where $R^{34}$ is nil; or $R^{34}$ is, together with L, an unsubstituted or substituted lower alkyl, cycloalkyl, or aryl; unsubstituted or substituted, saturated or unsaturated, branched or unbranched alkylamino; arylamino; alkoxy; hydroxy; heteroaryl; hetemcycloalkyl; alkenyl; or arylalkyl;

(2) $R^3$ is $R^{35}$—L—B, where $R^{35}$ is nil; or $R^{35}$ is, together with L, a lower alkyl, or an unsubstituted or substituted 5- or 6-membered heterocyclic ring containing from 1 to 3 oxygen, nitrogen, or sulfur atoms in the ring; or (3) $R^6$ is R36—L—B; where $R^{36}$ is nil; or $R^{36}$ is, together with L, an unsubstituted or substituted lower alkyl, cycloalkyl, or aryl; unsubstituted or substituted, saturated or unsaturated, branched or unbranched alkylamino; arylamino; alkoxy; hydroxy; heteroaryl; heterocycloalkyl; alkenyl; or arylalkyl; and (B) B is a structure according to Formula (III), where L is linked to $R^{14}$

(III)

wherein (1) $R^{10}$ is hydrogen or halogen; or $R^{10}$ is alkyl, alkenyl, heteroalkyl, heteroalkenyl, a carbocyclic ring, or a heterocyclic ring; that is unsubstituted or substituted with moieties selected from the group consisting of saturated and unsaturated, substituted and unsubstituted alkyl, a substituted and unsubstituted, saturated and unsaturated carbocyclic ring, a substituted and unsubstituted, saturated and unsaturated heterocyclic ring, hydroxy and short chain esters thereof, substituted and unsubstituted amino and acylated derivatives thereof, and mixtures thereof;

(2) $R^{11}$ is hydrogen; halogen; substituted or unsubstituted, saturated or unsaturated lower alkoxy, aryloxy, heteroalkoxy or heteroaryloxy containing from 1 to 4 heteroatoms selected from the group consisting of oxygen, nitrogen, sulfur, and mixtures thereof; or alkylacylamino, arylacylarrfino, heteroalkylacylamino or heteroarylacylamino containing from 1 to 4 heteroatoms selected from the group consisting of oxygen, nitrogen, sulfur, and mixtures thereof, where the acyl substituent is hydrogen or branched or cyclic, substituted or unsubstituted, saturated or unsaturated lower alkyl, aryl, heteroalkyl or heteroaryl containing from 1 to 4 heteroatoms selected from the group consisting of oxygen, nitrogen, sulfur, and mixtures thereof;

(3) bond "a" may be a single bond or may be nil; and bond "b" may be a single bond, double bond, or may be nil; except bond "a" and bond "b" are not both nil;

(4) $R^{12}$ may be —CH— or —CH$_2$—$R^{15}$, where $R^{15}$ is CH, O, or N, and $R^{15}$ is directly bonded to N" in Formula (III) to form a 5-membered ring;

(5) $R^{13}$ is —C(COOH)—; except if bond "b" is nil, then $R^{13}$ is —SO$_3$H; —PO(OR$^{16}$)OH, —C(O)NHSO$_2$N(R$^{16}$)(R$^{17}$), —OSO$_3$H, —CH(R$^{17}$)COOH, or —OCH(R$^{16}$)COOH; where $R^{16}$ is hydrogen, alkyl or aryl; and $R^{17}$ is hydrogen, alkyl, aryl, acyloxy, alkoxy or aryloxy; or $R^{16}$ and $R^{17}$ together comprise a 3- to 8-membered ring; and (6) $R^{14}$ is —W—C—C'''—(CH$_2$)$_n$—, —W—C'''—(CH$_2$)$_n$—, —W—C'''(R$^{18}$)—(CH$_2$)$_n$—; or —W—C'''=C—(CH$_2$)$_n$— (if bond "b" is not a double bond); where n is from 0 to 9; W is O, S(O)$_m$, or C(R$^{19}$), and m is from 0 to 2; $R^{18}$ is hydrogen, methyl, or methylene linked to $R^{13}$ to form a 3-membered ring (if bond "b" is not a double bond); $R^{19}$ is hydrogen, lower alkyl or lower alkoxy; and wherein C''' is directly linked to $R^{13}$ to form a 5- or 6-membered ring; except if bond "a" or bond "b" is nil, then $R^{14}$ is nil; and wherein L links said structure of Formula (I) to said structure of Formula (III); and L is L' or —S(O)$_m$—R$^{25}$—L'; and L' is —X$^1$—, —X$^2$—, —X$^3$—C(=Y)—Z$_q$—, —X$^4{}_q$—PO(Y',R$^{20}$)—Z'$_p$—, or X$^4{}_q$—SO$_2$—Z'$_p$—; where p, q, and r are, independently, 0 or 1;

(1) $R^{25}$ is unsaturated or saturated, cyclic or acyclic, unsubstituted or substituted alkyl or heteroalkyl;

(2) $R^{20}$ is hydrogen, substituted or unsubstituted lower alkyl, aryl, or acyl;

(3) $X^1$ is oxygen, S(O)$_m$, or a substituted or unsubstituted carbon;

(4) $X^2$ is nitrogen, N(R$^{21}$), N$^+$(R$^{21}$)(R$^{24}$), or R$^{23}$—N(R$^{22}$); where $R^{21}$ is $R^{20}$, hydroxy, alkoxy, aryloxy, or acyloxy, or is part of $R^{34}$ (if B is a substituent of R$^1$), is part of $R^{35}$ (if B is a substituent of R$^3$), or is part of $R^{36}$ (if B is a substituent of R$^6$); $R^{22}$ is hydrogen, unsubstituted or substituted lower alkyl or aryl, or is part of $R^{34}$ (if B is a substituent of R$^1$), part of $R^{35}$ (if B is a substituent of R$^3$), or is part of $R^{36}$ (if B is a substituent of R$^6$); and $R^{23}$ is N(R$^{24}$), oxygen or sulfur, where $R^{24}$ is hydrogen, unsubstituted or substituted lower alkyl, or unsubstituted or substituted aryl; and $X^2$ is linked to $R^{14}$ by a single or double bond;

(5) $X^3$ is oxygen, sulfur, NR$^{21}$, or R$^{23}$—NR$^{22}$;

(6) $X^4$ is oxygen, sulfur, or NR$^{22}$;

(7) Y is oxygen, sulfur, NR$^{21}$, or N$^+$(R$^{22}$)(R$^{24}$);

(8) Y' is oxygen, sulfur, or NR$^{22}$;

(9) Z is oxygen, sulfur, nitrogen, NR$^{21}$, or N(R$^{22}$)—R$^{23}$; and

(10) Z' is oxygen, sulfur, nitrogen, or NR$^{22}$; or a protected form, salt, ester or solvate thereof.

Where a lactam-quinolone is prepared, groups $R^{12}$, $R^{13}$, and $R^{14}$, together with bonds "a" and "b" of formula (III), form any of a variety of lactam-containing moieties known in the art to have antimicrobial activity. Such moieties wherein either bond "a" or bond "b" are nil (i.e., do not exist) are monocyclic; if both bonds exist, the structures are bicyclic. Preferably, bond "a" is a single bond and bond "b" is a double bond.

Preferred lactam moieties include the cephems, oxacephems and carbacephems of the representative formula:

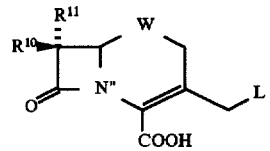

wherein, referring to formula (III), bond "a" is a single bond; bond "b" is a double bond; $R^{12}$ is —CH—; $R^{13}$ is —C(COOH)=; and $R^{14}$ is —W—C—C'''—(CH$_2$)$_n$—; where n=1, and W is S (for cephems), O (for oxacephems) or C(R$^{13}$) (for carbacephems).

Other preferred lactam moieties include the isocephems and iso-oxacephems of the representative formula:

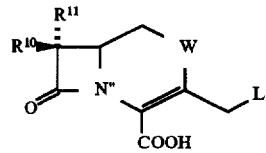

wherein, referring to formula (III), bond "a" is a single bond; bond "b" is a double bond; $R^{12}$ is —CH—; $R^{13}$ is —C(COOH)=; and $R^{14}$ is —C—W—C'''—(CH$_2$)$_n$—; where n=1, and W is S (for isocephems) or O (for isooxacephems).

Other preferred lactam-containing moieties include the penems, carbapenems and clavems, of the representative formula:

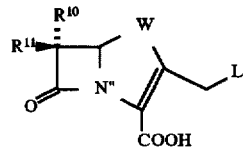

wherein, referring to formula (III), bond "a" is a single bond; bond "b" is a double bond; $R^{12}$ is —CH—; $R^{13}$ is —C(COOH)=; and $R^{14}$ is —W—C'''—(CH$_2$)$_n$—; where n=1, and W is S (for penems), C(R$^{19}$) (for carbapenems), or O (for clavems). Such lactam moieties are described in the following articles, all incorporated by reference herein: R. Wise, "In Vitro and Pharmacokinetic Properties of the Carbapenems", 30 *Antimicrobial Agents and Chemotherapy* 343 (1986); and S. McCombie et al., "Synthesis and In Vitro Activity of the Penera Antibiotics", 8 *Medicinal Research Reviews* 393 (1988).

Other preferred lactam-containing moieties of this invention include the penicillins of the representative formula:

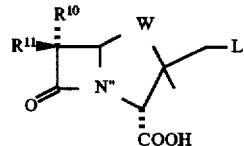

wherein, referring to formula (III), bond "a" is a single bond; bond "b" is a single bond; $R^{12}$ is —CH—; $R^{13}$ is —CH(COOH)—; and $R^{14}$ is —W—C'''(CH$_3$)—(CH$_2$)$_n$—; where n=1, and W is S.

Other preferred lactam-containing moieties include the monocyclic beta-lactams, of the representative formula:

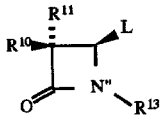

wherein, referring to formula (III), bond "a" is a single bond; bond "b" is nil; $R^{12}$ is —CH—; $R^{14}$ is covalent bond; and $R^{13}$ is —SO$_3$H (for a monobactam), —PO(OR$^{16}$)OH (for a monophospham); —C(O)NHSO$_2$N(R$^{16}$)(R$^{17}$) (for a monocarbam), —OSO$_3$H (for a monosulfactam), —CH(R$^{17}$)COOH (for nocardicins), or —OCH(R$^{16}$)COOH. Such lactam moieties are described in C. Cimarusti eta., "Monocyclic β-lactam Antibiotics", 4 *Medicinal Research Reviews* 1 (1984), incorporated by reference herein.

Other preferred lactam moieties include the monocyclic beta-lactams of the representative formula:

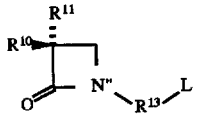

wherein referring to formula III, bond "a" is nil, bond "b" is a single bond; $R^{12}$ is —CH$_2$—; and $R^{14}$ is covalent bond.

Other preferred lactam moieties include the clavams of the representative formula:

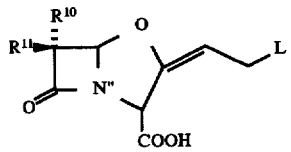

wherein, referring to formula (III), bond "a" is a single bond; bond "b" is a single bond; $R^{12}$ is —CH—; $R^{13}$ is —CH(COOH); and $R^{14}$ is W—C'''=C—(CH$_2$)$_n$—; where n=1, and W is O.

Other preferred lactam moieties include the 2,3-methyleno-penams and carbapenams of the representative formula:

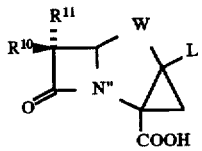

wherein, referring to formula (III), bond "a" is a single bond; bond "b" is a single bond; $R^{12}$ is —CH—; $R^{13}$ is —C(COOH); and $R^{14}$ is W—C'''CR$^{18}$)—, where n=1, and X is C(R$^{19}$) or sulfur, and $R^{18}$ is methylene linked to $R^{13}$ to from a 3-membered ring.

Lactam moieties of this invention also include the lactivicin analogs of the representative formula:

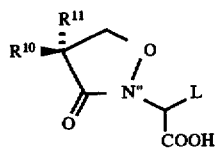

wherein, referring to formula (III), bond "a" is nil; bond "b" is a single bond; $R^{12}$ is —CH$_2$—R$^{15}$, where $R^{15}$ is O; $R^{13}$ is —CH(COOH); and $R^{14}$ is covalent bond.

Other lactam moieties include the pyrazolidinones of the representative formula:

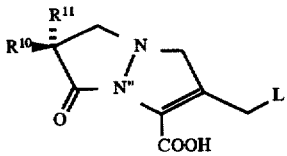

wherein, referring to formula (III), bond "a" is a single bond; bond "b" is a double bond; $R^{12}$ is —CH$_2$—R$^{15}$—, where $R^{15}$ is —N—; $R^{13}$ is —C(COOH); and $R^{14}$ is W—C'''—CH$_2$)$_n$—; where n=1, and X is C(R$^{19}$).

Other lactam moieties include the gamma-lactams of the representative formula:

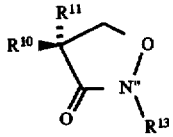

wherein, referring to formula (III), bond "a" is a single bond; bond "b" is nil; $R^{12}$ is —CH$_2$—R$^{15}$—, where $R^{15}$ is —CH—; $R^{13}$ is —SO$_3$H, —PO(OR$^{16}$)OH, —C(O)NHSO$_2$N(R$^{16}$)(R$^{17}$), —OSO$_3$H, —CH(R$^{17}$)COOH, or —OCH(R$^{16}$)COOH; and $R^{14}$ is covalent bond.

Preferred lactam-containing moieties include cephems, isocephems, isooxacephems, oxacephems, carbacephems, penicillins, penems, carbapenems, and monocyclic beta-lactams. Particularly preferred lactam-containing moieties for compounds made by this invention are penems, carbapenems, cephems, and carbacephems.

$R^{10}$, in formula (III), is any radical that may be substituted at the active stereoisomeric position of the carbon adjacent to the lactam carbonyl of an antimicrobially-active lactam. (As used herein, the term "antimicrobially-active lactam" refers to a lactam-containing compound, without a quinolonyl substituent moiety, which has antimicrobial activity.) This "active" position is beta (i.e., 7-beta) for cephems, oxacephems and carbacephems (for example). The active position is alpha for penems, carbapenems, clavems and clavams.

Appropriate $R^{10}$ groups will be apparent to one of ordinary skill in the art. Many such $R^{10}$ groups are known in the art, as described in the following documents (all of which are incorporated by reference herein): *Cephalosporins and Penicillins: Chemistry and Biology* (E. Flynn, editor, 1972); *Chemistry and Biology of β-Lactam Antibiotics* (R. Morin et al., editors, 1987); "The Cephalosporin Antibiotics: Seminar-in-Print", 34 *Drugs* (Supp. 2)1 (I. Williams, editor, 1987); *New Beta-Lactam Antibiotics: A Review from Chemistry of Clinical Efficacy of the New Cephalospodns* (H. Neu, editor, 1982); M. Sassiver et al., in *Structure Activity Relationships among the Semi-synthetic Antibiotics* (D. Perlman, editor, 1977). W. Durckheimer et al., "Recent Developments in the Field of Beta-Lactam Antibiotics", 24 *Angew. Chem. Int. Ed. Engl.* 180 (1985); G. Rolinson, "Beta-Lactam Antibiotics", 17 *J. Antimicrobial Chemotherapy* 5 (1986); European Patent Publication 187,456, Jung, published Jul. 16, 1986; and World Patent Publication 87/05297, Johnston et al., published Sep. 11, 1987.

For penems, carbapenems, clavems and clavans, $R^{10}$ is preferably lower alkyl, or hydroxy-substituted lower alkyl. Particularly preferred $R^{10}$ groups include hydrogen, hydroxymethyl, ethyl, [1(R)-hydroxyethyl], [1(R)-[(hydroxysulfonyl)oxyethyl]], and [1-methyl-1-hydroxyethyl].

Except for penems, carbapenems, clavems and clavams, preferred $R^{10}$ groups are amides, such as: acetylamino, preferably substituted with aryl, heteroaryl, aryloxy, heteroarylthio and lower alkylthio substituents; arylglycylamino, preferably N-substituted with heteroarylcarbonyl and cycloheteroalkylcarbonyl substituents; arylcarbonylamino; heteroarylcar-bonylamino; and lower alkoxyiminoacetylamino, preferably substituted with aryl and heteroaryl substituents.

Particularly preferred $R^{10}$ groups include amides of the general formula

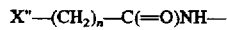

wherein n is from 0 to 9; and

X" is —$R^{26}$, —Y—$R^{27}$, —CH(Y—$R^{27}$)$R^{26}$), or —CH(Y—$R^{27}$)(Z—$R^{28}$); where (1) $R^{26}$ is hydrogen, or branched or cyclic, substituted or unsubstituted, saturated or unsaturated lower alkyl, aryl, or heteroalkyl or heteroaryl containing from 1 to 4 heteroatoms selected from the group consisting oxygen, nitrogen, sulfur, and mixtures thereof;

(2) Y and Z are, independently, —O—, —S—, —N($R^{29}$)—, —SO$_3$—, —COO—, or —C(=O)—;

(3) $R^{29}$ is hydrogen; branched or cyclic, substituted or unsubstituted, saturated or unsaturated, lower alkyl, aryl, heteroalkyl or heteroaryl containing from 1 to 4 heteroatoms selected from the group consisting of oxygen, nitrogen, sulfur, and mixtures thereof, —SO$_3$H; —C(=O)$R^{30}$; or a cyclic structure containing from 3 to 8 carbon or heteroatoms connected to $R^{27}$;

(4) $R^{30}$ is $R^{26}$; branched or cyclic, substituted or unsubstituted, saturated or unsaturated lower alkoxy, aryloxy, heteroalkoxy or heteroaryloxy containing from 1 to 4 heteroatoms selected from the group consisting of oxygen, nitrogen, sulfur, and mixtures thereof; alkylthio, arylthio, heteroalkylthio or heteroarylthio containing from 1 to 4 heteroatoms selected from the group consisting of oxygen, nitrogen, sulfur, and mixtures thereof, amino, mono- or di-substituted alkylamino; arylamino; or heteroalkylamino or heteroarylamino containing from 1 to 4 heteroatoms selected from the group consisting of oxygen, nitrogen, sulfur, and mixtures thereof; and (5) $R^{27}$ and $R^{28}$ are, independently, hydrogen (except when X" is —CH(Y$R^{27}$)(Z—$R^{28}$) and Y and Z are selected from the group consisting of —O—, —S—, N($R^{29}$), and mixtures thereof; branched or cyclic, substituted or unsubstituted, saturated or unsaturated, lower alkyl, aryl, heteroalkyl or heteroaryl containing from 1 to 4 heteroatoms selected from the group consisting of oxygen, nitrogen, sulfur, and mixtures thereof; —C(=O)$R^{30}$; a cyclic structure containing from 3 to 8 carbon or heteroatoms between $R^{27}$ and $R^{28}$.

Examples of such preferred $R^{10}$ groups include:

[(2-amino-5-halo-4-thiazolyl)acetyl]amino;
[(4-aminopyridin-2-yl)acetyl]amino;
[[(3,5-dichloro-4-oxo-1 (4H)-pyridinyl)acetyl]amino];
[[[2-(aminomethyl)phenyl]acetyl]amino];
[(1H-tetrazol-1-ylacetyl)amino];
[(cyanoacetyl)amino];
[(2-thienylacetyl)amino];
[[(2-amino-4-thiazoyl)acetyl]amino];
sydnone, 3-[-2-amino]-2-oxoethyl[sulfamoylphenylacetyl]amino;
[[(4-pyridinylthio)acetyl]amino];
[[[(cyanomethyl)thio]acetyl]amino];
(S)-[[[(2-amino-2-carboxyethyl)thio]acetyl]amino];
[[[(trifluoromethyl)thio]acetyl]amino]; and
(E)-[[[(2-aminocarbonyl-2-fluoroethenyl)thio]acetyl]amino];
[carboxyphenylacetyl]amino;
[(phenoxycarbonyl)phenylacetyl]amino;
[4-methyl-2,3-dioxo-1-piperazinecarbonyl-D-phenylglycyl]amino;
[[[3-(2-furylmethyleneamino)-2-oxo-1-imidazolidinyl]carbonyl]amino]phenyl]-acetyl]amino;
(R)-[(aminophenylacetyl)amino];
(R)-[[amino(4-hydroxyphenyl)acetyl]amino];
(R)-[(amino-1,4-cyclohexadien-1-ylacetyl)amino];
[(hydroxyphenylacetyl)amino];
(R)-[[[[(4-ethyl-2,3-dioxo-1-piperazinyl)carbonyl]amino] (4-hydroxyphenyl)acetyl]amino];
(R)-[[[[(5-carboxy-1H-imidazol-4-yl)carbonyl]amino]phenylacetyl]amino];
(R)-[[[[(4-hydroxy-6-methyl-3-pyridinyl)carbonyl]amino] (4-hydroxyphenyl)acetyl]amino];
(R)-[(phenylsulfoacetyl)amino];
(2R,3S)-[[2-[[(4-ethyl-2,3-dioxo-1-piperazinyl)carbonyl]amino]-3-hydroxy-1-oxobutyl]amino];
[[carboxy(4-hydroxyphenyl)acetyl]amino];
(R)-[[amino[3-[(ethylsulfonyl)amino]phenyl]acetyl]amino];
(R)-[[amino(benzo[b]thien-3-yl)acetyl]amino];
(R)-[[amino(2-naphthyl)acetyl]amino];
(R)-[[amino(2-amino-4-thiazolyl)acetyl]amino];
[[[[(6,7-dihydroxy-4-oxo-4H-1-benzopyran-3-yl)carbonyl]amino](4-hydroxyphenyl)acetyl]amino];
(R,R)-[[2-[4-[2-amino-2-carboxyethyloxycarbonyl]aminophenyl]-2-hydroxyacetyl]amino]; and
(S)-[[(5-hydroxy-4-oxo-1(4H)-pyridin-2-yl)carbonylamino (2-amino-4-thiazolyl)acetyl]amino].

Another class of preferred $R^{10}$ groups (for lactam-containing moieties other than penems, carbapenems, clavems and clavans) include those of the formula:

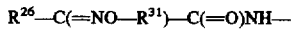

wherein $R^{31}$ is $R^{26}$ —C($R^{32}$)($R^{33}$)COOH, —C(=O)O—$R^{26}$, or —C(=O)NH—$R^{26}$; and where $R^{32}$ and $R^{33}$ are, independently, $R^{26}$, or are connected by a cyclic structure containing from 3 to 8 carbon or heteroatoms.

Examples of this preferred class of $R^{10}$ groups include:
2[(2-chloroacetamidothiaaol-4-yl)]-2-[(p-nitrobenzyloxycarbonyl)-methoxyimino]acetyl;
2-phenyl-2-hydroxyiminoacetyl;
2-thienyl-2-methoxyiminoacetyl; and
2-[4-(gamma-D-glutamyloxy) phenyl]-2-hydroxyiminoacetyl.

(Z)[[(2-amino-4-thiazolyl)(methoxyimino)acetyl]amino];

[[(2-furanyl(methoxyimino)acetyl]amino];

(Z)-[[(2-amino-4-thiazolyl)[(1-carboxy-1-methyl) ethoxyimino]acetyl]amino];

(Z)-[[(2-amino-4-thiazolyl)(1-carboxymethoxyimino) acetyl]amino];

[[(2-amino-4-thiazolyl)[(1H-imidazol-4-ylmethoxy)imino] acetyl]amino];

(Z)-[[(2-amino-4-thiazolyl-3-oxide)(methoxyimino)acetyl] amino]; and (S,Z)-[[(2-amino-4-thiazolyl)[carboxy(3,4-dihydroxyphenyl)-methoxyimino]acetyl]amino].

Suitable $R^{11}$ groups are among those well-known in the art, including those defined in the following documents (all incorporated by reference herein). W. Durckheimer et al., "Recent Developments in the Field of Beta-Lactam Antibiotics", 24 *Angew. Chem. Int. Ed. Engl.* 180 (1985); G. Rolinson, "Beta-Lactam Antibiotics", 17 *J. Antimicrobial Chemotherapy* 5 (1986); and European Patent Publication 187,456, Jung, published Jul. 16, 1986. Preferred $R^{11}$ groups include hydrogen, methoxy, ethoxy, propoxy, thiomethyl, halogen, cyano, formyl and formylamino. Particularly preferred $R^{11}$ groups include hydrogen, methoxy, halogen, and formylamino.

Preferred Formula (I) compounds made by the processes of the present invention include the following classes of compounds.

1. $A^1$ is —C($R^7$)—; $A^2$ is —CF—; and $A^3$ is —CH—;
2. $A^1$ is —CH—, —CF—, —CCl—; $A^2$ is —CF—; $A^3$ is —CH—; $R^4$ is OH and pharmaceutically-acceptable salts; $R^6$ is H; and $R^1$ is cyclopropyl, ethyl, 2,4-difluorophenyl, 4-fluorophenyl, or t-butyl;
3. $A^1$ is —N—; $A^2$ is —CF—; and $A^3$ is —CH—;
4. $A^1$ is —N—; $A^2$ is —CF—; $A^3$ is —CH—; $R^4$ is OH and pharmaceutically-acceptable salts; $R^6$ is H; and $R^1$ is cyclopropyl, ethyl, 2,4-difluorophenyl, 4-fluorophenyl, or t-butyl;
5. $R^1$, $R^3$, or $R^6$ is a lactam-containing moiety;
6. $A^1$ is —C($R^7$)— or —N—; $A^2$ is —CF—; $A^3$ is —CH—; and $R^3$ is a lactam-containing moiety; and
7. $A^1$ is —C($R^7$)— or —N—; $A^2$ is —CF—; $A^3$ is —CH—; and $R^6$ is a lactam-containing moiety.

As indicated hereinbefore, the compounds made according to the processes of this invention may be further reacted to yield other quinolone-containing compounds. Thus, the compounds prepared are useful as intermediates. These intermediates can be further reacted to yield other Formula (I) compounds. Alternatively, the compound may be further reacted to yield other than a Formula (I) compound. For example, the compounds may be further reacted to yield a compound where $A^1$ is —C($R^7$)— and $R^7$ and $R^1$ together comprise a heterocylic 6-membered, oxygen- (pyridobenzoxazine) or sulfur- (pyridobenzthiazine) containing ring including N' and $A^1$.

Synthetic methods for further reacting the compounds made by the processes of the present invention are well known in the art. References describing such methods include those listed hereafter, with respect to the discussion of the precursors of Formula (II).

Compounds of Formula (II)

The methods of the present invention involve cyclization of a quinolone precursor using an organosilicon compound. The precursor is a compound having a structure according to Formula (II)

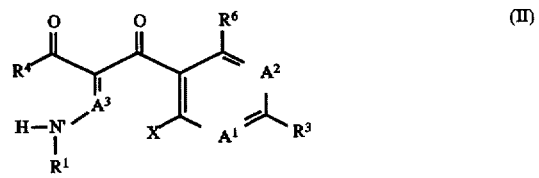

wherein (A)(1) $A^1$ is N or C($R^7$); where
  (a) $R^7$ is hydrogen, hydroxy, alkoxy, nitro, cyano, halogen, alkyl, or N($R^8$)($R^9$) (preferably hydrogen or halogen), and
  (b) $R^8$ and $R^9$ are, independently, $R^{8a}$; where $R^{8a}$ is hydrogen, alkyl, alkenyl, a carbocyclic ring, or a heterocyclic ring; or $R^8$ and $R^9$ together comprise a heterocyclic ring including the nitrogen to which they are bonded;

(2) $A^2$ is N or (preferably) C($R^2$); where $R^2$ is hydrogen or halogen;

(3) $A^3$ is N or (preferably) C($R^5$); where $R^5$ is hydrogen;

(4) $R^1$ is hydrogen, alkyl, heteroalkyl, a carbocyclic ring, a heterocyclic ring, alkoxy, hydroxy, alkenyl, arylalkyl, —N($R^8$)($R^9$), or a lactam-containing moiety (preferably alkyl or carbocyclic ring);

(5) $R^3$ is hydrogen, halogen, alkyl, a carbocyclic ring, a heterocyclic ring, or a lactam-containing moiety (preferably a heterocyclic ring or a lactam-containing moiety);

(6) $R^4$ is hydroxy;

(7) $R^6$ is hydrogen, halogen, nitro, hydrazino, alkoxyamino, —N($R^8$)($R^9$), or a lactam-containing moiety (preferably hydrogen or a lactam-containing moiety); and (8) X is a leaving group; except that if one of $R^1$, $R^3$, or $R^6$ is a lactam-containing moiety, then the other two cannot be a lactam-containing moiety;

(B) and (1) when $A^2$ is C($R^2$), $R^2$ and $R^3$ may together comprise —O—(CH$_2$)$_n$—O—, where n is from 1 to 4;

(2) when $A^3$ is C($R^5$), $R^4$ and $R^5$ may together comprise a heterocyclic ring including the carbon atoms to which $R^4$ and $R^5$ are bonded and the carbon atoms of Formula (II) to which said carbon atoms are bonded; and (3) when $A^1$ is C($R^7$), $R^3$ and $R^7$ may together comprise a heterocyclic ring including and $A^1$ and the carbon atom to which $R^3$ is bonded;

or a protected form, salt, biohydrolyzable ester, or solvate thereof.

The leaving group, X, can be any art-recognized leaving group. Preferred leaving groups include, for example, halogen (such as chlorine or fluorine), nitro, alkyl sulfonate (such as trifluoromethanesulfonate, methanesulfonate, or para-toluenesulfonate) or diazonium. More preferred are chlorine or fluorine. Most preferred is fluorine.

Procedures for preparing compounds useful as precursors in the methods of this invention (i.e., compounds of Formula (II)) are well known in the art. Such methods are described in the following references, all incorporated by reference herein (including articles listed within these references): U.S. Pat. No. 5,140,033, issued Aug. 18, 1992 to Schriewer et al.; U.S. Pat. No. 4,886,810, issued Dec. 12, 1989 to Matsumoto et al.; U.S. Pat. No. 4,885,386, issued Dec. 5, 1989 to Wemple et al.; U.S. Pat. No. 4,684,648, issued Aug. 4, 1987 to Tone et al.; European Patent Publication 522,277, Cecchetti et al., published Jan. 13, 1993; European Patent Publication 470,578, Yokomoto et al., published Feb. 12, 1992; European Patent Publication 319,906, Matsumoto et al., published Jun. 14, 1989; European Patent Publication 287,951, Ueda et al., published Oct. 26, 1988; European Patent Publication 195,316, Irikura et al., published Mar. 6, 1986; German Patent Publication DE-3702393, Schwiewer et al., published Aug. 11, 1988; German Patent Publication DE-3641312, Preiss, published Jun. 9, 1988; German Patent Publication DE-3601567, Petersen et al., published Jul. 23, 1987; German Patent Publication DE-3600891, Schriewer et al., published Jul. 16, 1987; German Patent Publication DE-3504643, Petersen et al., Aug. 14, 1986; German Patent Publication DE-3420743, Petersen et al., published Dec. 5, 1985; Japanese Patent Publication JP/02215749, Furumiya et al., published Aug. 28, 1990; Japanese Patent Publication JP/60172981, Hayakawa, published Sep. 6, 1985; World Patent Publication 92/03136, Chu et al., published Mar. 5, 1992; World Patent Publication 89/06649, Domagalia et al., published Jul. 27, 1989; Chu et al., "An Alternative Synthesis of Temafloxacin, a Potent Antibacterial Agent", 70(5) *Can. J. Chem.* 1323–27 (1992); Remuzon, "Fluoronaphthyridines and Quinolones as Antibacterial Agents", 34(1) *J. Med. Chem* 29–37 (1991); Cecchetti et al., "One-pot Synthesis of Rufloxacin", 21(22) *Synth. Commun.* 2301–08 (1991); Chu et al., "Synthesis of 4-oxo-4H quino[2,3,4-i,j] [1,4]benoxazine-5-carboxylic Acid Derivatives", 24(2) *J. Hetercycl. Chem.* 453–456 (1987); Egawa et al., "A New Synthesis of 7H-Pyrido[1,2,3,-de][1,4]benzoxazine Derivatives Including an Antibacterial Agent, Ofloxacin", 34(10) *Chem Pharm. Bull.* 4098–4102 (1986).

Additional references describing methods for preparing the compounds of Formula (II) are described in the following references, all incorporated by reference herein (including articles listed within these references): 31 *J. Med. Chem.*, 503–506 (1988); 32 *J. Med. Chem.*, 1313–1318 (1989); 1987 *Liebigs Ann. Chem.*, 871–879 (1987); 14 *Drugs Exptl. Clin. Res.*, 379–383 (1988); 31 *J. Med. Chem.*, 983–991 (1988); 32 *J. Med. Chem.*, 537–542 (1989); 78 *J. Pharm. Sci.*, 585–588 (1989); 26 *I. Het. Chem.*, (1989); 24 *J. Her. Chem.*, 181–185 (1987); U.S. Pat. No. 4,599,334; 35 *Chem. Pharm. Bull.*, 2281–2285 (1987); 29 *J. Med. Chem.*, 2363–2369 (1986); 31 *J. Med. Chem.*, 991–1001 (1988); 25 *J. Her. Chem.*, 479–485 (1988); European Patent Publication 266,576; European Patent Publication 251,308, 36 *Chem. Pharm. Bull.*, 1223–1228 (1988); European Patent Publication 227,088; European Patent Publication 227,039; European Patent Publication 228,661; 31 *J. Med. Chem.*, 1586–1590 (1988); 31 *J. Med. Chem.*, 1598–1611 (1988); 23 *J. Med. Chem.* 1358–1363 (1980); 21 *Progress in Drug Research*, 9–104 (1977).

Where the precursor of Formula (II) is a lactam-containing moiety (i.e., $R^1$, $R^3$, or $R^6$ is a lactam-containing moiety), procedures useful making such compounds are disclosed and claimed in copending application Ser. No. 08/289,960, by Randall et al., filed Aug. 2, 1994. That copending application also claims as intermediates the compounds of Formula (II) where $R^1$, $R^3$, or $R^6$ is a lactam-containing moiety.

The copending application relates to a process for making an intermediate compound having a structure according to the formula:

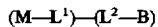

the method comprising the coupling of a compound having a structure according to Formula (II):

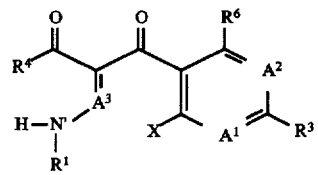

wherein
(A) (1) $A^1$ is N or $C(R^7)$; where
  (a) $R^7$ is hydrogen, hydroxy, alkoxy, nitro, cyano, halogen, alkyl, or $-N(R^8)(R^9)$, and
  (b) $R^8$ and $R^9$ are, independently, hydrogen, alkyl, alkenyl, a carbocyclic ring, or a heterocyclic ring; or $R^8$ and $R^9$ together comprise a heterocyclic ring including the nitrogen to which they are bonded;

(2) $A^2$ is N or $C(R^2)$; where $R^2$ is hydrogen or halogen;

(3) $A^3$ is N or $C(R^5)$; where $R^5$ is hydrogen;

(4) $R^1$ is hydrogen, alkyl, a carbocyclic ring, a heterocyclic ring, alkoxy, hydroxy, alkenyl, arylalkyl, or $-N(R^8)(R^9)$;

(5) $R^3$ is hydrogen, halogen, alkyl, a carbocyclic ring, or a heterocyclic ring;

(6) $R^4$ is hydroxy;

(7) $R^6$ is hydrogen, halogen, nitro, hydrazino or $-N(R^8)(R^9)$; and (8) X is a leaving group (B) and
(1) when $A^2$ is $C(R^2)$, $R^2$ and $R^3$ may together comprise $-O-(CH_2)_n-O-$, where n is from 1 to 4;

(2) when $A^3$ is $C(R^5)$, $R^4$ and $R^5$ may together comprise a heterocyclic ring; and (3) when $A^1$ is $C(R^7)$, $R^7$ and $R^3$ may together comprise a heterocyclic ring including $A^1$ and the carbon atom to which $R^3$ is bonded;

or a protected form, salt, ester, or solvate thereof; with a lactam-containing compound having a structure according to Formula (ii) wherein (I) M has a structure according to Formula (iv)

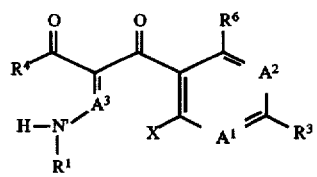

wherein
(A) (1) $A^1$ is N or $C(R^7)$; where
  (a) $R^7$ is hydrogen, hydroxy, alkoxy, nitro, cyano, halogen, alkyl, or $-N(R^8)(R^9)$, and
  (b) $R^8$ and $R^9$ are, independently, $R^{8a}$ where $R^{8a}$ is hydrogen, alkyl, alkenyl, a carbocyclic ring, or a heterocyclic ring; or $R^8$ and $R^9$ together comprise a heterocyclic ring including the nitrogen to which they are bonded;

(2) $A^2$ is N or $C(R^2)$; where $R^2$ is hydrogen or halogen;

(3) $A^3$ is N or $C(R^5)$; where $R^5$ is hydrogen;

(4) $R^1$ is hydrogen, alkyl, a carbocyclic ring, a heterocyclic ring, alkoxy, hydroxy, alkenyl, arylalkyl, or $-N(R^8)(R^9)$;

(5) $R^3$ is hydrogen, halogen, alkyl, a carbocyclic ring, or a heterocyclic ring;

21

(6) $R^4$ is hydroxy;
(7) $R^6$ is hydrogen, halogen, nitro, hydrazino, or —N($R^8$)($R^9$); and
(8) X is a leaving group;

(B) and
(1) when $A^2$ is C($R^2$), $R^2$ and $R^3$ may together comprise —O—(CH$_2$)$_n$—O—, where n is from 1 to 4;
(2) when $A^3$ is C($R^5$), $R^4$ and $R^5$ may together comprise a heterocyclic ring; and
(3) when $A^1$ is C($R^7$), $R^7$ and $R^3$ may together comprise a heterocyclic ring including $A^1$ and the carbon atom to which $R^3$ is bonded;

(C) and provided that one of $R^1$, $R^3$, or $R^6$ is a covalent bond to $L^1$;

(II) B has a structure according to Formula (ii)

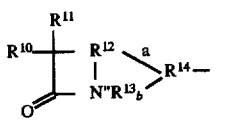
(ii)

wherein
(A) $R^{10}$ is hydrogen, halogen, alkyl, alkenyl, heteroalkyl, a carbocyclic ring, a heterocyclic ring, $R^8$—O—, $R^8$CH=N—, ($R^8$)($R^9$)N—, $R^{17}$—C(=CHR$^{20}$)—C(=O)NH—, $R^{17}$—C(=NO—$R^{19}$)—C(=O)NH—, or $R^{18}$—(CH$_2$)$_m$—C(=O)NH—; where
  (1) m is an integer from 0 to 9;
  (2) $R^{17}$ is hydrogen, alkyl, alkenyl, heteroalkyl, heteroalkenyl, a carbocyclic ring, or a heterocyclic ring;
  (3) $R^{18}$ is $R^{17}$, —$Y^1$, or —CH($Y^2$)($R^{17}$);
  (4) $R^{19}$ is $R^{17}$, arylalkyl, heteroarylalkyl, —C($R^{22}$)($R^{23}$)—COOH, —C(=O)O—$R^{17}$, or —C(=O)NH—$R^{17}$, where $R^{22}$ and $R^{23}$ are, independently, $R^{17}$ or together comprise a carbocyclic ring or a heterocyclic ring including the carbon atom to which $R^{22}$ and $R^{23}$ are bonded;
  (5) $R^{20}$ is $R^{19}$, halogen, —$Y^1$, or —CH($Y^2$)($R^{17}$);
  (6) $Y^1$ is —C(=O)O$R^{21}$, —C(=O)$R^{21}$, —N($R^{24}$)$R^{21}$, —S(O)$_p$ $R^{29}$, or —O$R^{29}$; and $Y^2$ is $Y^1$ or —OH, —SH, or —SO$_3$H;
    (a) p is an integer from 0 to 2;
    (b) $R^{24}$ is hydrogen; alkyl; alkenyl; heteroalkyl; heteroalkenyl; a carbocyclic ring; a heterocyclic ring; —SO$_3$H; —C(=O)$R^{25}$; or, when $R^{18}$ is —CH(N($R^{24}$)$R^{21}$)($R^{17}$), $R^{24}$ may comprise a moiety bonded to $R^{21}$ to form a heterocyclic ring; and
    (c) $R^{25}$ is $R^{17}$, NH($R^{17}$), N($R^{17}$)($R^{26}$), O($R^{26}$), or S($R^{26}$); where $R^{26}$ is alkyl, alkenyl, a carbocyclic ring, a heterocyclic ring, or when $R^{25}$ is —N($R^{17}$)($R^{26}$), $R^{26}$ may be a moiety bonded to $R^{17}$ to form a heterocyclic ring; and
  (7) $R^{21}$ is $R^{29}$ or hydrogen; where $R^{29}$ is alkyl; alkenyl; arylalkyl; heteroalkyl; heteroalkenyl; heteroarylalkyl; a carbocyclic ring; a heterocyclic ring; or, when Y is N($R^{24}$)$R^{21}$ and $R^{21}$ is $R^{29}$, $R^{21}$ and $R^{24}$ may together comprise a heterocyclic ring including the nitrogen atom to which $R^{24}$ is bonded;

(B) $R^{11}$ is hydrogen, halogen, alkoxy, or $R^{27}$C(=O)NH—, where $R^{27}$ is hydrogen or alkyl;
(C) bond "a" is a single bond or is nil; and bond "b" is a single bond, a double bond, or is nil; except bond "a" and bond "b" are not both nil;
(D) $R^{12}$ is —C($R^8$)—, or —CH$_2$—$R^{28}$—; where $R^{28}$ is —C($R^8$), —O—, or —N—, and $R^{28}$ is directly bonded

22 to N" in Formula (II) to form a 5-membered ring; except, if bond "a" is nil, then $R^{12}$ is
(1) —C($R^8$)($X^1$)—, where
  (a) $X^1$ is —$R^{21}$; —O$R^{30}$; —S(O)$_r$$R^{30}$, where r is an integer from 0 to 2; —OC(=O)$R^{30}$; or —N($R^{30}$)$R^{31}$; and
  (b) $R^{30}$ and $R^{31}$ are, independently, alkyl, alkenyl, a carbocyclic ring or a heterocyclic ring; or $R^{30}$ and $R^{31}$ together comprise a heterocyclic ring including the nitrogen atom to which $R^{30}$ and $R^{31}$ are bonded; or
(2) —CH$_2$—$R^{32}$—; where $R^{32}$ is —C($R^8$)($R^{21}$), —O—, or —NR$^8$, and $R^{32}$ is directly bonded to N" in Formula (II) to form a 5-membered ring;

(E)
(1) if bond "b" is a single bond, $R^{13}$ is —CH($R^{33}$); or, —C(O)NHSO$_2$—, if bond "a" is nil; or —C*($R^{33}$)— if $R^{14}$ contains a $R^{36}$ moiety; where $R^{33}$ is hydrogen or COOR$^{46}$ where $R^{46}$ is hydrogen, alkyl or alkenyl, and C* is linked to $R^{36}$ to form a 3-membered ring;
(2) if bond "b" is a double bond, $R^{13}$ is —C($R^{33}$)=; or
(3) if bond "b" is nil, $R^{13}$ is hydrogen, —SO$_3$H, PO(OR$^{34}$)OH, —C(O)NHSO$_2$N($R^{34}$)($R^{35}$), OSO$_3$H, —CH($R^{35}$)COOH, or —OCH($R^{34}$)—COOH; where $R^{34}$ is hydrogen, alkyl, alkenyl, a carbocyclic ring, or a heterocyclic ring; and $R^{35}$ is hydrogen, alkyl, alkenyl, or —NHR$^8$; or, if $R^{13}$ is —C(O)NH—SO$_2$N—($R^{34}$)($R^{35}$), $R^{34}$ and $R^{35}$ may together comprise a heterocyclic ring including the nitrogen to which $R^{34}$ and $R^{35}$ are bonded; and (F)
(1) if bond "a" or bond "b" is nil, then $R^{14}$ is a covalent bond;
(2) if bond "a" and "b" are single bonds, $R^{14}$ is —W—C'''=C($R^{8a}$)—$R^{37}$—, or —W—C'''($R^{36}$)—$R^{37}$—; or
(3) if bond "a" is a single bond and bond "b" is a double bond, $R^{14}$ is —C($R^8$)($R^{38}$)—W—C'''—$R^{37}$—; —W—C($R^8$)—($R^{38}$)—C'''—$R^{37}$—; or —W—C'''—$R^{37}$—;
(4) where
  (a) W is O; S(O)$_s$, where s is an integer from 0 to 2; or C($R^{38}$), where $R^{38}$ is hydrogen, alkyl or alkoxy;
  (b) $R^{36}$ is hydrogen; alkyl; alkenyl; —COOH; or, if $R^{13}$ is —C*($R^{33}$), $R^{36}$ may be linked to C* to form a 3-membered carbocyclic ring;
  (c) $R^{37}$ is covalent bond, alkyl, alkenyl, a carbocyclic ring, or a heterocyclic ring; and
  (d) C''' is directly bonded to $R^{13}$ to form a 5- or 6-membered ring; and (III)
(A) L is —C(=Z)—; —S(O)$_v$—; —N($R^{44}$)—; —N$^+$($R^{44}$)($R^{45}$)—; —N($R^{44}$)—N($R^{44}$)—; —O—; =N—; or a covalent bond; and L is bonded to $L^3$ and $L^4$; where
(1) Z is O, S, or $^+$N(H)$_2$;
(2) v is 0, 1 or 2;
(3) $R^{44}$ is hydrogen, substituted or unsubstituted lower alkyl, aryl, acyl, hydroxy, alkoxy, aryloxy, or acyloxy; and
(4) $R^{45}$ is hydrogen, unsubstituted or substituted lower alkyl, or substituted or unsubstituted aryl;

(B) $L^1$ is $L^3$ or $R^{15}L^3$; where
(1) when L is —C(=Z)—, $L^3$ is a covalent bond, oxygen, sulfur, or nitrogen; and when L is other than —C(=Z)—, $L^3$ is a covalent bond;
(2) $R^{15}$ is alkyl, alkenyl, heteroalkyl, a heterocyclic ring, a carbocyclic ring, or $R^{15}$ together with $L^3$ is a heteroalkyl or a heterocyclic ring; and (3) $L^1$ is bonded to Q at the point of attachment of $R^1$, $R^3$ or $R^6$, whichever is a covalent bond;

(C) $L^2$ is $L^4$, $-X^2-R^{39}-L^4$, or $-X^3-R^{39}-L^4$; where
  (1) when L is $-C(=Z)-$, $L^4$ is a covalent bond, oxygen, sulfur, or nitrogen; and when L is other than $-C(=Z)-$, $L^4$ is a covalent bond;
  (2) $X^2$ is oxygen, or $S(O)_v$, where v is 0, 1, or 2;
  (3) $X^3$ is nitrogen; $-N(R^{40})-$; $-N+(R^{41})(R^{42})-$; or $R^{43}-N(R^{41})$; and is linked to $R^{14}$ by a single or double bond; or, if $R^{14}$ is covalent bond, $X^3$ is linked to B by a single or double bond; where
    (a) $R^{40}$ is $R^8$; $-OR^8$; or $-C(=O)R^8$;
    (b) $R^{41}$ and $R^{42}$ are, independently, hydrogen; alkyl; alkenyl; carbocyclic rings; heterocyclic rings; or, if $R^6$ is $R^{16}X$, then $R^{41}$ and $R^{42}$ together with Q" may comprise a heterocyclic ring as $R^{16}$;
    (c) $R^{43}$ is $N(R^{41})$, oxygen or sulfur;
  (4) t is 0 or 1;
  (5) $R^{39}$ is alkyl, alkenyl, heteroalkyl, heteroalkenyl, carbocyclic ring, or a heterocyclic ring; and
  (6)
    (a) if bond "a" or bond "b" is nil, then $L^2$ is bonded directly to $R^{12}$ or $R^{13}$; or
    (b) if bond "a" and bond "b" are not nil, then $L^2$ is bonded to $R^{14}$;
(D) provided that if $L^1$, $L^2$ and $R^{37}$ are each a covalent bond, then L cannot be a covalent bond;
or a protected form, salt, pharmaceutically-acceptable salt, biohydrolyzable ester, or solvate thereof.

Methods of Manufacture:

The processes of this invention, when making a QLA, comprise the steps of (1) coupling a compound having a structure according to Formula (iii) with a lactam compound of the Formula (ii) to form an intermediate compound; and (2) cyclizing the intermediate by reaction with an organosilicon compound to give Q—L—B.

The intermediate compounds (M-$L^1$-L-$L^2$-B) of the present invention are prepared by the coupling step (1).

The identity of the compound of Formula (II) and the lactam compound used in coupling Step (1) will be dictated, in part, by the linking group (i.e., -$L^1$-L-$L^2$) of the desired intermediate or QLA end product. Using the present disclosure, those skilled in the art will recognize which materials will be utilized to prepare the desired intermediate or QLA according to the present invention. That is, the starting materials and resulting intermediates must be appropriately substituted to allow synthesis of the desired linking moiety.

The following general reaction schemes exemplify means for obtaining the various linking moieties described above. For each linking moiety, an exemplary reaction scheme is provide for making an intermediate of the formula (M -$L^1$)-L -($L^2$-B) (coupling step) and a QLA (the cyclization step).

For example, intermediates and QLAs having a carbamate linking moiety may be made according to the processes of the present invention as follows:

Step (1): (II)—NH+X—C(O)—O—CH$_2$—Lact→(iv)—N—C(O)—O—CH$_2$—Lact

Step (2): Cyclize to yield Quin—N—C(O)—O—CH$_2$—Lact where "(II)" represents a compound of Formula (II), which is described above; "(iv)" represents a moiety of Formula (iv), which is described above; X is a reactive leaving group (such as alkoxy, halo, or N-heteroalkyl); "Lact" generically represents an appropriately protected lactam-containing structure (such as carbapenem, penem, cephem, monocyclic beta-lactam, oxacephem, or carbacephem); and "Quin" represents an appropriately protected quinolone. The sequence can be envisioned as formation of the intermediate lactam carbonate derivative, followed by acylation of an amino functionality of a compound of Formula (II) to form a carbamate coupled lactam intermediate, followed by cyclization to form a carbamate-linked QLA.

When making carbamate-linked intermediates and QLAs, an optional step of reacting the compound of Formula (II) with an organosilicon compound may be performed prior to the coupling step (1). This step is illustrated in Examples 1 through 5 hereinbelow.

Alternately, "reversed" carbamate linking-moieties can be prepared by the following sequence:

Step (1): (II)—CH$_2$OC(=O)—X+H$_2$N—CH$_2$—Lact→Lact—CH$_2$—NHC(=O)O—CH$_2$—(iv)

Step (2): Cyclize to yield Lact—CH$_2$—NHC(=O)O—CH$_2$—Quin where "(II)" represents a compound of Formula (II), which is described above; "(iv)" represents a moiety of Formula (iv), which is described above; X is a reactive leaving group (such as alkoxy, halo, or N-heteroaryl); "Lact" generically represents an appropriately protected lactam-containing structure (such as a penem, carbapenem, cephem, or carbacephem); and "Quin" represents an appropriately protected quinolone. The sequence can be envisioned as formation of a carbonate derivative of a compound of Formula (H), followed by acylation of a lactam amino functionality to form a carbamate coupled conjugate of the lactam intermediate (step(1)), followed by cyclization to form a reversed carbamate linked QLA.

Lactam-Quinolones having a dithiocarbamate linking moiety may be made by the following general reaction sequence:

Step (1): M$^+$SC(=S)N—(II)+Lact—CH$_2$X →Lact—CH$_2$—SC(=S)N—(iv)

Step (2): Cyclize to yield Lact—CH$_2$—SC(=S)N—Quin where "(II)" represents a compound of Formula (II), which is described above, "(iv)" represents a moiety of Formula (iv), which is described above; X is a reactive leaving group (such as halo, a sulfonate ester, acetate, thiobenzoate or other activated hydroxyl functionality); "Lact" generically represents an appropriately protected lactam-containing structure (such as a penem, carbapenem, cephem monocyclic beta-lactam, oxacephem, or carbacephem); and "Quin" represents an appropriately protected quinolone. The sequence can be envisioned as formation of a dithiocarbamate salt of a compound of Formula (II), followed by nucelophilic displacement of the lactam X substituent to form a dithiocarbamate coupled conjugate of the lactam intermediate (intermediate), followed by cyclization to yield a dithiocarbamate linked QLA.

Alternatively, "reversed" dithiocarbamate conjugates can be prepared by the following sequence.

Lact—CH$_2$—NH$_2$+CS$_2$→Lact—CH$_2$—NHC(=S)S—M$^+$

Step (1): Lact—CH$_2$—NHC(=S)S—M$^+$+X—CH$_2$—(II) →Lact—CH$_2$—NH(C(=S)S—CH$_2$—(iv)

Step (2): Cyclize to give Lact—CH$_2$—NHC(=S)S—CH$_2$—Quin where "(II)" represents a compound of Formula (II), which is described above; "(iv)" represents a moiety of Formula (iv), which is described above, X is a reactive leaving group (such as halo, a sulfonate ester or other activated hydroxyl functionality); "Lact" generically represents an appropriately protected lactam-containing structure (such as a penem, carbapenem, cephem, oxacephem, or carbacephem); and "Quin" represents an appropriately protected quinolone. The sequence can be envisioned as formation of the lactam dithiocarbonate salt, followed by nucleophilic displacement of the suitable compound (II) X substituent to form a "reversed" dithiocarbamate coupled conjugate of the lactam intermediate (step (1)), followed by cyclization to form a reverse dithiocarbamate-linked QLA.

Lactam-quinolones having a thiourea or urea linking moiety may be made by the following general reaction sequence:

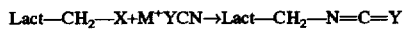

Step (1): Lact—$CH_2$—N=C=Y+HN—(II)→Lact—$CH_2$—NHC(=Y)N—(iv)

Step (2): Cyclize to yield Lact—$CH_2$—NH(C=Y)N—Quin (thiourea: Y=S; urea: Y=O)

where "(II)" represents a compound of Formula (II), which is described above; "(iv)" represents a moiety of Formula (iv), which is described above; X is a reactive leaving group (such as halo, a sulfonate ester, dichloroacetate, thiobenzoate or other activated hydroxyl functionality); and Y is either O or S. "Lact" generically represents an appropriately protected lactam-containing structure (such as a penem, carbapenem, cephem, monocyclic beta-lactam, oxacephem, or carbacephem), and "Quin" represents an appropriately protected quinolone. The sequence can be envisioned as formation of the intermediate lactam isothiocyanate (Y=S) or isocyanate (Y=O); followed by reaction with the amino substituent of a compound of Formula (II) to form a thiourea (Y=S) or urea (Y=O) coupled conjugate of the lactam and Formula II compound (intermediate) (step (1)), followed by cyclization to form a thiourea—(Y=S)— or urea—(Y=O) linked QLA.

Lactam-quinolones having an imine, amine or ammonium linking moiety may be made by the following general reaction sequence:

Step (1): Lact—$CH_2$HO+HN—(II)→Lact—CH=N—(iv)(an imine)→Lact—$CH_2$—N($R^{44}$)—(iv)(an amine) →Lact—$CH_2$—$N^+$($R^{44}$)($R^{45}$)—(iv) (an ammonium)

Step (2): cyclization of the amine or ammonium intermediate to yield Lact—CH=N—Quin, Lact—$CH_2$—N($R^{44}$)—Quin or Lact—$CH_2$—$N^+$($R^{44}$)($R^{45}$)—Quin, respectively where "(II)" represents a compound of Formula (II), which is described above; "(iv)" represents a moiety of Formula (iv), which is described above; $R^{44}$ and $R^{45}$ are described above; "Lact" generically represents an appropriately protected lactam-containing structure (such as a penem, carbapenem, cephem, oxacephem, or carbacephem; and "Quin" represents an appropriately protected quinolone. The sequence can be envisioned as the condensation of the imine coupled lactam conjugate. Reduction of the imine yields the corresponding amine coupled lactam intermediate lactam conjugate. Alkylation yields the corresponding quaternary ammonium-coupled lactam intermediate conjugate. Cyclization of the desired intermediate will yield an imine-, amine-, or ammonium-linked QLA.

Lactam-quinolones having an amine linking moiety may alternately be made by the following general reaction sequence:

Step (1): Lact—$CH_2$X+HN—(II)→Lact—$CH_2$—N($R^{44}$) (iv) (an imine)→

Step (2): cyclization of the amine to yield Lact—$CH_2$—N($R^{44}$)—Quin where "(II)" represents a compound of Formula (II), which is described above; "(iv)" represents a moiety of Formula (iv), which is described above; $R^{44}$ and $R^{45}$ are described above; "Lact" generically represents an appropriately protected lactam-containing structure (such as a penem, carbapenem, cephem, oxacephem, or carbacephem; X is a leaving group described above and "Quin" represents an appropriately protected quinolone.

Alternately, the quaternary ammonium conjugate can be prepared by the following general sequence:

Step (1): Lact—$CH_2$—X+($R^{44}$)($R^{45}$)N—(II)→Lact—$CH_2$—$N^+$($R^{44}$)($R^{45}$)—(iv)

Step (2): Cyclize to yield Lact—$CH_2$—$N^+$($R^{44}$)($R^{45}$)—Quin where "(II)" represents a compound of Formula (II), which is described above; "(iv)" represents a intermediate compound of Formula (iv), which is described above; $R^{44}$ and $R^{45}$ are described above; X is a reactive leaving group (such as halo, a sulfonate ester, or other activated hydroxyl functionality, etc.). This sequence can be envisioned as a quaternization of a tertiary and no group of a compound of Formula (II) with the lactam material to obtain the quaternary ammonium coupled conjugate between the lactam and compound of Formula (II) (step (1)), followed by cyclization to form the ammonium-linked QLA.

Lactam-quinolones having an amide linking moiety may be made by the following general sequence:

Step (1): Lact—$CH_2$—$NH_2$+X—C(=O)—(II)→Lact—$CH_2$—NHC(=O)—(iv)

Step (2): Cyclize to yield Lact—$CH_2$—NHC(=O)—Quin where "(II)" represents a compound of Formula (II), which is described above; "(iv)" represents an intermediate compound of Formula (iv), which is described above; X is a reactive leaving group (such as halo, HOBt ester, mixed anhydride or other activated carboxyl functionality); "Lact" generically represents an appropriately protected lactam-containing structure (such as penem, carbapenem, cephem, oxacephem, or carbacephem); and "Quin" represents an appropriately protected quinolone. The reaction can be envisioned as an acylation of the lactam amino substituent with the activated carboxyl group of a compound of Formula (II), to form an amide coupled conjugate of the lactam and Formula (II) compound (intermediate), followed by cyclization to form the amide-linked QLA.

Lactam-quinolones having a guanidinium linking moiety may be made by the following general reaction sequence:

Step (1): RSC(=$NH_2^+X^-$)N(iv)→Lact—$CH_2$—NHC($NH_2^+X^-$)N—(iv)

Step (2): Cyclize to yield Lact—$CH_2$—NHC(=$NH_2^+X^-$)N—Quin where "(II)" represents a compound of Formula (II), which is described above; "(iv)" represents an intermediate compound of Formula (iv), which is described above; "Lact" generically represents an appropriately protected lactam-containing structure (such as penem, carbapenem, cephem, oxacephem, or carbacephem); and "Quin" represents an appropriately protected quinolone. The sequence can be envisioned as formation of the isothiouronium salt of a compound of Formula (II), followed by reaction with the lactam amino substituent to form a guanidinium coupled conjugate of the lactam and compound of Formula (II) (intermediate), followed by cyclization to form a guanidinium-linked QLA.

Lactam-quinolones having a heteroarylium linking moiety may be made by the following general reaction sequence:

Step (1): Lact—$CH_2$—X+$N_{Het}$—(II)→Lact—$CH_2$—$N^+_{Het}$—(iv)

Step (2): Cyclize to yield Lact—$CH_2$—$N^+_{Het}$—Quin where "(II)" represents a compound of Formula (II), which is described above; "(iv)" represents an intermediate compound of Formula (iv), which is described above; X is a reactive leaving group (such as halo, a sulfonate ester, acetate, thiobenzoate or other activated hydroxyl functionality); "$N_{Het}$" is an heteroaryl moiety, $N^+_{Het}$ is a heteroaryl having a ring quaternary nitrogen atom, "Lact" genetically represents an appropriate protected lactam-containing structure (such as a penem, carbapenem, cephem, monocyclic beta-lactam, oxacephem, or carbacephem); and "Quin" represents an appropriately protected quinolone that contains a heteroaromatic nitrogen-containing substituent (for example, pyridine). The sequence can be envisioned as an alkylation of the heteroaromatic nitrogen-containing substituent of a compound of Formula (II) by the lactam to form the pyridinium-type conjugate (intermediate), followed by cyclization to form the pyridinium-linked QLA.

Lactam-quinolones having a xanthate linking moiety may be made by the following general reaction sequence:

Step (1): $M^+$ $^-$SC(=S)O(III)+Lact—$CH_2$—X→Lact—$CH_2$—SC(=S)O—(iv)

Step (2): Cyclize to form Lact—$CH_2$—SC(=S)O—Quin where "(II)" represents a compound of Formula (II), which is described above; "(iv)" represents an intermediate compound of Formula (iv), which is described above; X (such as halo, a sulfonate ester, acetate, thiobenzoate or other activated hydroxyl functionality); "Lact" generically represents an appropriately protected lactam-containing structure (such as penem, carbapenem, cephem, monocyclic beta-lactam, oxacephem, or carbacephem); and "Quin" represents an appropriately protected quinolone. The sequence can be envisioned as formation of the xanthate salt of a compound of Formula (II), followed by nucleophilic displacement of the lactam X substituent to form a xanthate coupled conjugate of the lactam and Formula (II) compound (intermediate), followed by cyclization to yield the xanthate-linked QLA.

Lactam-quinolones having a thioether, sulfoxide or sulfone linking moiety may be made by the following general reaction sequence:

Step (1): Lact—$CH_2$—X+HS—(II)→Lact—$CH_2$—S—(iv) (a thioether)→Lact—$CH_2$—SO—(iv)(a sulfoxide)→

Step (2): Cyclization of the thioether, sulfoxide or sulfone to form Lact—$CH_2$—S—Quin, Lact—$CH_2$—SO—Quin, or Lact—$CH_2SO_2$—Quin, respectively where "(II)" represents a compound of Formula (II), which is described above; "(iv)" represents an intermediate compound of Formula (iv), which is described above; X is a reactive leaving group (such as halo, a sulfonate ester, acetate, thiobenzoate or other activated hydroxyl functionality, etc.); "Lact" generically represents an appropriately protected lactam-containing structure (such as penera, carbapenem, cephem, monocyclic beta-lactam, oxacephem, or carbacephem); and "Quin" represents an appropriately protected quinolone. The sequence can be envisioned as nucleophilic displacement of the lactam X group with a thio-containing compound of Formula (II) to form the thioether coupled conjugate (intermediate). Oxidation of the thioether yields the corresponding sulfoxide conjugate. Further oxidation produces the sulfone lactam intermediate conjugate. Cyclization of the thioether, sulfoxide, or sulfone intermediate will form a thioether-linked, a sulfoxide-linked or-linked QLA, respectively.

Lactam-quinolones having an isothiouronium linking group may be made by the following general reaction sequence:

RC(=O)N=C=S+HN—(II)→$H_2$NC(=S)N—(II)

Step (1): $H_2$NC(=S)N—(II)+Lact—$CH_2$—X→Lact—$CH_2$—SC(=$NH_2^+X^-$)N—(iv)

Step (2): Cyclize to give Lact—$CH_2$—SC($CNH_2^+X^-$)N—Quin where "(II)" represents a compound of Formula (II), which is described above; "(iv)" represents an intermediate compound of Formula (iv), which is described above; X (such as halo, a sulfonate ester, acetate, thiobenzoate or other activated hydroxyl functionality); "Lact" generically represents an appropriately protected lactam-containing structure (such as penem, carbapenem, cephem, monocyclic beta-lactam, oxacephem, or carbacephem); and "Quin" represents an appropriately protected quinolone. The sequence can be envisioned as formation of the thioura-containing compound of Formula (II), followed by nucleophilic displacement of the lactam X substituent to form a isothiouronium coupled conjugate (intermediate), followed by cyclization to QLA.

In the reaction sequences described herein, certain functional groups contained in the Lact, (II) and (iv) structures, (such as carboxyl, hydroxyl, and amino groups) may need to be in a protected form. If various protecting groups are employed, then appropriate deprotecting chemistry, that will not decompose the coupled conjugate, may be required to obtain antibacterially active products. Depending on the $R^{10}$ group desired, the lactam starting material may be available from any of a variety of commercial sources. Synthetic methods for producing such lactams are well-known in the chemical literature. See, for example, *Antibiotics, Chemotherapeutics, and Antibacterial Agents for Disease Control*, pages 107–125 (M. Grayson, editor, 1982), incorporated by references herein.

Preferably, the processes of the present invention additionally comprise steps for protecting the lactam and compound of Formula (II) prior to the coupling step. In particular, the carboxylate groups at $R^4$ and $R^{13}$ are in a protected form, using, for example, an ester group.

Alternatively, the compound may be further reacted to form another QLA moiety that is known to have antimicrobial activity. For example, the QLA may be further reacted to yield a compound where $A^1$ is —C($R^7$)— and $R^7$ and $R^1$ together comprise a heterocyclic 6-membered, oxygen- (pyridobenzoxazine) sulfur-(pyridobenzthiazine) containing ring including N' and $A^1$.

A preferred process of this invention additionally comprises:

(a) a step, prior to said coupling step, wherein a compound of Formula (ii), a compound of Formula (II), or both are protected; and (b) deprotection steps, after said cyclization step, wherein the protection groups are removed.

Methods of Manufacture

The processes of the present invention comprise reacting one or more organosilicon compounds with a compound having a structure according to Formula (II). This reaction step provides a compound having a structure according to Formula (I). The processes may additionally comprise the use of known chemistry, subsequent to the reaction step, to provide a distinct compound of Formula (I), or another quinolone antimicrobial.

Any variety of known organosilicon compounds known in the art, including combinations thereof, may be used in the reaction step. Such silylation reagents include, for example, chlorotrimethylsilane, trimethylsilyl trifluoromethanesulfonate, N,O-bis(trimethylsilyl) acetamide, N,O-bis(trimethylsilyl)trifluoroacetamide, bis(trimethylsilyl)urea, hexamethyldisilazane, N-methyl-N-triimethylsilyltrifluoro-acetamide, 1-trimethylsilylimidazole, and mixtures thereof. More preferred include N,O-bis(trimethylsilyl)acetamide, N,O-bis(trimethylsilyl)trifluoroacetamide, N-methyl-N-trimethylsilyltrifluoroacetamide, and 1-trimethylsilylimidazole; and combinations of chlorotrimethylsilane with hexamethyldisilazane or N,O-bis(trimethylsilyl)acetamide. Most preferred are N,O-bis(trimethylsilyl)acetamide, N,O-bis(trimethylsilyl)trifluoroacetamide, and combinations of chlorotrimethylsilane with N,O-bis(trimethylsilyl)acetamide or hexamethyldisilazane. Use of the organosilicon compound in the reaction step may also yield a silyl ester of $R^4$ carboxylate, as a protecting group. This ester can then be removed, using well-known deprotection methods.

The processes of the present invention preferably comprise mixing a compound of Formula (II) with a solvent, followed by addition of one or more organosilicon compounds to the solution. Preferably, from about 1 to about 14 mole equivalents of the silyl-containing compound is added for each mole of the Formula (II) compound (i.e., a mole ratio of organosilicon compound to Formula (II) compound of from about 1:1 to about 14:1). More preferred is a mole ratio of from about 2:1 to about 12:1. Most preferred is a mole ratio of about 2:1 to about 6:1.

As indicated, the reaction is carried out after the substrate is mixed with any of a variety of known solvents. Such solvents include, but are not limited to: halocarbon solvents, such as methylene chloride, chloroform, and dichloroethane; ethers, such as diethyl ether and tetrahydrofuran (THF); aromatic solvents, such as benzene and toluene; alkyl nitriles, such as acetonitrile; and mixtures thereof. Halocarbon, ether and alkyl nitride solvents are preferred. Preferred solvents include methylene chloride, THF and acetonitrile, and mixtures thereof. Most preferred solvents include methylene chloride and acetonitrile, and mixtures thereof.

The reaction is carried out at a temperature sufficient to effect cyclization of Io the Formula (II) compound. The reaction is preferably carried out at temperatures greater than −15° C. More preferred is where the reaction is conducted at temperatures from about 0° C. to about 110° C. Most preferred reaction temperatures are from about 25° C. to about 50° C. Preferably, reagents are mixed in the reaction step so as to allow control of the temperature within these ranges.

The following non-limiting examples illustrate the processes of the present invention.

EXAMPLE 1

Synthesis of 1-cyclopropyl-6-fluoro-1,4-dihydro-7-(4-methyl-1-piperazinyl)-4-oxo-3-quinolinecarboxylic acid.

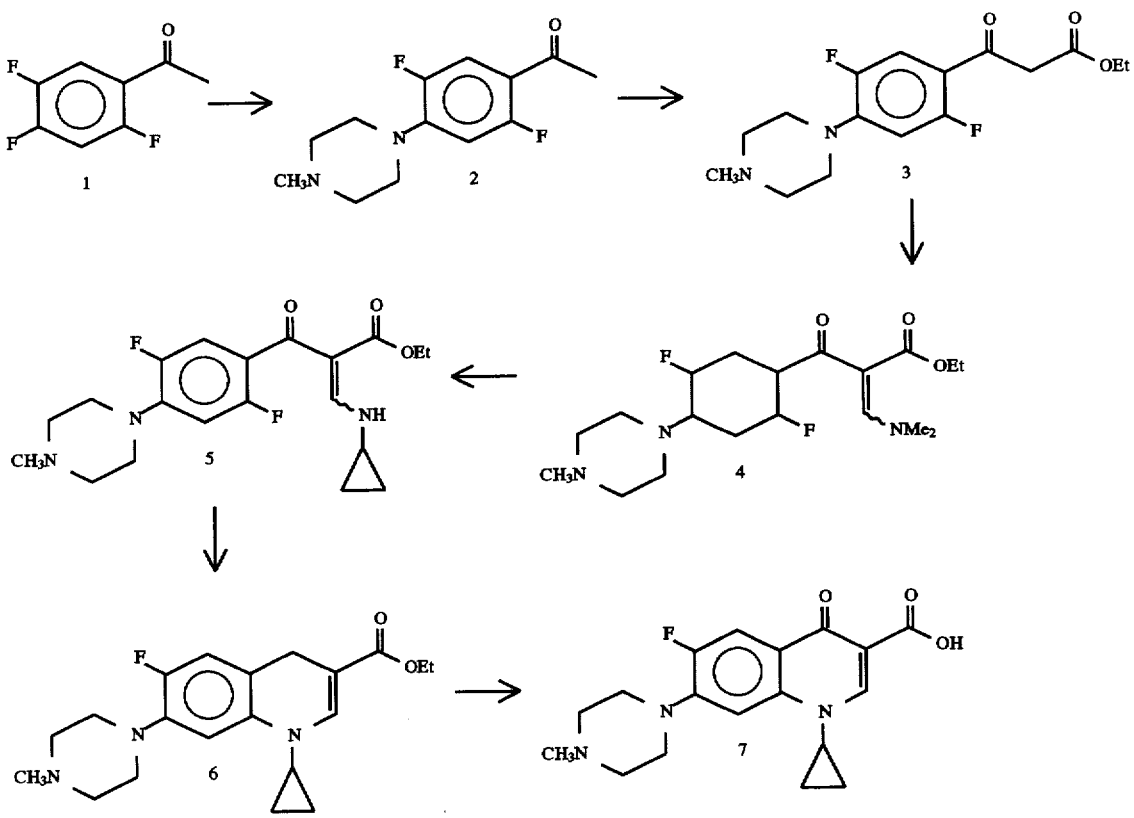

To a solution of 2,4,5-trifluoroacetophenone (15.0 g) (Compound 1) in N,N-dimethylformamide (DMF) (75 mL) is added 1-methylpiperazine (38.2 mL). The reaction mixture is heated (80°–90° C.) under $N_2$ for 1 hour and cooled to ambient temperature. The solvent is removed in vacuo and the mixture is partitioned between ethyl acetate (EtOAc) (75 mL) and H₂O (75 mL), and the EtOAc portion is washed with water (20 mL), dried (MgSO₄) and decolorized with activated carbon. The solvent is removed in vacuo and the residue is crystallized by addition of isopropyl ether to give, after filtration, Compound 2.

A 60% dispersion of NaH in oil (1.7 g) is washed with hexanes under N₂ and the hexanes are decanted off. The NaH is added portionwise to a cooled solution (0°–5° C.) of Compound 2 (5.0 g) and diethyl carbonate (9.5 mL) in tetrahydrofuran (THF) (50 mL) under N₂. The ice bath is removed and the reaction is allowed to warm to ambient temperature overnight. The reaction is poured into H₂O (170 mL) and the THF is removed in vacuo. The residue is extracted with EtOAc (100 mL), and the EtOAc portion is dried (MgSO₄) and decolorized with activated carbon. The solvent is removed in vacuo to give Compound 3.

To a solution of Compound 3 (5.7 g) in toluene (22.8 mL) is added N,N-dimethylformamide dimethylacetal (3.6 mL). The reaction is heated at reflux for 20 hours, under N₂, and cooled to ambient temperature. The mixture is concentrated in vacuo to provide crude Compound 4. Compound 4 is carried on directly to the next step by dissolving in ethanol (EtOH) (22.8 mL) and adding cyclopropylamine (1.9 mL) under N₂. The reaction is stirred for 3 hours, and the resulting slurry is cooled to 5° C. and filtered. The solid is washed with hexanes to give Compound 5.

To a solution of Compound 5 (100 mg) in CH₂Cl₂ (1 mL) is added N,O-bis(trimethylsilyl)acetamide (BSA) (0.38 mL). The reaction is stirred at ambient temperature for 22 hours under N₂. The reaction is quenched with water (1 mL) and diluted with CH₂Cl₂ (5 mL). The CH₂Cl₂ portion is separated and dried (MgSO₄), and the volatiles are removed in vacuo to obtain a solid. The solid is recrystallized from isopropyl ether to give Compound 6.

A suspension of Compound 6 (200 mg) in 6N HCl solution (15 mL) is heated at 110° C. under N₂. After 6 hours, the solvent is removed in vacuo, ethanol (20 mL) is added to the residue and the mixture is stirred at reflux for 15 minutes. The mixture is cooled to room temperature and the resulting solid is filtered to obtain Compound 7 as its hydrochloride salt.

EXAMPLE 2

Synthesis of 1-cyclopropyl-6-fluoro-1,4-dihydro-7-(4-methyl-1-piperazinyl)-4-oxo-3-quinolinecarboxylic acid.

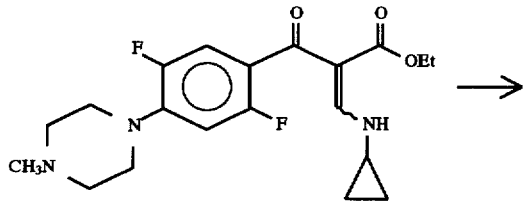

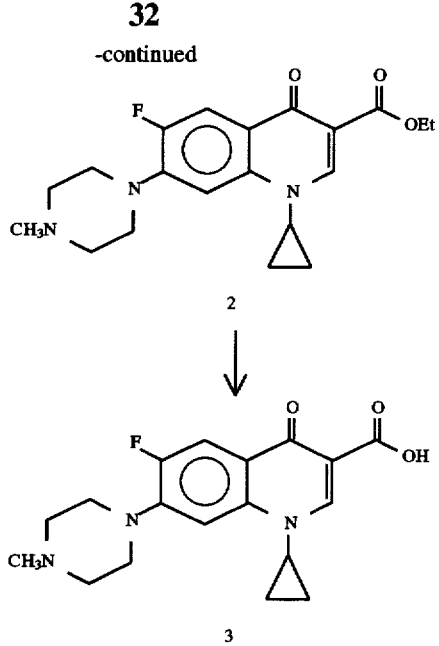

Compound 1 is prepared in the same manner as Compound 5 is prepared in Example 1 above.

To a solution of Compound 1 (100 mg) in CH₃CN (1 mL) is added N,O-bis(trimethylsilyl)acetamide (BSA) (0.19 mL). The reaction is stirred at ambient temperature for 20 hours under N₂. The reaction is quenched with water (1 mL) and the resulting slurry is concentrated in vacuo. The residue is recrystallized from ether (Et₂O) to give Compound 2.

A suspension of Compound 2 (200 mg) in 6N HCl solution (15 mL) is heated at 110° C. under N₂. After 6 hours, the solvent is removed in vacuo, ethanol (20 mL) is added to the residue and the mixture is stirred at reflux for 15 minutes. The mixture is cooled to room temperature and the resulting solid is filtered to obtain Compound 3 as its hydrochloride salt.

EXAMPLE 3

Synthesis of 1-cyclopropyl-6-fluoro-1,4-dihydro-7-(4-methyl-1-piperazinyl)-4-oxo-3-quinolinecarboxylic acid.

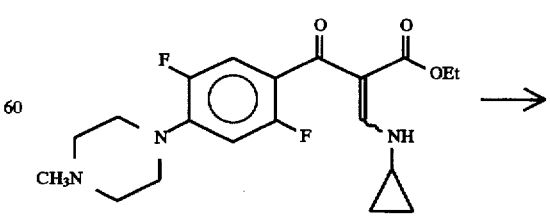

33
-continued

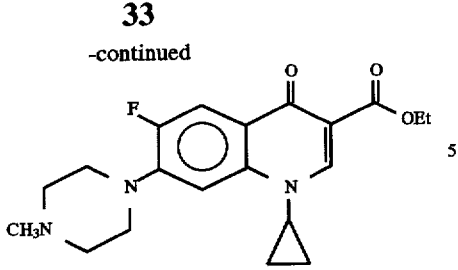

2

↓

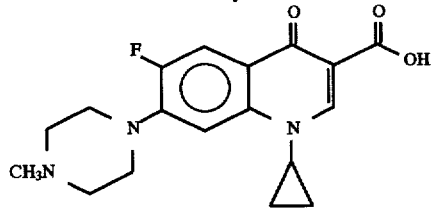

3

Compound 1 is prepared in the same manner as Compound 5 is prepared in Example 1 above.

To solution of Compound 1 (100 mg) in THF (1 mL) is added N,O-bis(trimethylsilyl)acetamide (BSA,) (0.19 mL) and trimethylchlorosilane (TMCS) (0.032 mL). The reaction is stirred at ambient temperature under $N_2$ for 20 hours and quenched with water (1 mL). The volatiles are removed in vacuo to provide a residue which is dissolved in $CH_2Cl_2$ (5 mL). The solution is washed with saturated $NaHCO_3$ solution (1 mL) and dried ($MgSO_4$). The solvent is removed in vacuo and the residue obtained is recrystallized from ether ($Et_2O$) to give Compound 2.

A suspension of Compound 2 (200 mg) in 6N HCl solution (15 mL) is heated at 110° C. under $N_2$. After 6 hours, the solvent is removed in vacuo, ethanol (20 mL) is added to the residue and the mixture is stirred at reflux for 15 minutes. The mixture is cooled to room temperature and the resulting solid is filtered to obtain Compound 3 as its hydrochloride salt.

EXAMPLE 4

Synthesis of 1-cyclopropyl-6-fluoro-1,4-dihydro-7-(4-methyl-1-piperazinyl)-4-oxo-3-quinolinecarboxylic acid.

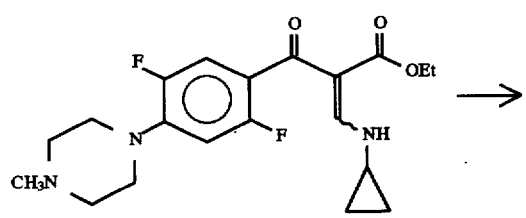

1

34
-continued

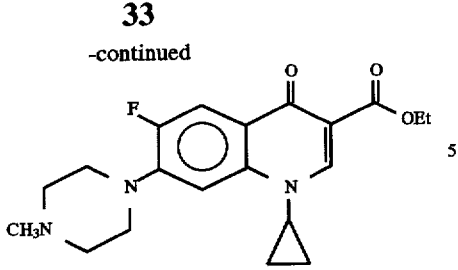

2

↓

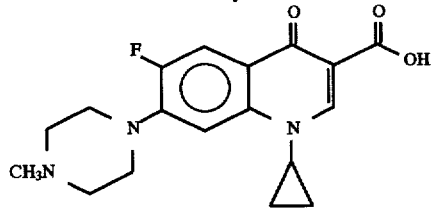

3

Compound 1 is prepared in the same manner as Compound 5 is prepared in Example 1 above.

To a solution of Compound 1 (100 mg) in $CH_2Cl_2$ (1 mL) is added N-methyl-N-trimethylsilyl-trifluoroacetamide (MSTFA) (0.102 mL). The reaction mixture is stirred at ambient temperatures under $N_2$ for 40 hours. The reaction is quenched with water (1.5 mL) and diluted with $CH_2Cl_2$ (5 mL). The $CH_2Cl_2$ portion is separated and dried ($Na_2SO_4$), and the volatiles are removed in vaeuo. The solid is recystallized from EtOAc/Hexane to give Compound 2.

A suspension of Compound 2 (200 mg) in 6N HCl solution (15 mL) is heated at 110° C. under $N_2$. After 6 hours, the solvent is removed in vacuo., ethanol (20 mL) is added to the residue and the mixture is stirred at reflux for 15 minutes. The mixture is cooled to room temperature and the resulting solid is filtered to obtain Compound 3 as its hydrochloride salt.

EXAMPLE 5

Synthesis of 1-cyclopropyl-6-fluoro-1,4-dihydro-7-(4-methyl-1-piperazinyl)-4-oxo-3-quinolinecarboxylic acid.

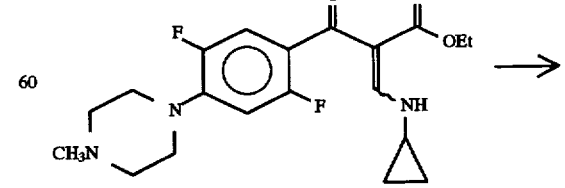

1

-continued

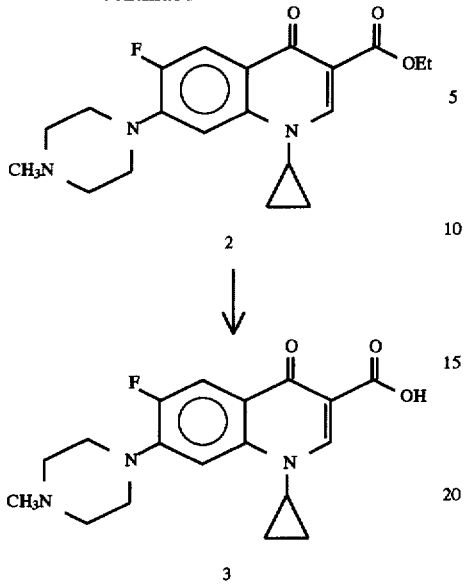

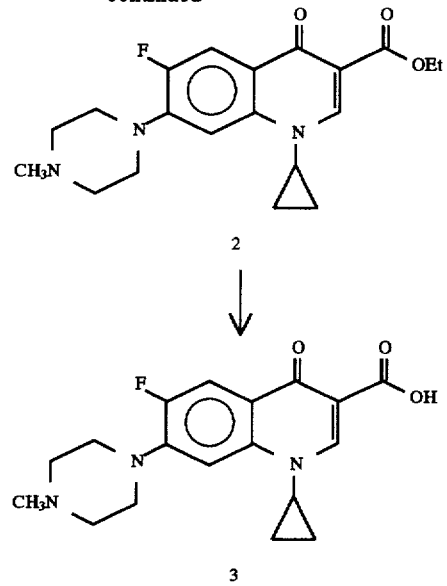

Compound 1 is prepared in the same manner as Compound 5 is prepared in Example 1 above.

To a solution of Compound 1 (100 mg) in $CH_2Cl_2$ (1 mL) is added 1-(trimethylsilyl)imidazole (TMSIM) (0.60 mL). The reaction mixture is heated to reflux for 30 hours under $N_2$. The reaction is quenched with water (1 mL) and diluted with $CH_2Cl_2$ (5 mL). The $CH_2Cl_2$ layer is separated and dried ($Na_2SO_4$), and the volatiles are removed in vacuo to obtain a solid. The solid is recystallized from EtOAc/Hexane to give Compound 2.

A suspension of Compound 2 (200 mg) in 6N HCl solution (15 mL) is heated at 110° C. under $N_2$. After 6 hours, the solvent is removed in vacuo, ethanol (20 mL) is added to the residue and the mixture is stirred at reflux for 15 minutes. The mixture is cooled to room temperature and the resulting solid is filtered to obtain Compound 3 as its hydrochloride salt.

EXAMPLE 6

Synthesis of 1-cyclopropyl-6-fluoro-1,4-dihydro-7-(4-methyl-1-piperazinyl)-4-oxo-3-quinolinecarboxylic acid

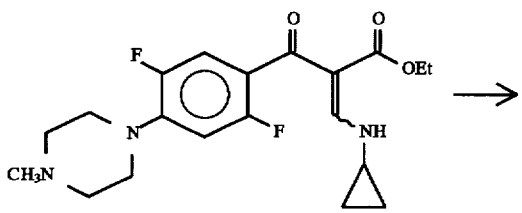

Compound 1 is prepared in the same manner as Compound 5 is prepared in Example 1 above.

To a solution of Compound 1 (100 mg) in $CH_2Cl_2$ (1 mL) is added hexamethyldisilazane (HMDS) (0.66 mL) and trimethylchlorosilane (TMCS) (0.1 mL). The reaction mixture heated to reflux for 30 hours under $N_2$. The reaction is quenched with water (1 mL) and diluted with $CH_2Cl_2$ (5 mL). The $CH_2Cl_2$ layer is separated and dried ($Na_2SO_4$), and the volatiles are removed in vacuo. The solid is recystallized from $Et_2O$ to give Compound 2.

A suspension of Compound 2 (200 mg) in 6N HCl solution (15 mL) is heated at 110° C. under $N_2$. After 6 hours, the solvent is removed in vacuo, ethanol (20 mL) is added to the residue and the mixture is stirred at reflux for 15 minutes. The mixture is cooled to room temperature and the resulting solid is filtered to obtain Compound 3 as its hydrochloride salt.

EXAMPLE 7

Synthesis of 1-cyclopropyl-6-fluoro-1,4-dihydro-7-(4-methyl-1-piperazinyl)-4-oxo-3-quinolinecarboxylic acid

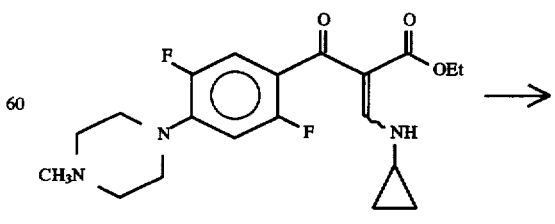

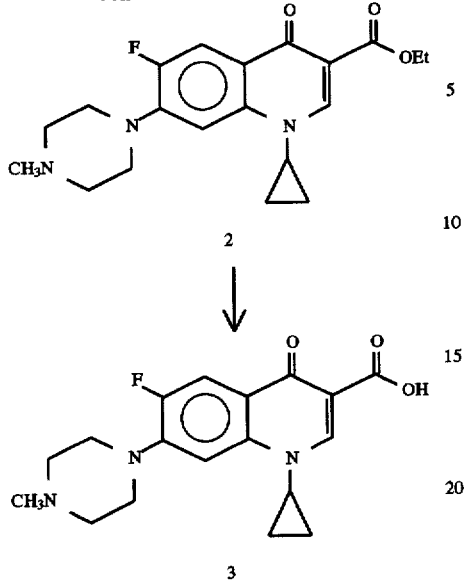

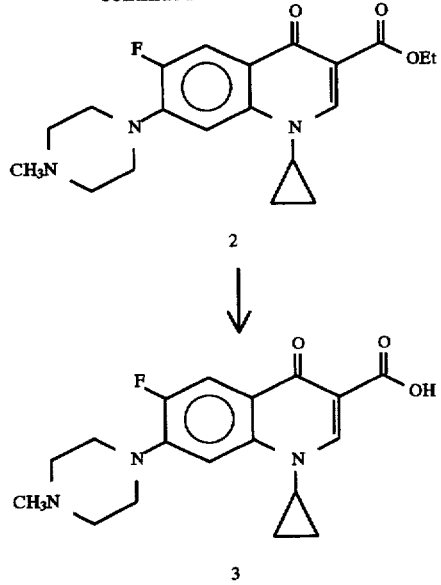

Compound 1 is prepared in the same manner as Compound 5 is prepared in Example 1 above.

To a solution of Compound 1 (100 mg) in $CH_2Cl_2$ (1 mL) is added hexamethyldisilazane (HMDS) (0.66 mL). The reaction minute is refluxed for 60 hours under $N_2$. The reaction is quenched with water (1 mL) and diluted with $CH_2Cl_2$ (5 mL). The $CH_2Cl_2$ layer is separated and dried ($Na_2SO_4$), and the volatiles are removed in vacuo to obtain a solid. The residue is recrystallized from isopropyl ether to give Compound 2.

A suspension of Compound 2 (200 mL) in 6N HCl solution (15 mL) is heated at 110° C. under $N_2$. After 6 hours, the solvent is removed in vacuo, ethanol (20 mL) is added to the residue and the mixture is stirred at reflux for 15 minutes. The mixure is cooled to room temperature and the resulting solid is filtered to obtain Compound 3 as its hydrochloride salt.

EXAMPLE 8

Synthesis of 1-cyclopropyl-6-fluoro-1,4-dihydro-7-(4-methyl-1-piperazinyl)-4-oxo-3-quinolinecarboxylic acid

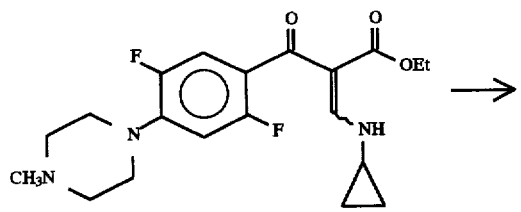

Compound 1 is prepared in the same manner as Compound 5 is prepared in Example 1 above.

To a solution of Compound 1 (100 mg) in $CH_2Cl_2$ (1 mL) is added N,O-bis(trimethylsilyl)trifluoroacetamide (BSTFA) (0.2 mL). The reaction mixture is stirred at ambient temperatures for 18 hours under $N_2$. The $CH_2Cl_2$ layer is separated and dried ($Na_2SO_4$), and the volatiles are removed in vacuo to obtain a solid. The residue is recrystallized from $H_2O$ and azeotroped with toluene (25 mL) to give Compound 2.

A suspension of Compound 2 (200 mg) in 6N HCl solution (15 mL) is heated at 110° C. under $N_2$. After 6 hours, the solvent is removed in vacuo, ethanol (20 mL) is added to the residue and the mixture is stirred at reflux for 15 minutes. The mixture is cooled to room temperature and the resulting solid is filtered to obtain Compound 3 as its hydrochloride salt.

EXAMPLE 9

Preparation of 1-cyclopropyl-6-fluoro-1,4-dihydro-4-oxo-7-(1-piperazinyl)-3-quinoline-carboxylic acid.

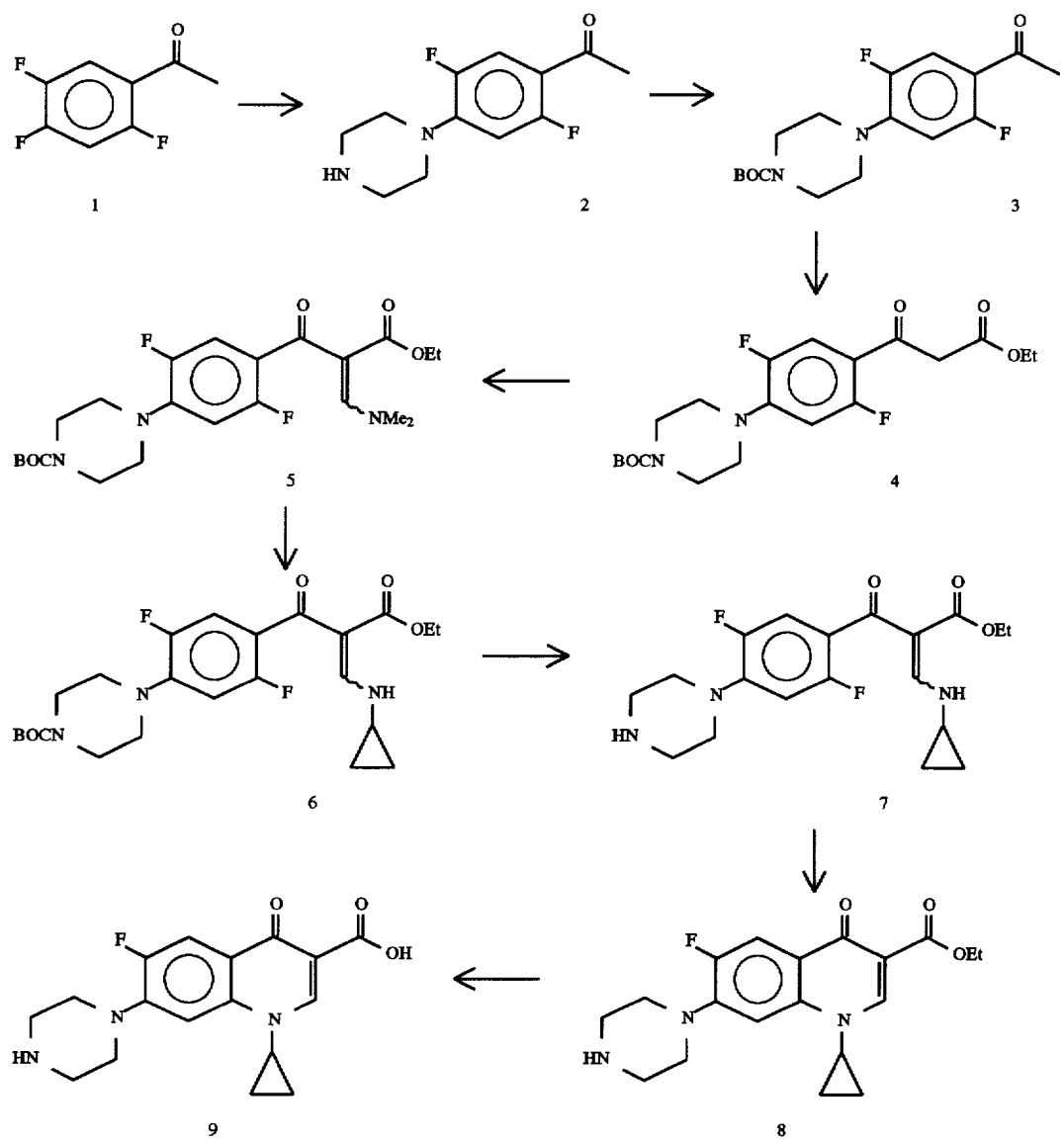

To a solution of 2,4,5-trifluoroacetophenone (15.0 g) (Compound 1) in THF (300 mL) is added piperazine (29.6 g). The mixture is refluxed under $N_2$ for 1 hour and the THF is removed under reduced pressure. The residue is slurried in EtOAc (150 mL), and the excess piperazine is filtered off and rinsed with EtOAc. The EtOAc filtrate is washed with water (2×150 mL) and the combined aqueous layers are extracted with EtOAc (75 mL). The combined EtOAc layers are dried ($MgSO_4$) and treated with activated charcoal. The solvents are evaporated in vacuo and the residue is crystallized from isopropyl ether to give Compound 2.

To a solution of Compound 2 (9.4 g) in $CHCl_3$ (141 mL) is added a solution of di-t-butylcarbonate (9.39 g) in $CHCl_3$ (50 mL). The reaction is stirred for 5 minutes under $N_2$ at ambient temperature and evaporated in vacuo. Hexanes are added to give Compound 3.

To a cooled solution of Compound 3 (10.0 g) in THF (100 mL) under $N_2$ at 0°–5° C. is added a 60% oil immersion of NaH (2.5 g), portionwise. The reaction mixture is stirred for 15 minutes and diethylcarbonate (14.2 mL) is added. The reaction is stirred for 18 hours under $N_2$ at ambient temperature and quenched with a 28:1 mixture of water and HOAc (100 mL). The organic portion is evaporated in vacuo and the residue is subjected to column chromatography (silica, 10:89:1% EtOAc/Hexane/HOAc). The residue is crystallized from hexanes to give Compound 4.

To a solution of Compound 4 (11.95 g) in toluene (47.8 mL) is added dimethylformamide dimethylacetal (5.95 mL). The reaction is heated to reflux for 20 hours under $N_2$ and concentrated in vacuo to obtain Compound 5, which is carried directly to the next step by dissolving in EtOH (47.8 mL) and adding cyclopropyl amine (3.2 mL). The mixture is stirred for 2 hours at ambient temperature under $N_2$. The volatiles are removed in vacuo and the residue is crystallized from 20% EtOAc/hexanes to give Compound 6.

To a cooled solution of Compound 6 (12.06 g) in anisole (97.7 mL) at 5°–10° C. is added trifluoroacetic acid (TFA) (97.7 mL). After stirring for 5 minutes under $N_2$, the ice bath is removed and the reaction is warmed to ambient temperature. After 2 hours, most of the TFA and some of the anisole is removed in vacuo. The residue is slurried in Et₂O (300 mL) and filtered. The solid is dissolved in a mixture of CH₂Cl₂ (100 mL) and saturated NaHCO₃ (100 mL) and stirred for 10 min. The CH₂Cl₂ portion is separated, dried (MgSO₄), treated with activated charcoal, and evaporated in vacuo. The residue is crystallized with hexane to give the mono-hydrate of Compound 7.

The mixture is cooled to room temperature and the resulting solid is filtered to obtain Compound 9 as its hydrochloride salt.

EXAMPLE 10

Preparation of 6, 8-difluoro-1-(2-fluoroethyl)-1,4-dihydro-7-(4-methyl-1-piperazinyl)-4-oxo-3-quinolinecarboxylic acid.

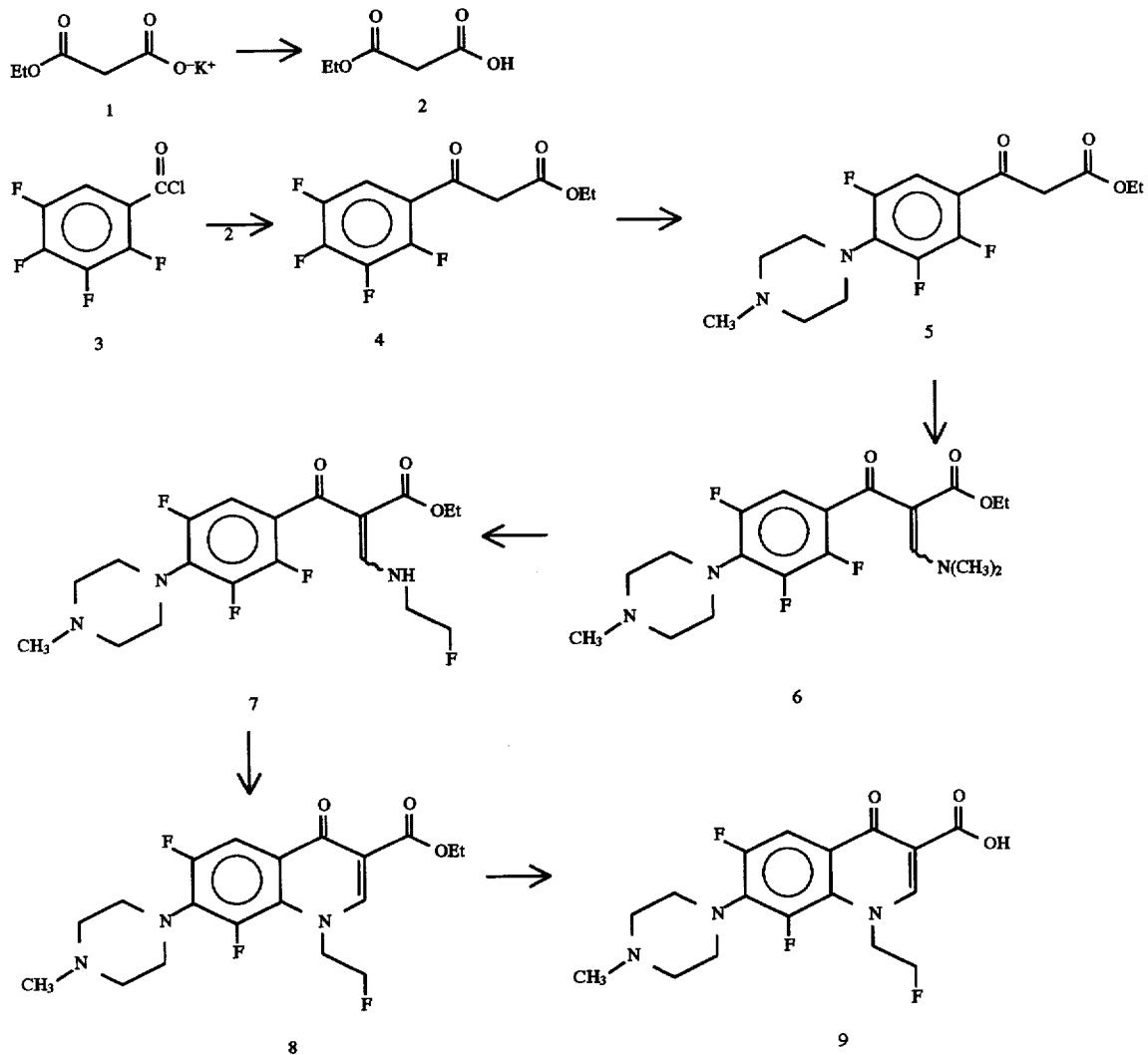

Compound 7 (100 mg) is dissolved in dichloroethane (4 mL) and dried (Na₂SO₄). The solution is transferred to a second vessel, under N₂, and N,O-bis(trimethylsilyl) acetamide (0.4 mL) is added. The reaction is stirred at ambient temperatures overnight under N₂. The reaction is quenched with water (2 mL) and the organic portion is separated and dried (MgSO₄). The solvent is evaporated in vacuo to give Compound 8.

A suspension of Compound 8 (90 mg) in 6N HCl solution (10 mL) is heated at 110° C. under N₂. After 6 hours, the solvent is removed in vacuo, ethanol (10 mL) is added to the residue and the mixture is stirred at reflux for 15 minutes.

To a cooled solution of potassium ethyl malonate (20 g) (Compound 1) in water (12.5 mL) is added 12N HCl (10.1 mL) at a rate which allows the temperature to be maintained between 5°–10° C. Once the addition is complete, the KCl formed is filtered and rinsed with ether (40 mL). The ethereal portion of the filtrate is separated and the aqueous portion is extracted with Et₂O (3×15 mL). The combined ether layers are dried (MgSO₄) and the solvent removed in vacuo to give Compound 2.

To a cooled (–30° C.) solution of 2,2-biquinoline (7.9 mg) and Compound 2 (8.2 g) in THF (95 mL), under N₂, is added 2.5M n-BuLi in hexane until a pink color persists at –5° C.

(approximately 50 mL). The mixture is cooled to –50° C. and a solution of 2,3,4,5-tetrafluorobenzoyl chloride (4.0 mL) (Compound 3) in THF (45 mL) is added dropwise so that the temperature is maintained at –50° C. After 30 minutes, the mixture is allowed to warm to ambient temperature and is quenched with 1M HCl (130 mL) at a rate which allows the temperature to be maintained at about 30° C. The organic layer is separated and the aqueous layer is extracted with Et$_2$O (4×40 mL). The combined organic layers are washed with 10% aqueous NaHCO$_3$ (3×100 mL) and brine (3×100 mL). The organic portion is dried (MgSO$_4$) and treated with activated charcoal. After removal of the solvents in vacuo, the residue obtained is subjected to column chromatography (silica, 5% EtOAc/hexane) to give a mixture of Compound 4 and its enol ether, which is used directly in the next step.

To a solution of Compound 4 (3.5 g) in THF (70 mL) is added 1-methylpiperazine (5.88 mL). The reaction is heated at reflux, under N$_2$, for 1 hour and the volatiles are removed in vacuo. The residue obtained is dissolved in EtOAc (40 mL), washed with water (4×35 mL), and dried (MgSO$_4$). The solvent is removed in vacuo and the oil obtained is subjected to column chromatograpy (silica, 1:5:94 HOAc/ MeOH/CH$_2$Cl$_2$) to give a mixture of Compound 5 and its enol ether, which is used directly in the next step.

To a solution of Compound 5 (1.08 g) in toluene (8 mL) is added dimethylformamide dimethylacetal (0.65 mL). The reaction is heated at reflux under N$_2$ for 2 hours and the volatiles are removed in vacuo to give Compound 6, which is used directly in the next step To a solution of Compound 6 (1.02g) in EtOH (7 mL) is added 2-fluoroethylamine hydrochloride (0.431 g). The reaction is stirred at ambient temperatures for 2 hours under N$_2$. The volatiles are removed in vacuo and the residue obtained is dissolved in a mixture of EtOAc (50 mL) and 0.1N NaOH solution (10 mL). The organic layer is separated and washed with 0.1N NaOH solution (3×30 mL), water (3×30 mL) and brine (3×30 mL). The organic portion is dried (Na$_2$SO$_4$) and the solvent is removed in vacuo. The solid is recrystallized from isopropylether to give Compound 7.

To a solution of Compound 7 (0.495 g) in CH$_3$CN (10 mL) is added N,O-bis(trimethylsilyl)-acetamide (0.88 mL). The reaction is stirred for 2 hours at room temperature under N$_2$. The volatiles are removed in vacuo and the residue obtained is dissolved in CH$_2$Cl$_2$ (20 mL). The solution is washed with water (3×5 mL) and dried (Na$_2$SO$_4$), and the volatiles are removed in vacuo. The residue obtained is reslurried in isopropylether to give Compound 8.

A suspension of Compound 8 (300 mg) in 6N HCl solution (22 mL) is heated at 110° C. under N$_2$. After 6 hours, the solvent is removed in vacuo, ethanol (25 mL) is added to the residue and the mixture is stirred at reflux for 15 minutes. The mixture is cooled to room temperature and the resulting solid is filtered to obtain 6,8-difluoro-1-(2-fluoroethyl)-1,4-dihydro-7-(4-methyl-1-piperazinyl)-4-oxo-3-quinolinecarboxylic acid (Compound 9) as its hydrochloride salt.

EXAMPLE 11

Preparation of 1-cyclopropyl-6-fluoro-1,4-dihydro-4-oxo-7-(1-piperazinyl)-3-quinolinecarboxylic acid as the hydrochloride salt.

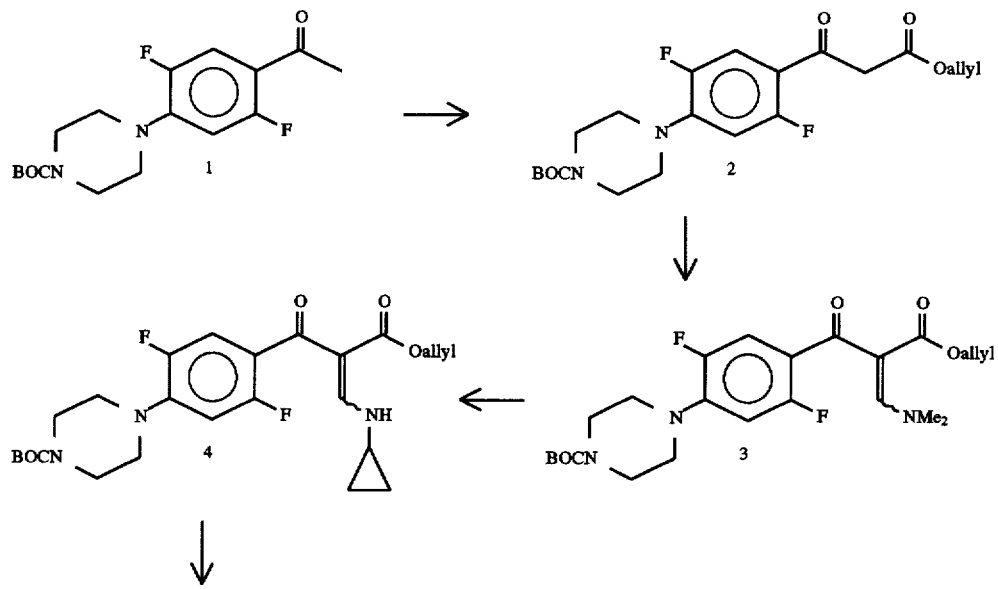

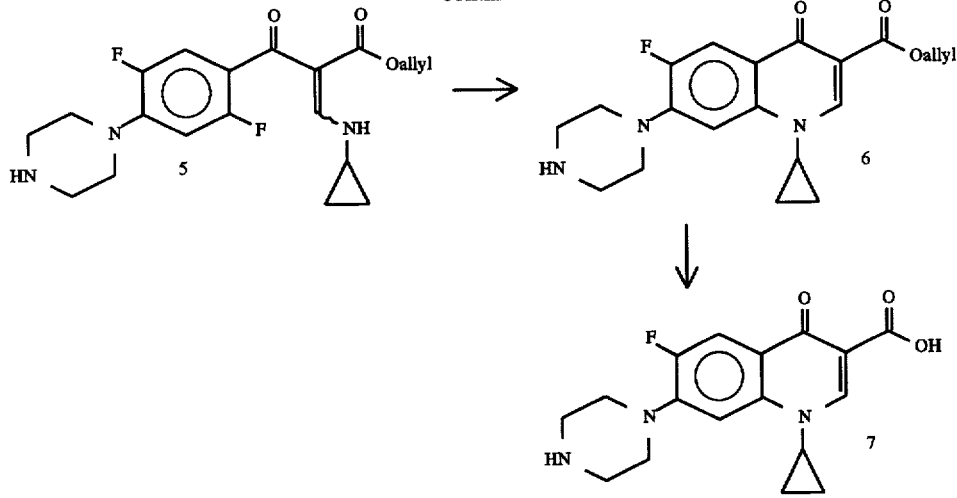

To a cooled solution of Compound 1 (10.0 g) (prepared in the same manner as Compound 3 in Example 9) in THF (100 mL) under $N_2$ at 0°–5° C. is added a 60% oil immersion of NaH (2.5 g), portionwise. The reaction mixture is stirred for 15 minutes and diallylcarbonate (16.9 mL) is added. The reaction is stirred for 18 hours under $N_2$ at ambient temperature and quenched with a 28:1 mixture of water and HOAc (100 mL). The organic portion is evaporated in vacuo and the residue is subjected to column chromatography (silica). The residue is crystallized from hexanes to give Compound 2.

To a solution of Compound 2 (10.5 g) in toluene (42 mL) is added dimethylformamide dimethylacetal (5.1 mL). The reaction is heated to reflux for 20 hours under $N_2$ and concentrated in vacuo to obtain Compound 3, which is carried directly to the next step by dissolving in EtOH (42 mL) and adding cyclopropyl amine (2.73 mL). The mixture is stirred for 2 hours at ambient temperature under $N_2$. The volatiles are removed in vacuo and the residue is crystallized from 20% EtOAc/hexanes to give Compound 4.

To a cooled solution of Compound 4 (9.75 g) in anisole (79 mL) at 5°–10° C. is added trifluoroacetic acid (TFA) (79 mL). After stirring for 5 minutes under $N_2$, the ice bath is removed and the reaction is warmed to ambient temperature. After 2 hours, most of the TFA and some of the anisole is removed in vacuo. The residue is slurried in $Et_2O$ (250 mL) and filtered. The solid is dissolved in a mixture of $CH_2Cl_2$ (80 mL) and saturated $NaHCO_3$ (80 mL) and stirred for 10 min. The $CH_2Cl_2$ portion is separated, dried ($MgSO_4$), treated with activated charcoal, and evaporated in vacuo. The residue is crystallized with hexane to give the monohydrate of Compound 5.

Compound 5 (100 mg) is dissolved in dichloroethane (4 mL) and dried ($Na_2SO_4$). The solution is transferred to a second vessel, under $N_2$, and N,O-bis(trimethylsilyl) acetamide (0.4 mL) is added. The reaction is stirred at ambient temperatures overnight under $N_2$. The reaction is quenched with water (2 mL) and the organic portion is separated and dried ($MgSO_4$). The solvent is evaporated in vacuo to give Compound 6.

A suspension of Compound 6 (90 mg) in 6N HCl solution (10 mL) is heated at 110° C. under $N_2$. After 6 hours, the solvent is removed in vacuo, ethanol (10 mL) is added to the residue and the mixture is stirred at reflux for 15 minutes. The mixture is cooled to room temperature and the resulting solid is filtered to obtain 1-cyclopropyl-6-fluoro-1,4-dihydro-4-oxo-7-(1-piperazinyl)-3-quinolinecarboxylic acid (Compound 7) as its hydrochloride salt.

The following compounds are prepared according to Examples 1–11 with substantially similar results.

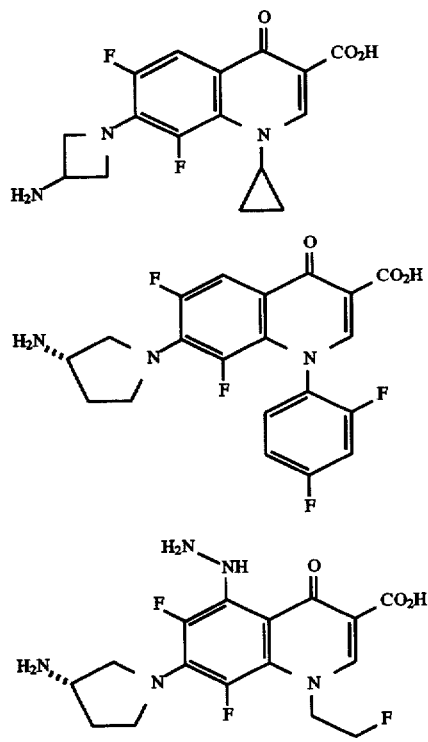

47
-continued
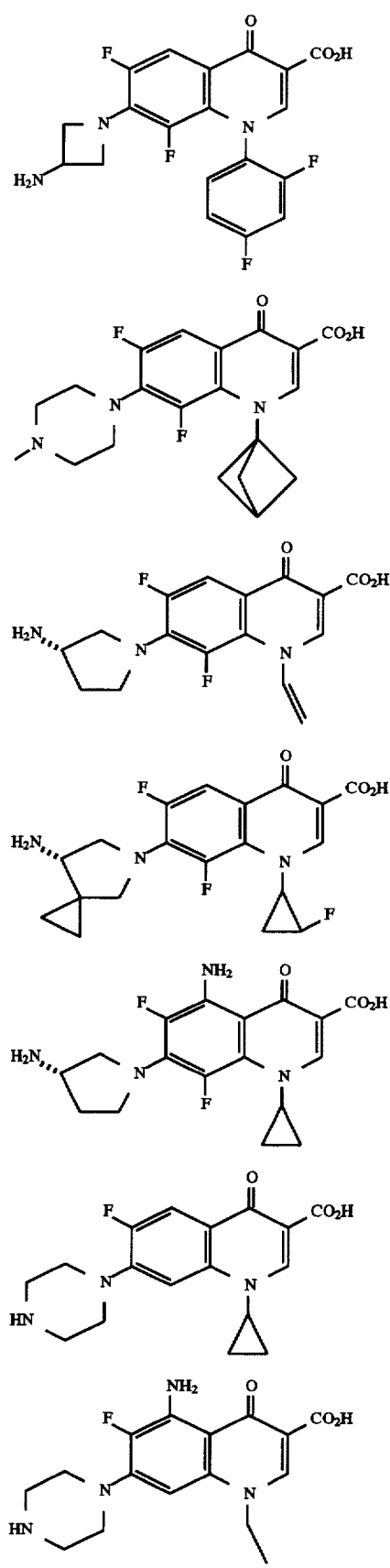
48
-continued
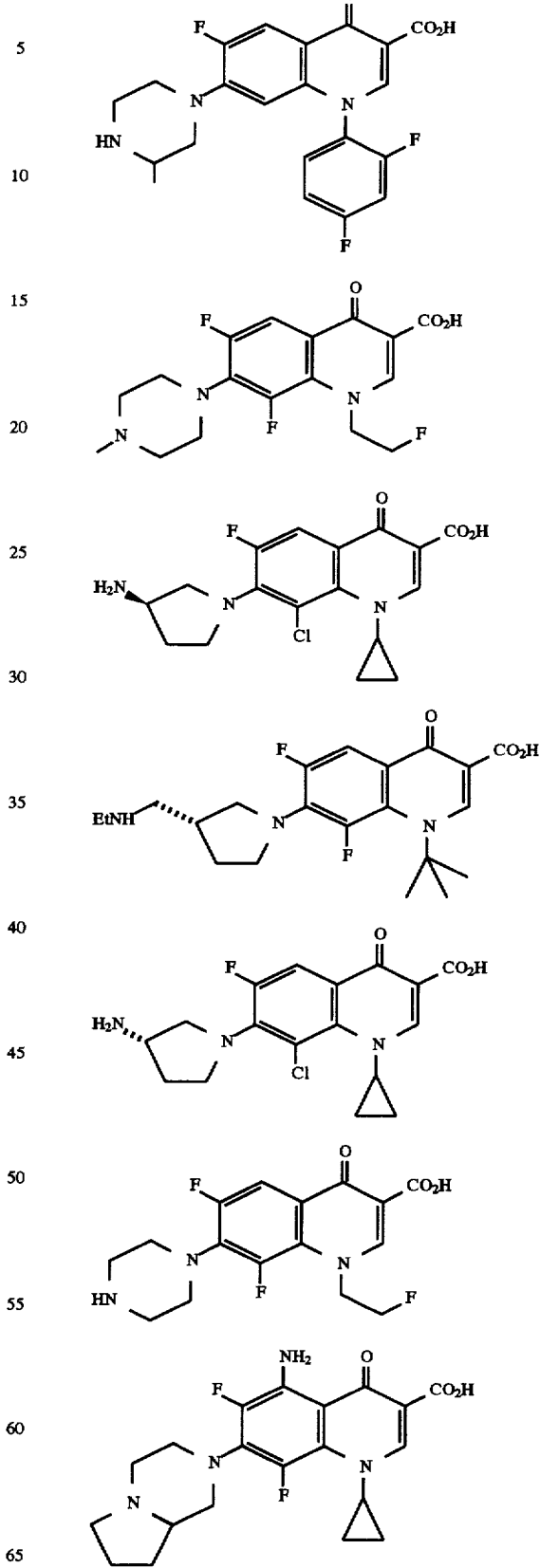

49
-continued
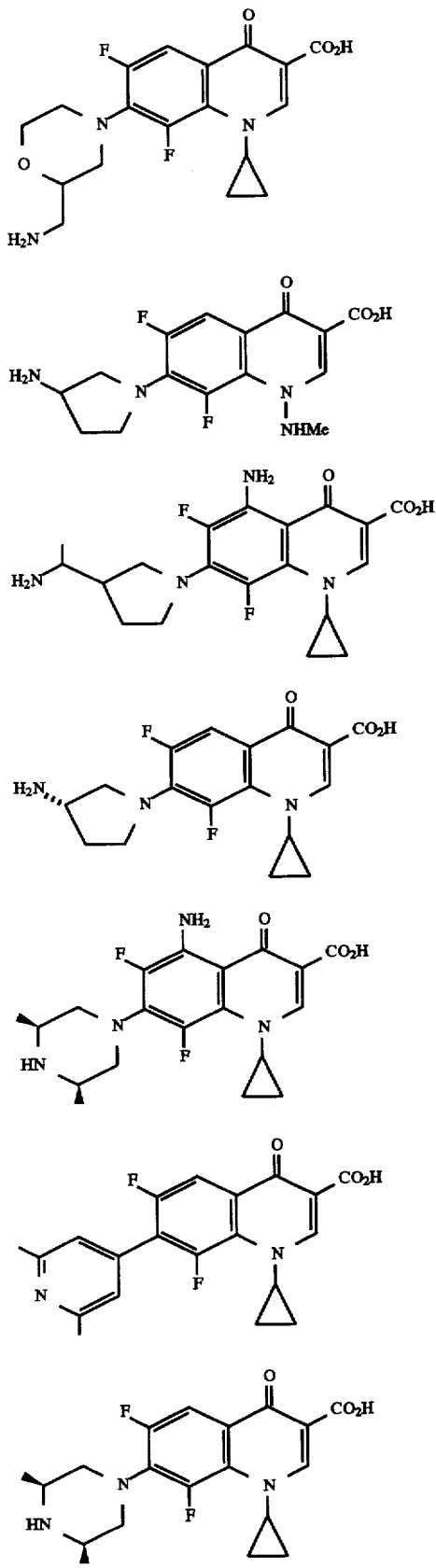
50
-continued
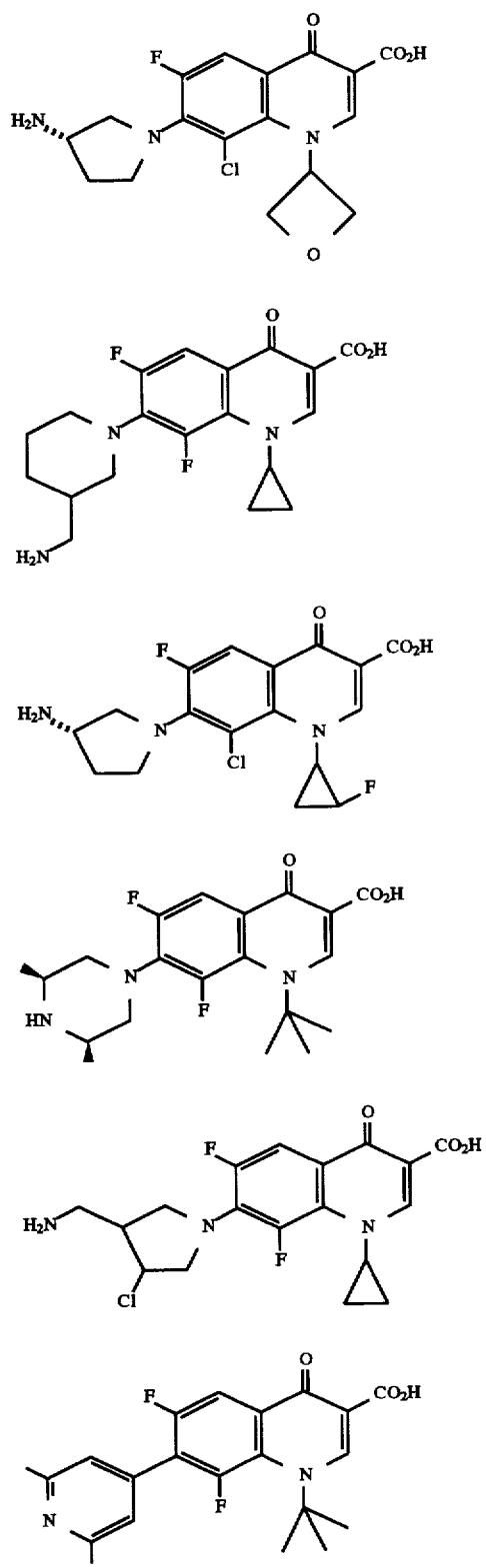

-continued

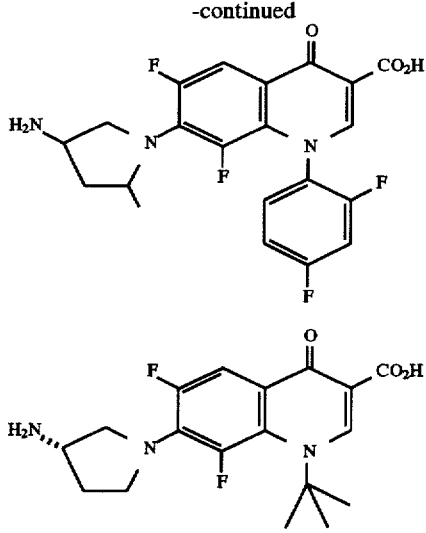

EXAMPLE 12

Synthesis of 9-fluoro-2,3-dihydro-3-methyl-10-(4-methyl-1-piperazinyl)-7-oxo-7H-pyrido[1,2,3-de]-1,4-benzoxazine-6-carboxylic acid.

volatiles are removed in vacuo. The residue obtained is dissolved in EtOAc (100 mL), and the solution is washed with $H_2O$ (3×30 mL) and brine (3×30 mL). The organic portion is dried ($MgSO_4$) and the solvent is removed in vacuo to provide Compound 2, which is used directly in the next step.

To a solution of Compound 2 (1.3 g) in $CH_3CN$ (10 mL) is added N,O-bis(trimethylsilyl)acetamide (2.3 mL). The reaction is stirred for 2.5 hours under $N_2$. The volatiles are removed in vacuo and the residue obtained is dissolved in $CH_2Cl_2$ (50 mL). The solution is washed with $H_2O$ (3×10 mL), dried ($MgSO_4$), and treated with activated charcoal. The volatiles are removed in vacuo. Compound 3 is crystallized from isopropylether.

To a solution of Compound 3 (0.15 g) in dioxane (3 mL) is added a 60% immersion of NaH in oil (0.0176 g). The reaction is heated to 75° C. and stirred 1.5 hours under $N_2$. The reaction is poured into ice water (10 mL) and the aqueous solution is extracted with EtOAc (3×20 mL). The organic portion is dried ($Na_2SO_4$) and the solvent is removed in vacuo. The residue obtained is crystallized from EtOAc to give Compound 4.

A suspension of Compound 4 (95 mg) in 6N HCl solution

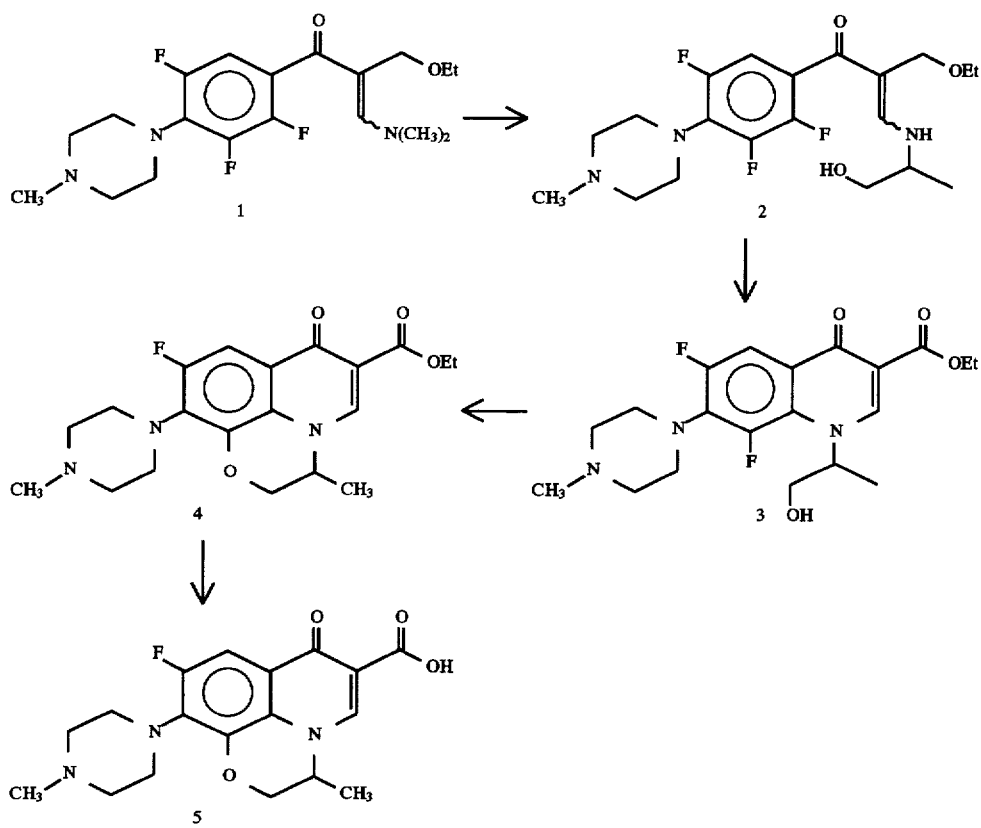

Compound 1 is prepared according to the same procedure as Compound 6 in Example 10 above.

To a solution of Compound 1 (1.2 g) in EtOH (10 mL) is added (+)-2-amino-1-propanol (0.26 mL). The reaction is stirred at ambient temperature for 2 hours under $N_2$ and the (10 mL) is heated at 110° C. under $N_2$. After 6 hours, the solvent is removed in vacuo, ethanol (11 mL) is added to the residue and the mixture is stirred at reflux for 15 minutes. The mixture is cooled to room temperature and the resulting solid is filtered to obtain 9-fluoro-2,3-dihydro-3-methyl-10-

(4-methyl-1-piperazinyl)-7-oxo-7H-pyrido[1,2,3-de]-1,4-benzoxazine-6-carboxylic acid (Compound 5) as its hydrochloride salt.

The following compounds are prepared according to Example 12 with substantially similar results.

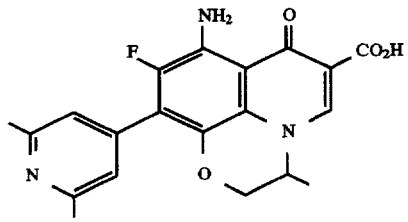

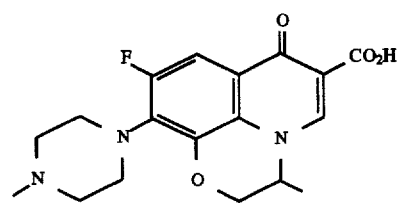

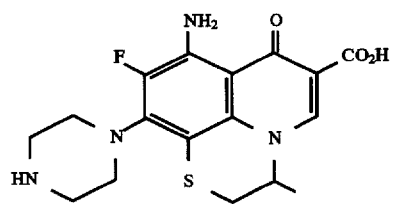

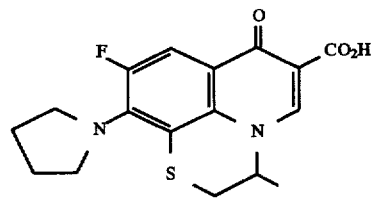

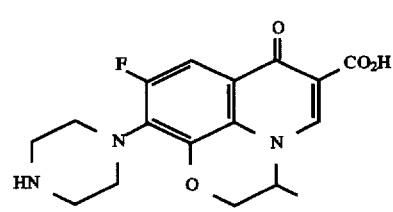

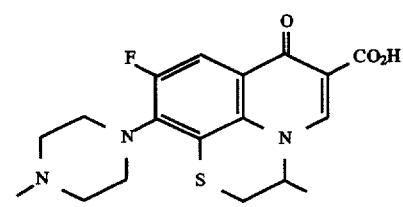

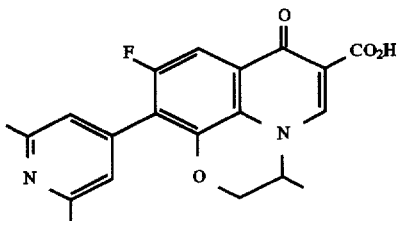

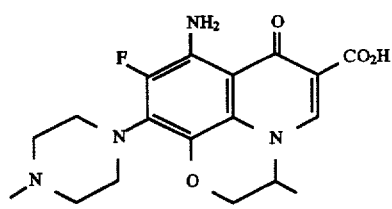

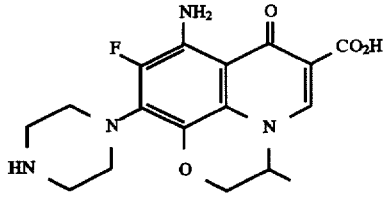

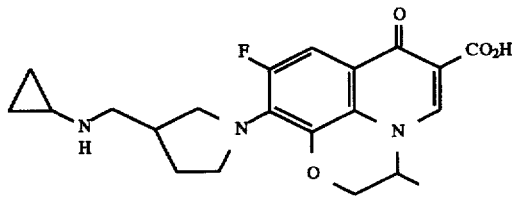

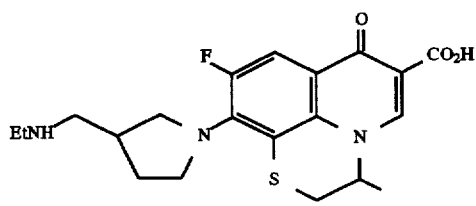

EXAMPLE 13

Synthesis of 1-ethyl-6,7,8-trifluoro-1,4-dihydro-4-oxo-3-quinolinecarboxylic acid. This compound, and its analogs, are useful intermediates for making antimicrobial quinolones, using known chemistry.

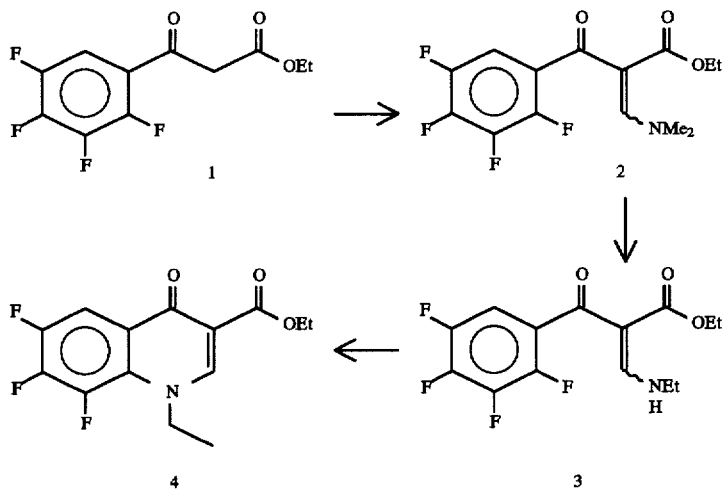

Comound 1 is synthesized using the reaction sequence for preparing Compound 4 in Example 10.

To a solution of Compound 1 (1.39 g) in toluene (12 mL) is added dimethylformamide dimethylacetal (1.08 mL). The reaction is heated at 90° C. for hours under $N_2$ and the volatiles are removed in vacuo to give Compound 2, which is used directly in the next step.

To a solution of Compound 2 (0.32 g) in EtOH (3 mL) is added ethylamine hydrochloride (0.09 g). The reaction is stirred for 20 hours and the volatiles are removed in vacuo. The residue obtained is dissolved in EtOAc (25 mL) and the solution is washed with 0.1M NaOH (3×30 mL), $H_2O$ (3×25 mL), and brine (3×25 mL). The organic portion is dried ($MgSO_4$) and the solvent is removed in vacuo to provide Compound 3.

To a solution of Compound 3 (0.144 g) in $CH_3CN$ (4 mL) is added N,O-bis(trimethylsilyl)acetamide (BSA) (0.67 mL). The reaction is stirred for 20 hours at ambient temperature, cooled to 0° C., and filtered to provide the ethyl ester of 1-ethyl-6,7,8-trifluoro-1,4-dihydro-4-oxo-3-quinolinecarboxylic acid (Compound 4).

EXAMPLE 14

Synthesis of 1-cyclopropyl-6,7-difluoro-1,4-dihydro-4-oxo-3-quinoline-carboxylic acid. This compound, and its analogs, are useful intermediates for making antimicrobial quinolones, using known chemistry.

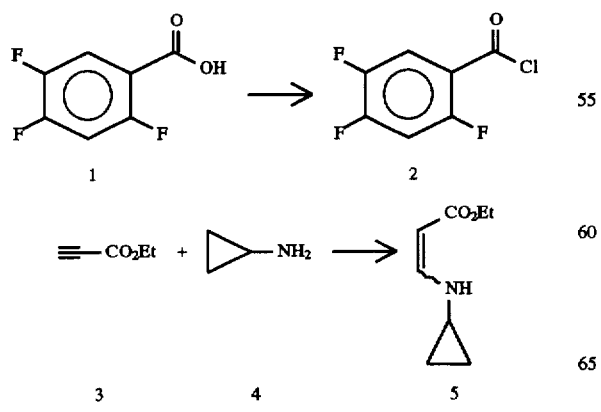

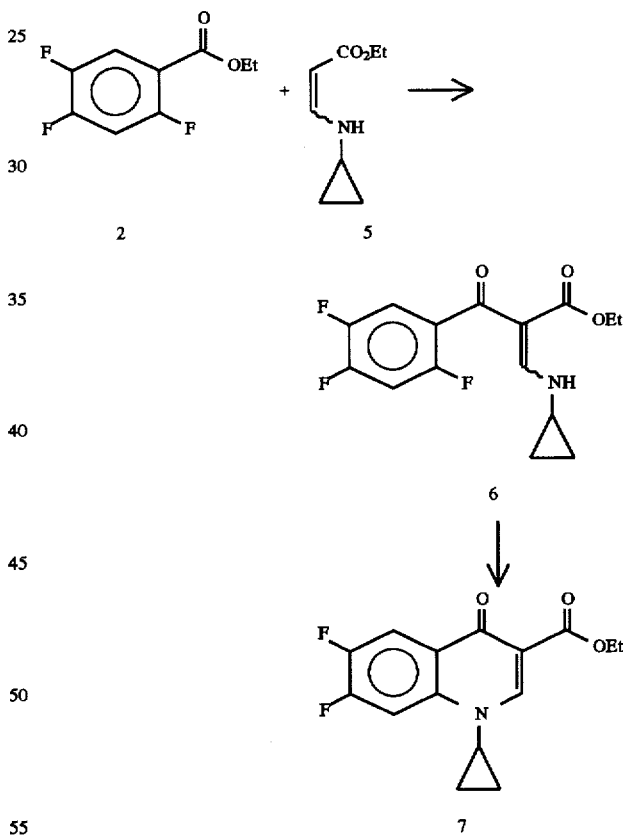

To $SOCl_2$ (12.4 mL) is added 2,4,5-trifluorobenzoic acid (10 g) (Compound 1). The reaction is stirred at reflux for 20 hours under $N_2$ and the volatiles are removed in vacuo. The residue obtained is vacuum distilled (0.4 mm Hg) at 39°–42° C. to give Compound 2.

To a cooled (5° C.) solution of ethylpropiolate (5.0 g) (Compound 3) in THF (25.5 mL) is added a solution of cyclopropylamine (3.5 mL) (Compound 4) in THF (4.5 mL) at a rate which allows the temperature to be maintained at about 5° C. The reaction is stirred for 1 hour at 5° C., under $N_2$, and is then allowed to slowly warm to ambient temperature over 2 hours, whereupon it is allowed to stir at ambient temperature for 20 hours. The volatiles are removed in vacuo and the residue is vacuum distilled (0.5 mm Hg) at 55°–70° C. to give Compound 5.

To a cooled (15°–20° C.) Solution of Compound 2 (1.5 g) in dioxane (2 mL) is added dropwise a solution of Compound 5 (1.2 g) and TEA (1.1 mL) in dioxane (2.6 mL) at a rate which allows the temperature to be maintained below 20° C. The reaction is stirred at ambient temperature under $N_2$ for 20 hours and the precipitate that is formed is filtered. Hexanes (20 mL) are added to the filtrate and the additional precipitate that forms is filtered off. The volatiles are removed in vacuo and the residue is subjected to column chromatography (silica, 20% EtOAc/hexanes) to give Compound 6.

To a solution of Compound 6 (1.0 g) in $CH_3CN$ (30 mL) is added N,O-bis(trimethylsilyl)acetamide (4.3 mL). The reaction is stirred at ambient temperatures under $N_2$ for 2 hours. The solution is cooled and the precipitate that forms is filtered and washed with cold $CH_3CN$ to give the ethyl ester of 1-cyclopropyl-6,7-difluoro-1,4-dihydro-4-oxo-3-quinolinecarboxylic acid (Compound 7).

EXAMPLE 15

Synthesis of the ethyl ester of 7-chloro-1-(2,4-difluorophenyl)-6-fluoro-1,4-dihydro-4-oxo-1,8-napthyridine-3-carboxylic acid. This compound, and its analogs, are useful intermediates for making antimicrobial quinolones, using known chemistry.

Solid sodium ethoxide (424.5 g) is added in portions (20 min) via a Gooch tube to a vigorously stirred, cold (ice bath) solution of ethyl fluoroacetate (450 g) and ethyl formate (525 g) under argon. The ice bath is removed and the reaction mixture is stirred for 3.5 h at room temperature. Malondiamide (745.5 g) is added in portions over 10 min with the aid of 5.4 L of absolute EtOH to wash in the solid. The mixture is slowly heated to reflux where upon the mixture becomes a thick paste. The reaction mixture is cooled in an ice bath and water (4.23 L) is added over 10 min. followed by addition of conc. HCl (843 mL), while stirring and cooling. The mixture is filtered and the solid is washed successively with $H_2O$ and EtOH to give Compound 1.

In an argon purged 5-L 3-neck flask is added Compound 1 (300 g) and phosphorus pentachloride (1200 g). The mixture is stirred thoroughly and is slowly heated to 110° C. and maintained at 110° C. for about 1 h. The mixture is distilled under partial vacuum to remove $POCl_3$. The concentrated residue is mixed with cold water (3 L) and stirred. The mixture is filtered and the solid is washed successively with $H_2O$ (2×1 L) and isopropyl alcohol-$H_2O$ (1:1) to give, after vacuum drying, Compound 2.

A solution of Compound 2 (200 g) in concentrated sulfuric acid (1.35 L) is heated at 90° C. for 1.5 h. The solution is cooled to about 60° C. and $H_2O$ (2.67 L) is slowly added while maintaining the temperature below 95° C. The reaction mixture is heated at 100° C. for 3 h and then stored overnight at 5° C. The mixture is filtered, and the solid is air dried to give crude Compound 3. Compound 3 is purified by mixing with 5 L of EtOAc and adding decolorizing carbon

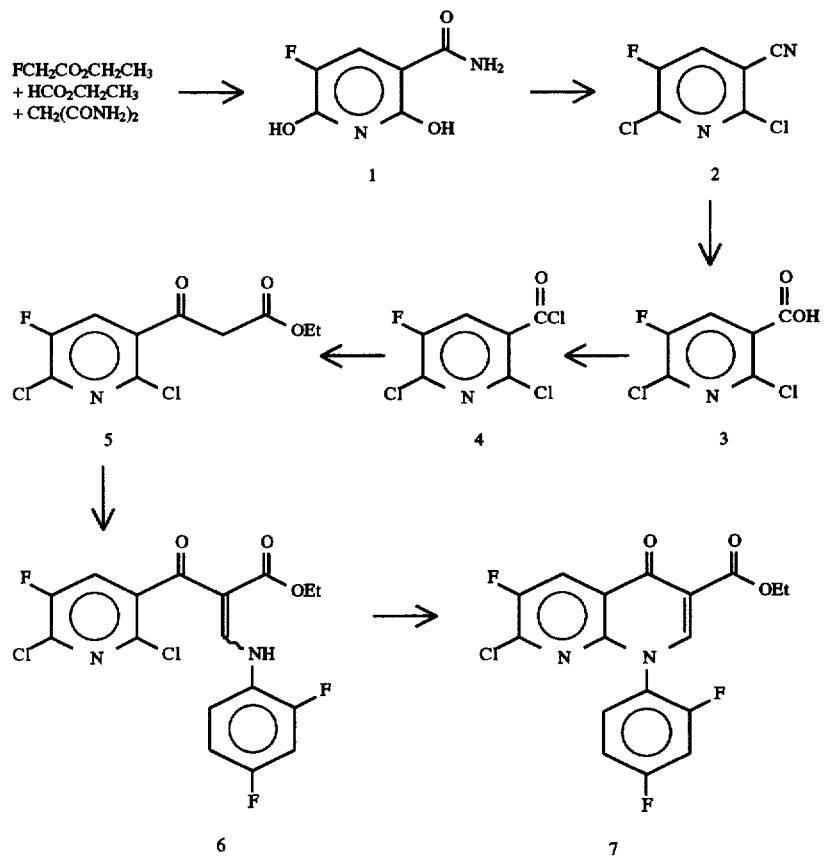

(100 g). The mixture is filtered, and the filtrate is concentrated in vacuo to 3 L. The solution is diluted with hexanes (7 L) and further evaporated to 2 L. An additional 4 L of hexanes is added. The solid is collected and washed with hexanes (1 L) to give Compound 3.

A mixture of Compound 3 (140 g) and thionyl chloride (250 mL) is stirred and heated at reflux for 2 h. The solution is cooled and evaporated in vacuo. The residue is evaporated further with toluene (3×600 mL, freshly filtered through anhydrous $Na_2SO_4$) to give the crude Compound 4, which is used immediately in the subsequent step.

A 2.5M solution of n-butyl lithium (1270 mL) in hexanes is added over 2.5 h to a stirred solution of ethyl hydrogen malonate (197.1 g) in THF (3.4 L) at −50° to −65° C. under an Ar atmosphere. The cooling bath is replaced with warm water to bring the temperature to −5° C. The pasty mixture is recooled in the dry ice-acetone bath, and the crude Compound 4 in THF (250 mL) is added dropwise (1.5 h) while keeping the temperature below −50° C. After the addition is complete, the cooling bath is removed, and the reaction mixture is left to warm to room temperature overnight. The mixture is poured in about 4 equal portions to a rapidly stirred solution of conc. HCl (270 mL) and $H_2O$ (2.5 L). The mixture is stirred for about 30 min and the temperature rises to 34° C. The layers are separated, and the aqueous layer is extracted (by stirring) with EtOAc (2×2 L). The combined organic material is washed with saturated aqueous $NaHCO_3$ (1.8 L and 2×1 L). These aqueous washes are back extracted with EtOAc (800 mL). The combined EtOAc solutions are dried over $Na_2SO_4$ then concentrated in vacuo to a residue. This material is chromatographed on a 1.4 kg silica gel column eluted with $CH_2Cl_2$. The fractions containing purified product are combined and concentrated in vacuo to give (after cold hexane trituration) Compound 5 as crystals.

A mixture of Compound 5 (160.5 g), triethyl orthoformate (145 mL) and acetic anhydride (350 mL) is stirred and heated at 130° C. for 1 h. Approximately 230 mL of volatile distillate is collected in a Dean-Stark trap. The solution is cooled and evaporated in vacuo. The residue is dissolved in $CH_2Cl_2$ (600 mL) and cooled in an ice bath. A solution of 2,4-difluoroaniline (72.6 g) in $CH_2Cl_2$ (300 mL) is added with continued ice bath cooling. After a few minutes, the solution is left to warm to room temperature overnight. The mixture of crystals is concentrated further in vacuo to a paste. The mixture is diluted with hexane (1.8 L) and filtered. The solid is chromatographed on a 1.4 kg column of silica gel with $CH_2Cl_2$. The eluate is concentrated in vacuo to a paste which is diluted with hexane (1.5 L). The mixture is filtered to afford a Compound 6.

To a solution of Compound 6 (100 mg) in acetonitrile (0.7 mL) is added N,O-bis(trimethylsilyl)acetamide (0.24 mL). The reaction is stirred for 48 hours at ambient temperature under $N_2$ whereupon the reaction is diluted with $CH_2Cl_2$ (5 mL). The mixture is then washed with water (2×2 mL) and the organic portion is dried ($Na_2SO_4$). Evaporation of the volatiles in vacuo provides a residue that is crystallized from isopropyl ether to provide the ethyl ester of 7-chloro-1-(2, 4-difluorophenyl)-6-fluoro-1,4-dihydro-4-oxo-1,8-napthyridine-3-carboxylic acid (Compound 7).

EXAMPLE 16

Synthesis of the ethyl ester of 1-(tert-butyl)-7-chloro-6-fluoro-1,4-dihydro-4-oxo-1,8-napthyridine-3-carboxylic acid. This compound, and its analogs, are useful intermediates for making antimicrobial quinolones, using known chemistry.

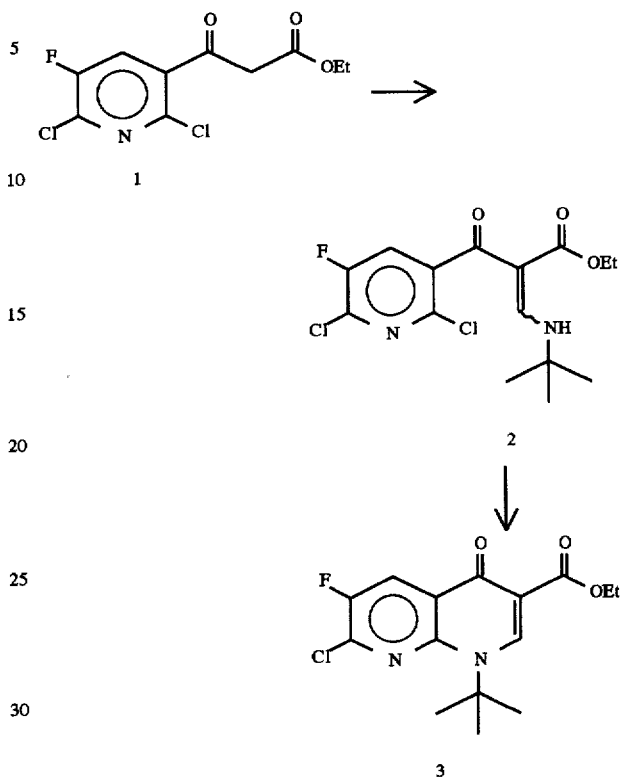

Compound 1 is prepared according to the same process as Compound 5 in Example 15 above.

To a solution of Compound 1 (1.4 g) in triethylorthoformate (1.36 mL) is added acetic anhydride (4.33 mL). The mixture is fitted with a Dean-Stark trap and stirred at 130° C. for 1.5 hours under $N_2$. The volatiles removed in vacuo and the residue is dissolved in $CH_2Cl_2$ (8.2 mL). The solution obtained is cooled to 0° C. and tert-butylamine is added (0.72 mL). The reaction is stirred at 0° C. for 5 minutes under $N_2$, allowed to warm to ambient temperature and stirred for 1 hour. The volatiles are removed in vacuo and the residue is dissolved in $CH_2Cl_2$. A small amount of silica gel is added to the solution and the solvent is removed in vacuo. The solid mixture is then applied to a column of silica gel and eluted with $CH_2Cl_2$. The appropriate fractions are evaporated in vacuo to provide Compound 2.

To a solution of Compound 2 (100 mg) in $CH_3CN$ (0.6 mL) is added N,O-bis(trimethylsilyl)acetamide (0.2 mL). The mixture is stirred for 48 hours at ambient temperature under $N_2$. The mixture is diluted with $CH_2Cl_2$ (5 mL) and washed with water (3×2 mL). The organic portion is dried ($Na_2SO_4$) and the volatiles are removed in vacuo. The residue obtained is crystallized from isopropylether to obtain the ethyl ester of 1-(tert-butyl)-7-chloro-6-fluoro-1,4-dihydro-4-oxo-1,8-napthyridine-3-carboxylic acid (Compound 3).

The following compounds are made according to Examples 15 and 16 with substantially similar results.

61
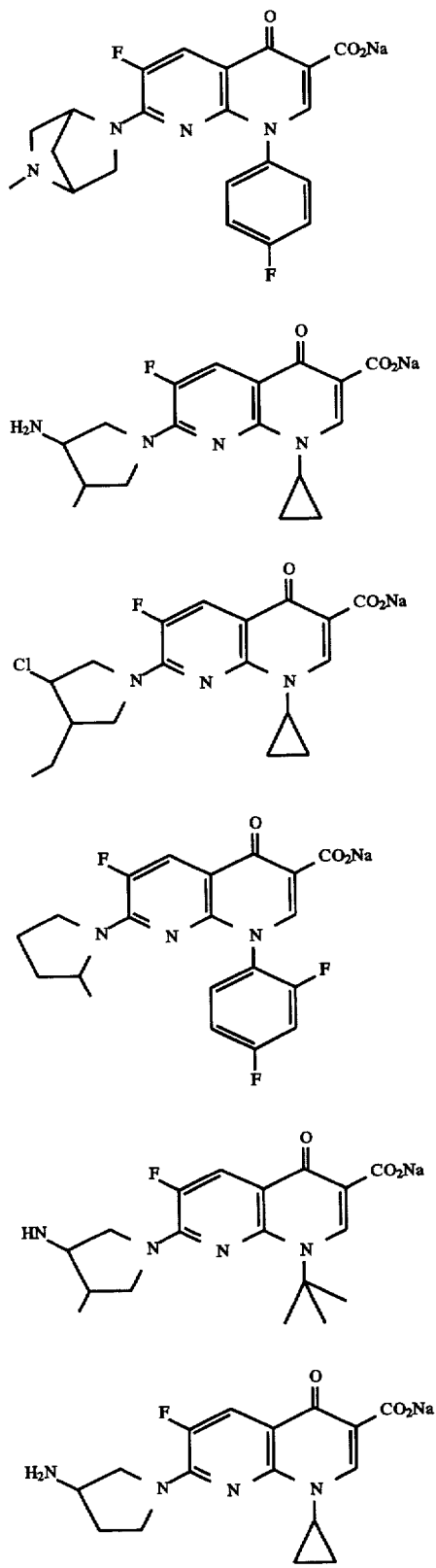
62
-continued
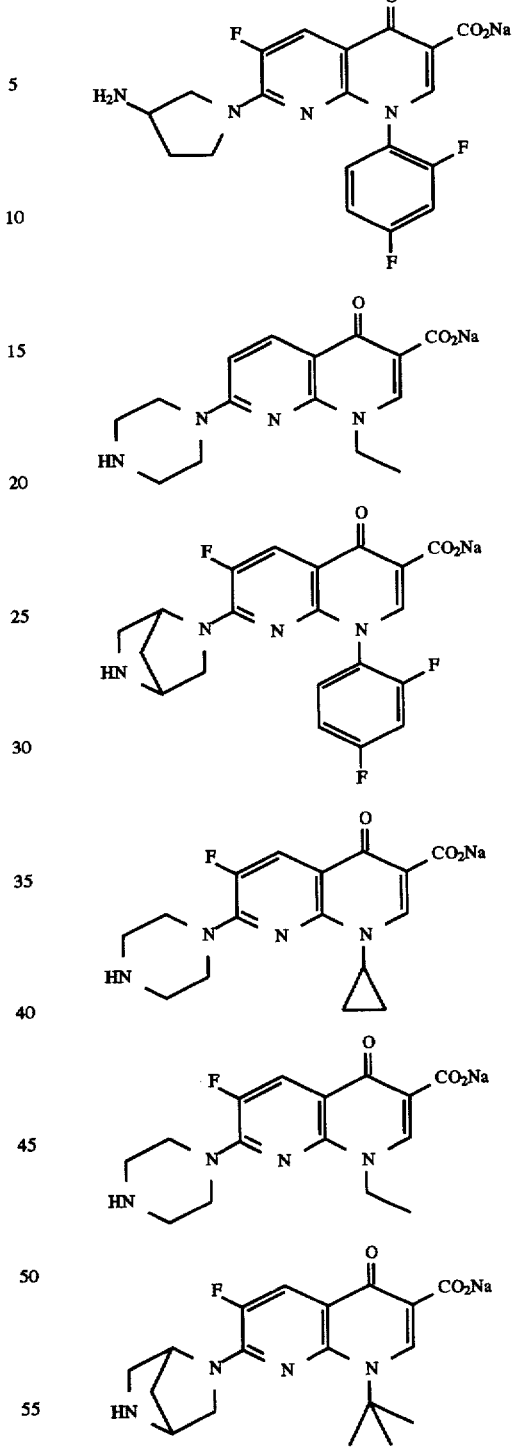
EXAMPLE 17
Synthesis of [5R-[5α,6α(R*)]]-3-[[[4-(3-Carboxy-1-cyclopropyl-6-fluoro-1,4-dihydro-4-oxo-7-quinolinyl)-1-piperazinyl]carbonyloxy]methyl]-6-(1-hydroxyethyl)-7-oxo-4-thia-1-azabicyclo[3.2.0]hept-2-ene-2-carboxylic acid.

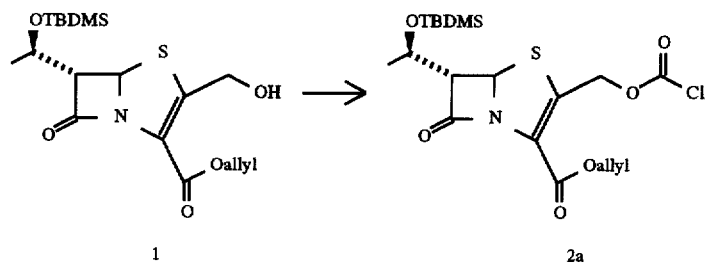
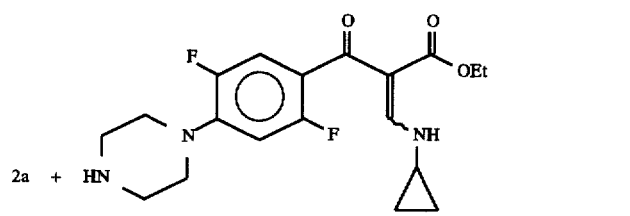
↓
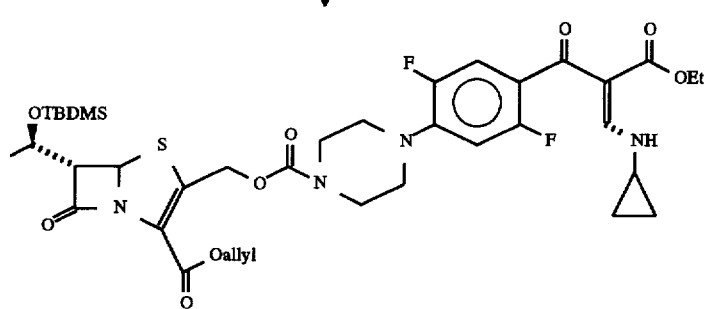
↓
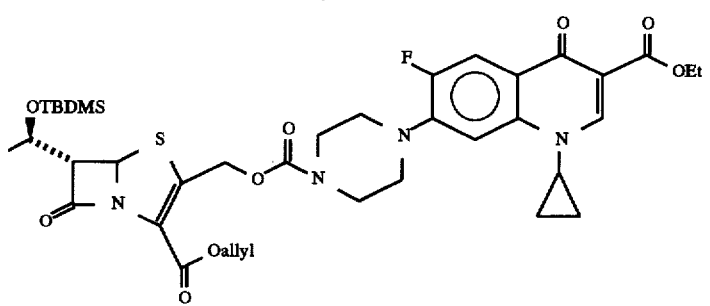
↓

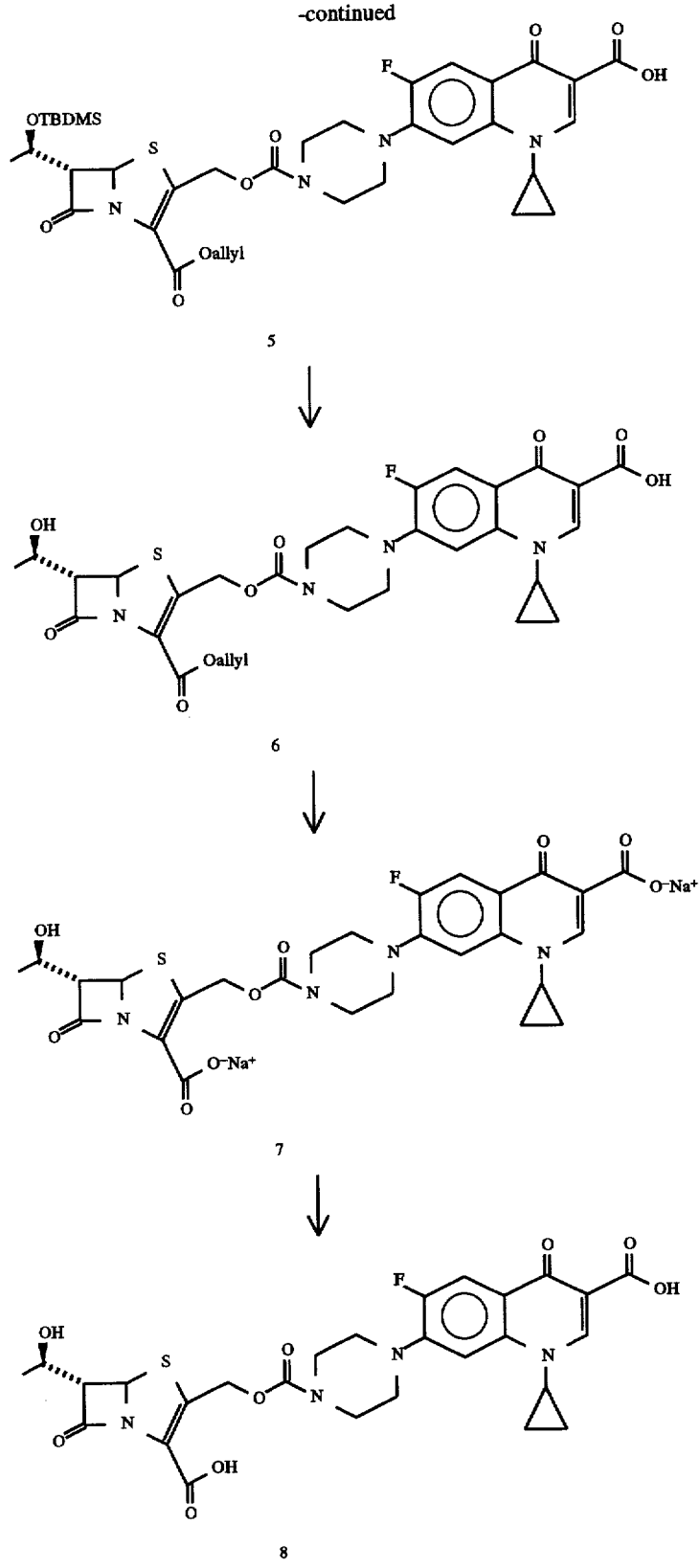
A solution of Compound 2b (2.1 g) in CH$_2$Cl$_2$ (50 mL), prepared in the same manner as Compound 7 in Example 9, is dried (Na$_2$SO$_4$) and the dried solution is transferred to a second vessel, under N$_2$. The solution is cooled (−15° C.) and N,O-bis(trimethylsilyl)acetamide (2.7 mL) is added. The mixture is allowed to stir for 15 minutes under N$_2$ to yield a silylated form of 2b, which is used without further characterization.

In a third vessel, a solution of Compound 1 (2.06 g) in $CH_2Cl_2$ (50 mL) prepared according to U.S. Pat. No. 4,631,150, Battistini et al., issued Dec. 23, 1986 (incorporated by reference herein), is dried ($Na_2SO_4$) and the dried solution is transferred to a fourth vessel, under $N_2$. N,N-diisopropylethylamine (1.05 mL) is added and the solution is stirred for 15 minutes at ambient temperature, under $N_2$, and cooled to −78° C. In a fifth vessel, to cooled (−78° C.) $CH_2Cl_2$ (40 mL,) is added 20% phosgene in toluene (3.45 mL) under $N_2$. The forementioned solution of Compound 1 is added dropwise while maintaining the solution temperature at less than −60° C. The reaction is stirred for 15 minutes and warmed to −15° C. to provide Compound 2a, which is then reacted in situ by dropwise addition of the forementioned solution of Compound 2b, while maintaining the temperature below −15° C. The reaction is stirred at −15° C. under $N_2$ until complete. The reaction mixture is quenched with water (160 mL), warmed to 0° C. and stirred 10 minutes. The organic portion is separated and dried with ($Na_2SO_4$). The volatiles are evaporated in vacuo and the residue is subjected to column chromatography (silica) to give Compound 3.

To a solution of Compound 3 (1.2 g) in $CH_3CN$ (21 mL) is added bis(trimethylsilyl) acetamide (BSA) (1.09 mL). The reaction mixture is stirred under $N_2$ at ambient temperature until complete. The reaction is quenched with water (21 mL), and the resulting slurry is filtered and washed with a mixture of water and $CH_3CN$ (5:1) to provide Compound 4.

To a solution of Compound 4 (1.1 g) in benzene (25 mL) is added bis(tributyltin) oxide (1.43 mL), under $N_2$. The mixture is heated to reflux until completion, whereupon the volatiles are removed in vacuo and the residue obtained is subjected to column chromatography (silica) to provide Compound 5.

To a solution of Compound 5 (0.9 g) in THF (8 mL) and acetic acid (0.62 mL) is added tetra-n-butyl ammonium fluoride (3.21 mL of a 1M solution in THF), under $N_2$. The mixture is stirred at ambient temperature overnight and, upon completion, is diluted with ether (15 mL). The solution is stirred for a half-hour, allowing the product to crystallize. The slurry is filtered through troyfelt and the solid residue is washed with ether to obtain Compound 6.

To a solution of Compound 6 (0.75 g) in $CH_2Cl_2$ (45 mL) is added tetrakis(triphenylphosphine)palladium (0) (135 mg), under $N_2$. The mixture is cooled (−10 to −5° C.) and a cooled solution (<−10° C.) of sodium ethylhexanoate (389 mg) in THF (22 mL) is added dropwise. The mixture is stirred for approximately 30 minutes, whereupon the resulting slurry is filtered and washed successively with $CH_2Cl_2$ and acetone, to obtain Compound 7.

To a solution of Compound 7 (0.55 g) in absolute ethanol (77 mL) is added highly acidic ion-exchange resin (1.1 g, Amberlite IR-120-plus), under $N_2$. The mixture is stirred at ambient temperature for approximately 5 hours, whereupon it is filtered through a sintered glass filtration funnel to remove the resin. The filtrate is reduced in vacuo to approximately one third of its volume, whereupon water (27 mL) is added. The mixture is stirred for a few minutes and then filtered. The solid obtained is washed with water and dried in vacuo overnight to obtain [5R-[5α,6α(R*)]]-3-[[[4-(3-Carboxy-1-cyclopropyl-6-fluoro-1,4-dihydro-4-oxo-7-quinolinyl)-1-piperazinyl]carbonyloxy]methyl]-6-(1-hydroxyethyl)-7-oxo-4-thia-1-azabicyclo[3.2.0]hept-2-ene-2-carboxylic acid (Compound 8).

EXAMPLE 18

Synthesis of [5R-[5α,6α(R*)]]-3-[[[4-(3-Carboxy-1-cyclopropyl-6-fluoro-1,4-dihydro-4-oxo-7-quinolinyl)-1-piperazinyl]carbonyloxy]methyl]-6-(1-hydroxyethyl)-7-oxo-4-thia-1-azabicyclo[3.2.0]hept-2-ene-2-carboxylic acid.

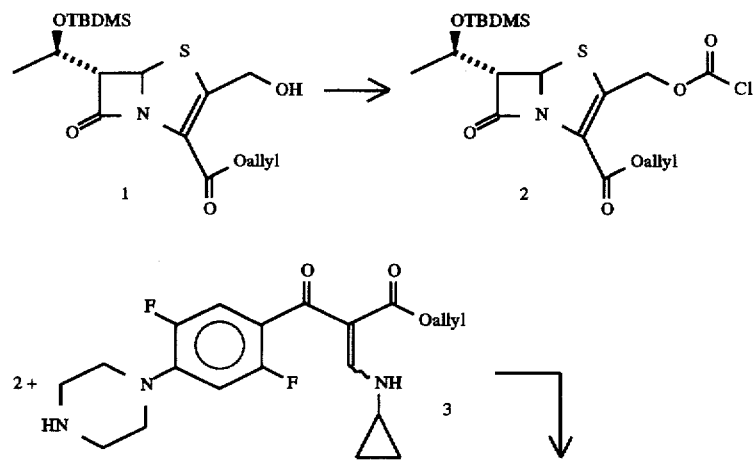

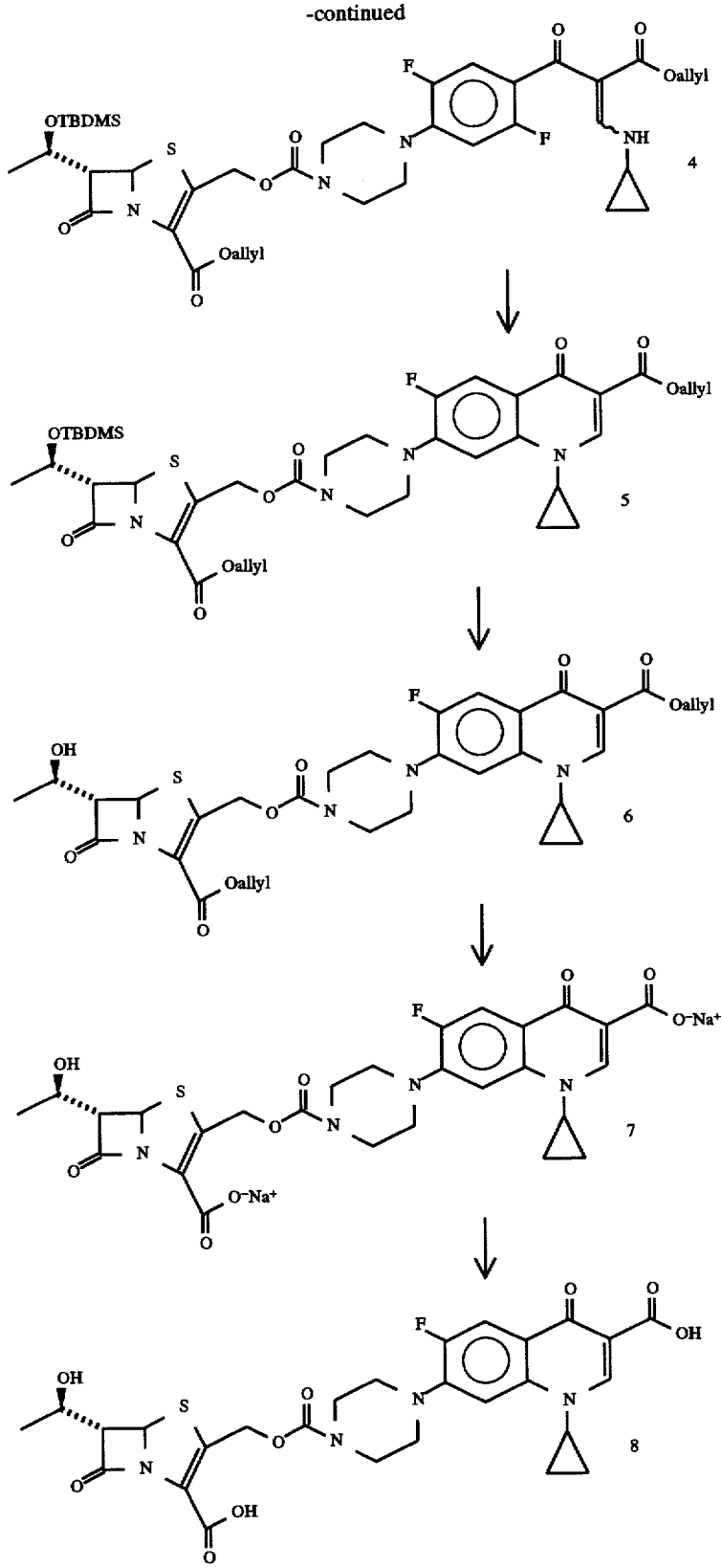
Compound 3 (2.2 g), prepared in the same manner as Compound 5 in Example 11, is dissolved in CH$_2$Cl$_2$ (55 mL) and activated 4A molecular sieves (500 mg) are added under N$_2$. After stirring for 30 minutes at room temperature, the solution is transferred via canula to a second vessel. The solution is cooled (−15° C.) and N,O-bis(trimethylsilyl)

acetamide (2.75 mL) is added under $N_2$. The mixture is allowed to stir for 15 minutes under $N_2$.

Concurrent with this procedure, Compound 1 (2.09 g), prepared according to U.S. Pat. No. 4,631,150, Battistini et al., issued Dec. 23, 1986 (incorporated by reference herein), is dissolved in $CH_2Cl_2$ (55 mL) in a third vessel and activated 4A molecular sieves (500 mg) are added, under $N_2$. After stirring for 30 minutes, the solution is transferred via canula to a fourth vessel and N,N-diisopropylethylamine (1.08 mL) is added under $N_2$. The solution is stirred for 15 minutes at ambient temperature and cooled to –78° C. In a fifth vessel, to cooled (–78° C.) $CH_2Cl_2$ (45 mL) is added 20% phosgene in toluene (3.5 mL) under $N_2$. The forementioned solution of Compound 2 is added dropwise while maintaining the solution temperature at less than –60° C. The reaction is stirred for 15 minutes and warmed to –15° C. to provide Compound 2 which is then reacted in situ by dropwise addition of the forementioned solution of Compound 3, while maintaining the temperature below –15° C. The reaction is stirred at –15° C. under $N_2$ until complete. The reaction mixture is quenched with water (30 mL), warmed to 0° C. and stirred 10 minutes. The organic portion is separated and dried with ($Na_2SO_4$). The volatiles are evaporated in vacuo and the residue is subjected to column chromatography (silica) to give Compound 4.

To a solution of Compound 4 (2.1 g) in $CH_3CN$ (30 mL) is added BSA (1.89 mL). The reaction mixture is stirred under $N_2$ at ambient temperature until complete. The reaction is quenched with water (30 mL), and the resulting slurry is filtered and washed with a mixture of water and $CH_3CN$ (5:1) giving Compound 5.

To a solution of Compound 5 (1.8 g) in THF (16 mL) and acetic acid (1.25 mL) is added tetra-n-butyl ammonium fluoride (6.1 mL of a 1M solution in THF), under $N_2$. The mixture is stirred at ambient temperature overnight and, upon completion, is diluted with ether (25 mL). The solution is stirred for a half-hour, allowing the product to crystallize. The slurry is filtered through troyfelt and the solid residue is washed with ether to obtain Compound 6.

To a solution of Compound 6 (1.4 g) in $CH_2Cl_2$ (85 mL) is added tetrakis(triphenylphosphine)palladium (0) (240 mg), under $N_2$. The mixture is cooled (–10 to –5° C.) and a cooled solution (<–10° C.) of sodium ethylhexanoate (681 mg) in THF (42 mL) is added dropwise. The mixture is stirred for approximately 30 minutes, whereupon the resulting slurry is filtered and washed successively with $CH_2Cl_2$ and acetone, to obtain Compound 7.

To a solution of Compound 7 (0.9 g) in absolute ethanol (126 mL) is added highly acidic ion-exchange resin (1.8 g, Amberlite IR-120-plus), under $N_2$. The mixture is stirred at ambient temperature for approximately 5 hours, whereupon it is filtered through a sintered glass filtration funnel to remove the resin. The filtrate is reduced in vacuo to approximately one third of its volume, whereupon water (45 mL) is added. The mixture is stirred for a few minutes and then filtered. The solid obtained is washed with water and dried in vacuo overnight to obtain [5R-[5α, 6α(R*)]]-3-[[[4-(3-Carboxy-1-cyclopropyl-6-fluoro-1,4-dihydro-4-oxo-7-quinolinyl)-1-piperazinyl]carbonyloxy]methyl]-6-(1-hydroxyethyl)-7-oxo-4-thia-1-azabicyclo[3.2.0]hept-2-ene-2-carboxylic acid (Compound 8).

EXAMPLE 19

Synthesis of [4R-[4α,5β,6β(R*)]]-3-[[[4-(3-Carboxy-1-cyclopropyl-6-fluoro-1,4-dihydro-4-oxo-7-quinolinyl)-1-piperazinyl]carbonyloxy]methyl]-6-(1-hydroxyethyl)-7-oxo-4-thia-1-azabicyclo[3.2.0]hept-2-ene-2-carboxylic Acid, Disodium salt.

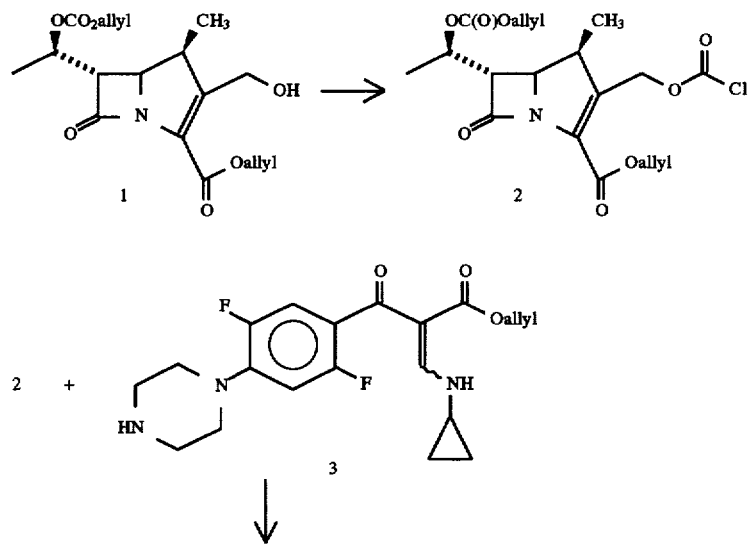

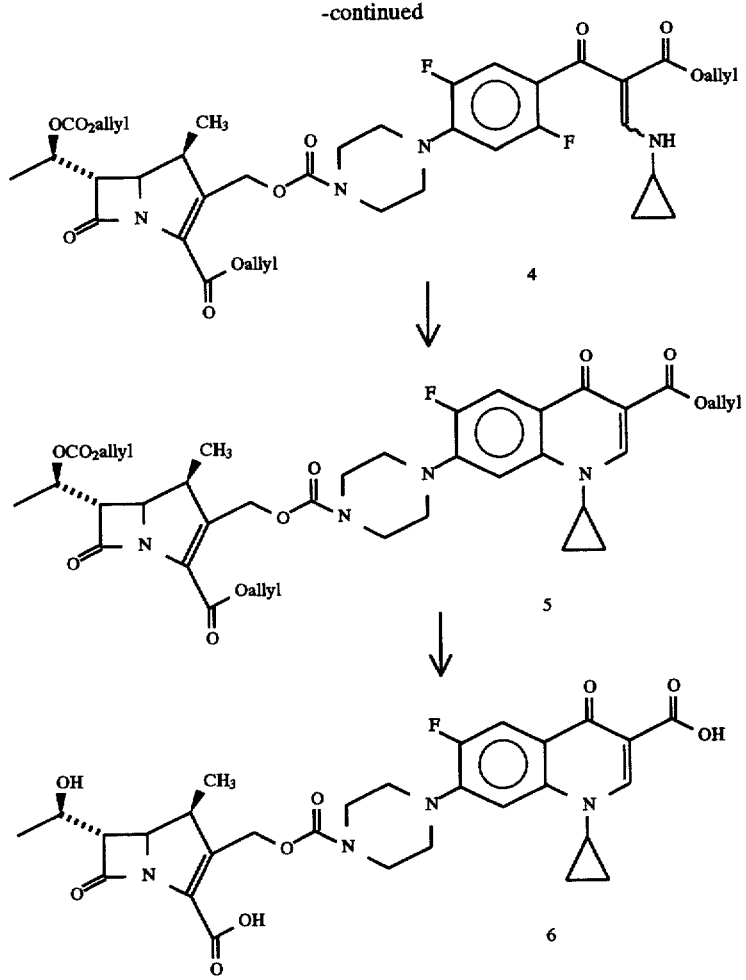

Compound 3 (1.2 g), prepared in the same manner as Compound 5 in Example 11, is dissolved in CH$_2$Cl$_2$ (30 mL) and dried, under N$_2$, with activated molecular sieves. The solution is transferred to a second vessel and cooled (−15° C.). N,O-bis(trimethylsilyl)acetamide (1.5 mL) is added and the mixture is allowed to stir for 15 minutes under N$_2$.

In a third vessel, Compound 1 (1.12 g), prepared according to Schmitt et al., 41 *J. Antibiot.* 780–787 (1988) (incorporated by reference herein), is dissolved in CH$_2$Cl$_2$ (30 mL) and dried, under N$_2$, with activated molecular sieves. The solution is transferred, under N$_2$, to a fourth vessel and N,N-diisopropylethylamine (0.58 mL) is added. The solution is stirred for 15 minutes at ambient temperature, under N$_2$, and cooled to −78° C. In a fifth vessel, to cooled (−78° C.) CH$_2$Cl$_2$ (25 mL) is added 20% phosgene in toluene (1.86 mL) under N$_2$. The forementioned solution of Compound 1 is added dropwise while maintaining the solution temperature at less than −60° C. The reaction is stirred for 15 minutes and warmed to −15° C. to provide Compound 2 which is then reacted in situ by dropwise addition of the forementioned solution of Compound 3, while maintaining the temperature below −15° C. The reaction is stirred at −15° C. under N$_2$ until complete. The reaction mixture is quenched with water (90 mL), warmed to 0° C. and stirred 10 minutes. The organic portion is separated and dried with (Na$_2$SO$_4$). The volatiles are evaporated in vacuo and the residue is subjected to column chromatography (silica) to give Compound 4.

To a solution of Compound 4 (2.15 g) in CH$_3$CN (40 mL) is added N,O-bis(trimethylsilyl)acetamide (2.04 mL). The reaction mixture is stirred under N$_2$ at ambient temperature until complete. The reaction is quenched with water (10 mL), and the resulting slurry is filtered and washed with a mixture of water and CH$_3$CN (5:1) giving Compound 5.

To a cooled (0° C.) Solution of Compound 5 (1.9 g) in CH$_2$Cl$_2$ (75 mL) is added bis(triphenylphosphine) palladium-dichloride (78 mg), followed by water (3.5 mL). To this solution is added tributyltin hydride (4 mL) in one portion. The mixture is stirred at 0° C. for 2 hours, whereupon sodium ethylhexanoate (715 mg) is added. The mixture is stirred for 20 minutes and the precipitate is partitioned between CH$_2$Cl$_2$ (350 mL) and water (450 mL). The aqueous phase is separated and lyophilized to provide a crude residue which is triturated with acetone (450 mL) to provide a solid that is subjected to column chromatography (reverse-phase silica) to provide [4R-[4α,5β,6β(R*)]]-3-[[[4-(3-Carboxy-1-cyclopropyl-6-fluoro-1,4-dihydro-4-oxo-7-quinolinyl)-1-piperazinyl]carbonyloxy]-methyl]-6-(1-hydroxyethyl)-7-oxo-4-thia-1-azabi-cyclo[3.2.0]hept-2-ene-2-carboxylic Acid, Disodium salt (Compound 6).

EXAMPLE 20

Synthesis of [6R-[6α,7β]]-3-[[[4-(3-Carboxy-1-cyclopropyl-6-fluoro-1,4-dihydro-4-oxo-7-quinolinyl)-1-piperazinyl]carbonyloxy]methyl]-8-oxo-7-[(2- thienylacetyl)amino]-5-thia-1-azabicyclo[4.2.0]oct-2-ene-2-carboxylic Acid, Disodium Salt.
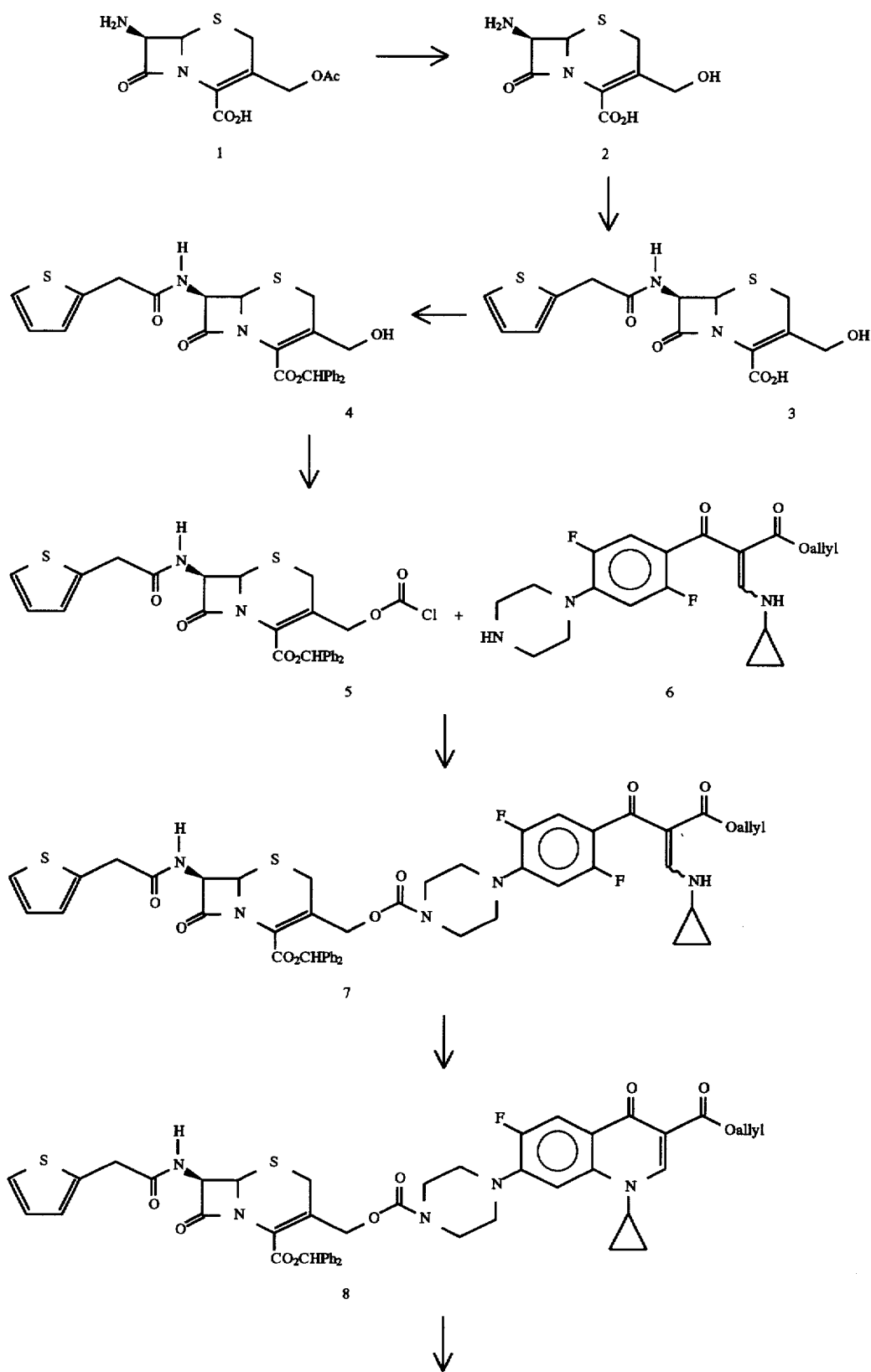

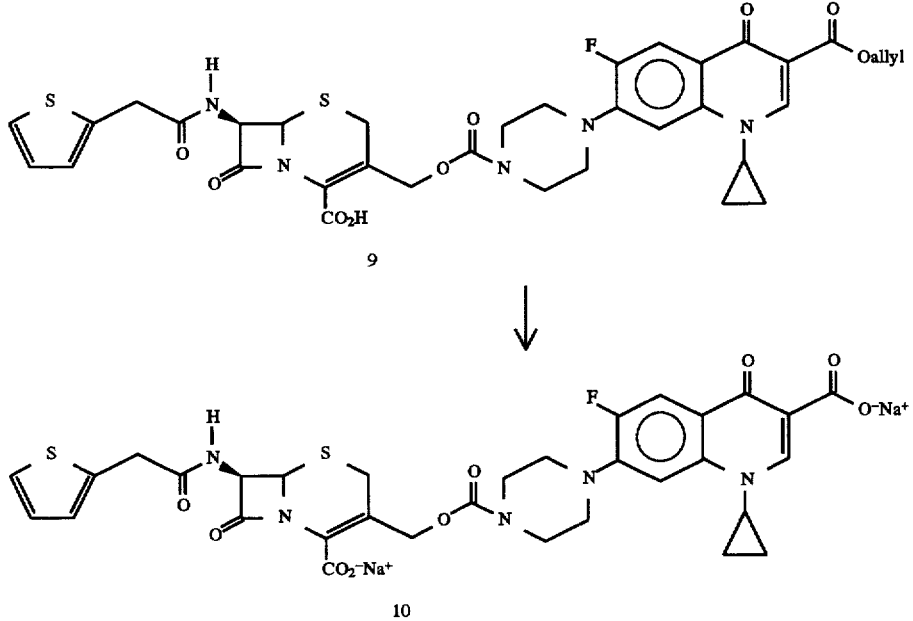

To a cooled (−5° C.) suspension of 7-aminocephalosporanic acid (20 g) (Compound 1) in methanol (38 mL) is added 1N NaOH (73.5 mL) over 30 minutes. Additional 1N NaOH (73.5 mL) is then added over 7 minutes at 2°–5° C. to provide Compound 2. Compound 2 is further reacted in situ by addition of acetone (50 mL) and NaHCO₃ (18.51 g) followed by dropwise addition of 2-thiopheneacetyl chloride (9 mL) over 30 minutes at 0°–5° C., while maintaining a pH of 7 by simultaneous addition of NaHCO₃. The solution is washed with EtOAc (100 mL) and the layers are separated. The aqueous phase is layered with EtOAc (160 mL) and the resulting mixture is acidified at 0° C. with concentrated HCl. The layers are separated and the aqueous phase is extracted with EtOAc (160 mL). The combined EtOAc layers are filtered and the volatiles removed in vacuo to near dryness. The precipitate that results is filtered and dried in in vacuo to provide Compound 3.

To a solution of benzophenone hydrazone (10 g) in CH₂Cl₂ (51 mL) is added a 1% w/v solution of iodine in CH₂Cl₂ (2.05 mL) and 1,1,3,3-tetramethylguanidine (6.43 g). 3-Chloroperoxybenzoic acid (9.7 g) is then added in small portions at room temperature. The solvent is removed in vacuo to provide diphenyl diazomethane. A solution of diphenyl diazomethane (8.78 g) in EtOAc (19 mL) is then added to a cooled (5° C.) solution of Compound 3 in THF (150 mL) and EtOAc (150 mL). The mixture is stirred until completion whereupon it is evaporated to dryness in vacuo. THF (64 mL) is added and the insolubles are filtered off The filtrate is evaporated in vacuo until crystals begin to form. EtOAc (64 mL) is then added and the mixture is stirred for 1.5 hours at 0°–5° C. The resulting solid is filtered to provide Compound 4.

Compound 6 (1.9 g), prepared in the same manner as Compound 5 in Example 11, is dissolved in CH₂Cl₂ (58 mL) and activated 4A molecular sieves (500 mg) are added under N₂. After stirring for 30 minutes at room temperature, the solution is transferred via canula to a second vessel. The solution is cooled (−15° C.) and N,O-bis(trimethylsilyl) acetamide (2.37 mL) is added under N₂. The mixture is allowed to stir for 15 minutes under N₂. Concurrent with this procedure, to a cooled (0° C.) solution of Compound 4 (2.52 g) in CH₂Cl₂ (48 mL) in a third vessel is added activated 4A molecular sieves (500 mg), under N₂. After stirring for 30 minutes, the solution is transferred via canula to a fourth vessel and N,N-diisopropylethylamine (0.93 mL) is added under N₂. The solution is stirred for 15 minutes at 0° C. and cooled to −78° C. In a fifth vessel, to cooled (−78° C.) CH₂Cl₂ (40 mL) is added 20% phosgene in toluene (3 mL) under N₂. The forementioned solution of Compound 4 is added dropwise while maintaining the solution temperature at less than −60° C. The reaction is stirred for 15 minutes and warmed to −15° C. to provide Compound 5, which is then reacted in situ by dropwise addition of the forementioned solution of Compound 6, while maintaining the temperature below −15° C. The reaction is stirred at −15° C. under N₂ until complete. The reaction mixture is quenched with water (30 mL), warmed to 0° C. and stirred 10 minutes. The organic portion is separated and dried with (Na₂SO₄). The volatiles are evaporated in vacuo and the residue is subjected to column chromatography (silica) to give Compound 7.

To a solution of Compound 7 (2.9 g) in CH₃CN (55 mL) is added N,O-bis(trimethylsilyl)acetamide (2.27 mL). The reaction mixture is stirred under N₂ at ambient temperature until complete. The reaction is quenched with water (55 mL), and the resulting slurry is filtered and washed with a mixture of water and CH₃CN (5:1) giving Compound 8.

To a cooled (−15° C.) solution of Compound 8 (2.2 g) in anhydrous anisole (22 mL) is added TFA (22 mL), dropwise. The cooling bath is removed and the mixture is stirred for 30 minutes. The volatiles are removed in vacuo and ether (75 mL) is added to the residue. The mixture is stirred under N₂ for 30 minutes and the resulting solid is filtered to obtain Compound 9.

To a solution of Compound 9 (1.6 g) in CH₂Cl₂ (90 mL) is added tetrakis(triphenylphosphine)palladium (0) (246 mg), under N₂. The mixture is cooled (−10 to −5° C.) and a cooled solution (<−10° C.) of sodium ethylhexanoate (708 mg) in THF (45 mL) is added dropwise. The mixture is stirred for approximately 30 minutes, whereupon the resulting slurry is filtered and washed successively with CH₂Cl₂ and acetone, to provide [6R-[6α,7β]]-3-[[[4-(3-Carboxy-1-cyclopropyl-6-fluoro-1,4-dihydro-4-oxo-7-quinolinyl)-1-piperazinyl]-carbonyloxy]-methyl]-8-oxo-7-[(2-thienylacetyl)amino]-5-thia-1-azabicyclo-[4.2.0]oct-2-ene-2-carboxylic Acid, Disodium Salt (Compound 10).

EXAMPLE 21

Synthesis of [6R-[6α,7β]]-3-[[[4-[3-Carboxy-1-(1,1-dimethylethyl)-6-fluoro-1,4-dihydro-4-oxo-1,8-napthyridine-7-yl]-1-piperazinyl]carbonyloxy]methyl]-8-oxo-7-[(2-thienylacetyl)amino]-1-azabicyclo[4.2.0]oct-2-ene-2-carboxylic Acid, Disodium Salt

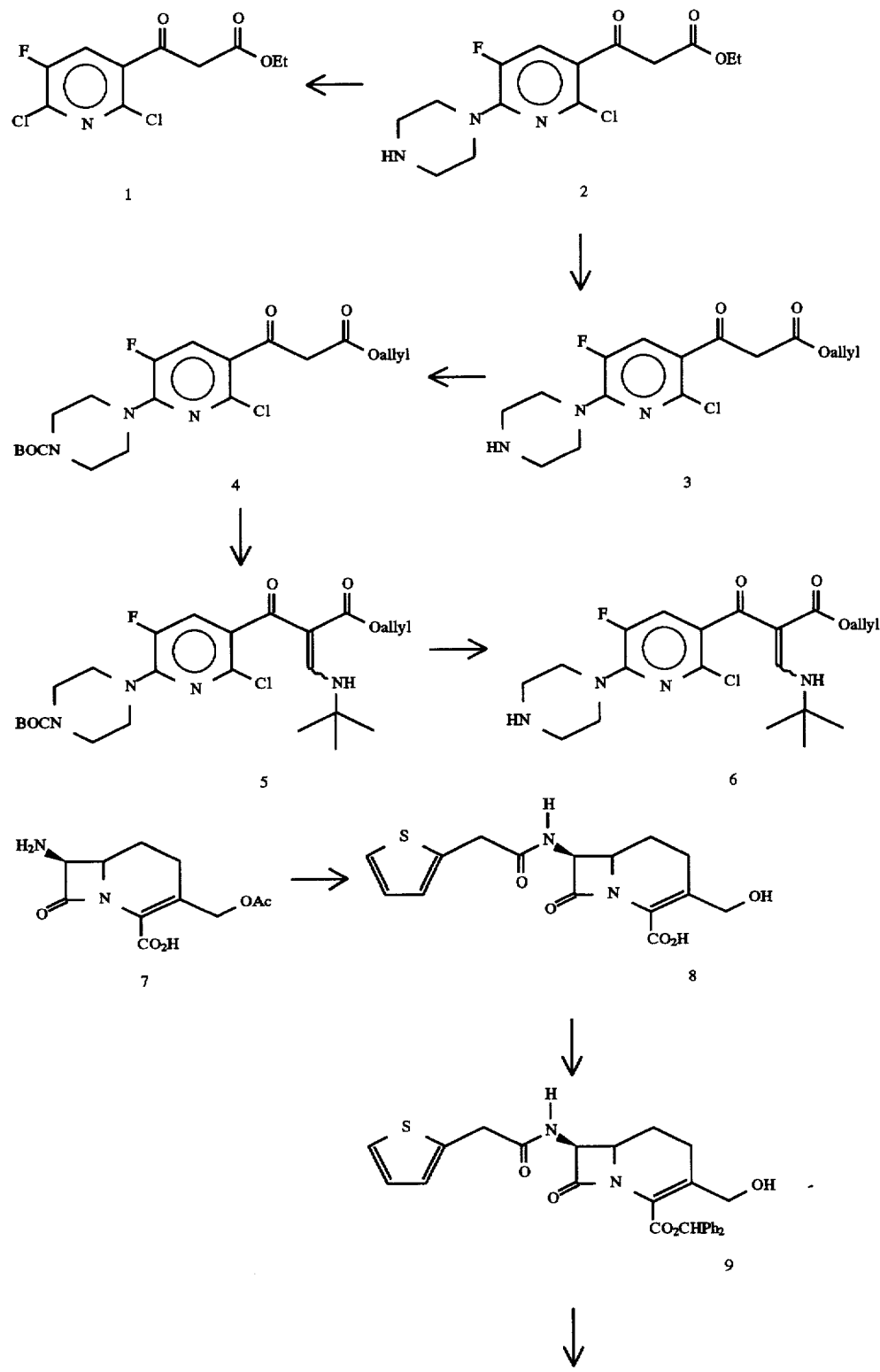

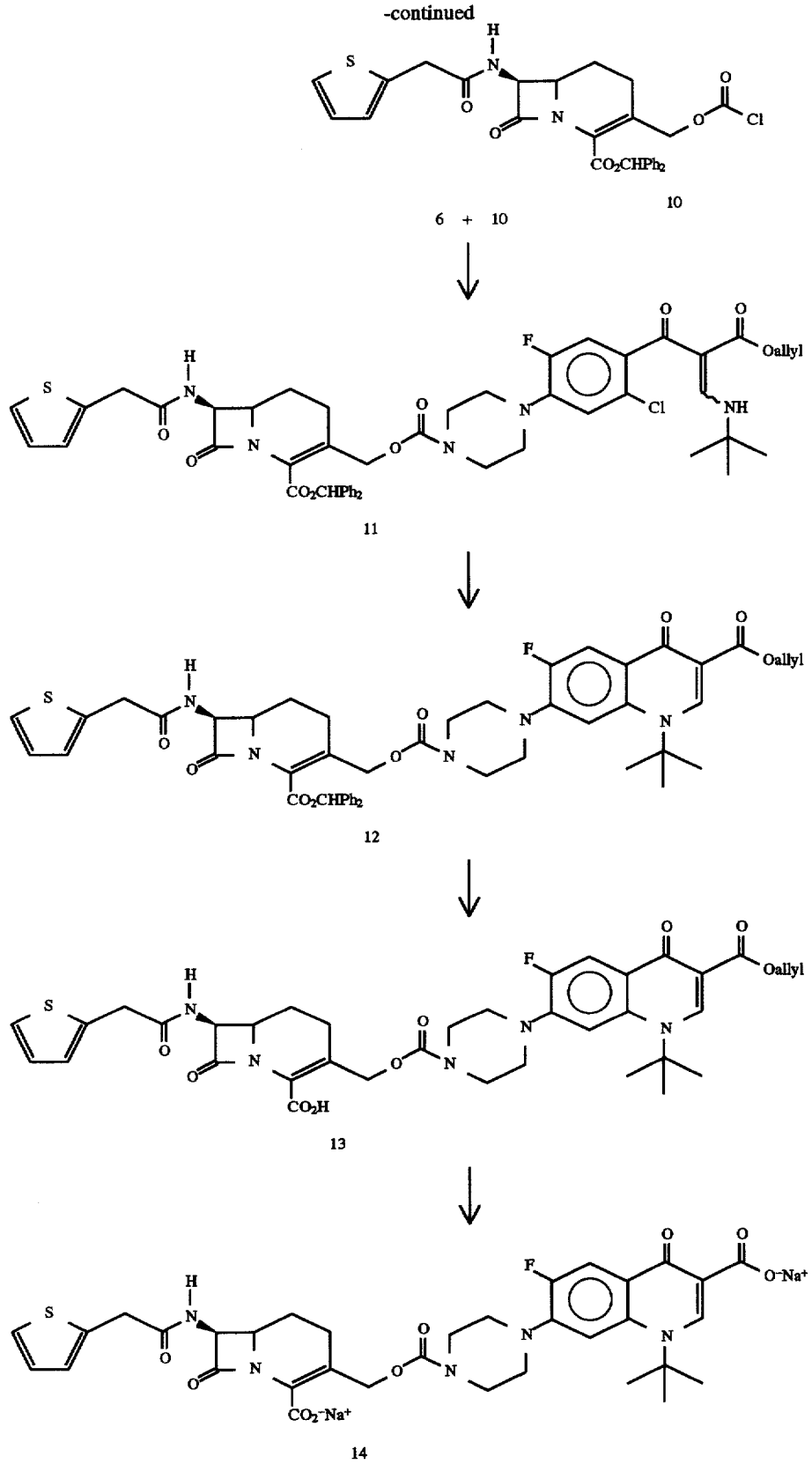
To a solution of Compound 1 (18.0 g) (which is prepared in the same manner as Compound 5 in Example 15 above) in THF (360 mL) is added piperazine (22 g). The mixture is refluxed under $N_2$ until complete and the THF is removed under reduced pressure. The residue is slurried in EtOAc (175 mL), and the excess piperazine is filtered off and rinsed with EtOAc. The EtOAc filtrate is washed with water (2×175 mL) and the combined aqueous layers are extracted with EtOAc (100 mL). The combined EtOAc layers are dried (MgSO$_4$) and treated with activated charcoal. The solvents are evaporated in vacuo and the residue is crystallized from isopropyl ether to give Compound 2.

To a solution of allyl alcohol (84 g) in toluene (120 mL) is added 4-dimethylaminopyridine (2.2 g), under N$_2$. Compound 2 (20 g)is added and the mixture is heated to reflux. Upon completion, the reaction mixture is cooled and saturated ammonium chloride (300 mL) is added, followed by the addition of EtOAc (350 mL). The layers are separated and the EtOAc portion is washed with water (4×100 mL) and brine (2×75 mL), and dried (MgSO$_4$). The solvents are removed in vacuo and the residue is subjected to column chromatography (silica) to provide Compound 3.

To a solution of Compound 4 (21 g) in CHCl$_3$ (400 mL) is added a solution of di-t-butylcarbonate (15 mL) in CHCl$_3$ (75 mL), under N$_2$. The reaction is stirred for 5 minutes under N$_2$ at ambient temperature and evaporated in vacuo. Hexanes are added to the residue to give Compound 4.

To a solution of Compound 3 (17.8 g) in triethylorthoformate (10.9 mL) is added acetic anhydride (34.8 mL). The mixture is fitted with a Dean-Stark trap and stirred at 130° C. for 1.5 hours under N$_2$. The volatiles removed in vacuo and the residue is dissolved in CH$_2$Cl$_2$ (65 mL). The solution obtained is cooled to 0° C. and tert-butylamine is added (5.8 mL). The reaction is stirred at 0° C. for 5 minutes under N$_2$, allowed to warm to ambient temperature and stirred for 1 hour. The volatiles are removed in vacuo and the residue obtained is subjected to column chromatography (silica) to provide Compound 5.

To a cooled solution of Compound 5 (12 g) in anisole (90 mL) at 5°–10° C. is added TFA (90 mL). After stirring for 5 minutes under N$_2$, the ice bath is removed and the reaction is warmed to ambient temperature. After 2 hours, most of the TFA and some of the anisole is removed in vacuo. The residue is slurried in Et$_2$O (300 mL) and filtered. The solid is dissolved in a mixture of CH$_2$Cl$_2$ (100 mL) and saturated NaHCO$_3$ (100 mL) and stirred for 10 min. The CH$_2$Cl$_2$ portion is separated, dried (MgSO$_4$), treated with activated charcoal, and evaporated in vacuo. The residue is crystallized with hexane to give Compound 6.

To a cooled (−5° C.) suspension of (±)-7β[-amino-1-methylenedethiacephalosporanic acid (21.5 g) (Compound 7), prepared as described in R. Guthikonda et al., 96 J. Am. Chem. Soc. 7584 (1974), in methanol (44 mL) is added 1N NaOH (84.53 mL) over 30 minutes. Additional 1N NaOH (84.53 mL) is then added over 8 minutes at 2°–5° C. The mixture is further reacted in situ by addition of acetone (58 mL) and NaHCO$_3$ (21.29 g) followed by dropwise addition of 2-thiopheneacetyl chloride (10.4 mL) over 30 minutes at 0°–5° C., while maintaining a pH of 7 by simultaneous addition of NaHCO$_3$. The solution is washed with EtOAc (110 mL) and the layers are separated. The aqueous phase is layered with EtOAc (170 mL) and the resulting mixture is acidified at 0° C. with concentrated HCl. The layers are separated and the aqueous phase is extracted with EtOAc (170 mL). The combined EtOAc layers are filtered and the volatiles removed in vacuo to near dryness. The precipitate that results is filtered and dried in in vacuo to provide Compound 8.

To a solution of benzophenone hydrazone (11.3 g) in CH$_2$Cl$_2$ (58 mL) is added a 1% w/v solution of iodine in CH$_2$Cl$_2$ (2.3 mL) and 1,1,3,3-tetramethylguanidine (7.29 g). 3-Chloroperoxybenzoic acid (11 g) is then added in small portions at room temperature. The solvent is removed in vacuo to provide diphenyl diazomethane. A solution of diphenyl diazomethane (10 g) in EtOAc (22 mL) is then added to a cooled (5° C.) solution of Compound 8 (9.7 g) in THF (170 mL) and EtOAc (170 mL). The mixture is stirred until completion whereupon it is evaporated to dryness in vacuo. THF (73 mL) is added and the insolubles are filtered off. The filtrate is evaporated in vacuo until crystals begin to form. EtOAc (73 mL) is then added and the mixture is stirred for 1.5 hours at 0°–5° C. The resulting solid is filtered to provide Compound 9.

Compound 6 (7.1 g) is dissolved in CH$_2$Cl$_2$ (160 mL) and activated 4A molecular sieves (1.5 g) are added under N$_2$. After stirring for 30 minutes at room temperature, the solution is transferred via cannula to a second vessel. The solution is cooled (−15° C.) and N,O-bis(trimethylsilyl) acetamide (8.17 mL) is added under N$_2$. The mixture is allowed to stir for 15 minutes under N$_2$. Concurrent with this procedure, Compound 9 (9.1 g) is dissolved in CH$_2$Cl$_2$ (160 mL) in a third vessel and activated 4A molecular sieves (1.5 g) are added, under N$_2$. After stirring for 30 minutes, the solution is transferred via cannula to a fourth vessel and N,N-diisopropylethylamine (3.21 mL) is added under N$_2$. The solution is stirred for 15 minutes at ambient temperature and cooled to −78° C. In a fifth vessel, to cooled (−78° C.) CH$_2$Cl$_2$ (150 mL) is added 20% phosgene in toluene (10.4 mL) under N$_2$. The forementioned solution of Compound 9 is added dropwise while maintaining the solution temperature at less than −60° C. The reaction is stirred for 15 minutes and warmed to −15° C. to provide Compound 10 which is then reacted in situ by dropwise addition of the forementioned solution of Compound 6, while maintaining the temperature below −15° C. The reaction is stirred at −15° C. under N$_2$ until complete. The reaction mixture is quenched with water (150 mL), warmed to 0° C. and stirred 10 minutes. The organic portion is separated and dried (Na$_2$SO$_4$). The volatiles are evaporated in vacuo and the residue is subjected to column chromatography (silica) to give Compound 11.

To a solution of Compound 11 (12.1 g) in CH$_3$CN (140 mL) is added N,O-bis(trimethylsilyl)acetamide (9 mL). The reaction mixture is stirred under N$_2$ at ambient temperature until complete. The reaction is quenched with water (140 mL), and the resulting slurry is filtered and washed with a mixture of water and CH$_3$CN (5:1) giving Compound 12.

To a cooled (−15° C.) solution of Compound 12 (8.6 g) in anhydrous anisole (80 mL) is added TFA (80 mL), dropwise. The cooling bath is removed and the mixture is stirred for 30 minutes. The volatiles are removed in vacuo and ether (200 mL) is added to the residue. The mixture is stirred under N$_2$ for 30 minutes and the resulting solid is filtered to obtain Compound 13.

To a solution of Compound 13 (6.4 g) in CH$_2$Cl$_2$ (340 mL) is added tetrakis(triphenylphosphine)palladium (0) (932 mg), under N$_2$. The mixture is cooled (−10 to −5° C.) and a cooled solution (<−10° C.) of sodium ethylhexanoate (2.68 g) in THF (170 mL) is added dropwise. The mixture is stirred for approximately 30 minutes, whereupon the resulting slurry is filtered and washed successively with CH$_2$Cl$_2$ and acetone to provide [6R-[6α,7β]]-3-[[[4-[3-Carboxy-1-(1,1-dimethylethyl)-6-fluoro-1,4-dihydro-4-oxo-1,8-napthyridine-7-]-1-piperazinyl]-carbonyloxy]methyl]-8-oxo-7-[(2-thienylacetyl)amino]-1-azabicyclo[4.2.0]oct-2-ene-2-carboxylic Acid, Disodium Salt (Compound 14).

The following compounds are made according to Examples 17–21, with substantially similar results.
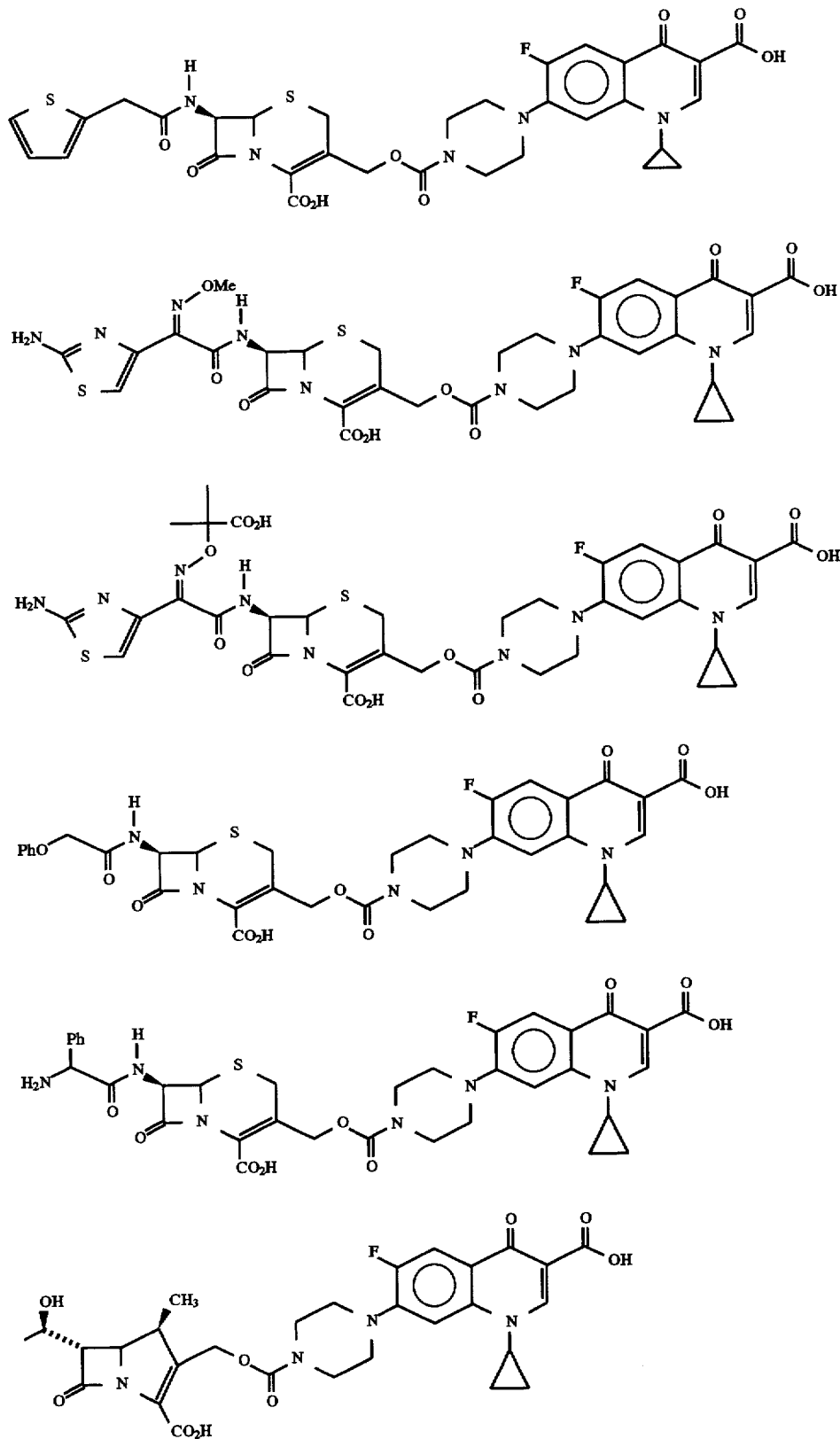

-continued
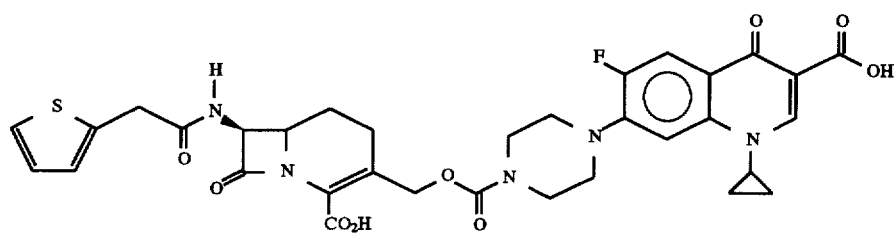
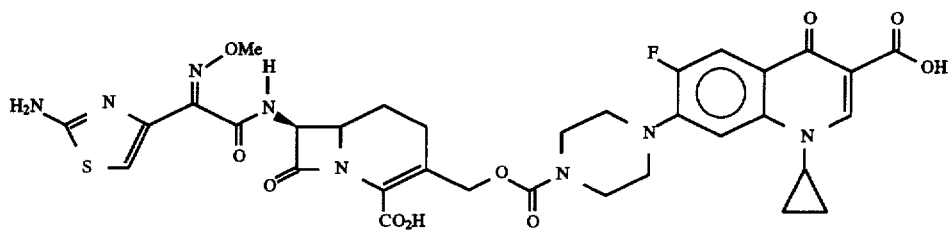
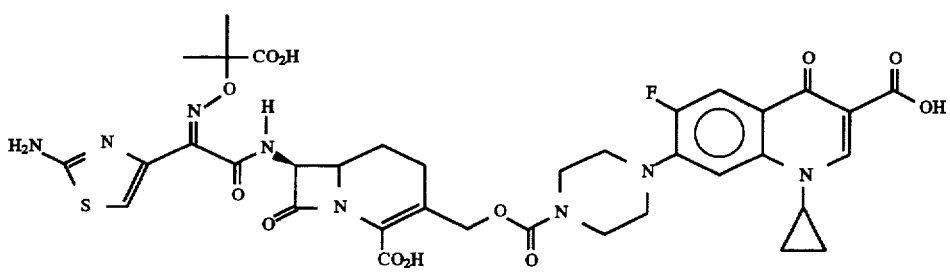
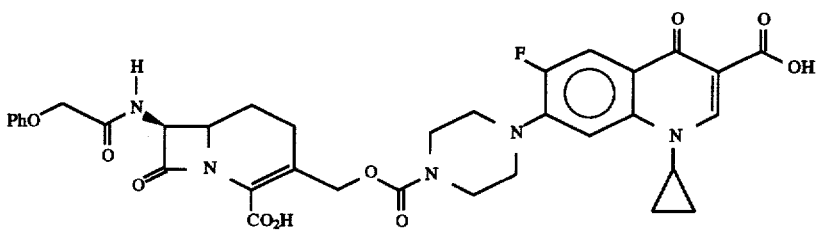
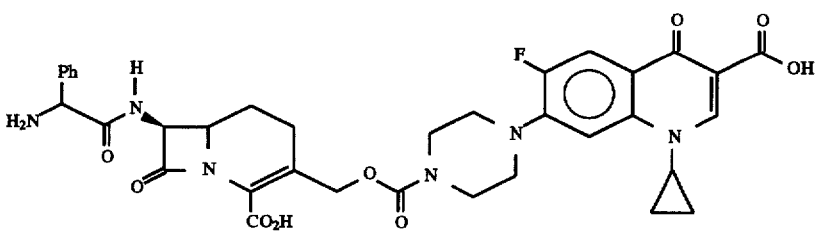
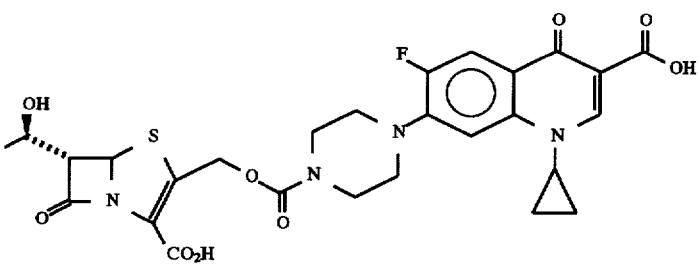

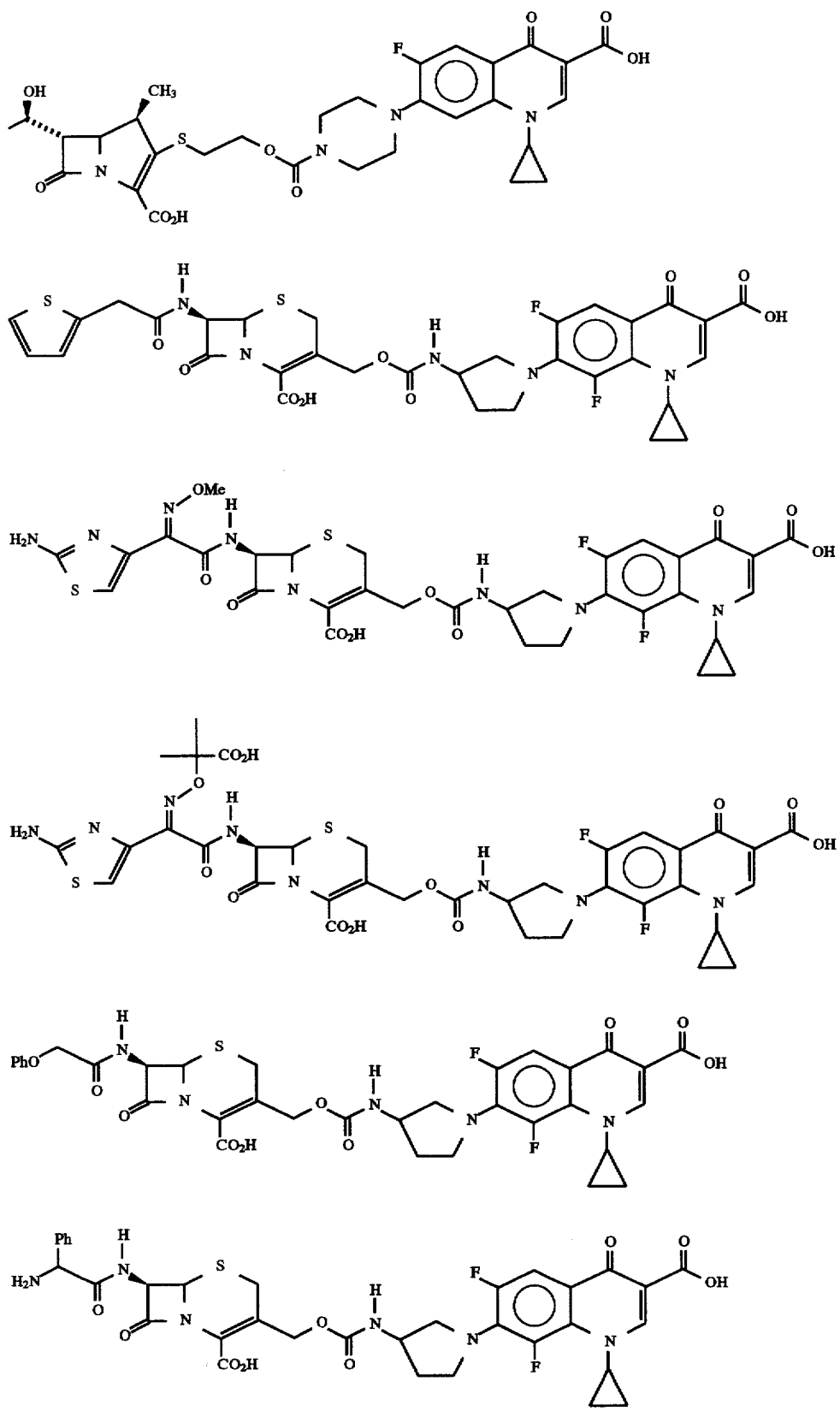

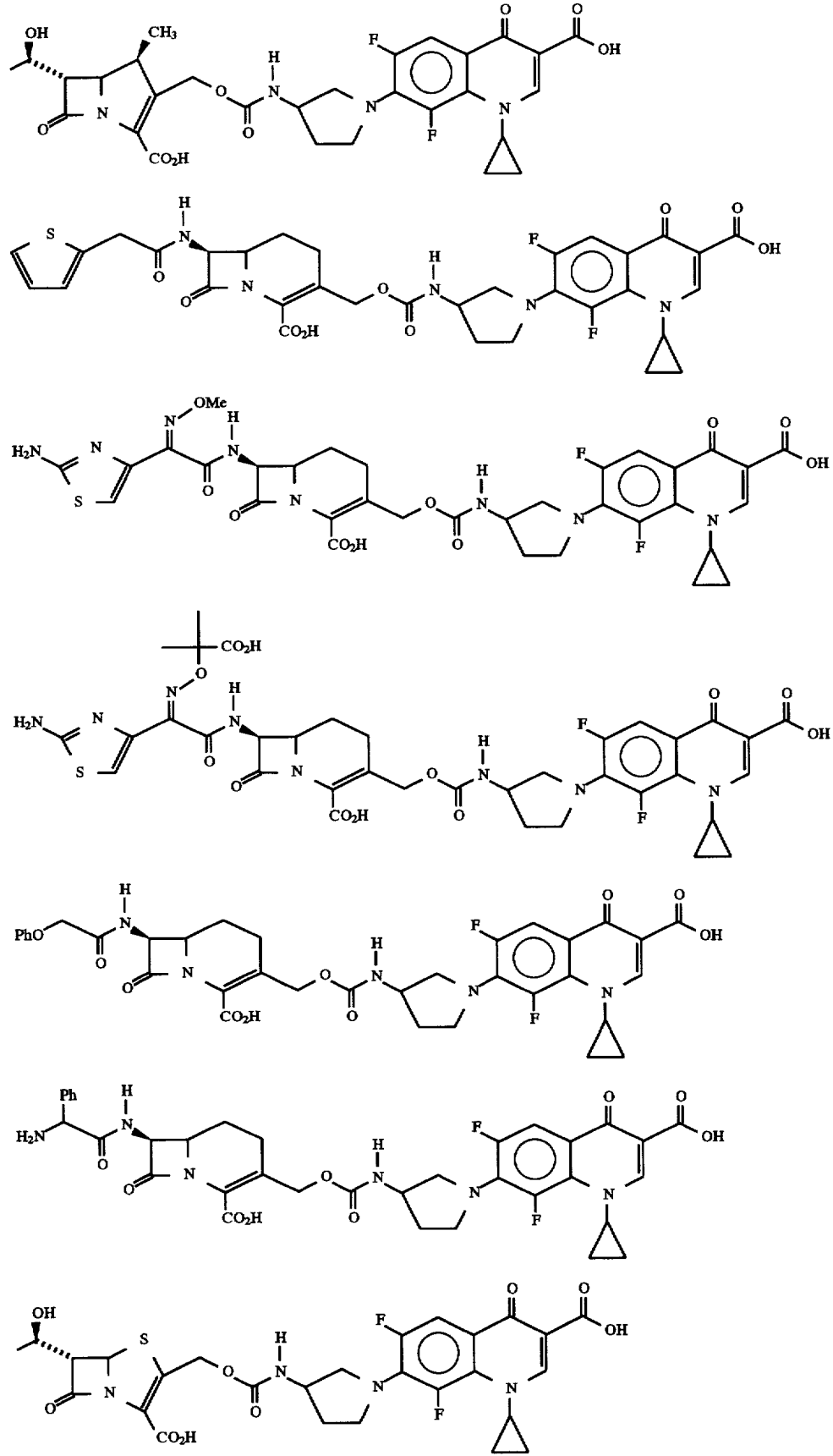

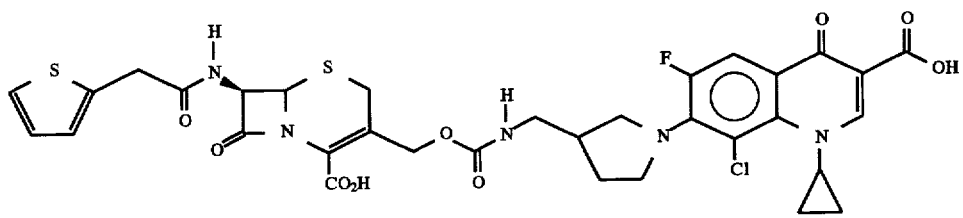
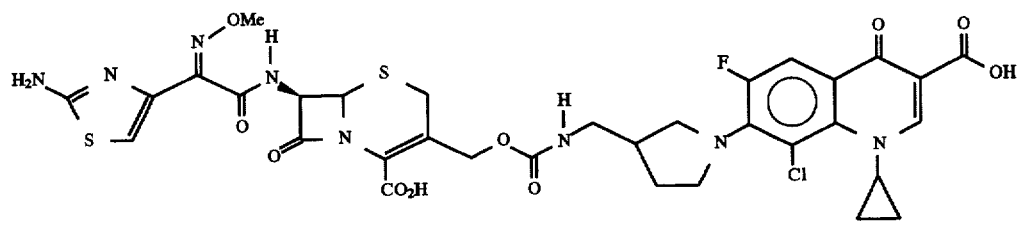
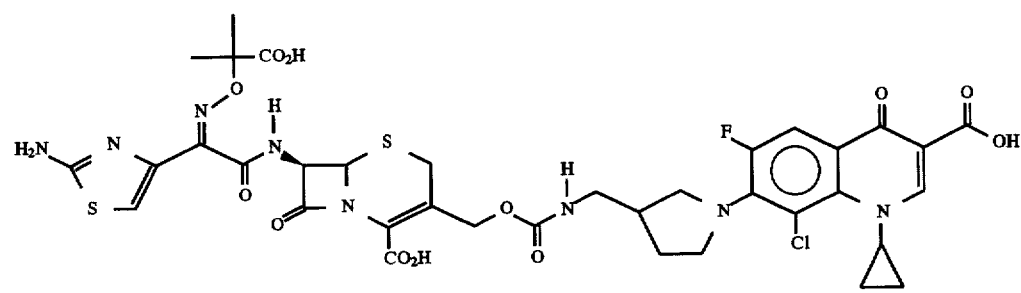
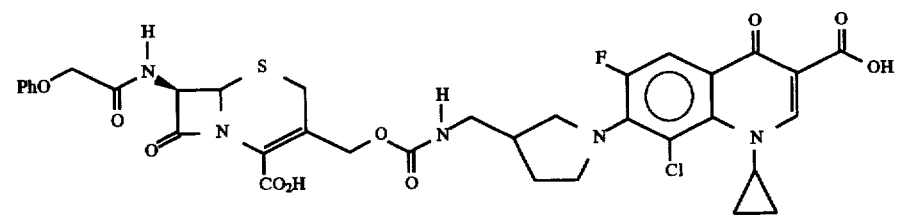
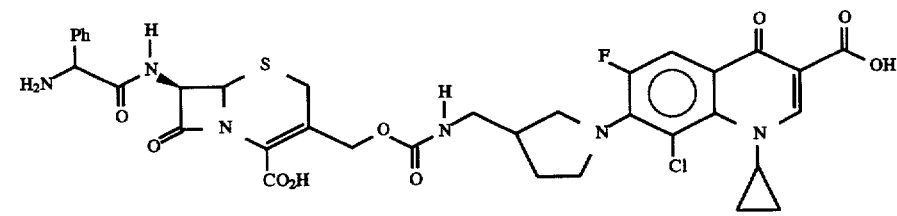
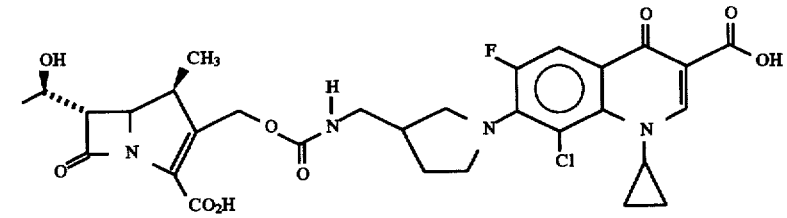
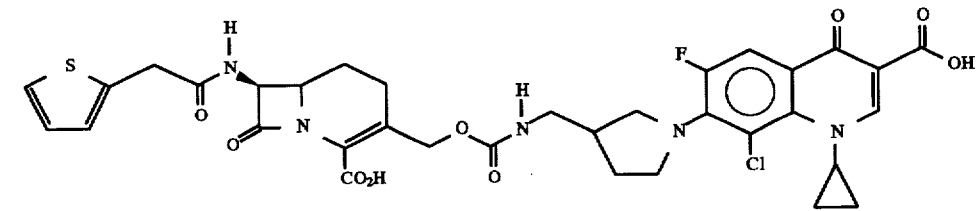

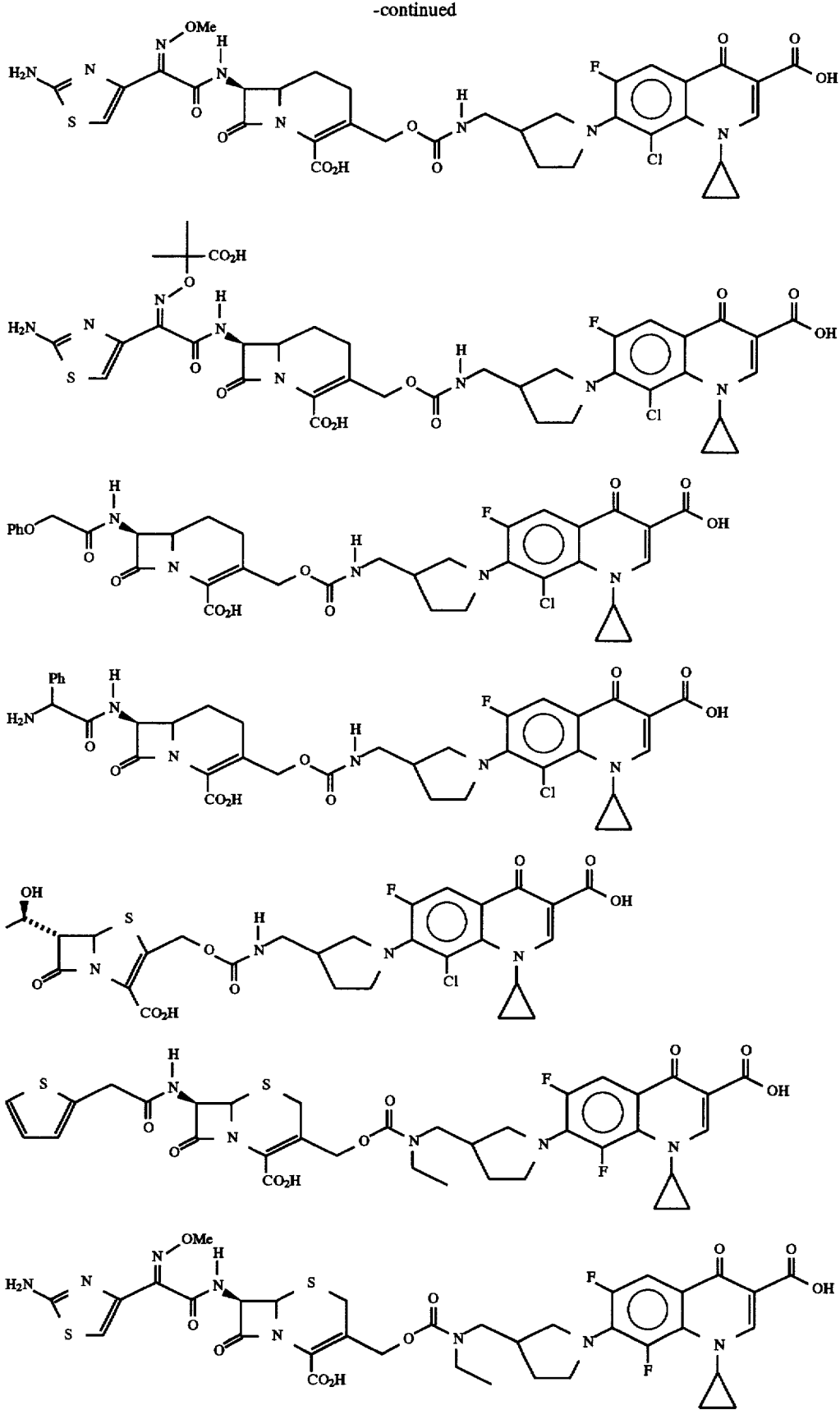

-continued
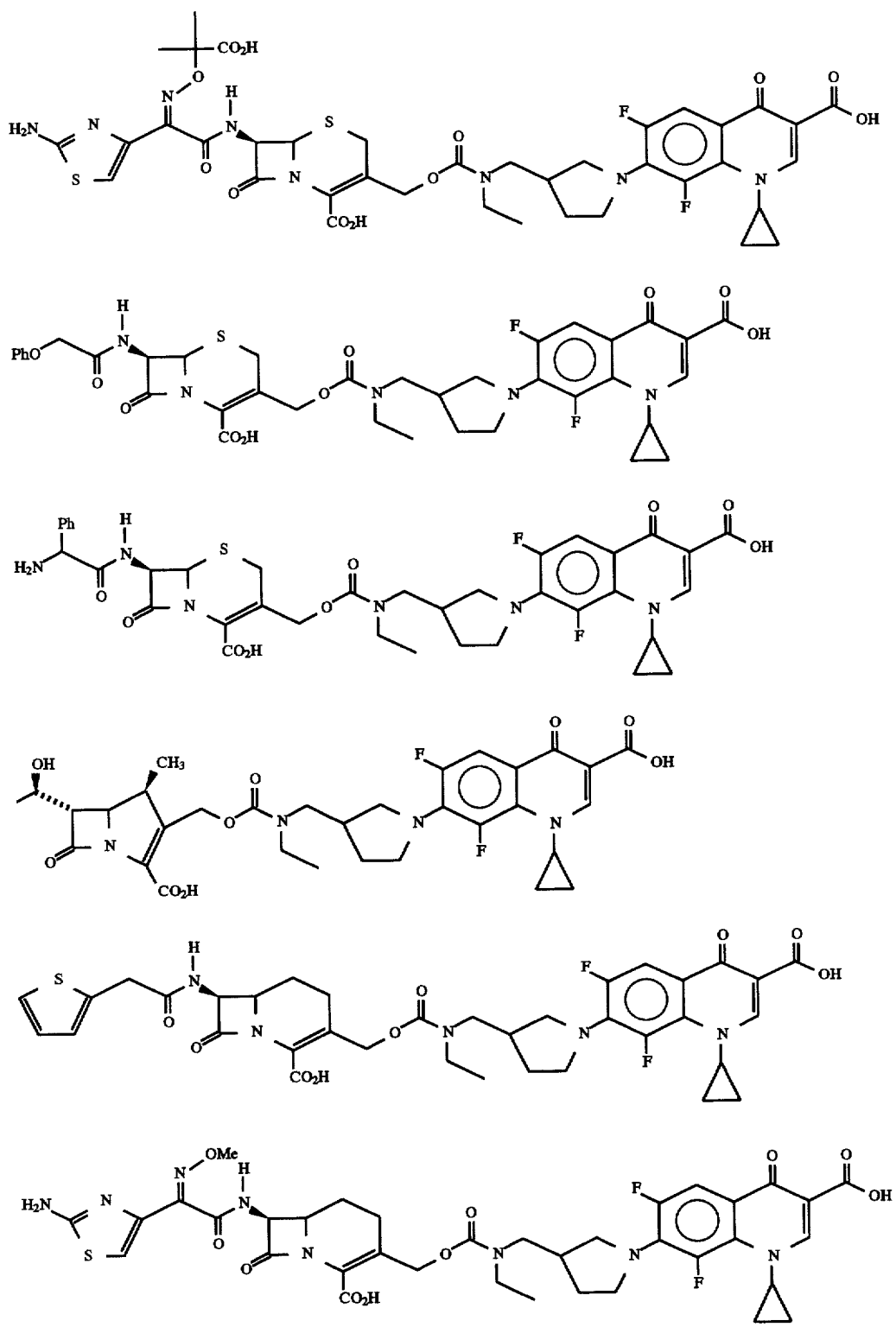

-continued
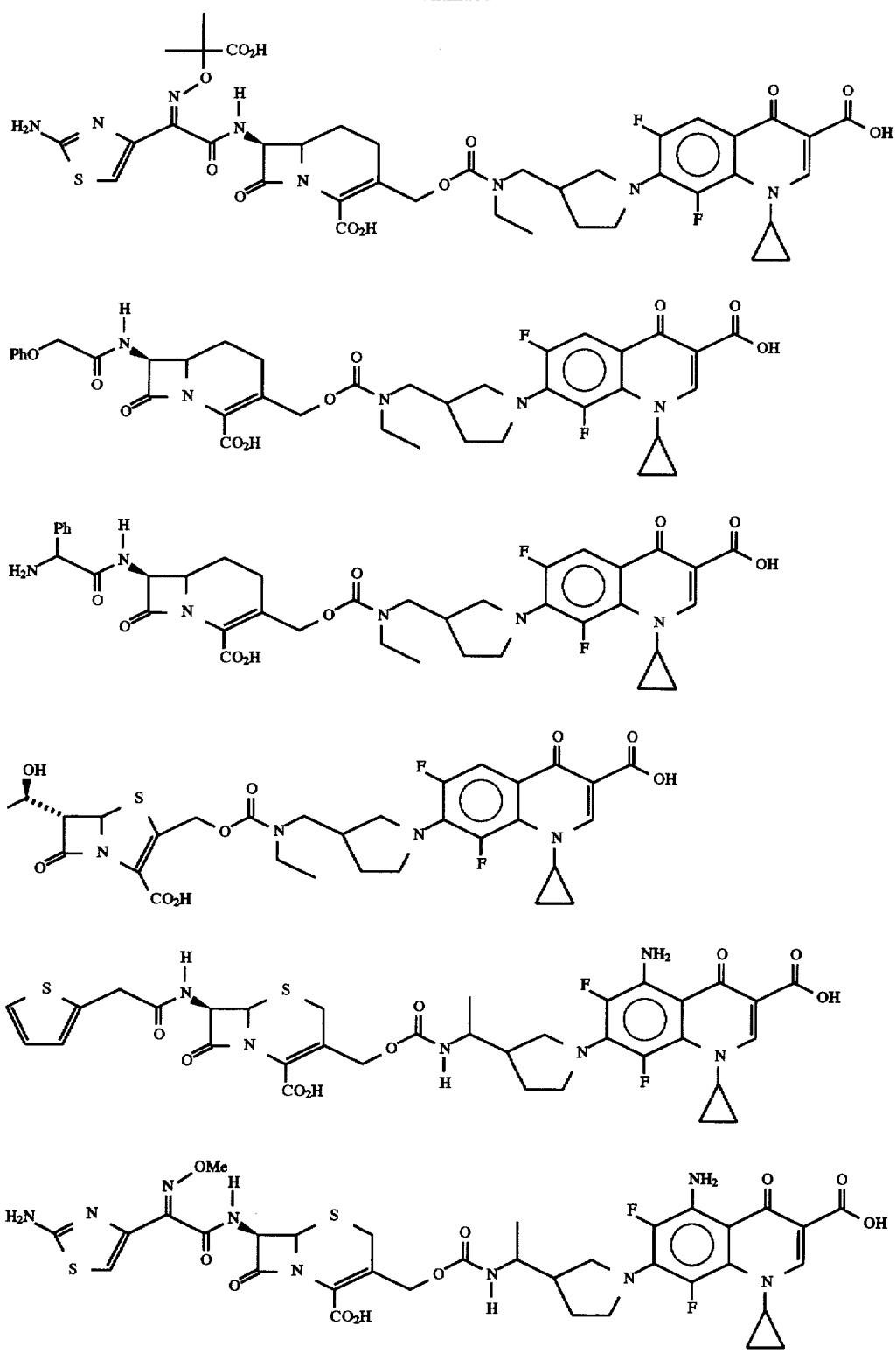

-continued
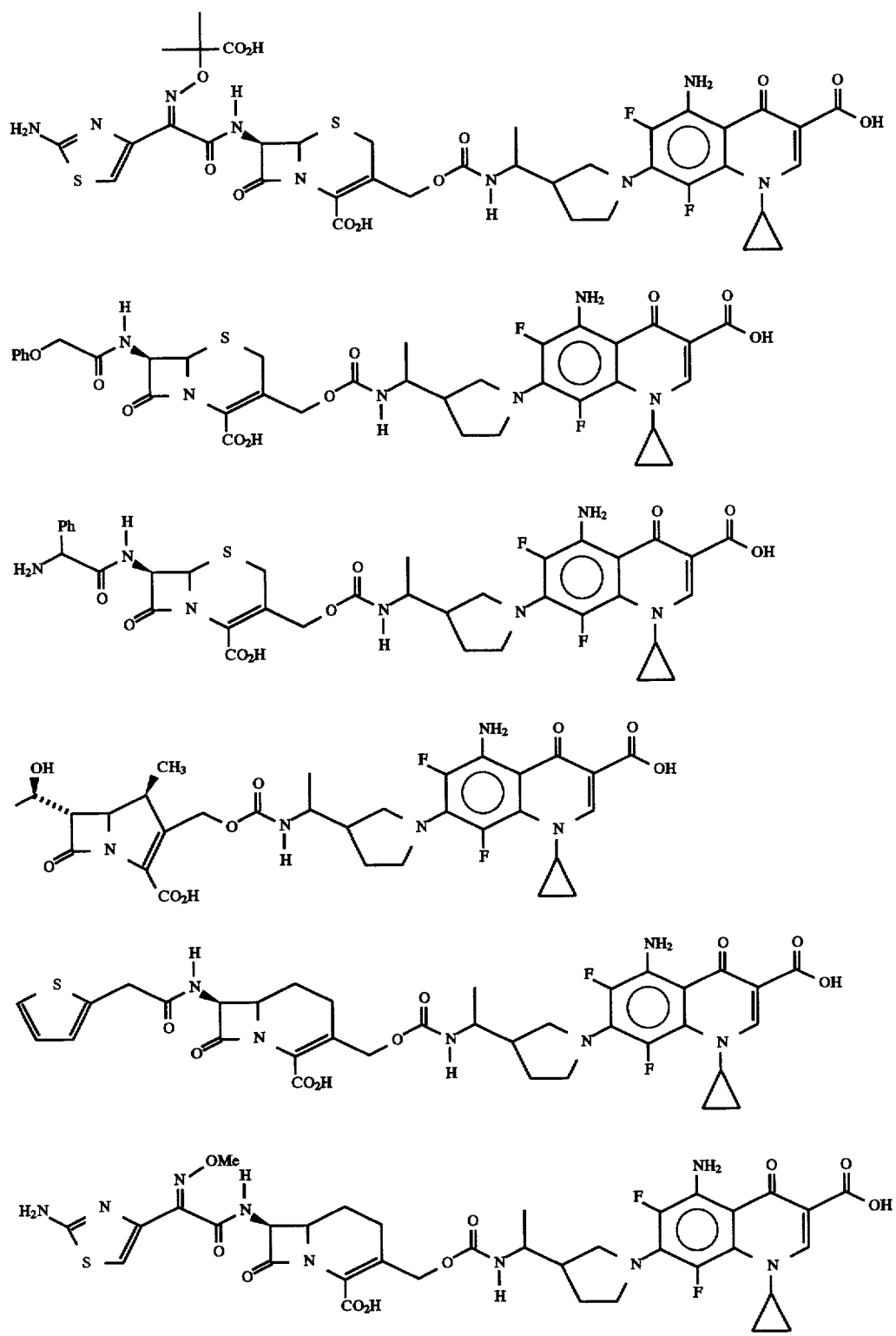

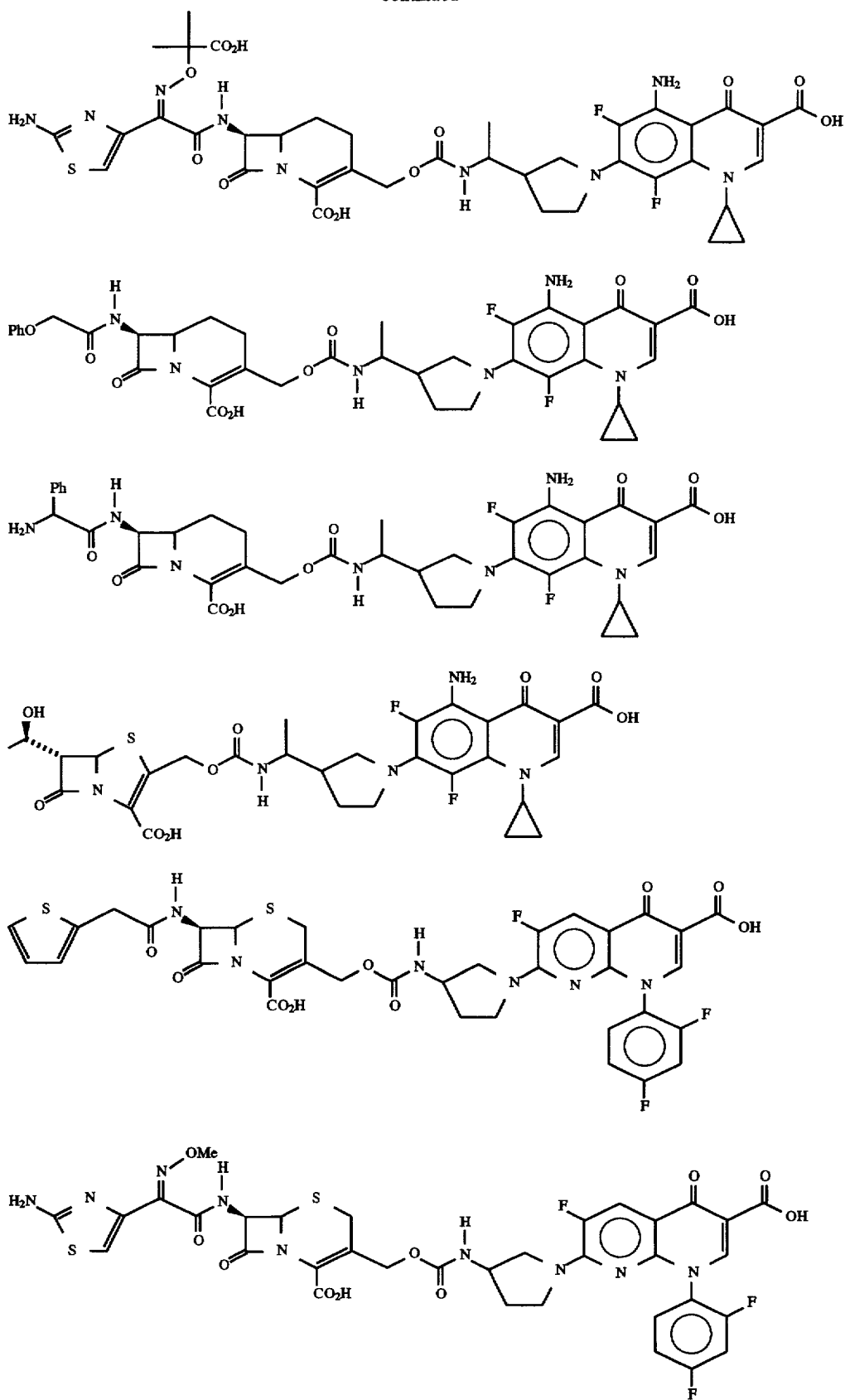

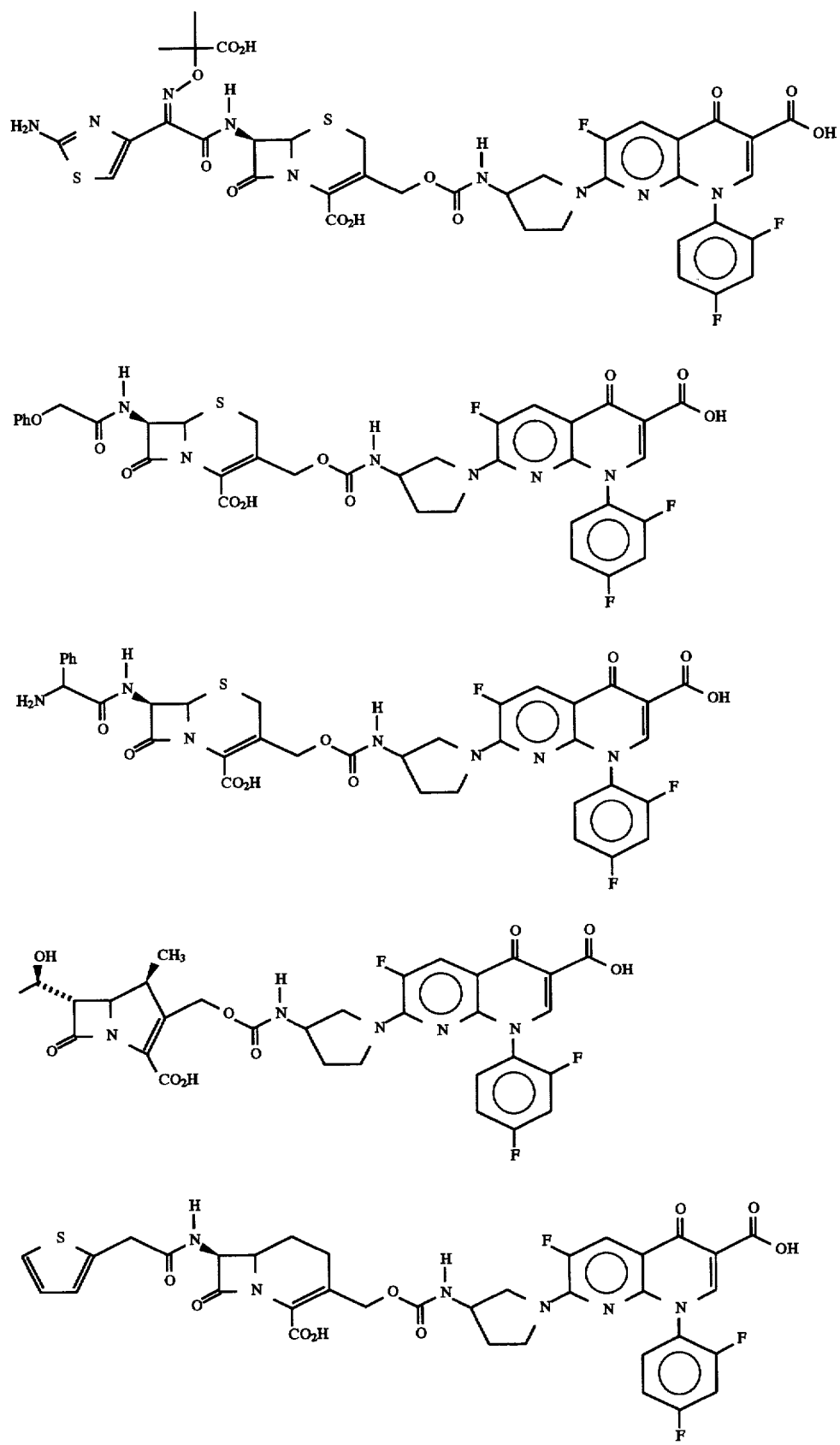

-continued
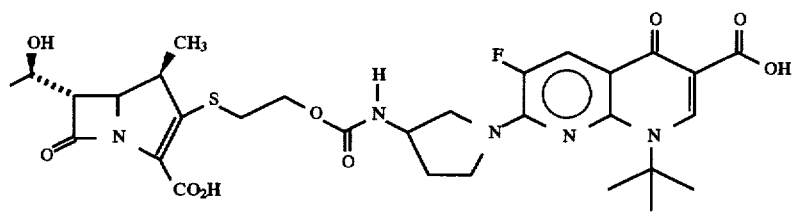
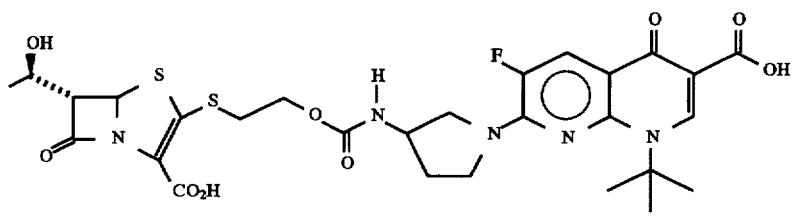
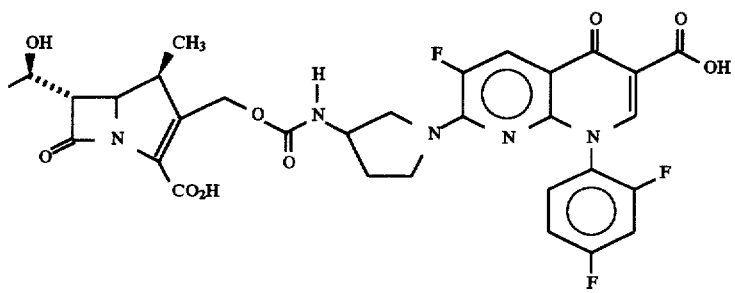
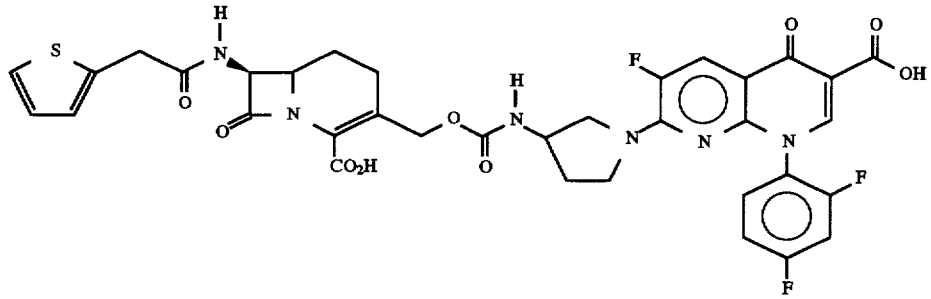
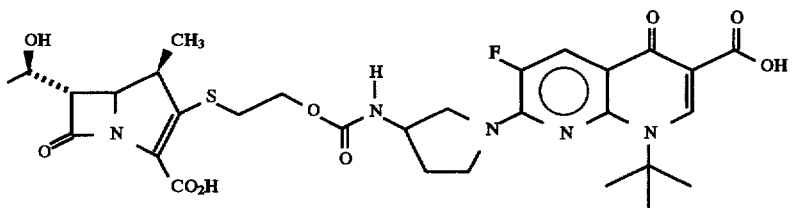
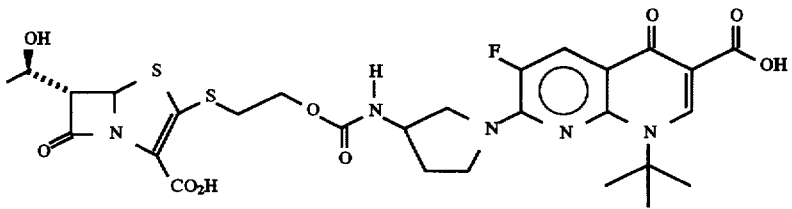

-continued
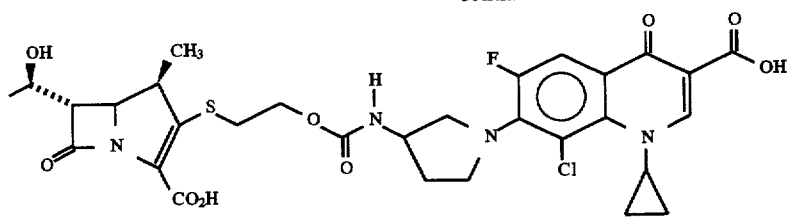
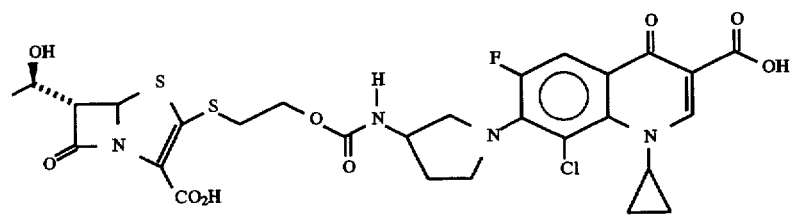
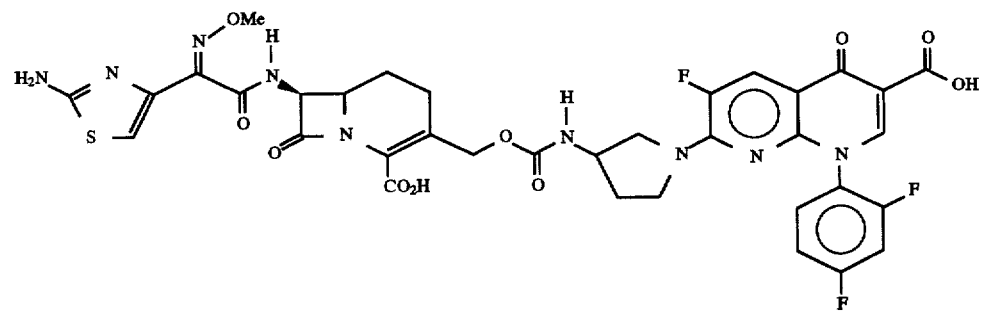
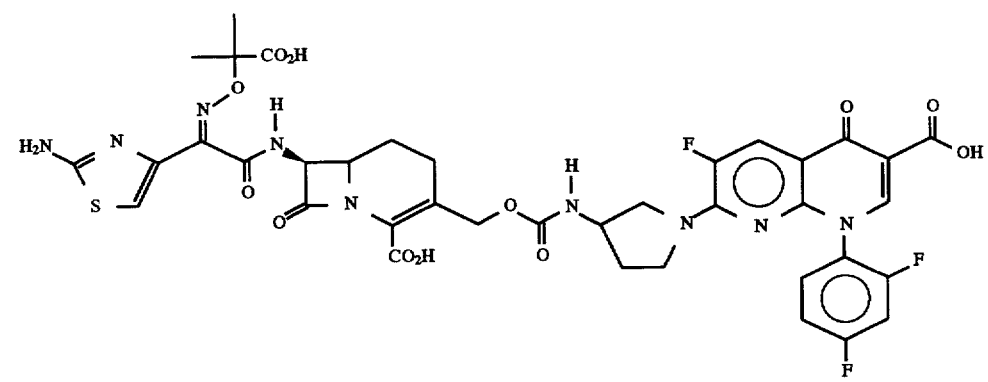
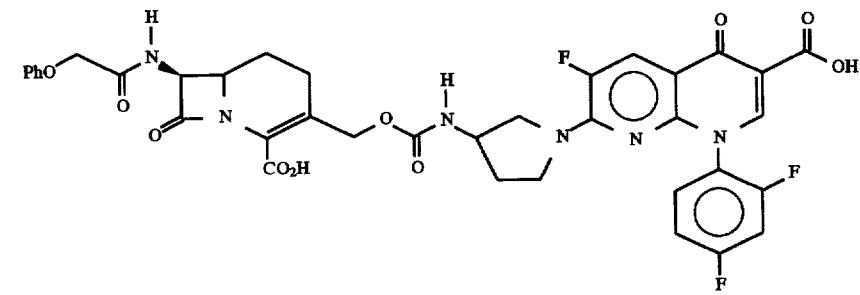

-continued
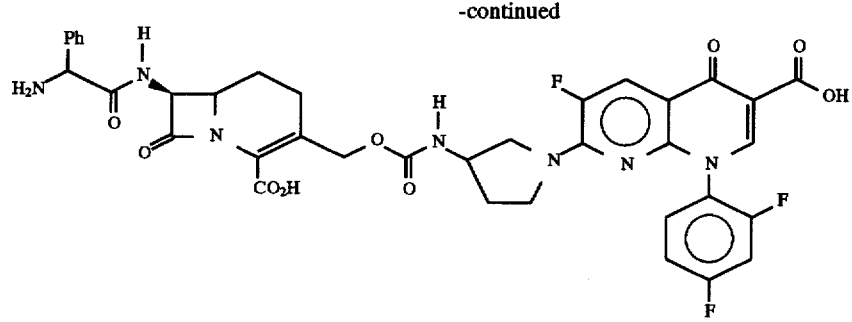
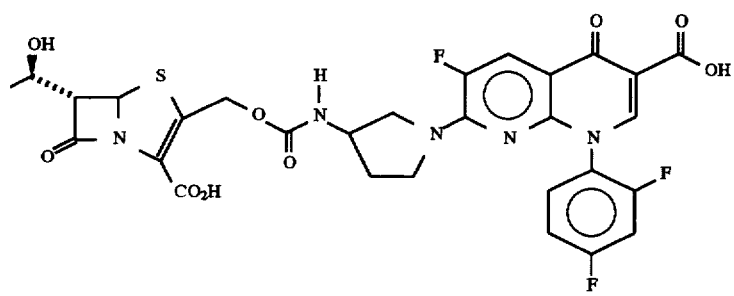
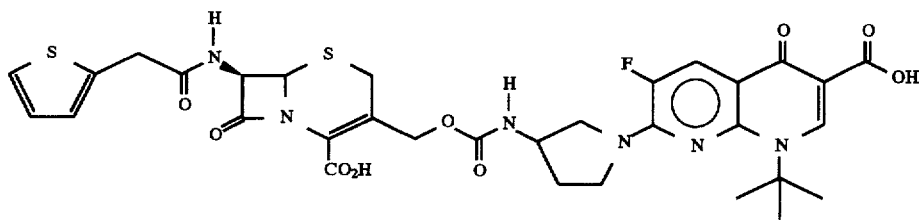
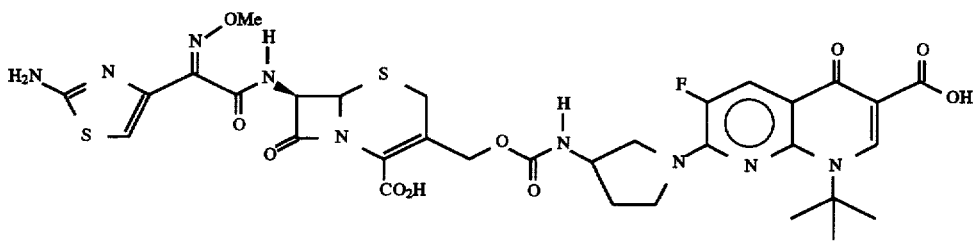
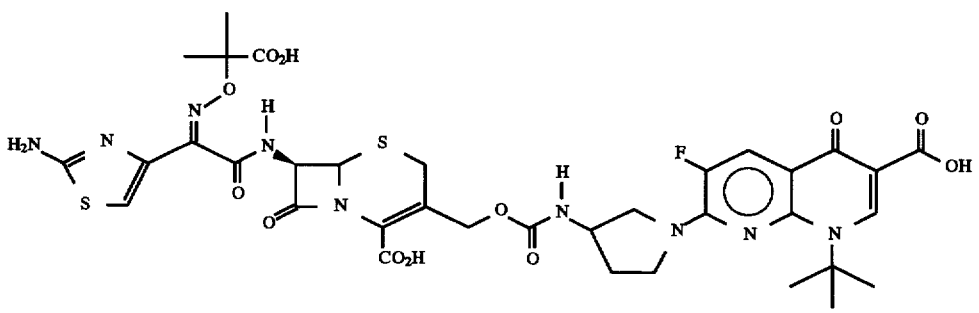
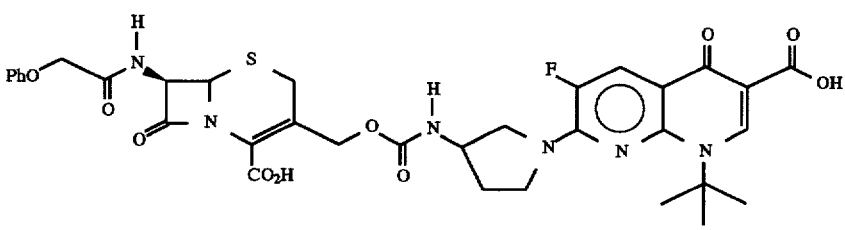

-continued
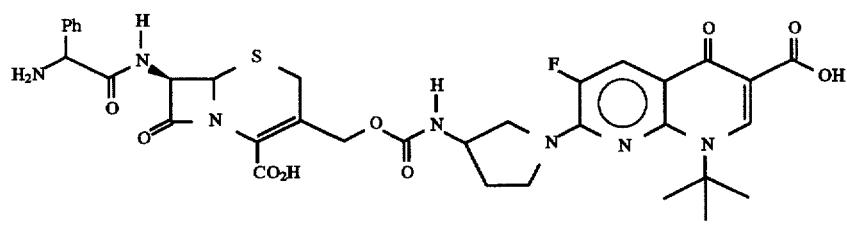
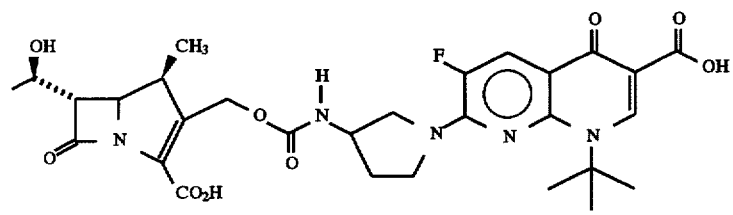
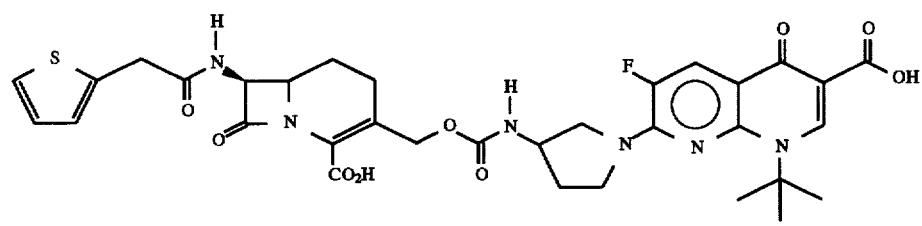
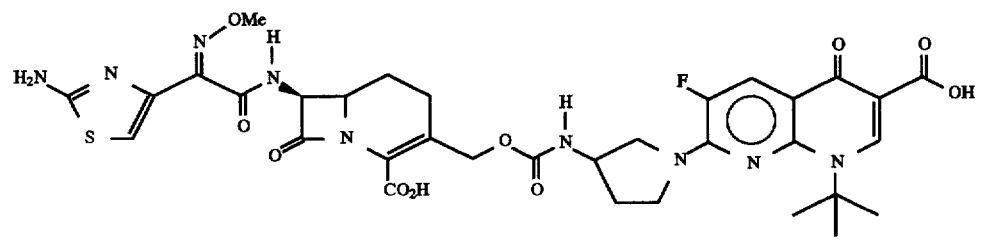
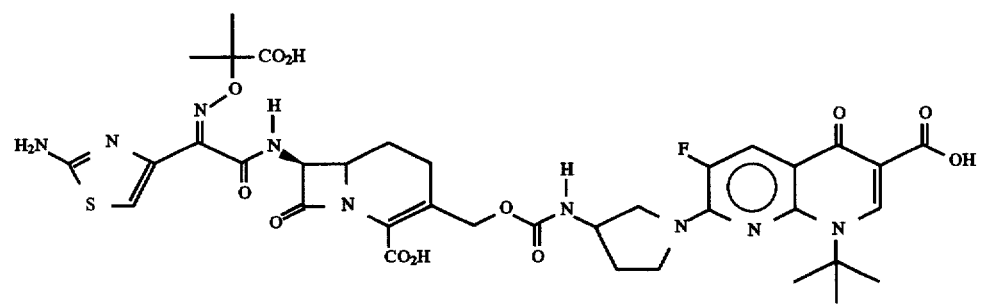
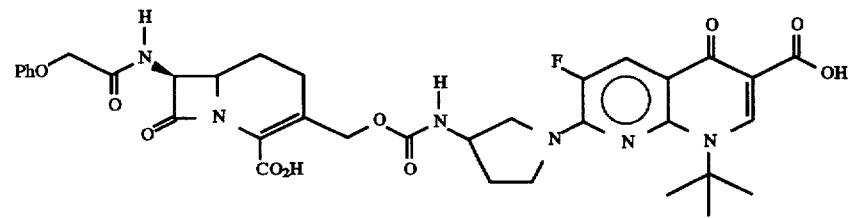

-continued
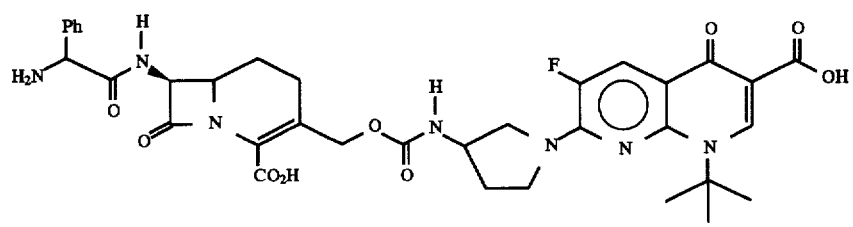
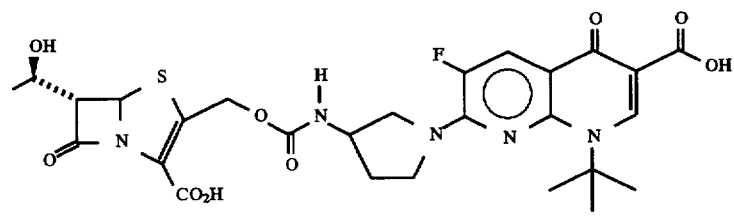
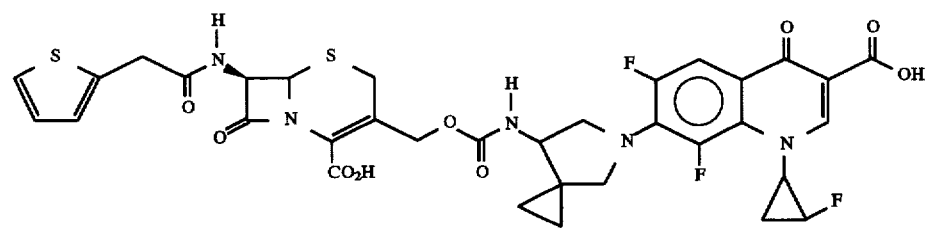
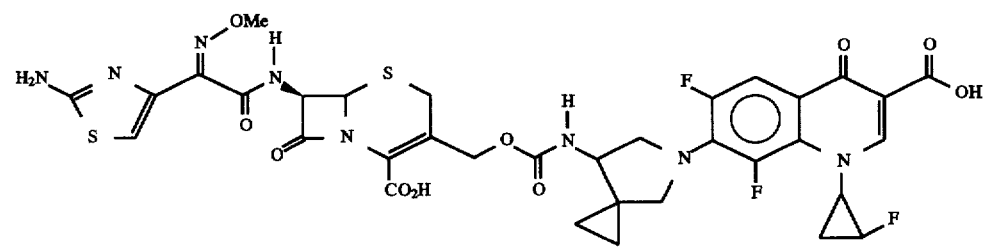
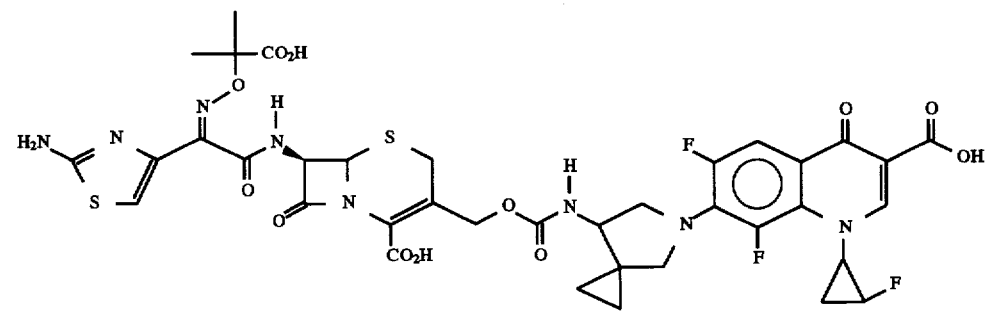
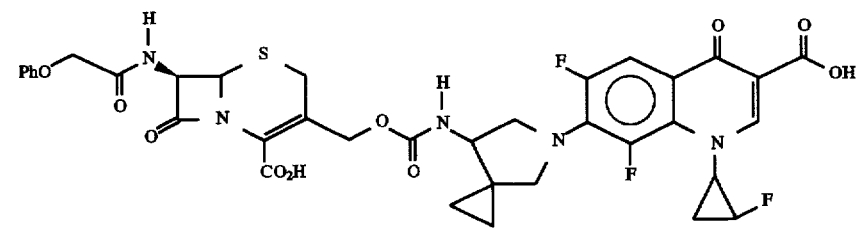

-continued
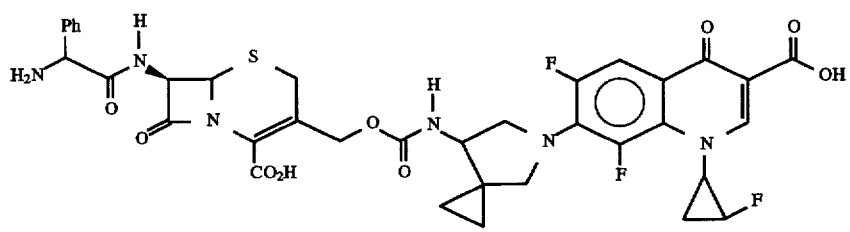
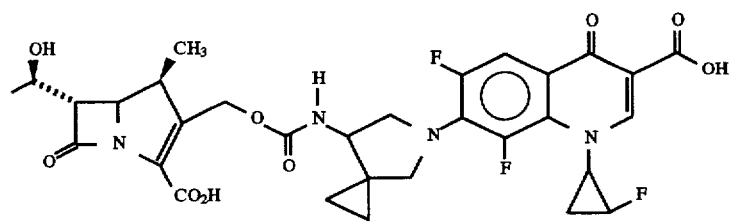
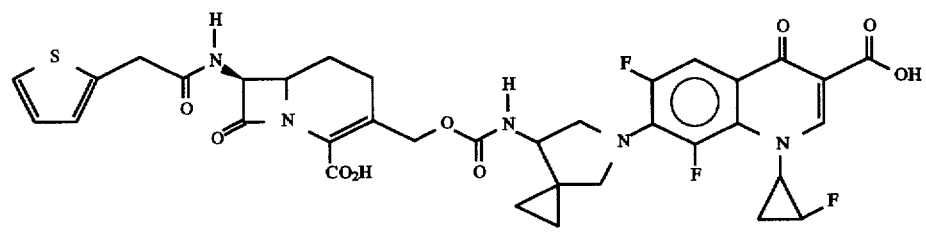
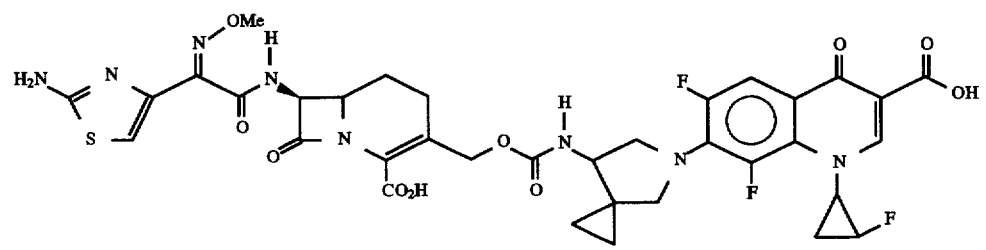
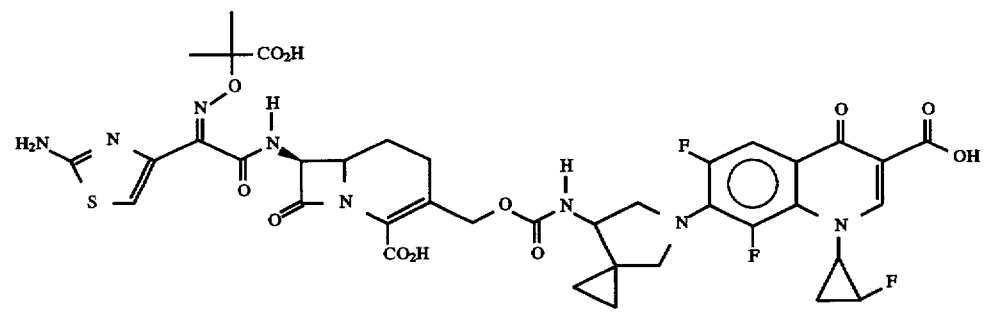
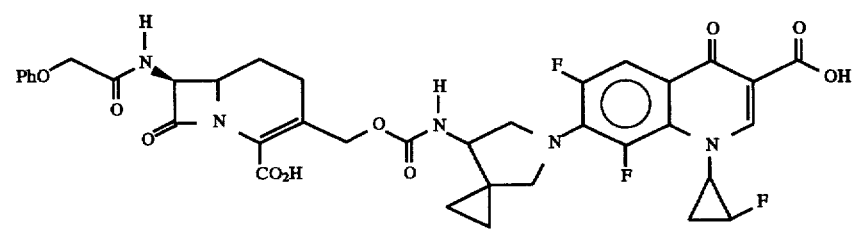

-continued
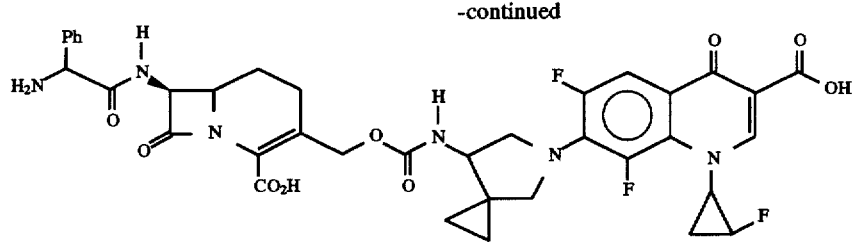
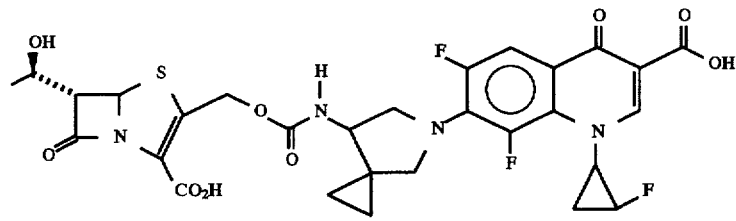
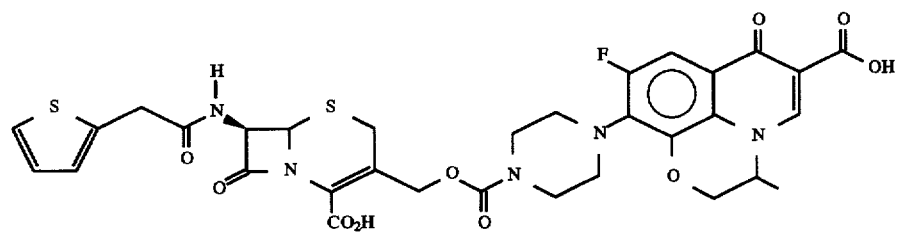
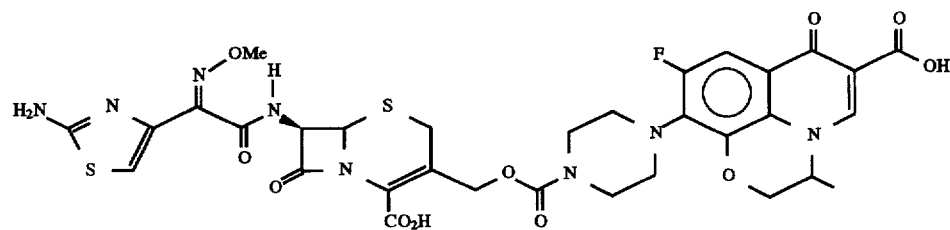
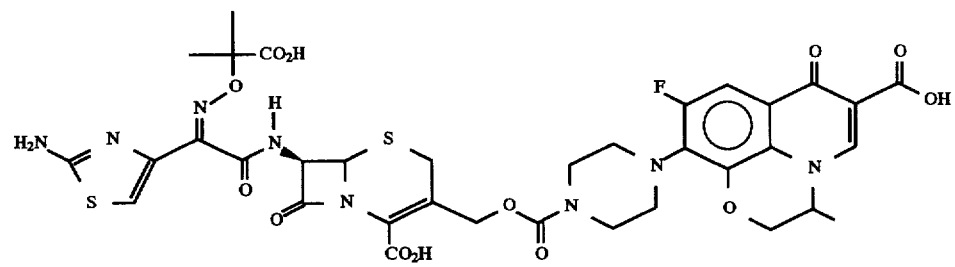
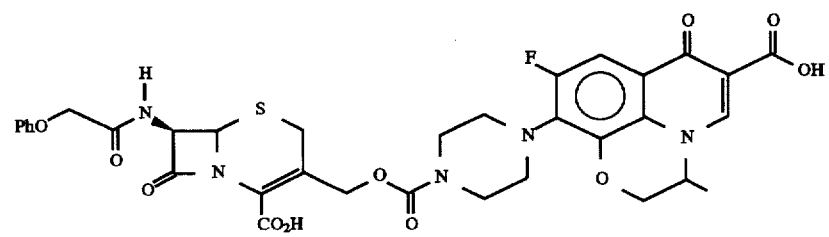
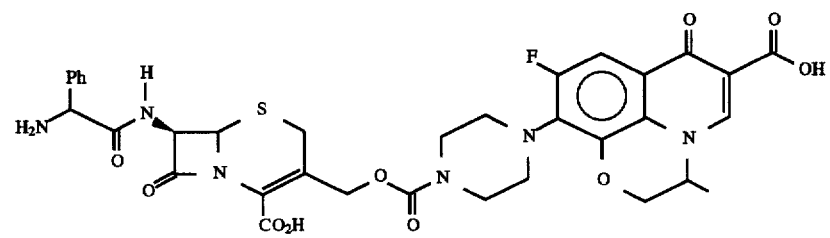

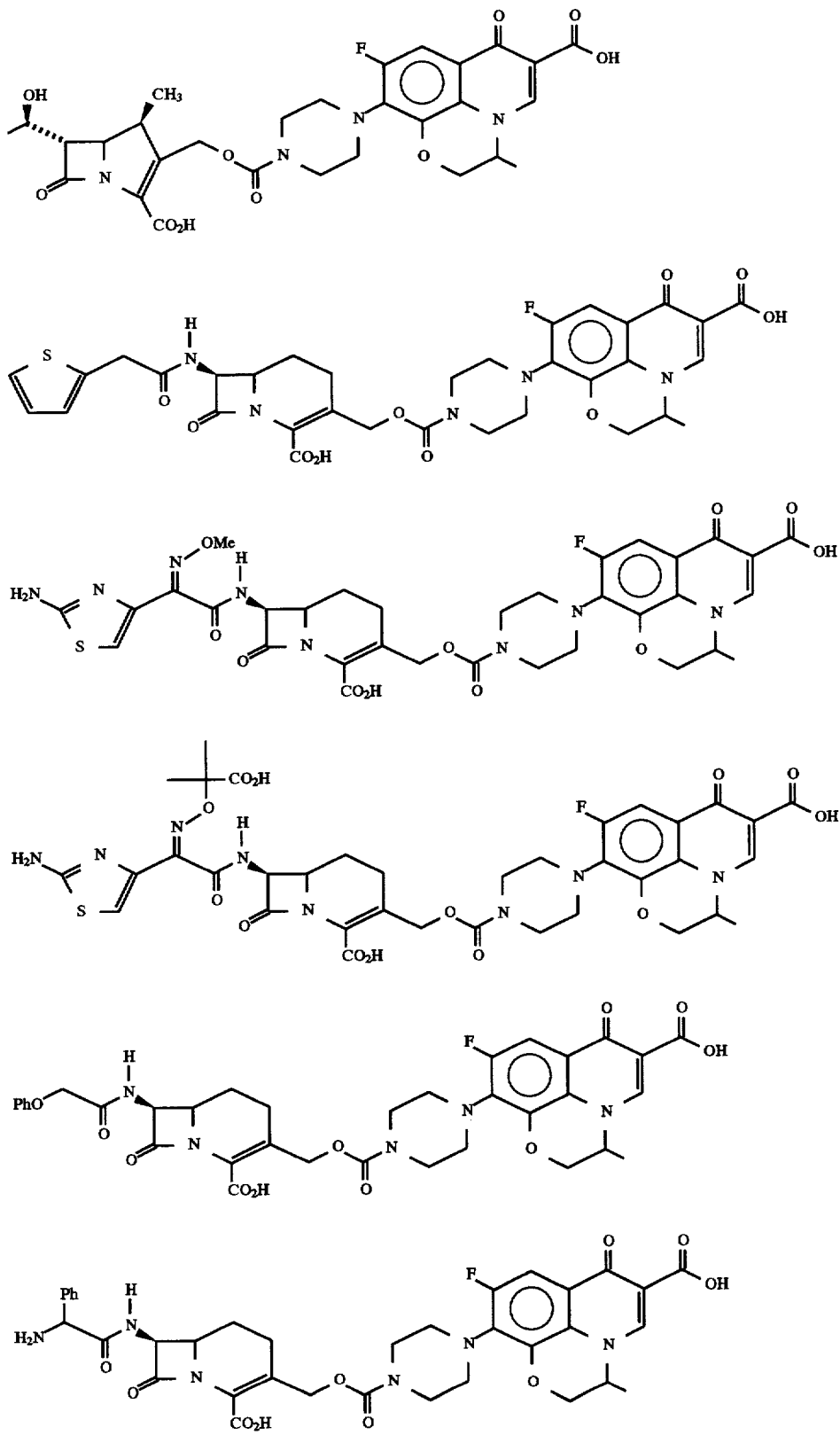

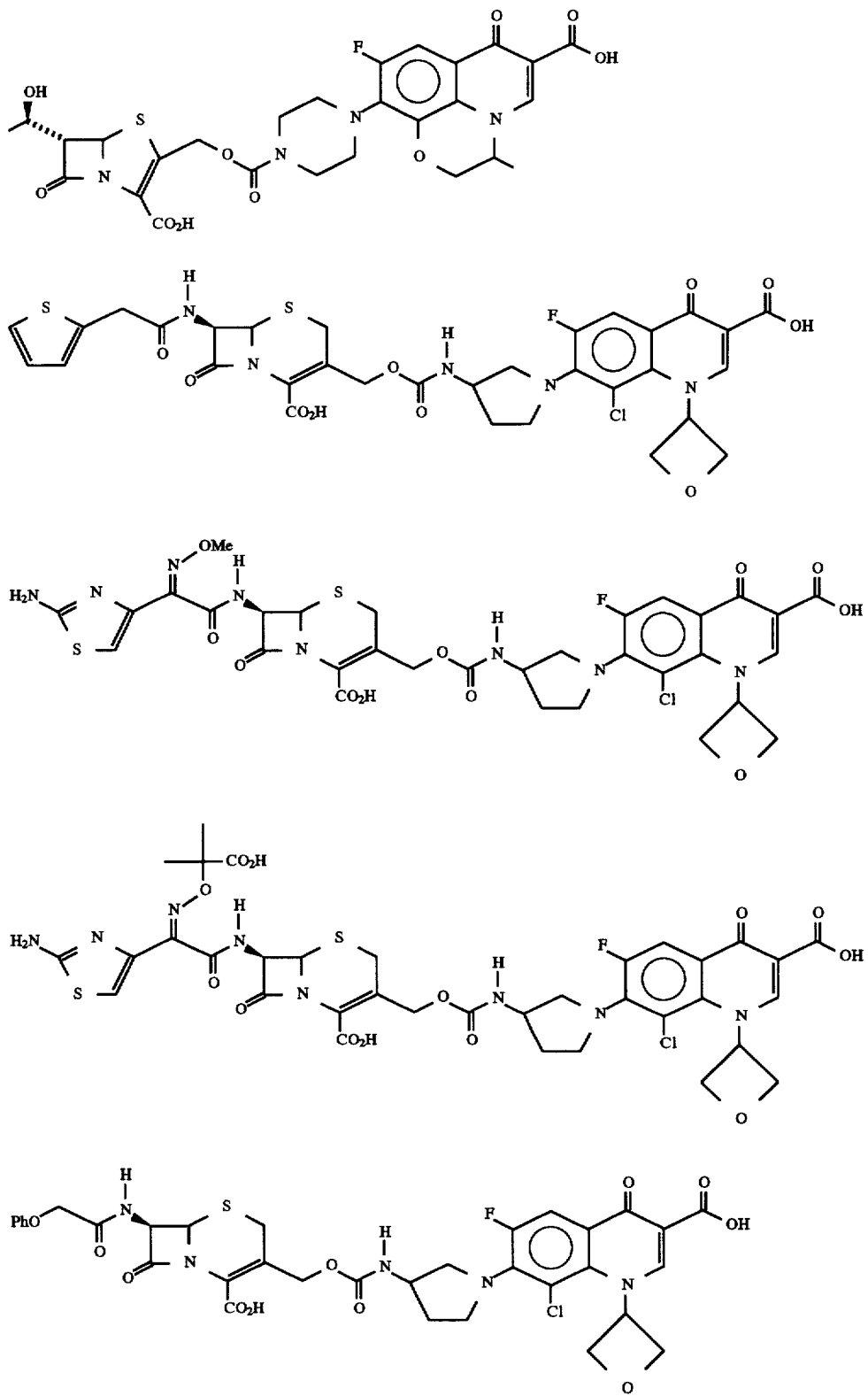

-continued
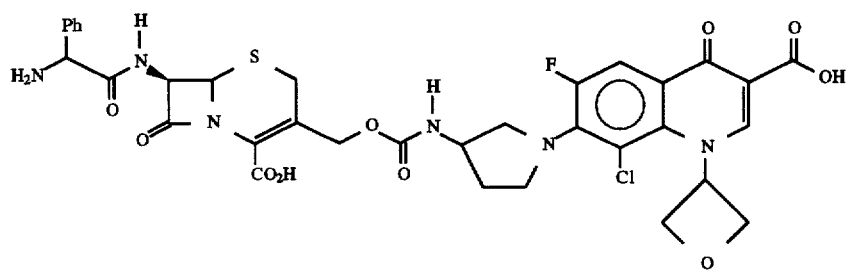
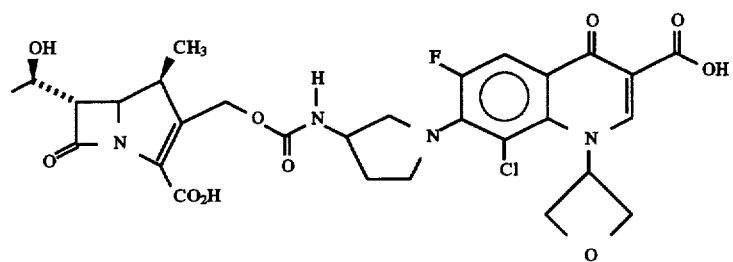
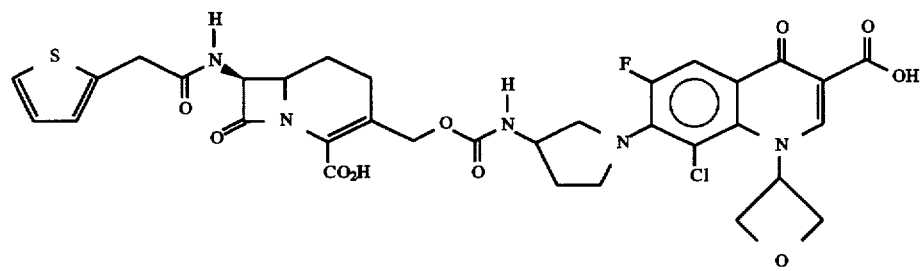
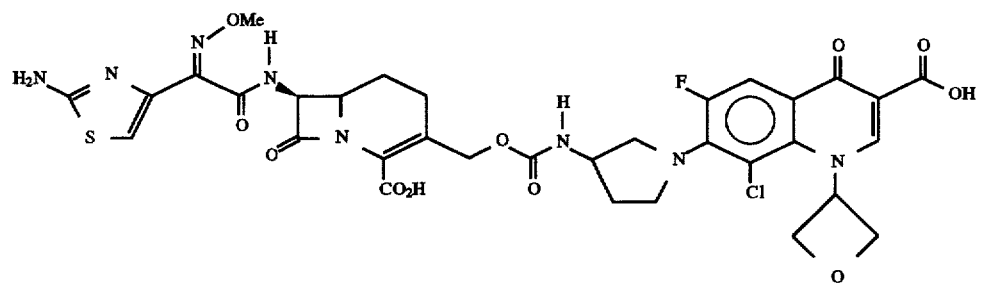
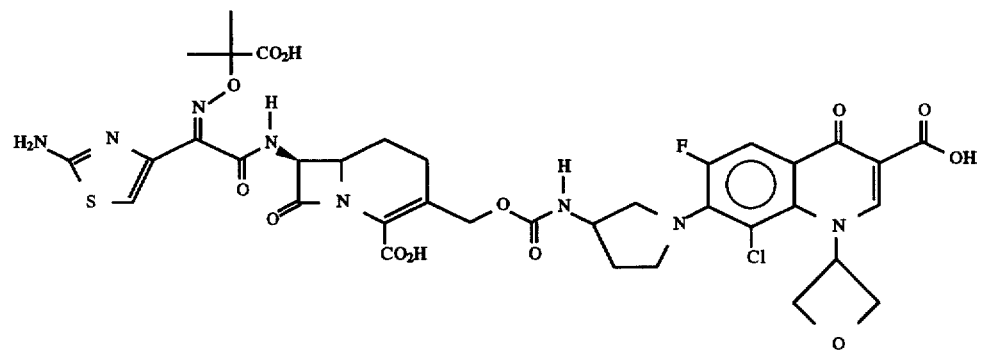

-continued
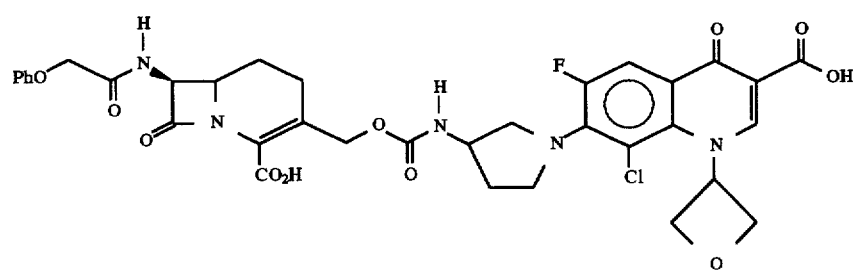
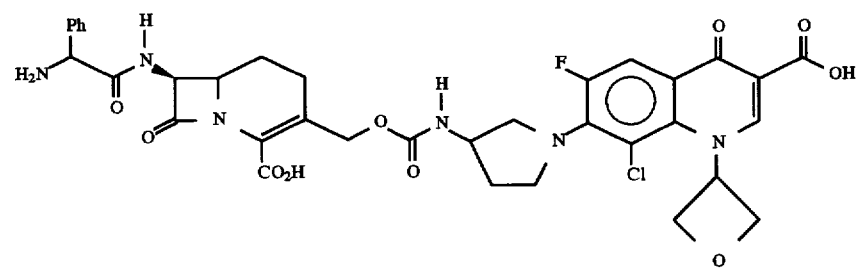
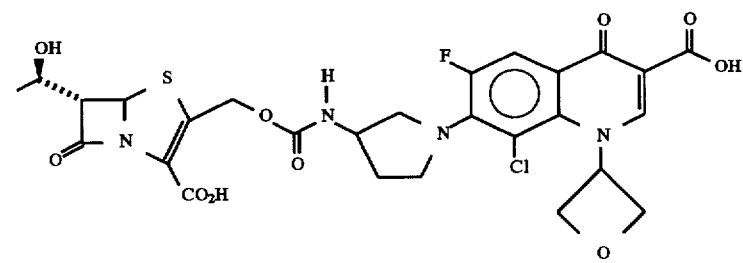
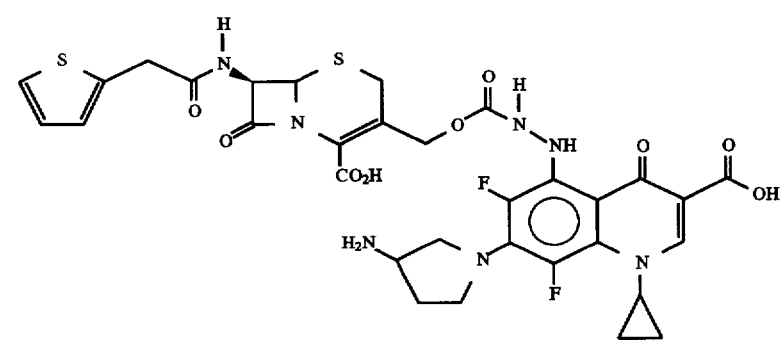
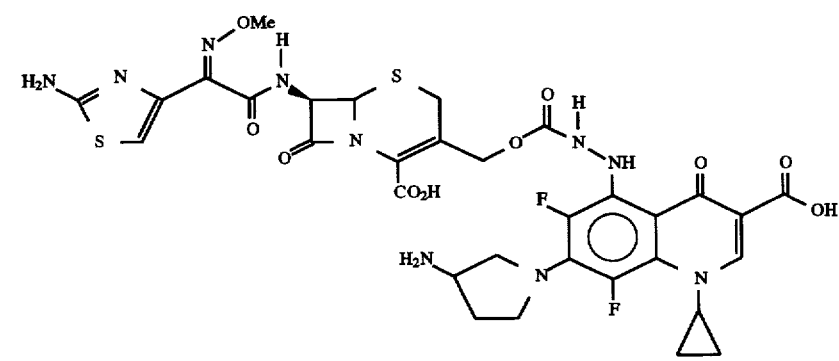

-continued
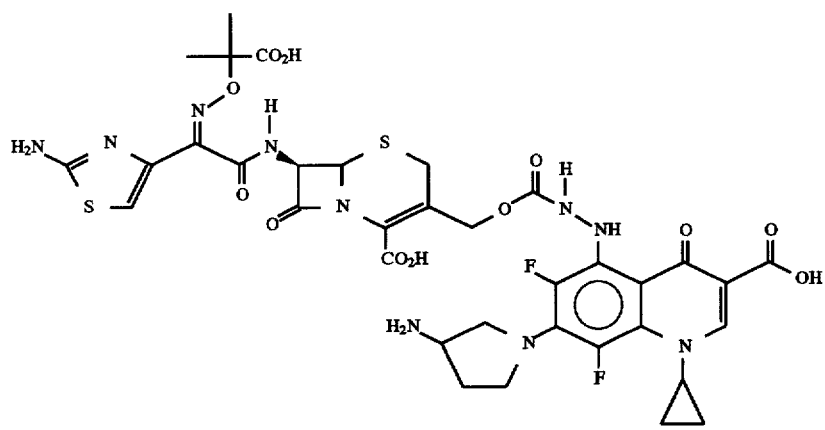
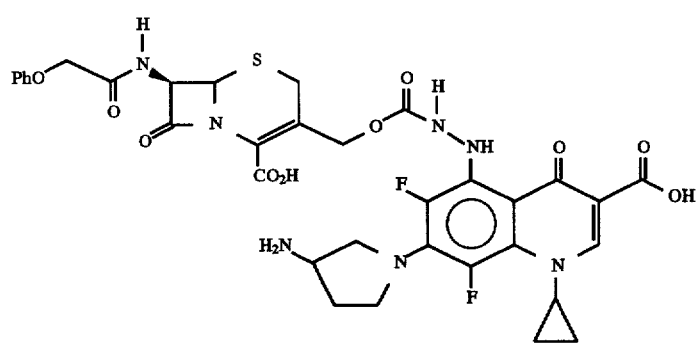
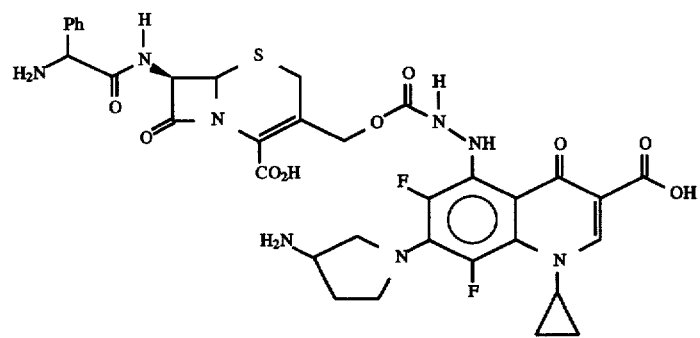
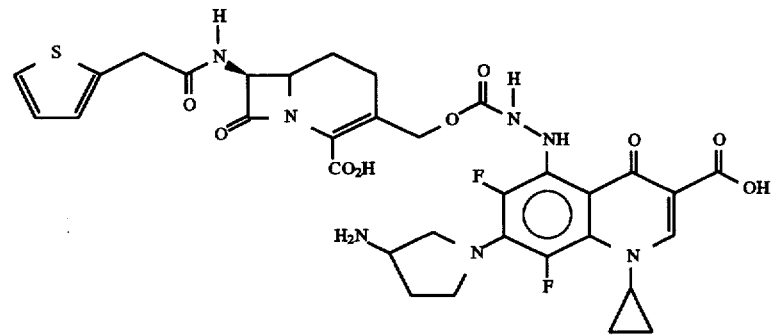

-continued
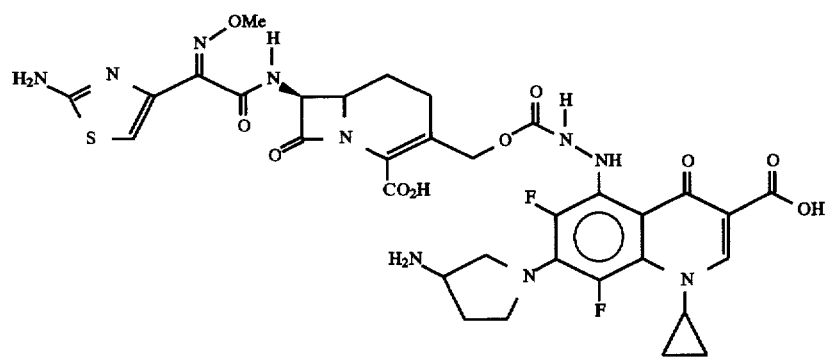
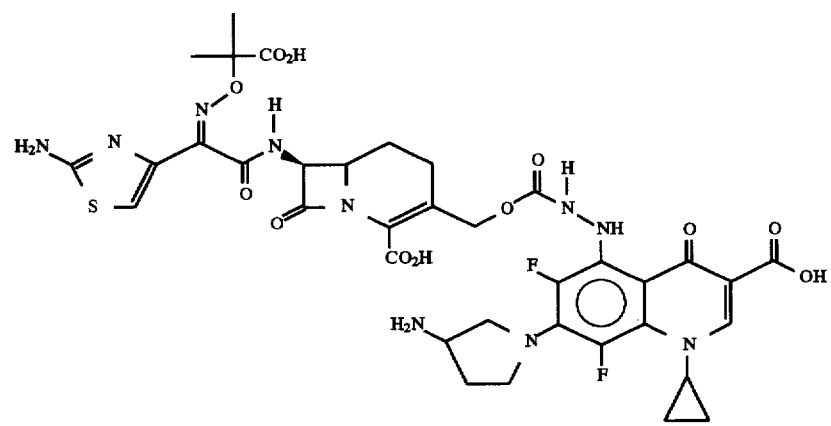
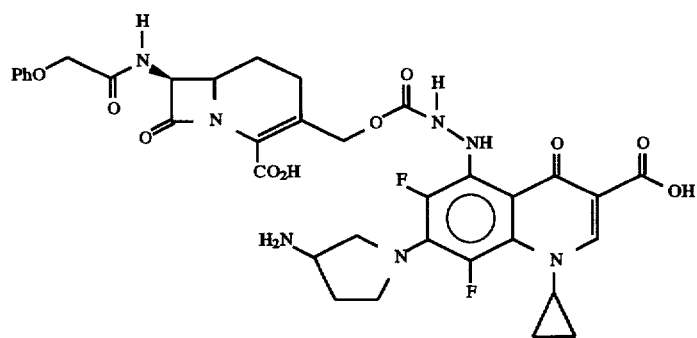
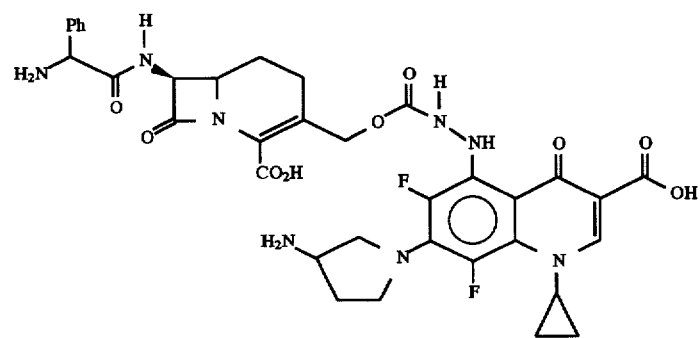

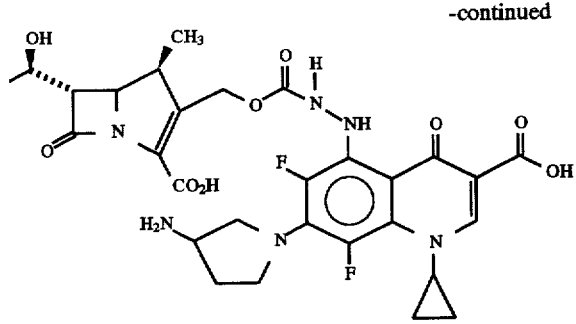
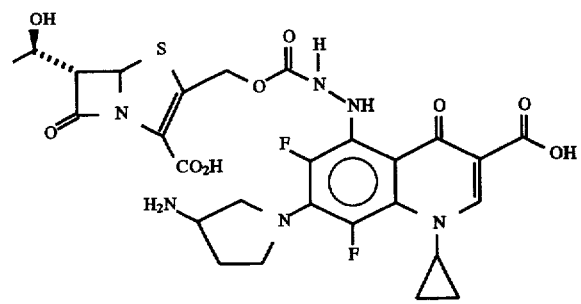
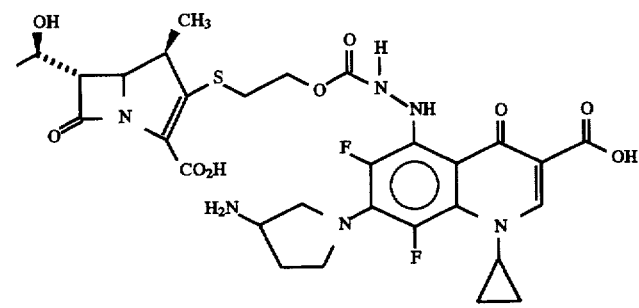
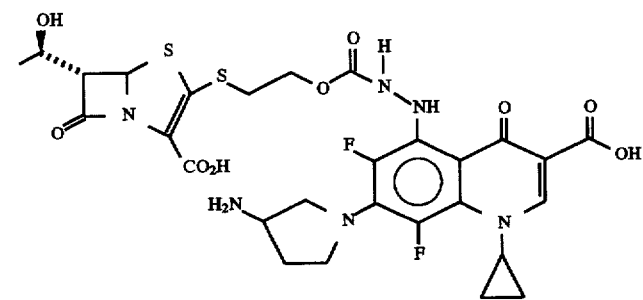
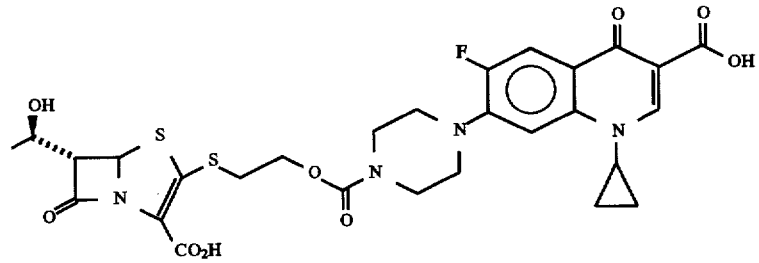
EXAMPLE 22
Synthesis of [5R-[5α,6α(R*)]]-3-[[4-(3-Carboxy-1-cyclopropyl-6-fluoro-1,4-dihydro-4-oxo-7-quinolinyl)-1-piperazinyl]methyl]-6-(1-hydroxyethyl)-7-oxo-4-thia-1-azabicyclo[3.2.0]hept-2-ene-2-carboxylic Acid, Disodium Salt.

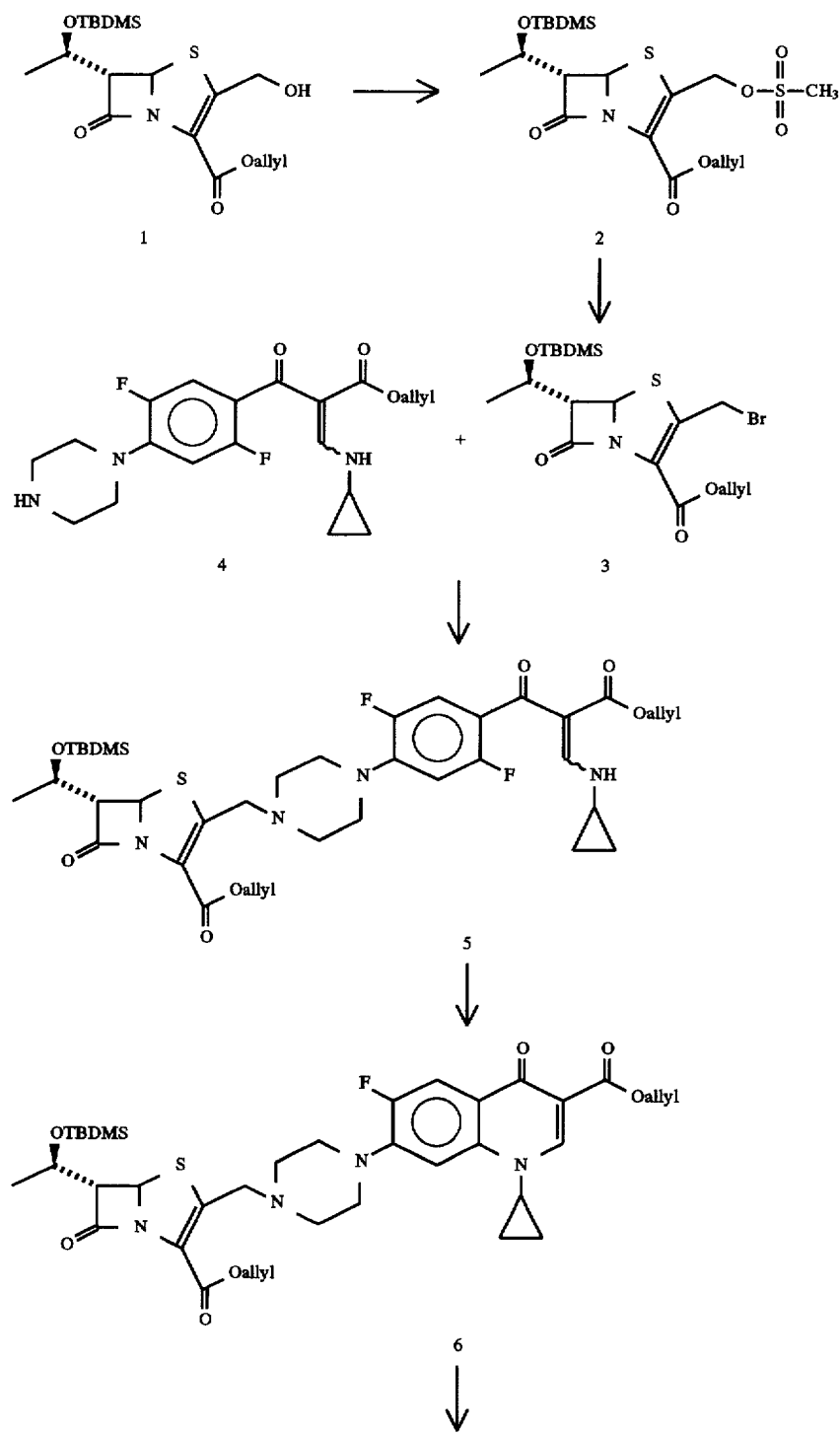

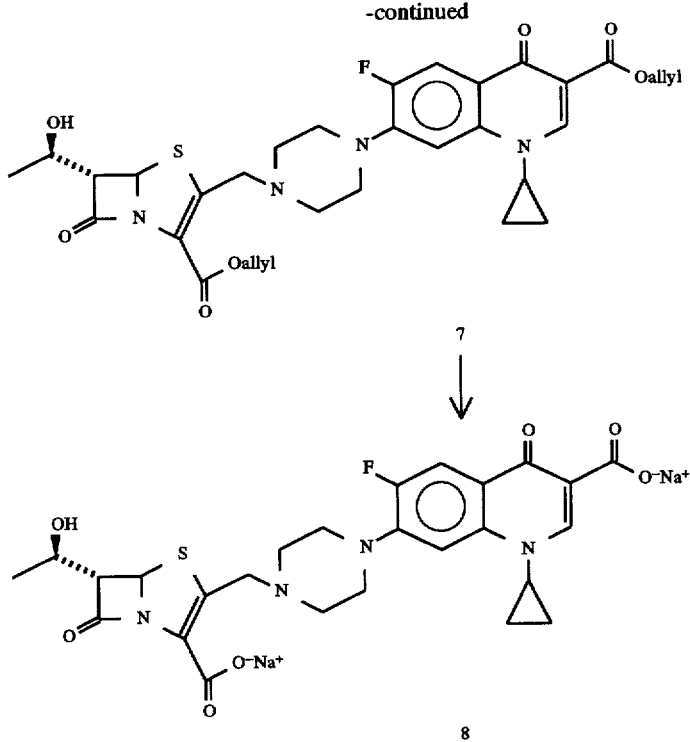

To a cooled (0° C.) solution of Compound 1 (4.2 g), prepared according to U.S. Pat. No. 4,631,150, Battistini et al., issued Dec. 23, 1986 (incorporated by reference herein), in $CH_2Cl_2$ (75 mL) is added methanesulfonyl chloride (1.05 mL), dropwise, followed by the dropwise addition of triethylamine (1.43 mL), under $N_2$. The mixture is stirred at 0° C. for 40 minutes whereupon a 5% solution of $NaHCO_3$ (60 mL) is added. After stirring at 0° C. for 10 minutes, the organic layer is separated and washed with dilute brine (2×30 mL). The organic portion is dried ($Na_2SO_4$) and the volatiles are removed in vacuo to provide Compound 2.

To a solution of Compound 2 (4.3 g) in DMSO (40 mL) is slowly added a solution of $CaBr_2$ (1.89 g) in DMSO (38 mL), under $N_2$. The reaction mixture is stirred for 3 hours, whereupon the mixture is diluted with EtOAc (175 mL) and poured over an ice/water mixture (175 mL). The mixture is stirred for 5 minutes whereupon the organic layer is separated and the aqueous layer is extracted with EtOAc (2×40 mL). The organic portion is washed with brine (2×60 mL) and dried ($Na_2SO_4$). The solvents are removed in vacuo to provide Compound 3.

To a solution of Compound 4 (1.9 g), prepared in the same manner as Compound 5 in Example 11, in a 1:1 mixture of DMF and $CH_2Cl_2$ (60 mL) is slowly added a solution of Compound 3 (2.32 g) in a 1:1 mixture of DMF and $CH_2Cl_2$ (30 mL), under $N_2$. N,N-Diisopropylethylamine (0.98 mL) is added dropwise and the reaction is allowed to stir at ambient temperature until complete. Upon completion, methanol (15 mL) is added and the mixture is stirred for 15 minutes. The volatiles are removed in vacuo until a small mount of DMF remains whereupon methanol (150 mL) is added. The mixture is stirred for 5 minutes and filtered to obtain Compound 5.

To a solution of Compound 5 (2.2 g) in $CH_3CN$ (35 mL) is added N,O-bis(trimethylsilyl)acetamide (2.17 mL). The reaction mixture is stirred under $N_2$ at ambient temperature until complete. The reaction is quenched with water (30 mL), and the resulting slurry is filtered and washed with a mixture of water and $CH_3CN$ (5: 1) giving Compound 6.

To a solution of Compound 6 (1.7 g) in THF (15 mL) and acetic acid (1.18 mL) is added tetra-n-butyl ammonium fluoride (5.76 mL of a 1M solution in THF), under $N_2$. The mixture is stirred at ambient temperature overnight and, upon completion, is diluted with ether (25 mL). The solution is stirred for a half-hour, allowing the product to crystallize. The slurry is filtered through troyfelt and the solid residue is washed with ether to obtain Compound 7.

To a solution of Compound 7 (1.32 g) in $CH_2Cl_2$ (80 mL) is added tetrakis(triphenylphosphine)palladium (0) (227 mg), under $N_2$. The mixture is cooled (−10 to −5° C.) and a cooled solution (<−10° C.) of sodium ethylhexanoate (643 mg) in THF (40 mL) is added dropwise. The mixture is stirred for approximately 30 minutes, whereupon the resulting slurry is filtered and washed successively with $CH_2Cl_2$ and acetone, to obtain [5R-[5α,6α(R*)]]-3-[[4-(3-Carboxy-1-cyclopropyl-6-fluoro-1,4-dihydro-4-oxo-7-quinolinyl)-1-piperazinyl]methyl]-6-(1-hydroxyethyl)-7-oxo-4-thia-1-azabicyclo[3.2.0]hept-2-ene-2-carboxylic Acid, Disodium Salt (Compound 8).

EXAMPLE 23

Synthesis of [6R-[6α,7β]]-3-[[4-(3-Carboxy-1-cyclopropyl-6,8-difluoro-1,4-dihydro-4-oxo-7-quinolinyl)-1-piperazinyl]]methyl]-8-oxo-7-[2-(phenoxyacetyl)-amino]-1-azabicyclo[4.2.0]oct-2-ene-2-carboxylic Acid, Disodium Salt.

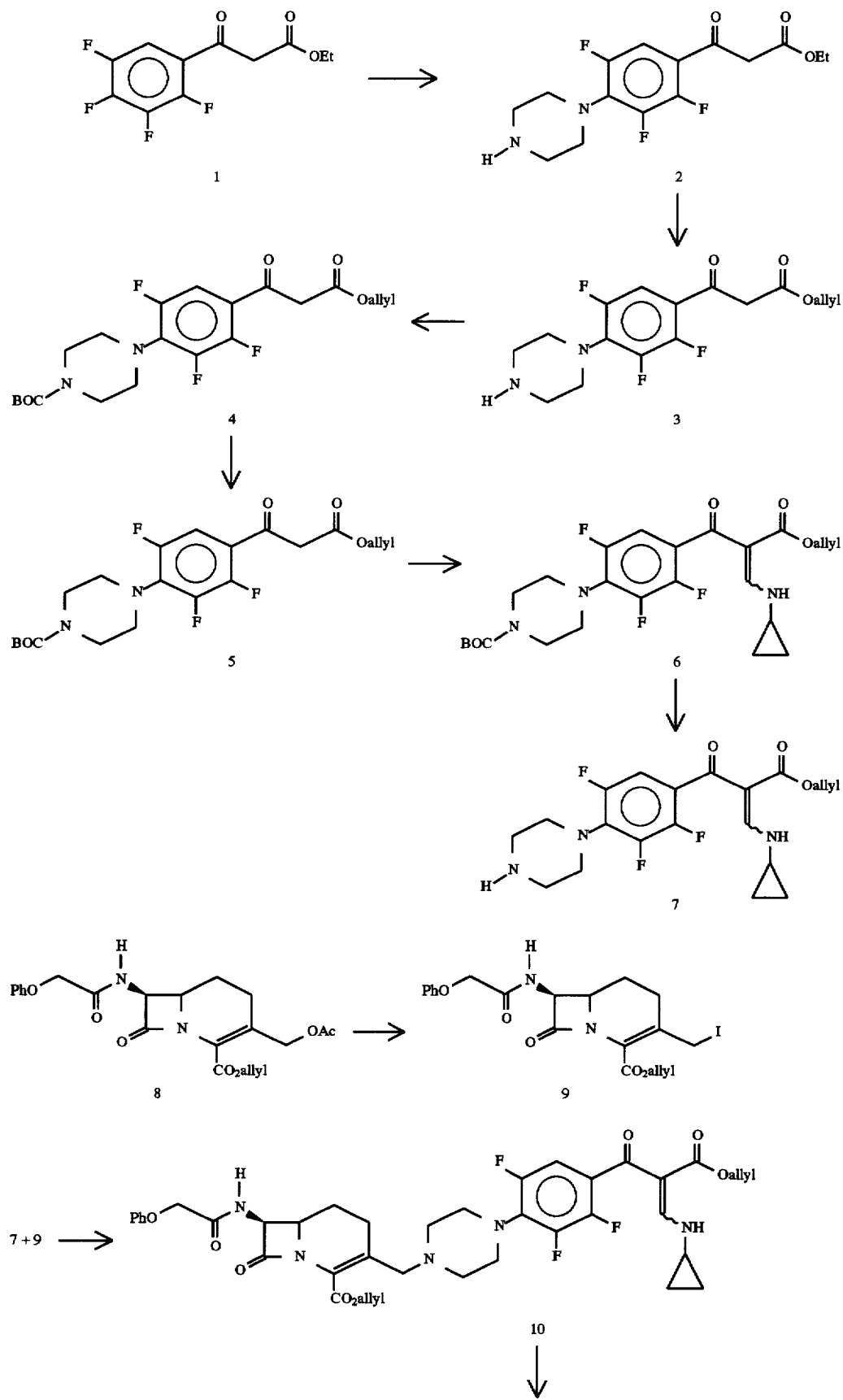

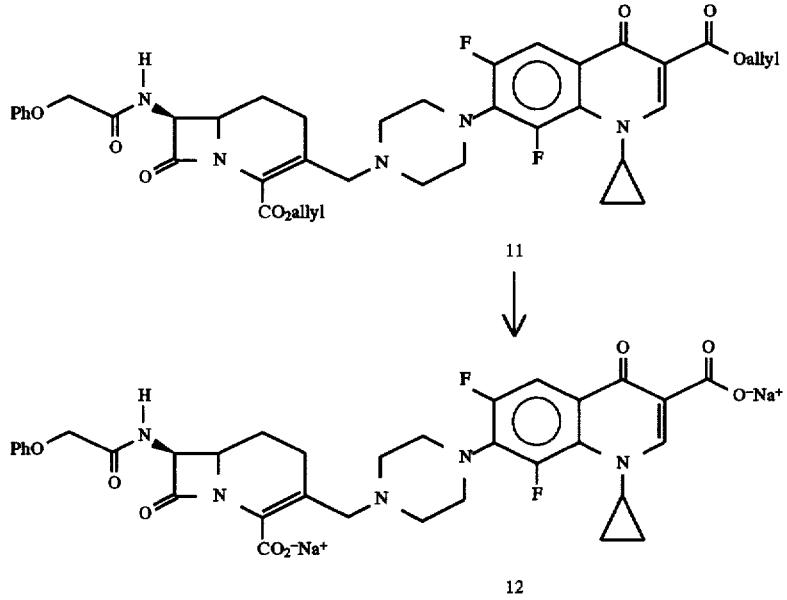

To a solution of Compound 1 (12.3 g) (prepared in the same manner as Compound 4 in Example 10) in THF (240 mL) is added piperazine (16 g). The reaction is heated at reflux, under $N_2$, until completion, whereupon the volatiles are removed in vacuo. The residue obtained is dissolved in EtOAc (150 mL), washed with water (4×50 mL), and dried ($MgSO_4$). The solvent is removed in vacuo and the residue obtained is subjected to column chromatography (silica) to give a mixture of Compound 2 and its enol ether which is used directly in the next step.

To a solution of allyl alcohol (24 mL) in toluene (70 mL) is added 4-dimethylaminopyridine (1.3 g), under $N_2$. Compound 2 (11.9 g) is added and the mixture is heated to reflux. Upon completion, the reaction mixture is cooled and saturated ammonium chloride (175 mL) is added, followed by the addition of EtOAc (200 mL). The layers are separated and the EtOAc portion is washed with water (4×60 mL) and brine (2×45 mL), and dried ($MgSO_4$). The solvents are removed in vacuo and the residue is subjected to column chromatography (silica) to provide a mixture of Compound 3 and its enol ether which is used directly in the next step.

To a solution of Compound 3 (10.1 g) in $CHCl_3$ (150 mL) is added a solution of dibutylcarbonate (7.5 mL) in $CHCl_3$ (25 mL). The reaction is stirred for 5 minutes under $N_2$ at ambient temperature and the volatiles are removed in vacuo. Hexanes are added to give Compound 4.

To a solution of Compound 4 (10.6 g) in toluene (40 mL) is added dimethylformamide dimethylacetal (4.9 mL). The reaction is heated at reflux under $N_2$ for 2 hours and the volatiles are removed in vacuo to give crude Compound 5. The crude compound is carried directly to the next step by dissolving in EtOH (47 mL) and adding cyclopropyl amine (2.65 mL). The mixture is stirred for 2 hours at ambient temperature under $N_2$. The volatiles are removed in vacuo and the residue is crystallized from 20% EtOAc/hexanes to give Compound 6.

To a cooled solution of Compound 6 (9.1 g) in anisole (70 mL) at 5°–10° C. is added TFA (70 mL). After stirring for 5 minutes under $N_2$, the ice bath is removed and the reaction is warmed to ambient temperature. After 2 hours, most of the TFA and some of the anisole is removed in vacuo. The residue is slurried in $Et_2O$ (250 mL) and filtered. The solid is dissolved in a mixture of $CH_2Cl_2$ (100 mL) and saturated $NaHCO_3$ (100 mL) and stirred for 10 min. The $CH_2Cl_2$ portion is separated, dried ($MgSO_4$), and treated with activated charcoal. The volatiles are removed in vacuo and the residue obtained is crystallized with hexane to give Compound 7.

To a cooled (0° C.) solution of allyl (7S, 6R)-7-(phenoxyacetamido)-3-(acetoxy-methyl)-1-carba-1-dethia-3-cephem-4-carboxylate (4.2 g) (Compound 8), prepared as described in L. Blaszczak et al., 33 J. Am. Chem. Soc. 1656 (1990), in $CH_2Cl_2$ (30 mL) is added iodotrimethylsilane (2.07 mL). The mixture is stirred at 0° C. for 0.5 hour and then at ambient temperature for 1 hour. The volatiles are removed in vacuo to provide crude Compound 9 which is used directly in the next step. In a second vessel, to a solution of Compound 7 (4 g) in DMF (30 mL) and $CH_2Cl_2$ (30 mL) is added activated molecular sieves (1 g), under $N_2$. After stirring for 30 minutes, the solution is transferred to a third vessel and diisopropylethylamine (1.72 mL) is added, under $N_2$. The mixture is cooled (–40° C.) and, after stirring for 0.5 hour, a solution of the forementioned crude Compound 9 in DMF (30 mL) and $CH_2Cl_2$ (30 mL) is slowly added. The mixture is stirred for 1 hour at –40° C. and then stirred at 0° C. for 1 hour and allowed to warm to ambient temperature. Upon completion, the reaction is diluted with $CH_2Cl_2$ (100 mL) and washed with 1M HCl (2×80 mL) and brine (2×80 mL). The organic portion is separated and the solvents are removed in vacuo to provide a residue that is subjected to column chromatography (silica) to provide Compound 10.

To a solution of Compound 10 (4.1 g) in $CH_3CN$ (60 mL) is added N,O-bis(trimethylsilyl)acetamide (3.9 mL). The reaction mixture is stirred under $N_2$ at ambient temperature until complete. The reaction is quenched with water (60 mL), and the resulting slurry is filtered and washed with a mixture of water and $CH_3CN$ (5:1) to provide Compound 11.

To a solution of Compound 11 (3.8 g) in $CH_2Cl_2$ (210 mL) is added tetrakis(triphenylphosphine)palladium (0) (580 mg), under $N_2$. The mixture is cooled (–10 to –5° C.)

and a cooled solution (<−10° C.) of sodium ethylhexanoate (1.67 mg) in THF (105 mL) is added dropwise. The mixture is stirred for approximately 30 minutes, whereupon the resulting slurry is filtered and washed successively with $CH_2Cl_2$ and acetone, to obtain [6R-[6α,7β]]-3-[[4-(3-Carboxy-1-cyclopropyl-6,8-difluoro-1,4-dihydro-4-oxo-7-quinolinyl)-1-piperazinyl]]-methyl]-8-oxo-7-[2-(phenoxyacetyl)amino]-1-azabicyclo[4.2.0]oct-2-ene-2-carboxylic Acid, Disodium Salt (Compound 12).

The following compounds are made according to Examples 22–23, with substantially similar results.

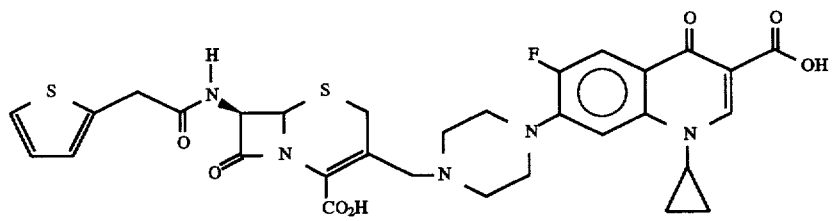

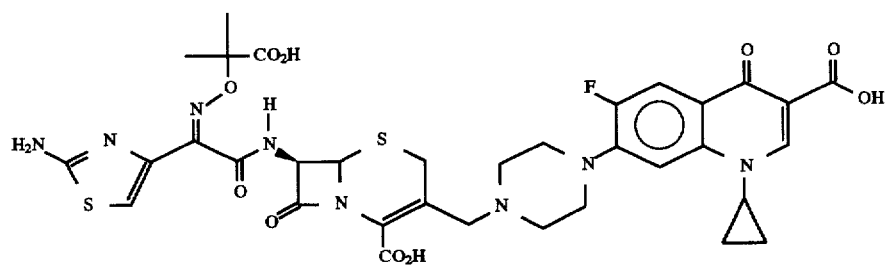

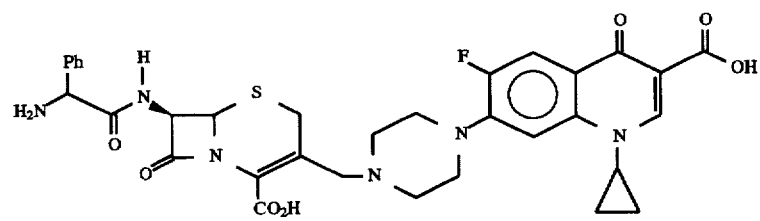

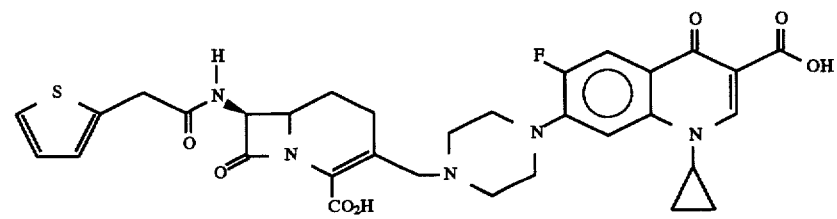

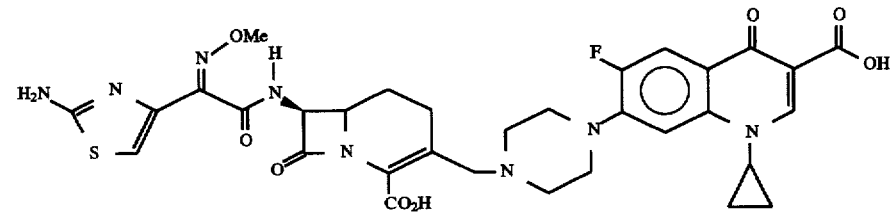

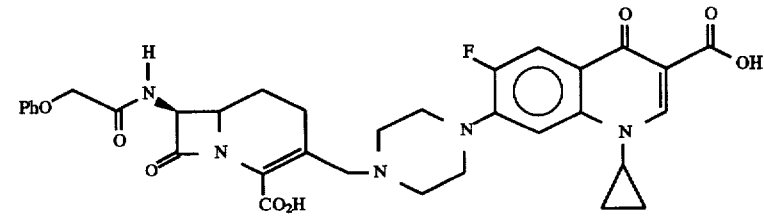

-continued
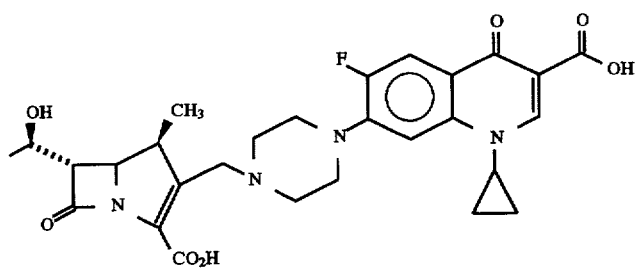
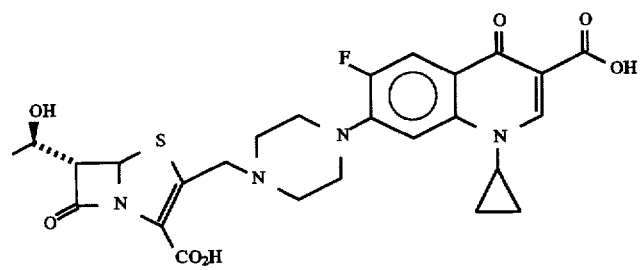
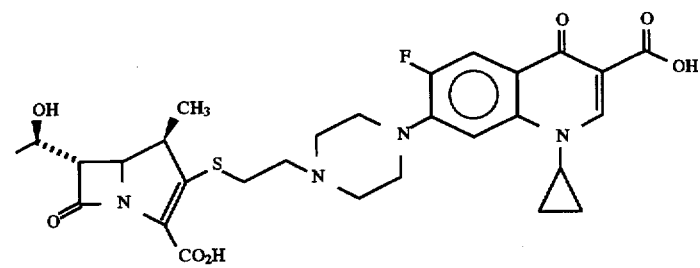
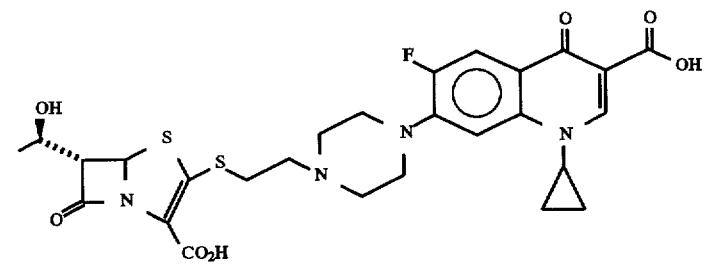
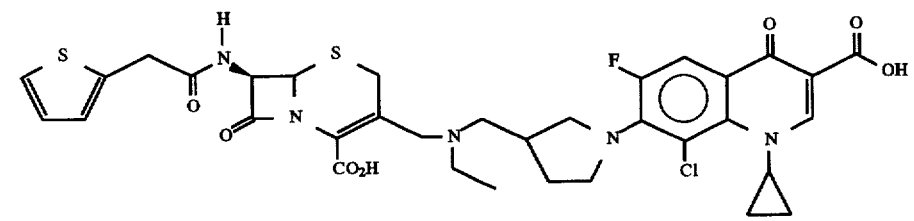
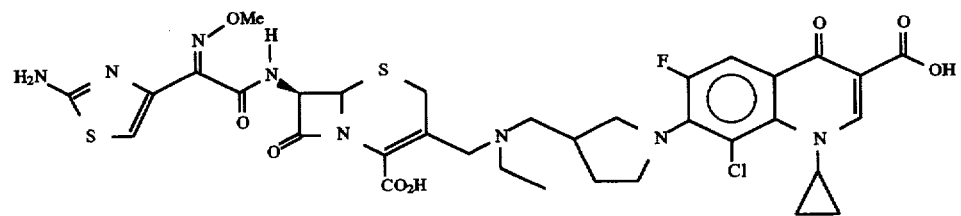

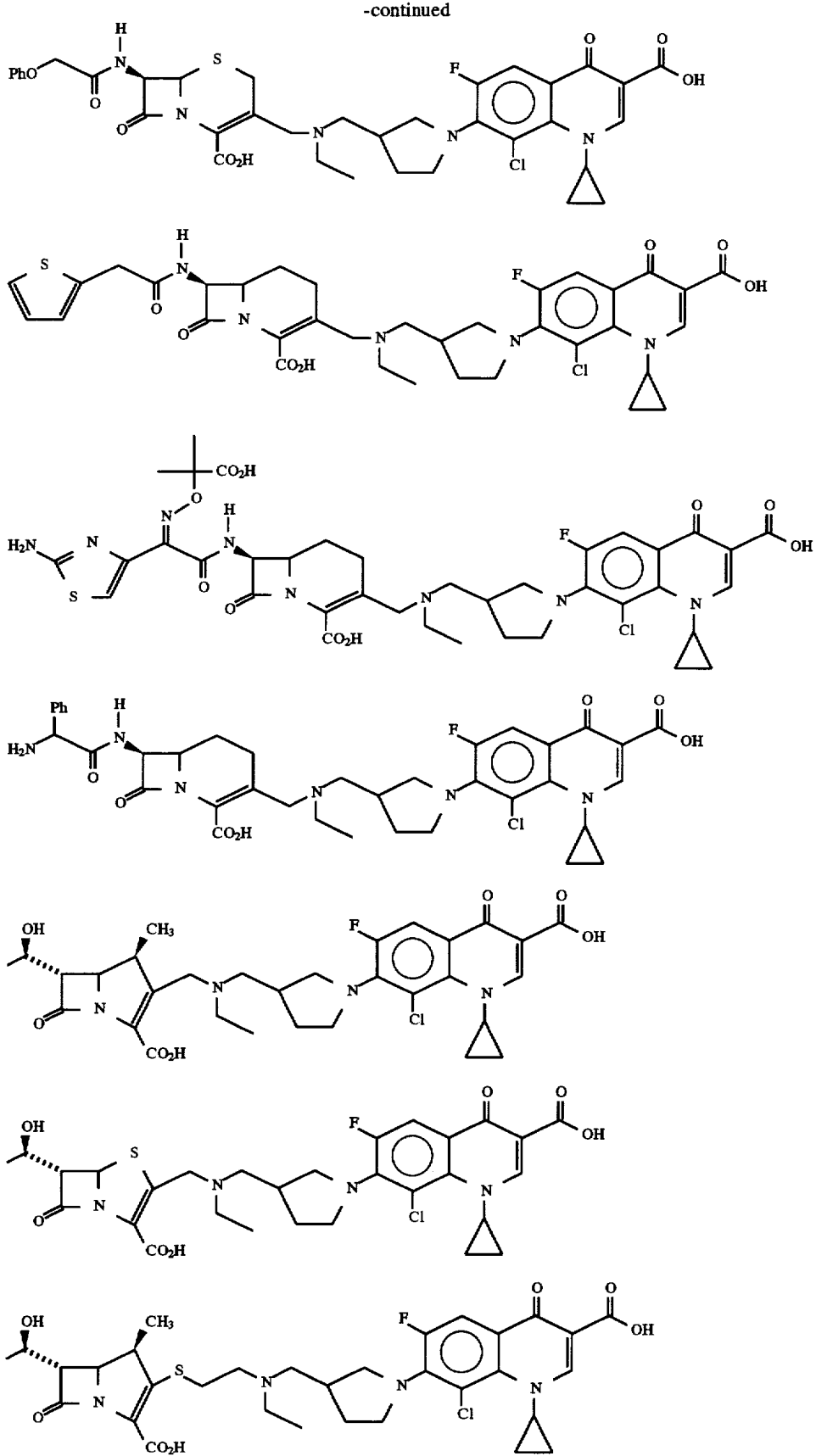

-continued
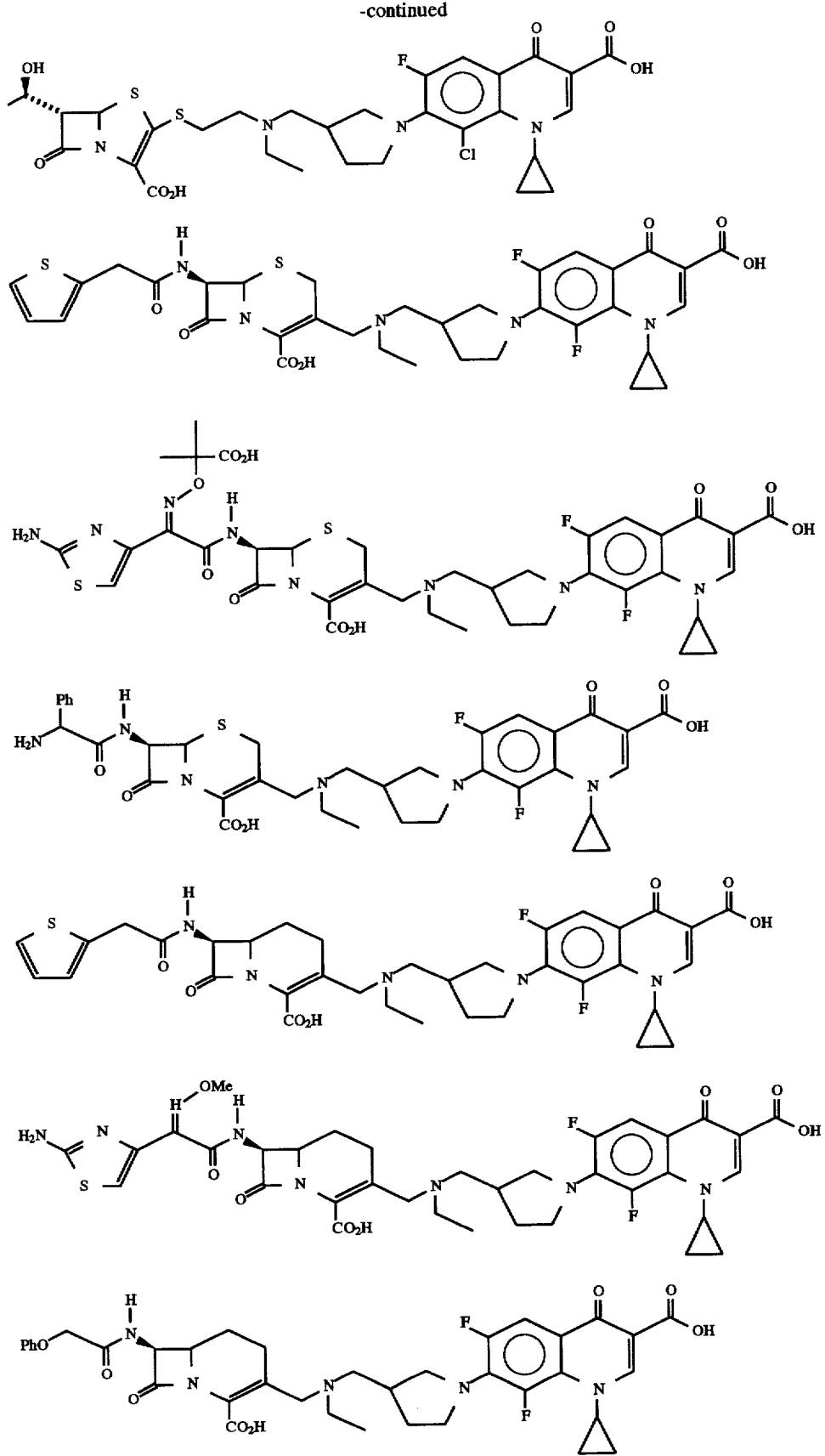

-continued
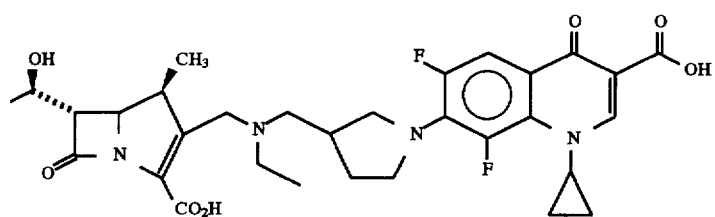
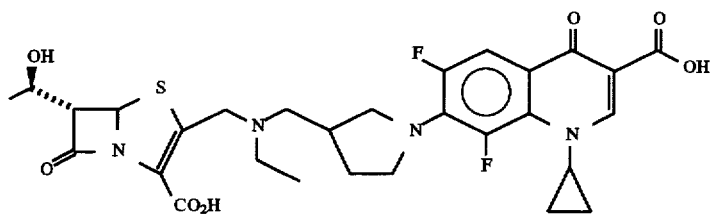
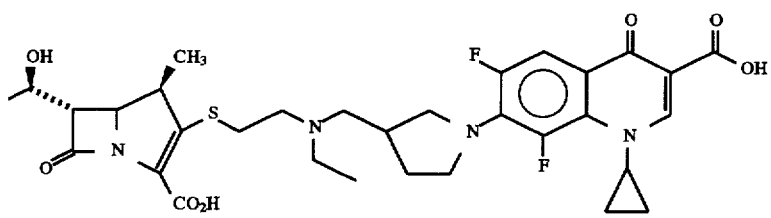
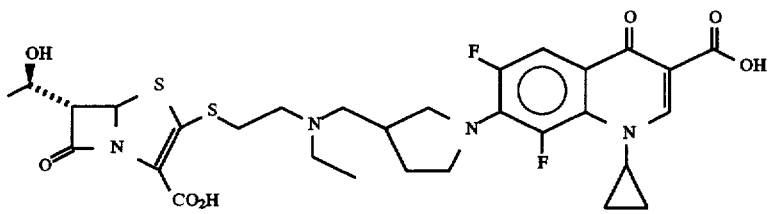
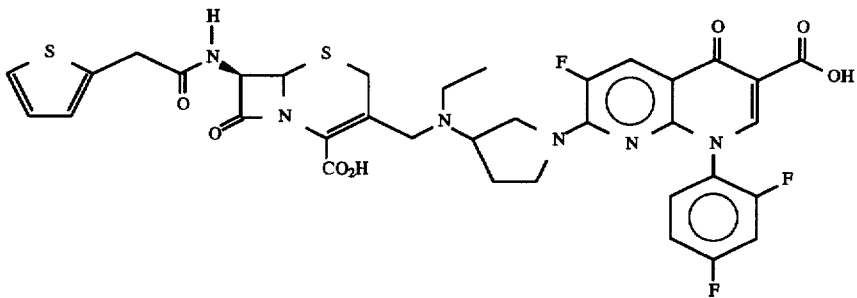
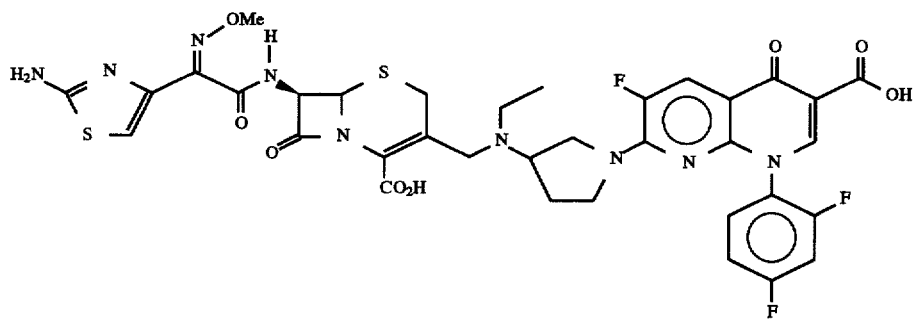

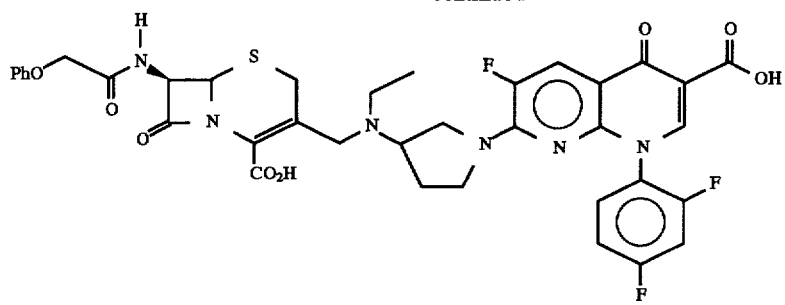
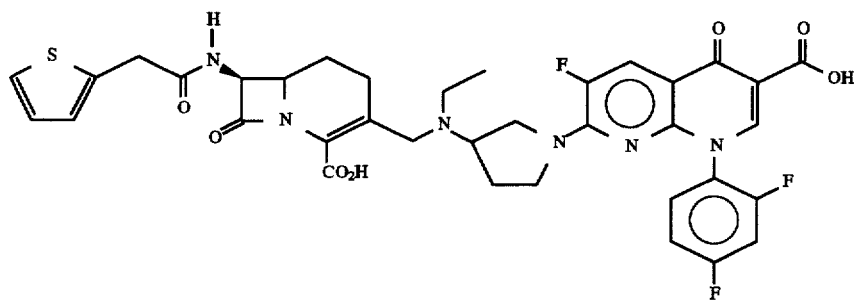
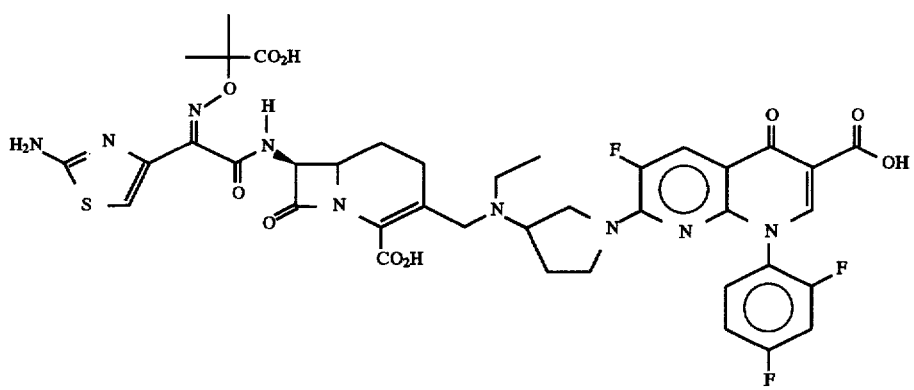
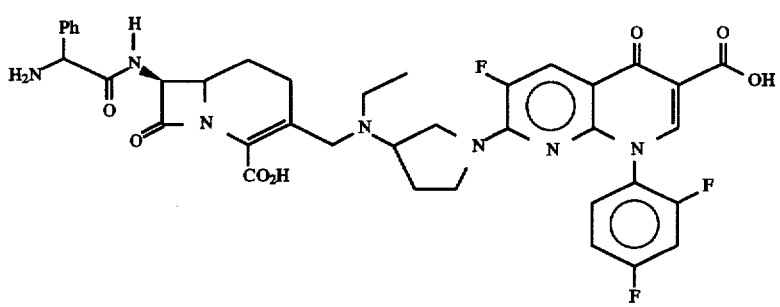
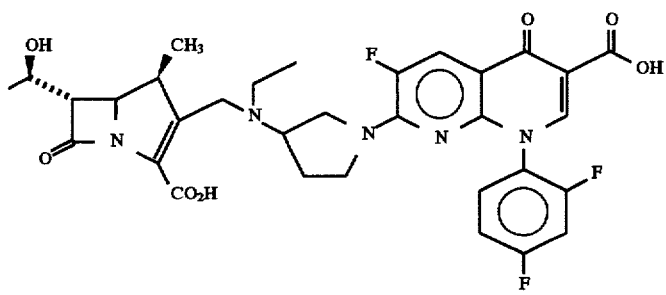

-continued
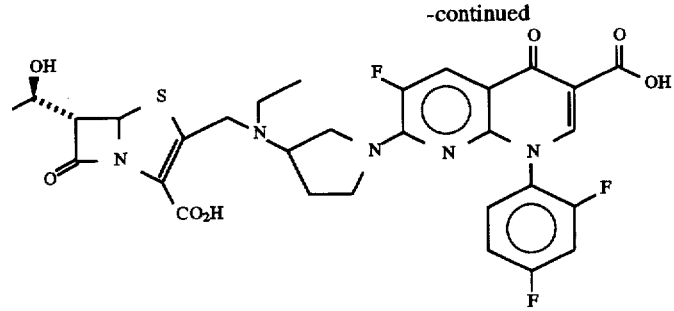
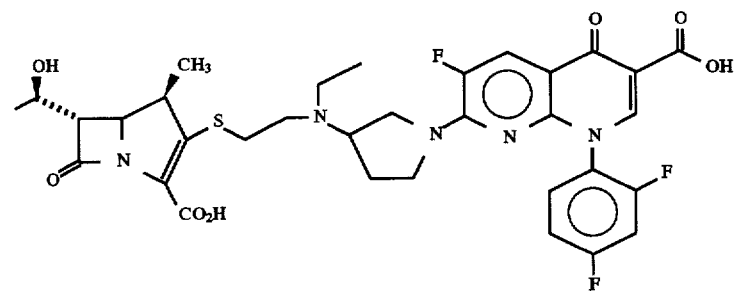
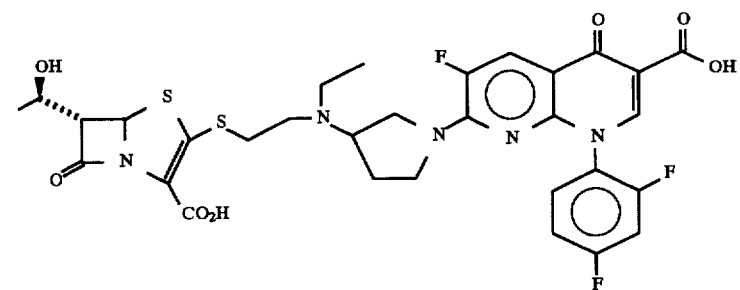
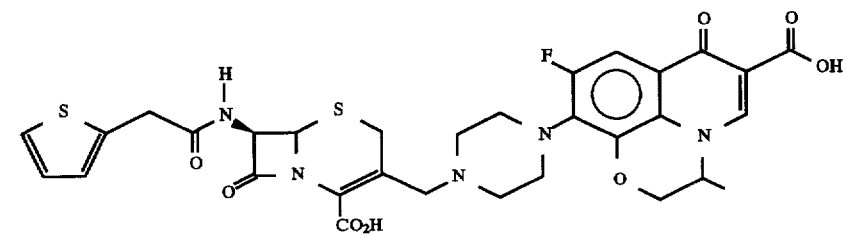
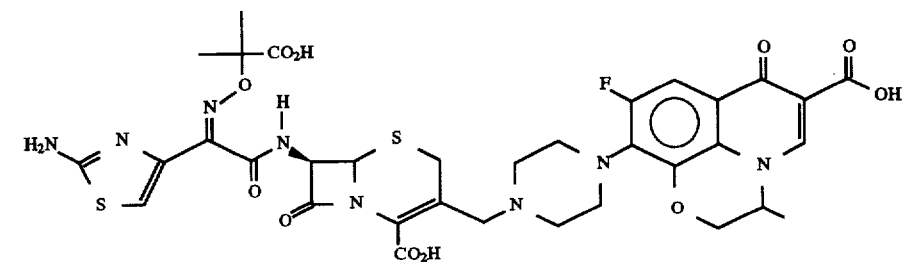
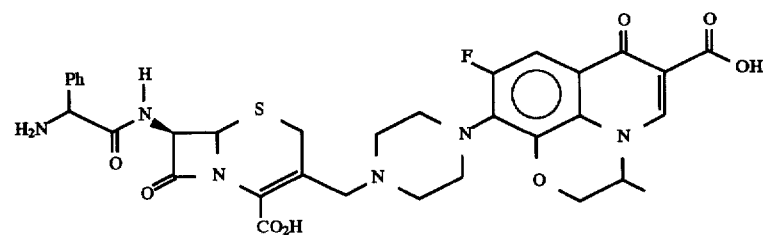

-continued
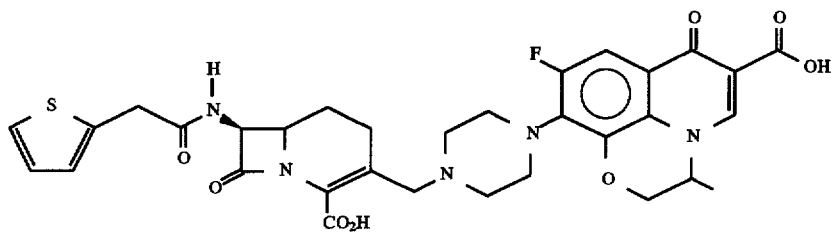
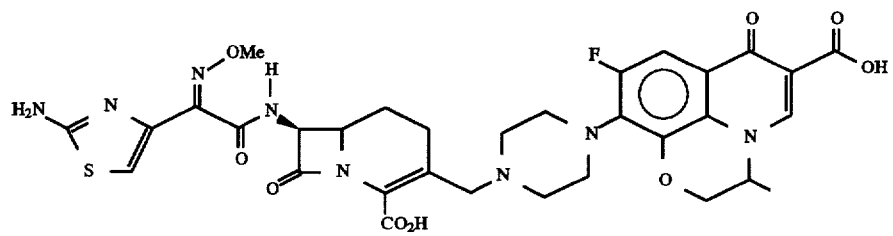
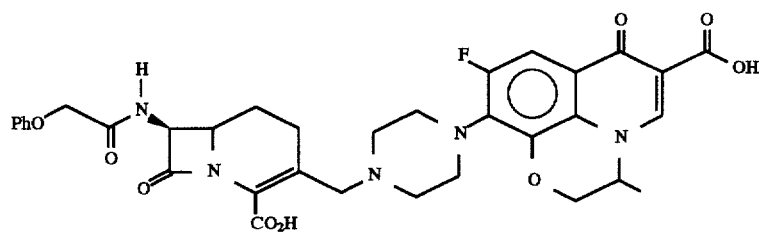
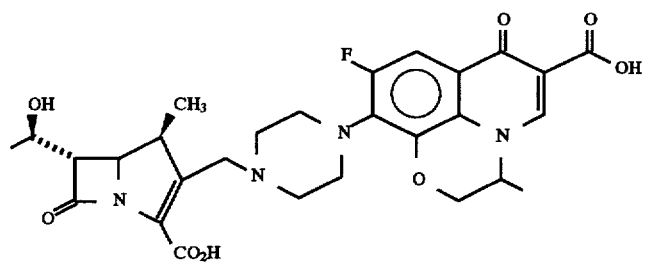
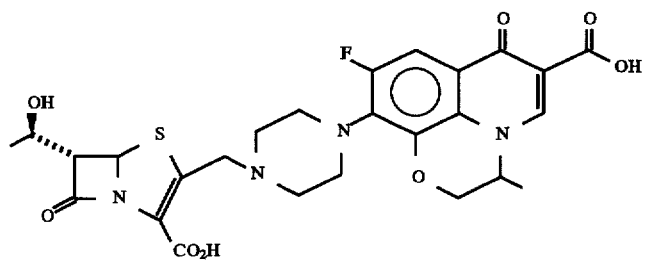
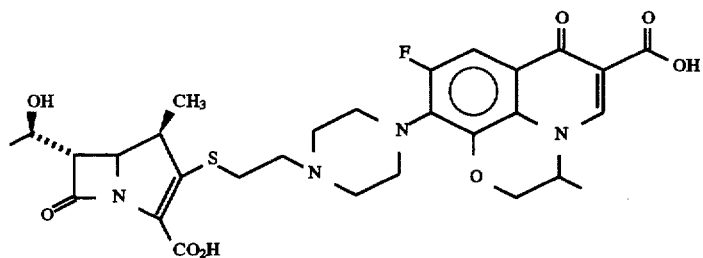

-continued
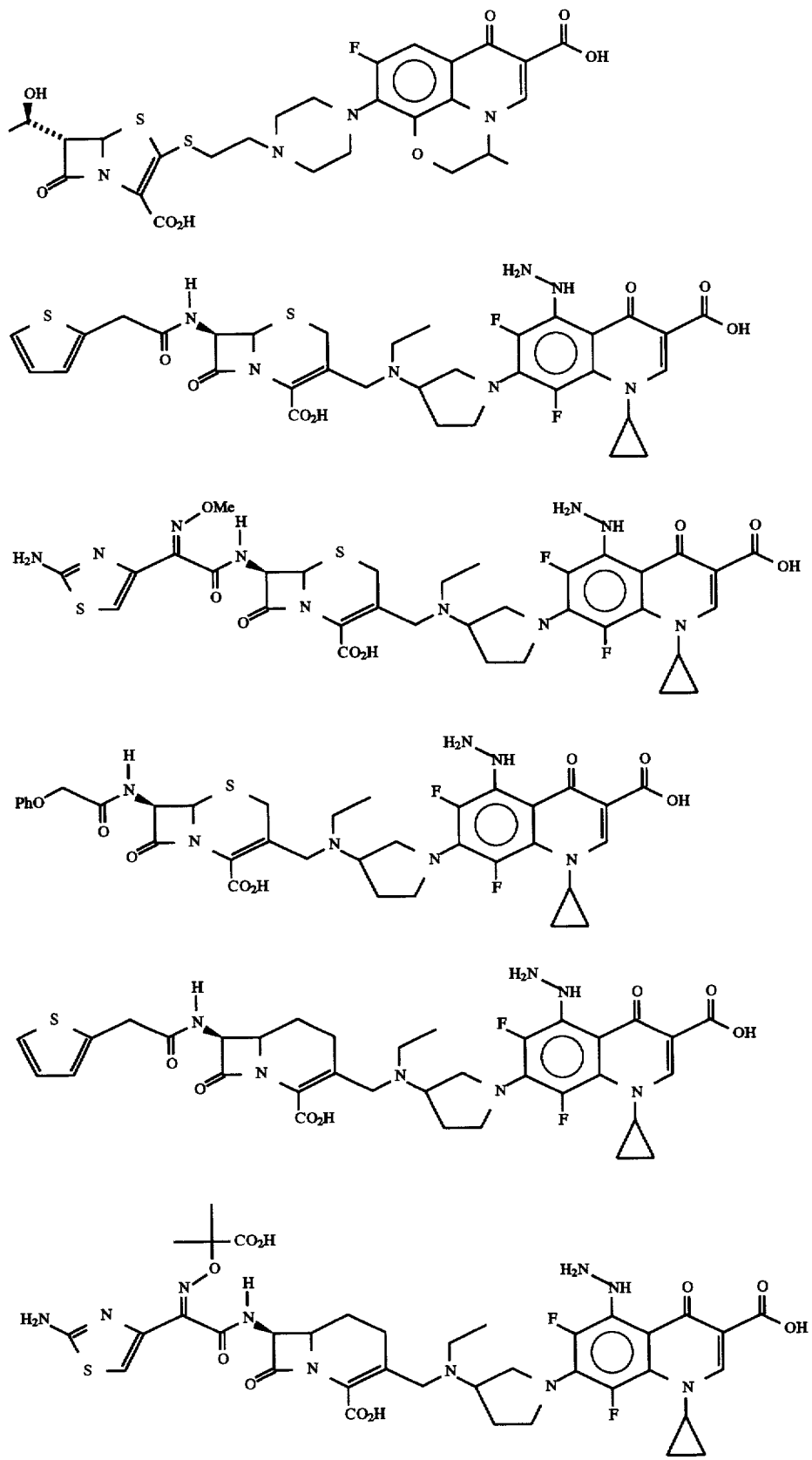

-continued
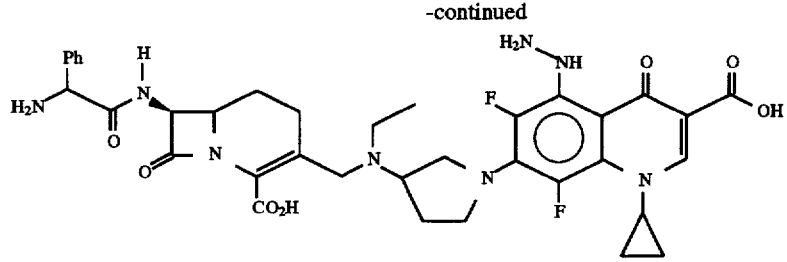
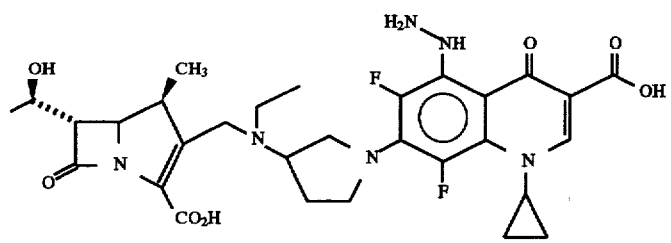
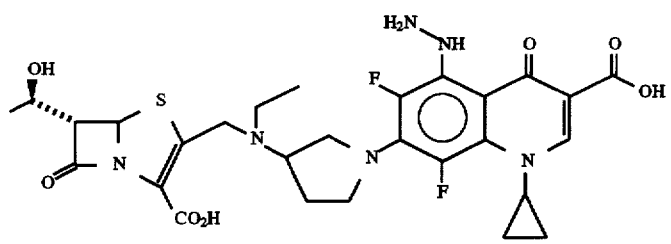
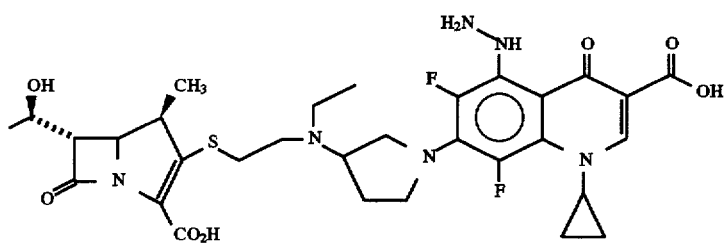
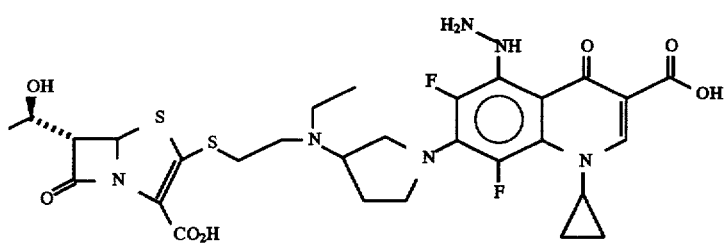
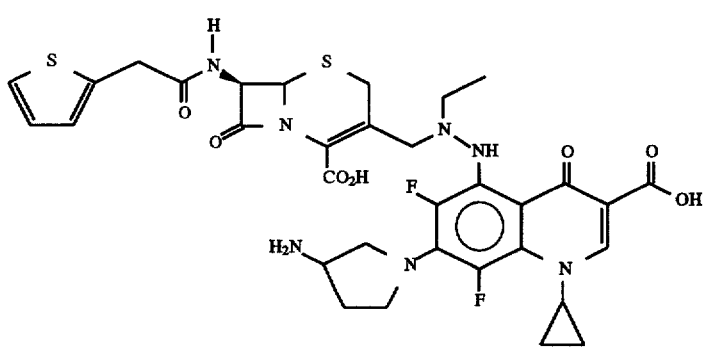

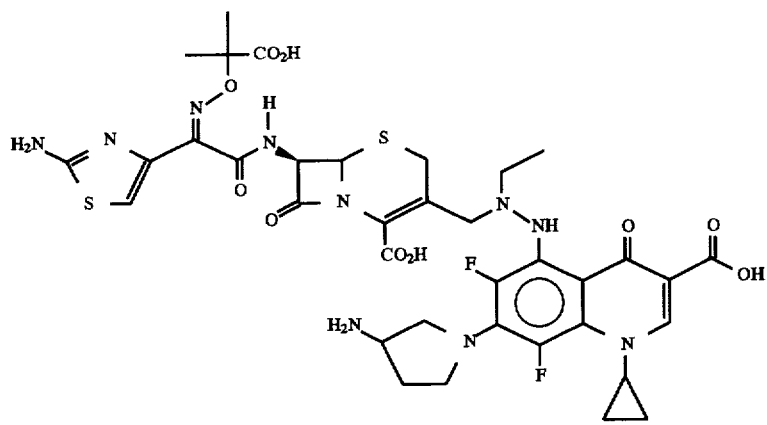
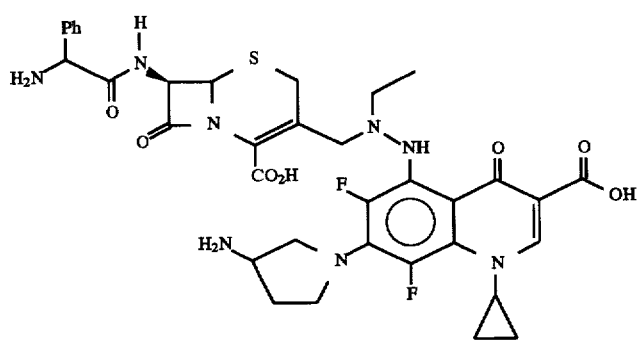
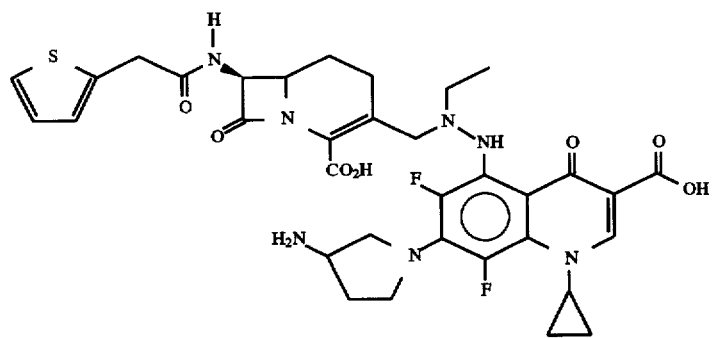
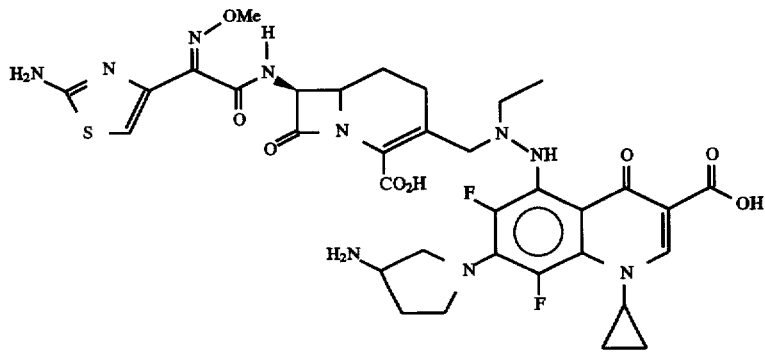

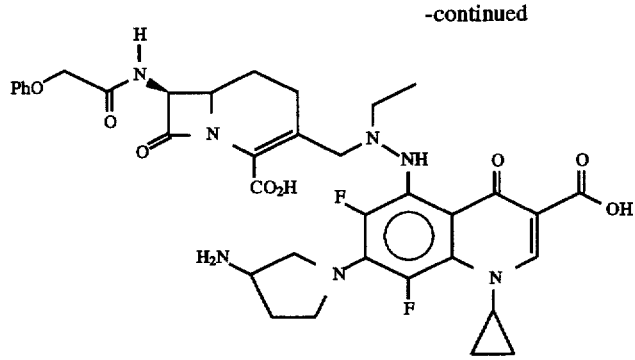
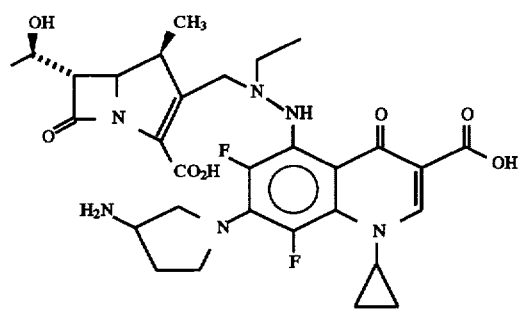
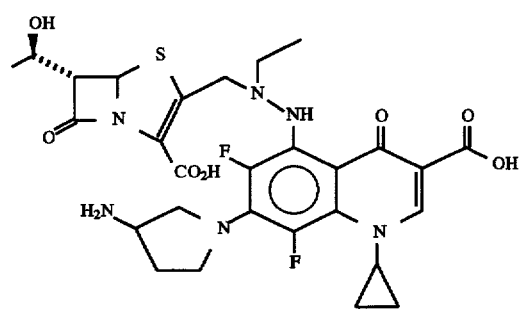
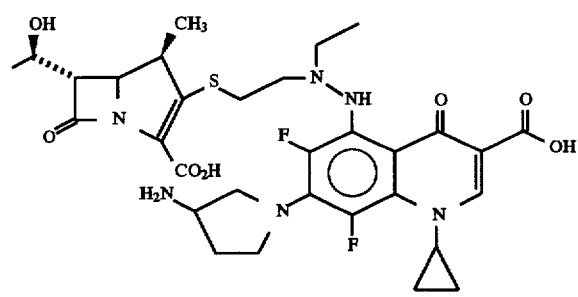
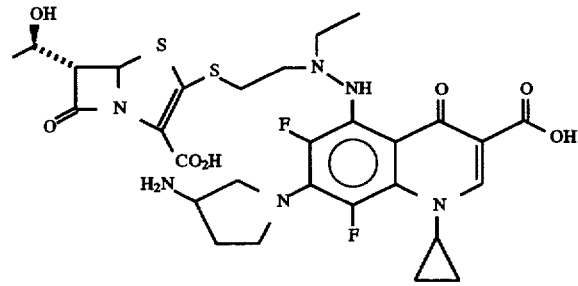
EXAMPLE 24
Synthesis of [4S-[3(R*),4α, 5β,6β(S*)]]-3-[[[1-[3-Carboxy-1-(2,4-difluorophenyl)-6-fluoro-1,4-dihydro-4-oxo-1,8-napthyridine-7-yl]-3-pyrrolidinyl]-amino]methyl]-6-(1-hydroxyethyl)-4-methyl-7-oxo-1-azabicyclo [3.2.0] hept-2-ene-2-carboxylic Acid, Disodium salt.

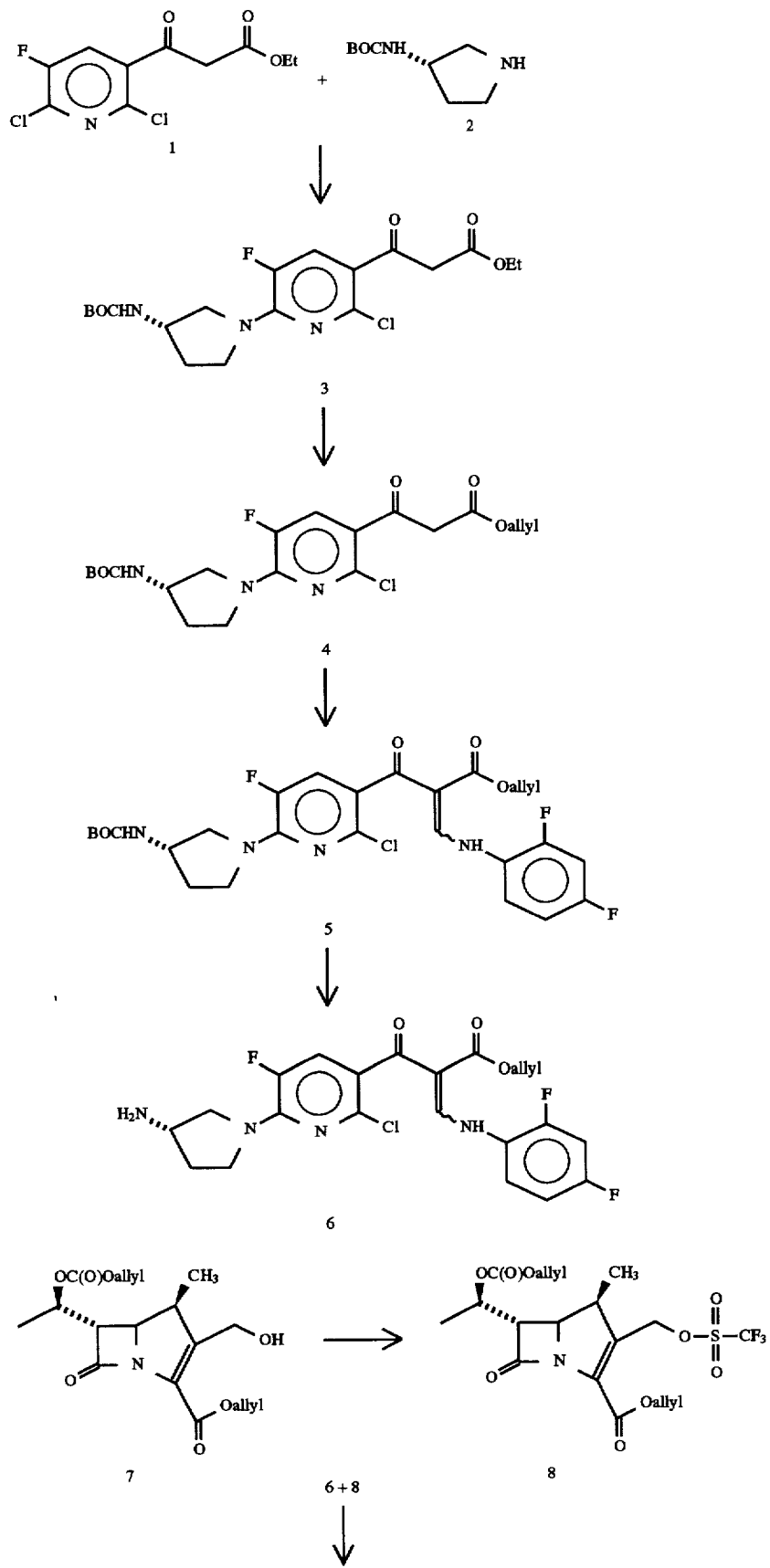

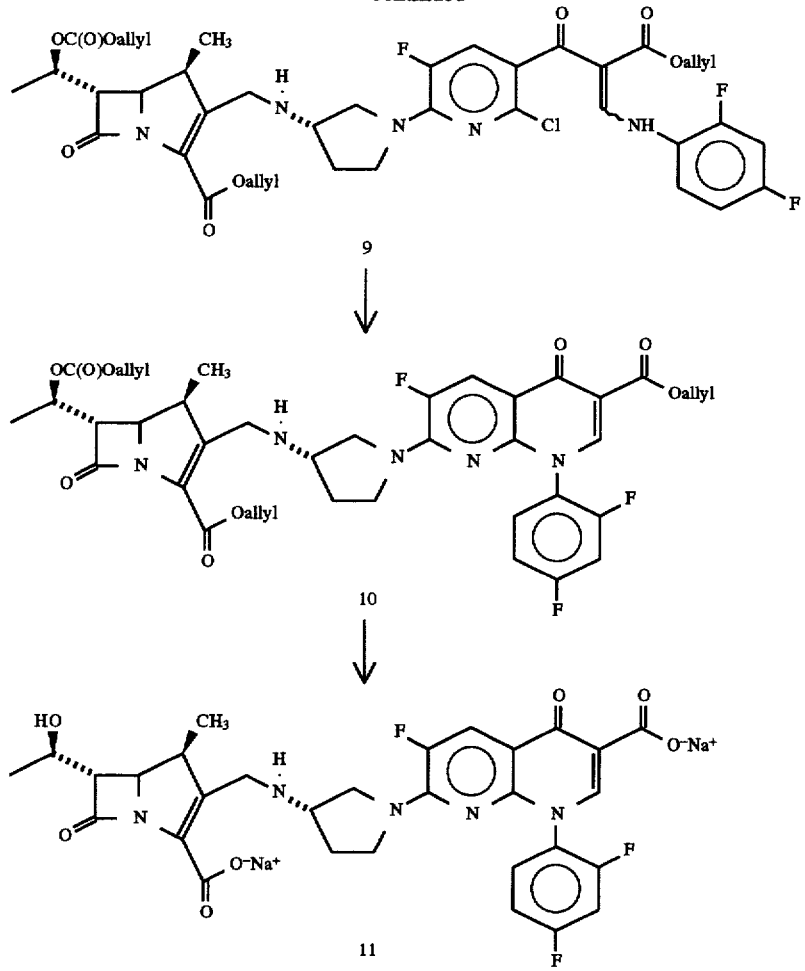

To a solution of Compound 1 (12.5 g) (which is prepared in the same manner as Compound 5 in Example 15 above) in THF (250 mL) is added (S)-(−)-3-(tert-butoxycarbonylamino)pyrrolidine (33.25 g) (Compound 2). The mixture is refluxed under $N_2$ until complete and the THF is removed under reduced pressure. The residue is slurried in EtOAc (125 mL), and the excess pyrrolidine is filtered off and rinsed with EtOAc. The EtOAc filtrate is washed with water (2×125 mL) and the combined aqueous layers are extracted with EtOAc (70 mL). The combined EtOAc layers are dried ($MgSO_4$) and treated with activated charcoal. The solvents are evaporated in vacuo and the residue is crystallized from isopropyl ether to give Compound 3.

To a solution of allyl alcohol (17 mL) in toluene (75 mL) is added 4-dimethylaminopyridine (0.95 g), under $N_2$. Compound 3 (13.1 g) is added and the mixture is heated to reflux. Upon completion, the reaction mixture is cooled and saturated ammonium chloride (125 mL) is added, followed by the addition of EtOAc (150 mL). The layers are separated and the EtOAc portion is washed with water (4×50 mL) and brine (2×40 mL), and dried ($MgSO_4$). The solvents are removed in vacuo and the residue is subjected to column chromatography (silica) to provide Compound 4.

To a solution of Compound 4 (8.65 g) in triethylorthoformate (4.6 mL) is added acetic anhydride (14.6 mL). The mixture is fitted with a Dean-Stark trap and stirred at 130° C. for 1.5 hours under $N_2$. The volatiles removed in vacuo and the residue is dissolved in $CH_2Cl_2$ (30 mL). The solution obtained is cooled to 0° C. and 2,4-difluoroaniline is added (2.4 mL). The reaction is stirred at 0° C. for 5 minutes under $N_2$, allowed to warm to ambient temperature and stirred for 1 hour. The volatiles are removed in vacuo and the residue obtained is subjected to column chromatography (silica) to provide Compound 5.

To a cooled solution of Compound 5 (6.1 g) in anisole (40 mL) at 5°–10° C. is added TFA (40 mL). After stirring for 5 minutes under $N_2$, the ice bath is removed and the reaction is warmed to ambient temperature. After 2 hours, most of the TFA and some of the anisole is removed in vacuo. The residue is slurried in $Et_2O$ (125 mL) and filtered. The solid is dissolved in a mixture of $CH_2Cl_2$ (75 mL) and saturated $NaHCO_3$ (50 mL) and stirred for 10 min. The $CH_2Cl_2$ portion is separated, dried ($MgSO_4$), treated with activated charcoal, and evaporated in vacuo. The residue is crystallized with hexane to give Compound 6.

To a cooled (−78° C.) solution of Compound 7 (3.56 g), prepared as described in Schmitt et al., *J. Antibiot.*, 41, 780–787, 1988. (incorporated by reference herein), in $CH_2Cl_2$ (14 mL) is added diisopropylethylamine (1.54 mL), followed by the dropwise addition of trifluoromethanesulfonic anhydride (1.49 mL). The reaction is stirred at −78° C. for 1.5 hours to provide Compound 8 which is reacted in situ by the dropwise addition of a solution of Compound 6

(4.9 g) and diisopropylethylamine (1.54 mL) in $CH_2Cl_2$ (18 mL). The reaction is stirred at −78° C. until completion, whereupon the cooling bath is removed and water (2 mL) is slowly added. When the temperature reaches −40° C., more water (40 mL) and $CH_2Cl_2$ (150 mL) is added. The mixture is quickly separated and the organic portion is quickly washed successively with cold water (2×50 mL), 10% $NaHCO_3$ (3×50 mL) and water (50 mL). The organic portion is dried ($Na_2SO_4$) and the volatiles are removed in vacuo. The residue obtained is subjected to column chromatography (silica) to obtain Compound 9.

To a solution of Compound 9 (4.1 g) in $CH_3CN$ (55 mL) is added N,O-bis(trimethylsilyl)acetamide (3.35 mL). The reaction mixture is stirred under $N_2$ at ambient temperature until complete. The reaction is quenched with water (55 mL), and the resulting slurry is filtered and washed with a mixture of water and $CH_3CN$ (5:1) giving Compound 10.

To a solution of Compound 10 (3.3 g) in $CH_2Cl_2$ (160 mL) is added tetrakis(triphenylphosphine)palladium (0) (433 mg), under $N_2$. The mixture is cooled (−10 to −5° C.) and a cooled solution (<−10° C.) of sodium ethylhexanoate (1.25 g) in THF (80 mL) is added dropwise. The mixture is stirred for approximately 30 minutes, whereupon the resulting slurry is filtered and washed successively with $CH_2Cl_2$ and acetone to provide [4S-[3(R*),4α,5β,6β(S*)]]-3-[[[1-[3-Carboxy-1-(2,4-difluorophenyl)-6-fluoro-1,4-dihydro-4-oxo-1,8-napthyridine-7-yl]-3-pyrrolidinyl]-amino]methyl]-6-(1-hydroxy-ethyl)-4-methyl-7-oxo-1-azabicyclo[3.2.0]hept-2-ene-2-carboxylic Acid, Disodium salt (Compound 11).

EXAMPLE 25

Synthesis of [6R-[3(S*),6α,7β]]-3-[[[1-[3-Carboxy-1-(1,1-dimethylethyl)-6-fluoro-1,4-dihydro-4-oxo-1,8-napthyridin-7-yl]-3-pyrrolidinyl]amino]methyl]-8-oxo-7-[(2-thienylacetyl)amino]-5-thia-1-azabicyclo[4.2.0]oct-2-ene-2-carboxylic Acid

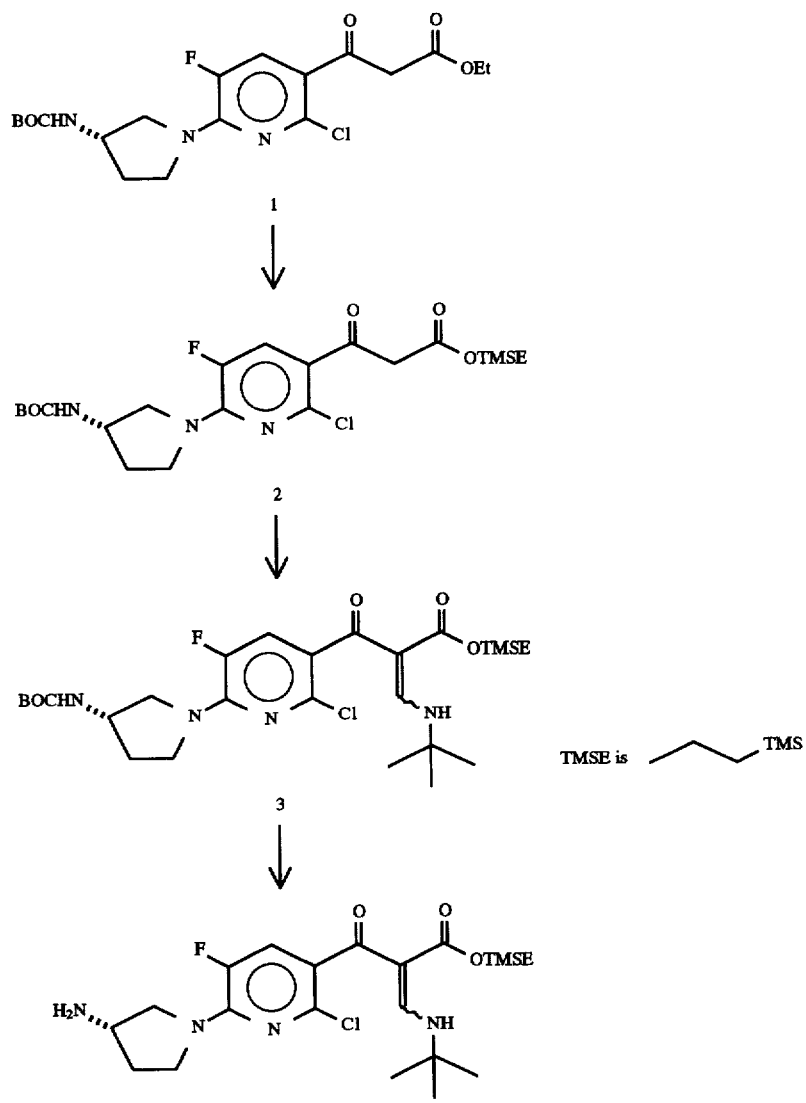

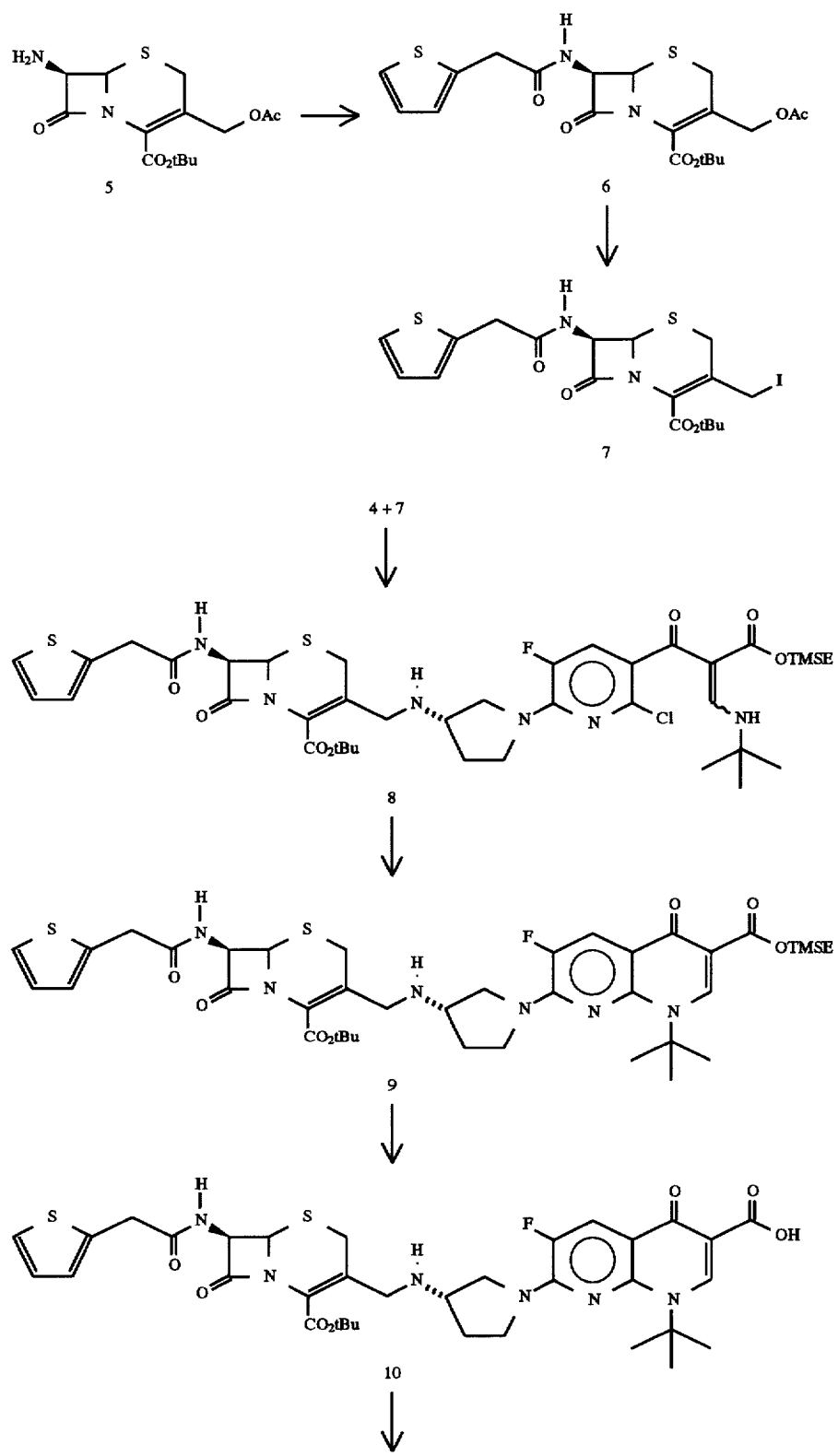

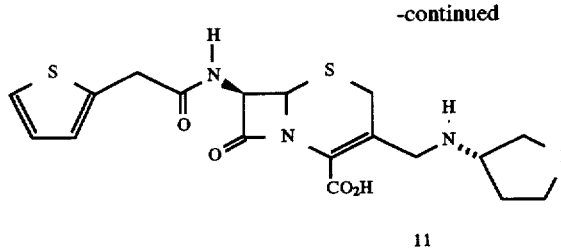
11

To a solution of 2-(trimethylsilyl)ethanol (33 mL) in toluene (80 mL) is added 4-dimethylaminopyridine (0.82 g), under $N_2$. Compound 1 (11.4 g) (prepared in the same manner as Compound 3 in Example 24) is added and the mixture is heated to reflux. Upon completion, the reaction mixture is cooled and saturated ammonium chloride (125 mL) is added, followed by the addition of EtOAc (150 mL). The layers are separated and the EtOAc portion is washed with water (4×50 mL) and brine (2×40 mL), and dried ($MgSO_4$). The solvents are removed in vacuo and the residue is subjected to column chromatography (silica) to provide Compound 2.

To a solution of Compound 2 (10.2 g) in triethylorthoformate (4.8 mL) is added acetic anhydride (15.4 mL). The mixture is fitted with a Dean-Stark trap and stirred at 130° C. for 1.5 hours under $N_2$. The volatiles removed in vacuo and the residue is dissolved in $CH_2Cl_2$ (35 mL). The solution obtained is cooled to 0° C. and tert-butylamine is added (2.6 mL). The reaction is stirred at 0° C. for 5 minutes under $N_2$, allowed to warm to ambient temperature and stirred for 1 hour. The volatiles are removed in vacuo and the residue obtained is subjected to column chromatography (silica) to provide Compound 3.

To a cooled solution of Compound 3 (9.8 g) in anisole (60 mL) at 5°–10° C. is added TFA (60 mL). After stirring for 5 minutes under $N_2$, the ice bath is removed and the reaction is warmed to ambient temperature. After 2 hours, most of the TFA and some of the anisole is removed in vacuo. The residue is slurried in $Et_2O$ (175 mL) and filtered. The solid is dissolved in a mixture of $CH_2Cl_2$ (110 mL) and saturated $NaHCO_3$ (75 mL) and stirred for 10 min. The $CH_2Cl_2$ portion is separated, dried ($MgSO_4$), treated with activated charcoal, and evaporated in vacuo. The residue is crystallized with hexane to give Compound 4.

To a cooled (0° C.) solution of tert-butyl 7-aminocephalosporanate (30 g) (Compound 5), prepared as described in R. J. Stealman, 9 *J. Med. Chem.* 444 (1966), which is incorporated by reference herein, in THF (1.5L) is added a solution of sodium bicarbonate (12.93 g) in water (1.5 L). To this mixture is added a solution of 2-thiopheneacetyl chloride (13.1 mL). The ice bath is removed and the reaction is stirred at room temperature until complete. The volatiles are removed in vacuo until an aqueous mixture is obtained. This mixture is extracted with EtOAc (4×500 mL) and the combined EtOAc layers are dried ($MgSO_4$). The EtOAc is removed in vacuo until approximately 200 mL of EtOAc remains. Hexane is added to this solution, until a precipitate begins to form. The mixture is then cooled to −20° C. and held at this temperature for 16 hours. The resulting slurry is filtered and washed with hexanes to provide Compound 6.

To a solution of Compound 6 (10 g) in $CH_2Cl_2$ (150 mL) is slowly added iodotrimethylsilane (3.5 mL), under $N_2$. After stirring for 30 minutes, additional iodotrimethylsilane (1.85 mL) is added and stirring is continued for 30 minutes more. The reaction is quenched by slowly adding a cold 5% solution of sodium thiosulfate (50 mL). The $CH_2Cl_2$ portion is washed with a cold 5% solution of sodium thiosulfate (50 mL), a cold solution of 5% $NaHCO_3$ (50 mL), cold water (50 mL) and brine (2×50 mL). The $CH_2Cl_2$ solution is dried and the volatiles are removed in vacuo until about one third of the solvent remains. The resulting solution is cooled and product crystallized by the addition of hexanes to provide Compound 7.

To a cooled (−40° C.) solution of Compound 4 (2.26 g) in DMF (13 mL) and $CH_2Cl_2$ (13 mL) is added diisopropylethylamine (0.71 mL), under $N_2$. After stirring for 30 minutes, a solution of Compound 7 (2.1 g) in DMF (13 mL) and $CH_2Cl_2$ (13 mL) is slowly added. The mixture is stirred for 1 hour at -40° C. and then stirred at 0° C. for 1 hour, and allowed to warm to ambient temperature. Upon completion, the reaction is diluted with $CH_2Cl_2$ (100 mL) and washed with cold 1M HCl (2×80 mL) and cold brine (2×80 mL). The organic portion is separated and the solvents are removed in vacuo to provide a residue that is subjected to column chromatography (silica) to provide Compound 8.

To a solution of Compound 8 (3.45 g) in $CH_3CN$ (40 mL) is added N,O-bis(trimethylsilyl)acetamide (3.56 mL). The reaction mixture is stirred under $N_2$ at ambient temperature until complete. The reaction is quenched with water (40 mL), and the resulting slurry is filtered and washed with a mixture of water and $CH_3CN$ (5: 1) to provide Compound 9.

To a cooled (0° C.) solution of Compound 9 (2.7 g) in THF (50 mL) is added a solution of tetra-n-butyl ammonium fluoride (10.4 mL of a 1M solution in THF), under $N_2$. The mixture is stirred at 0° C. for 30 minutes and then warmed to ambient temperature. Upon completion, hexamethyldisiloxane (2.27 mL) is added and the mixture is stirred for an additional 30 minutes. The volatiles are removed in vacuo to provide a residue which is crystallized by the addition of ether to provide Compound 10.

To a cooled (−15° C.) solution of Compound 10 (1.6 g) and triethylsilane 0.22 mL) in $CH_2Cl_2$ (30 mL) is slowly added trifluoroacetic acid (33 mL), under $N_2$. After 30 minutes at −15° C., the mixture is allowed to warm to ambient temperature. Upon completion, the mixture is cooled to 0° C. and is crystallized by the addition of cold ether to provide Compound 11.

The following compounds are prepared according to Examples 24 and 25, with substantially similar results.

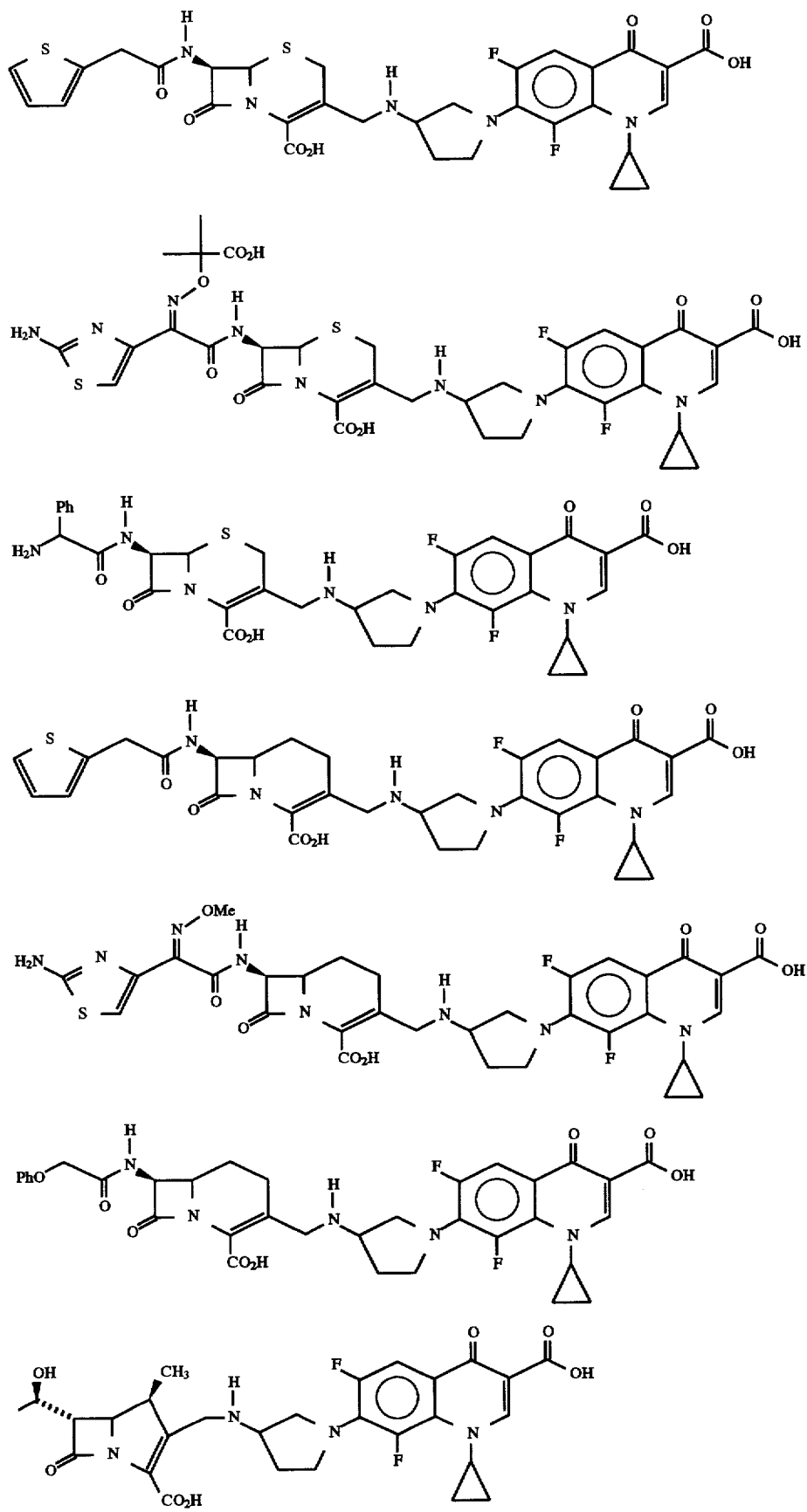

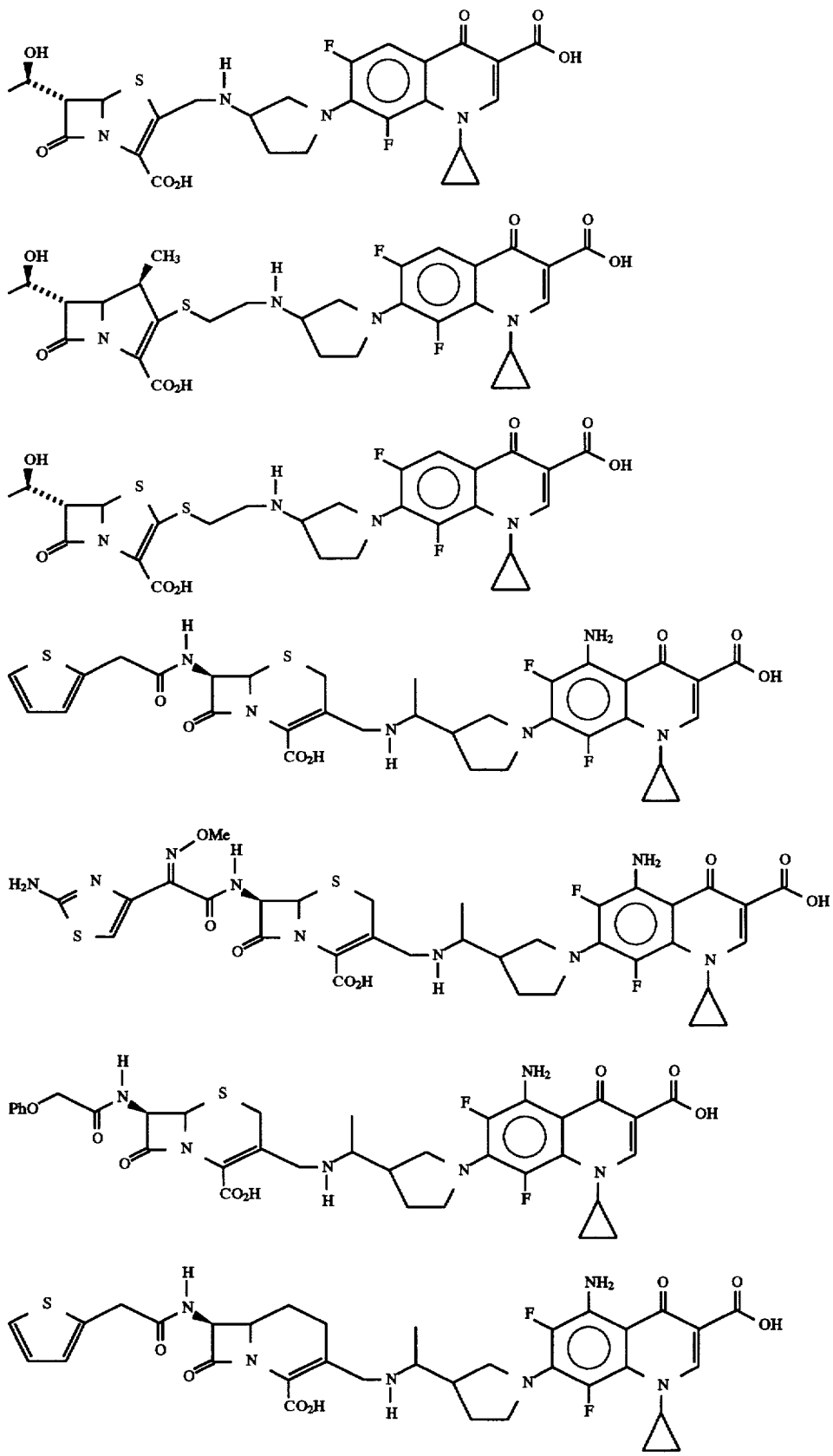

-continued
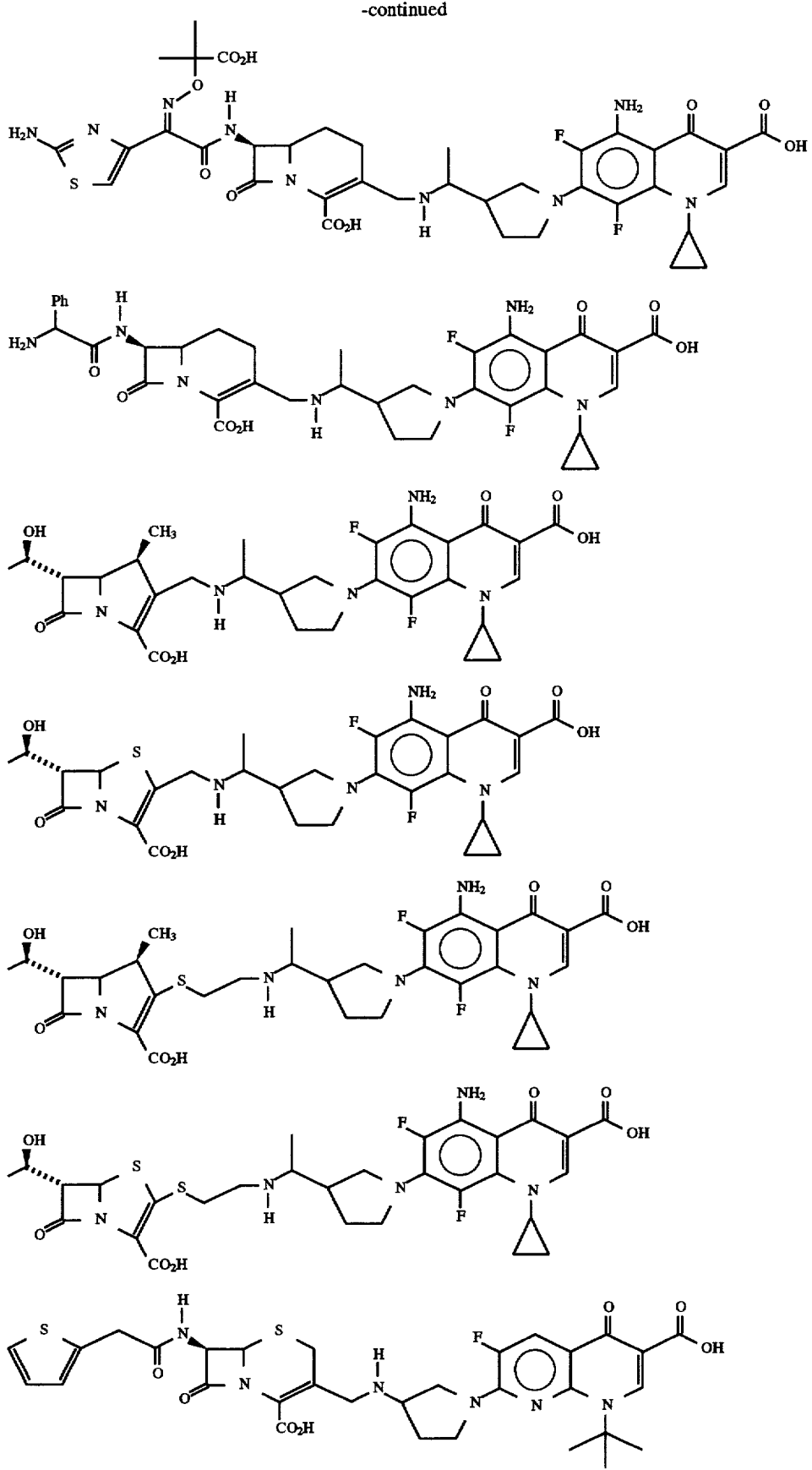

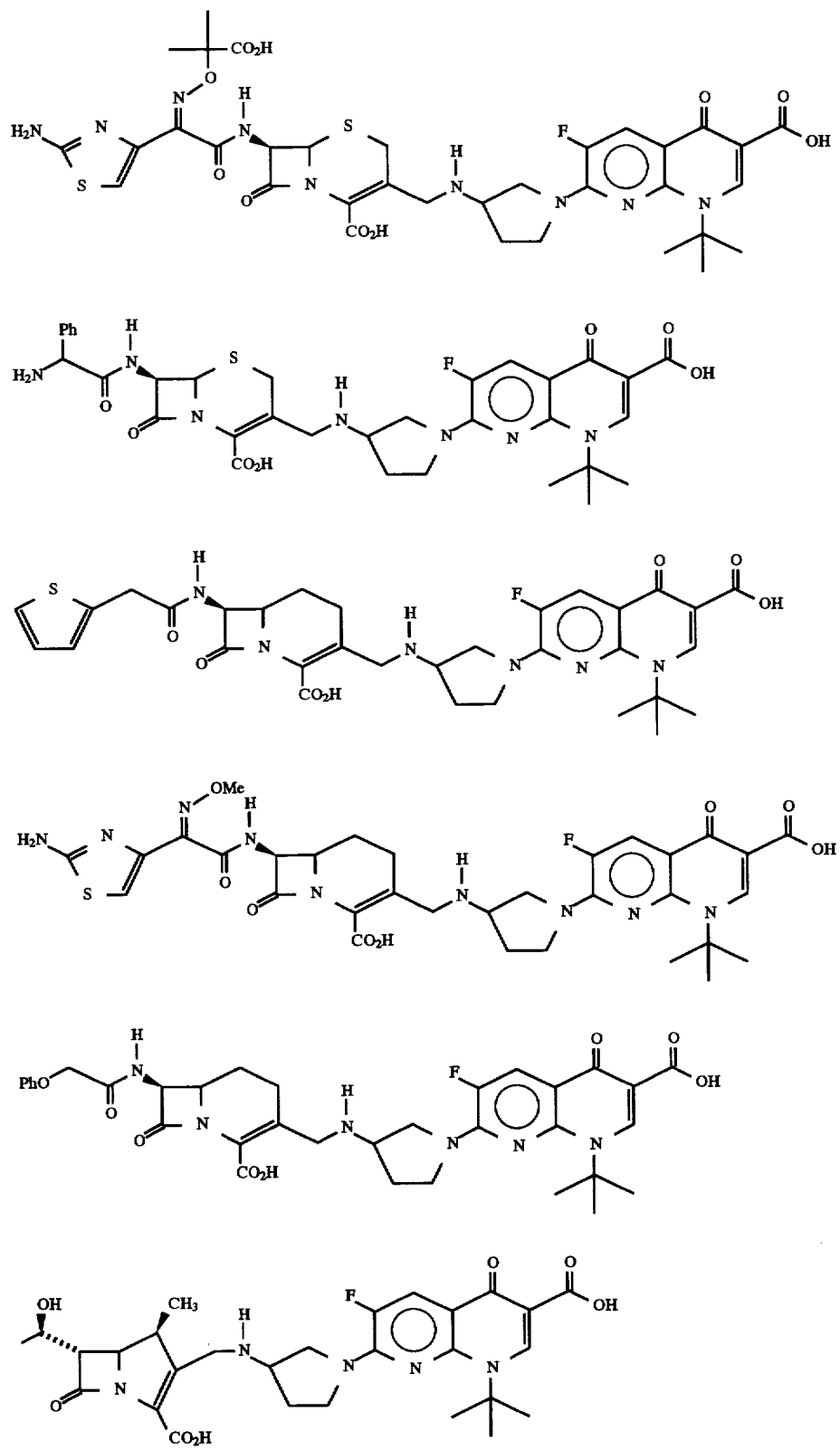

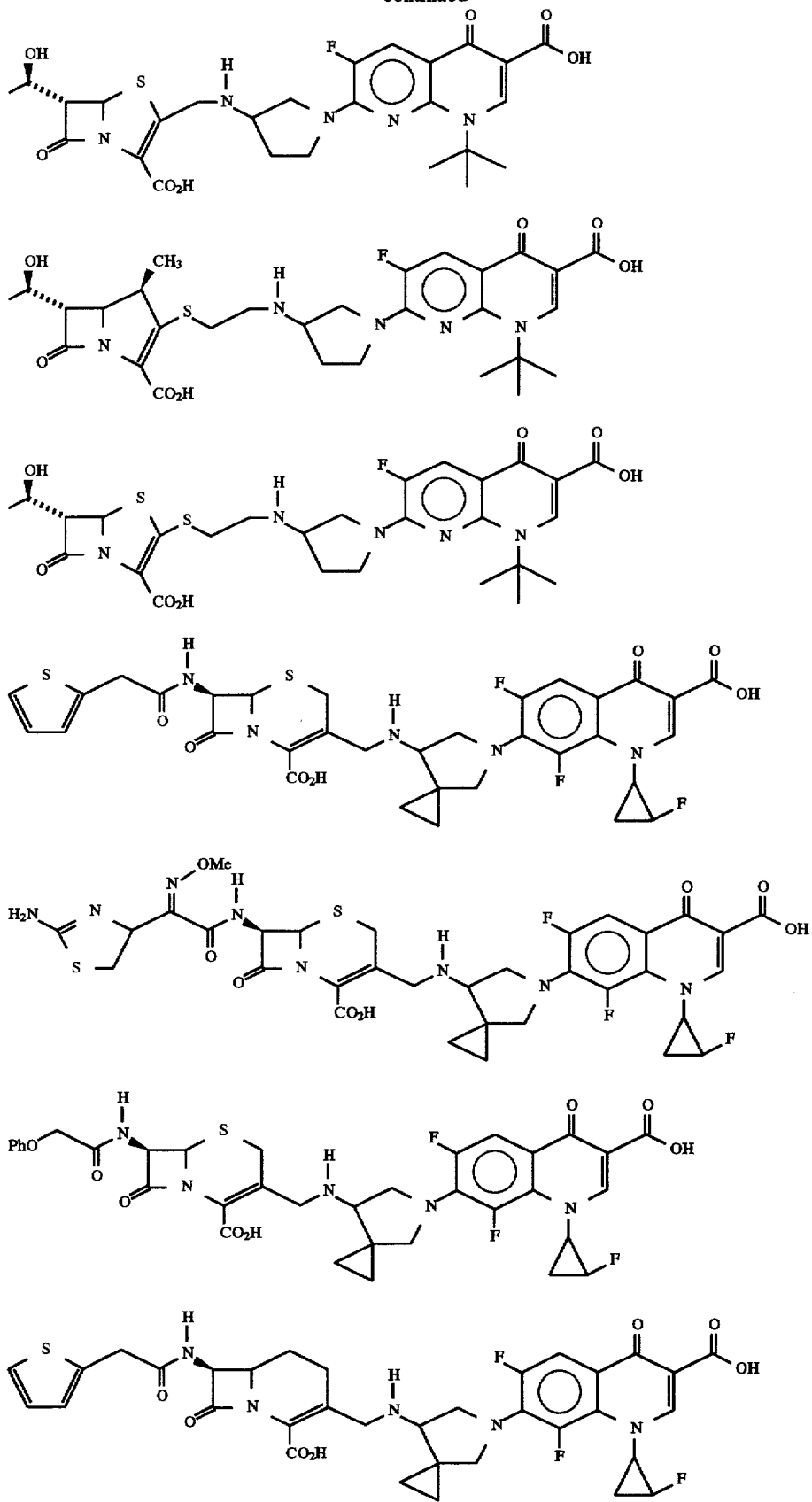

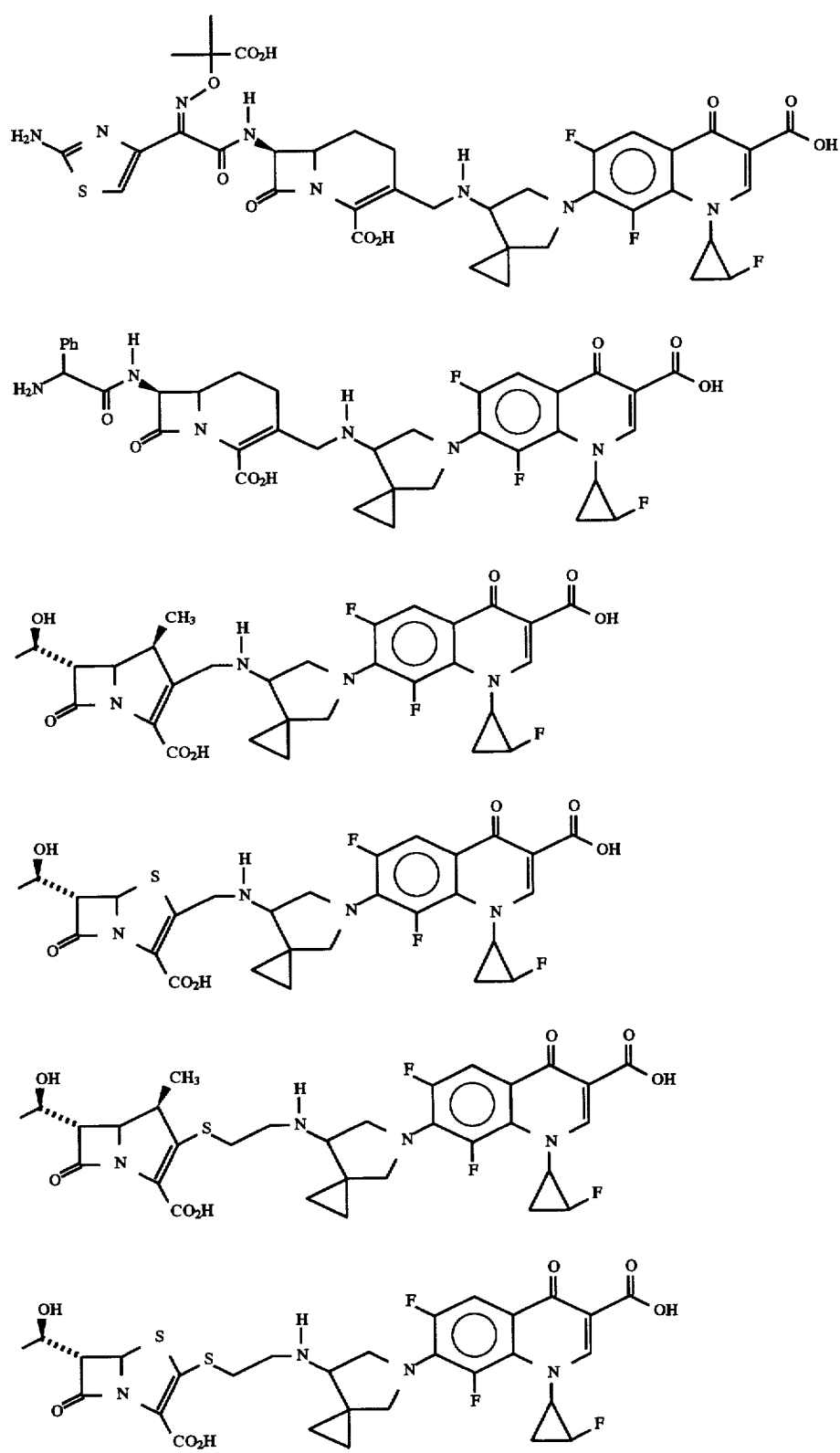

-continued
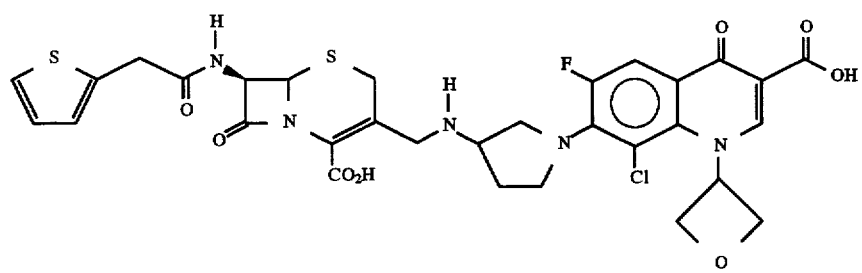
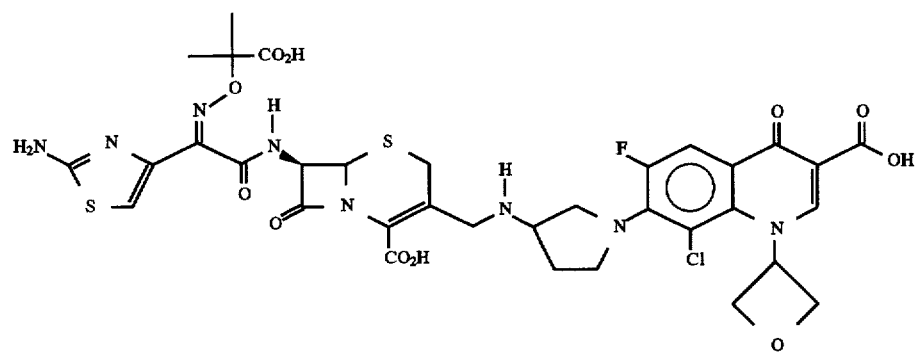
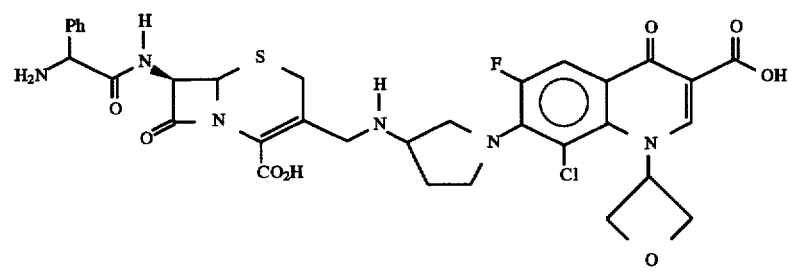
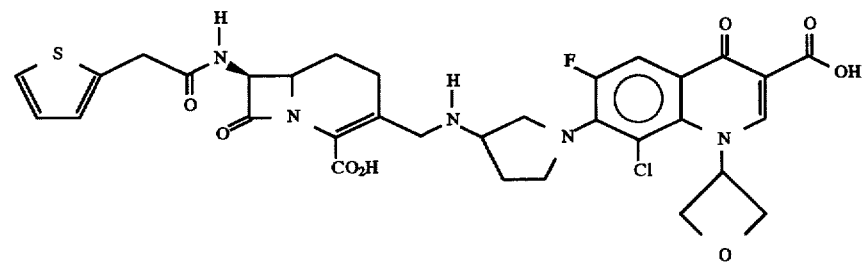
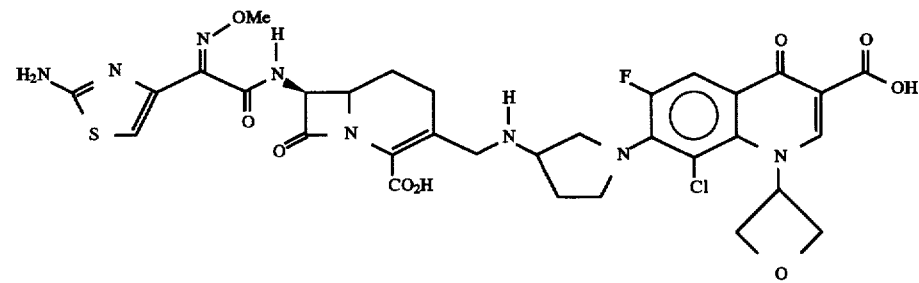

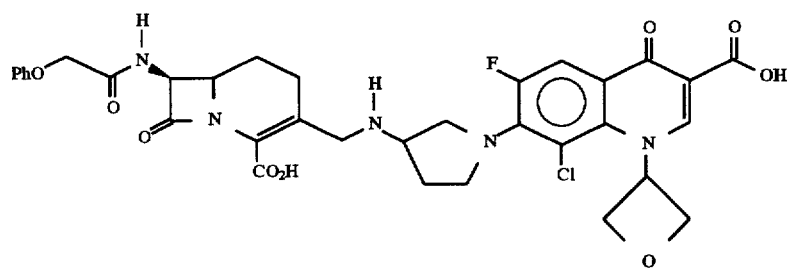
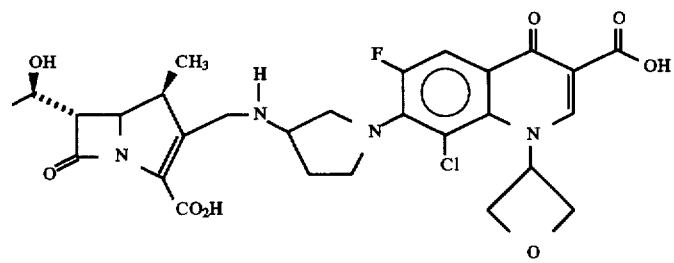
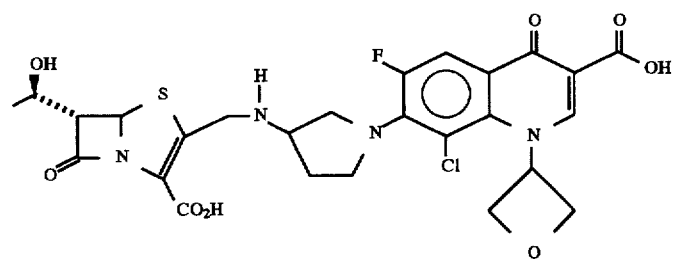
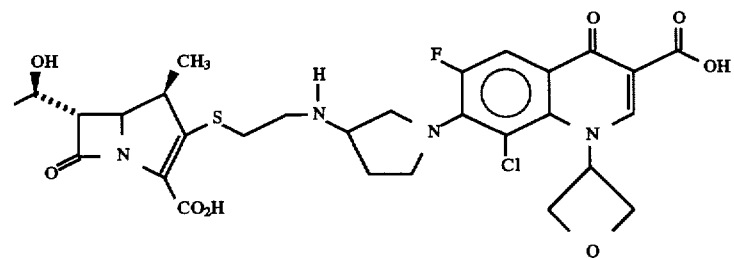
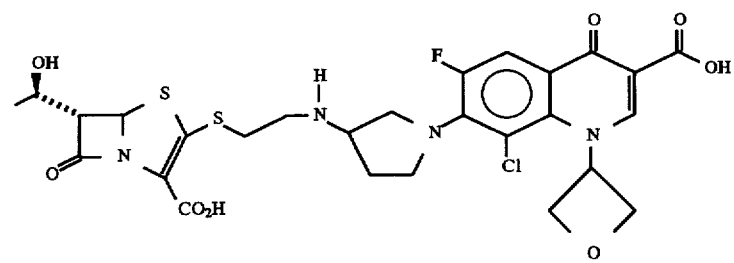
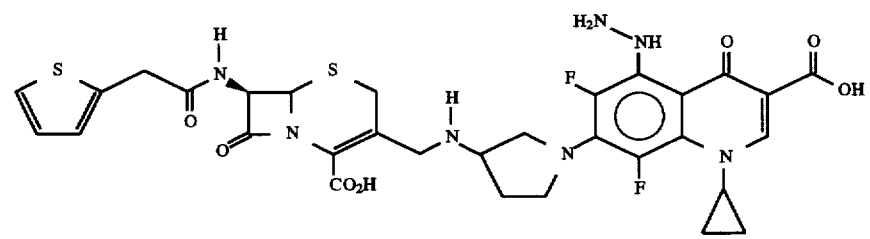

-continued
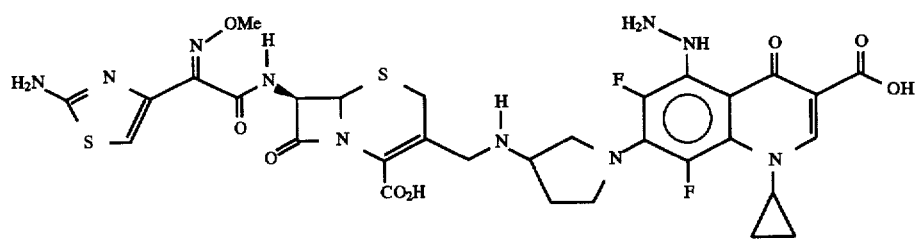
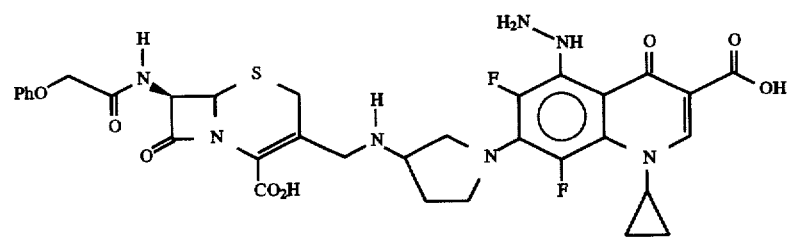
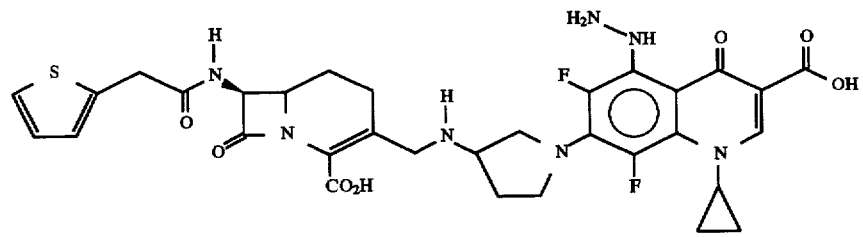
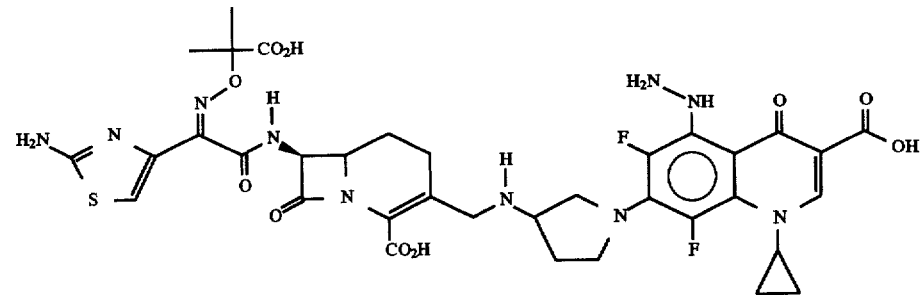
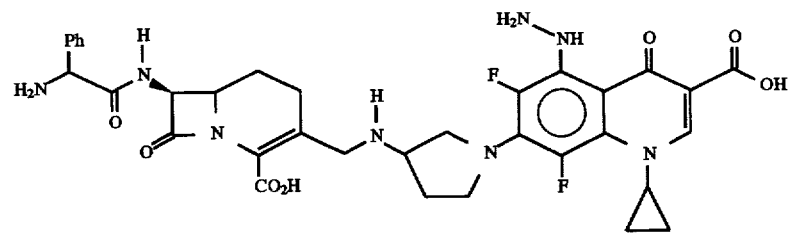
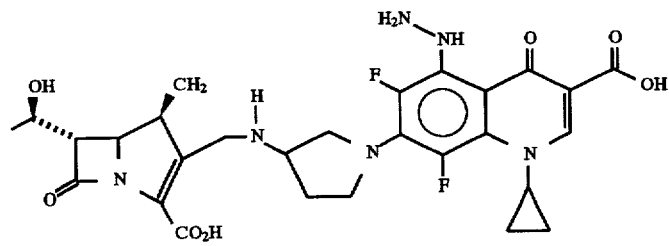

-continued
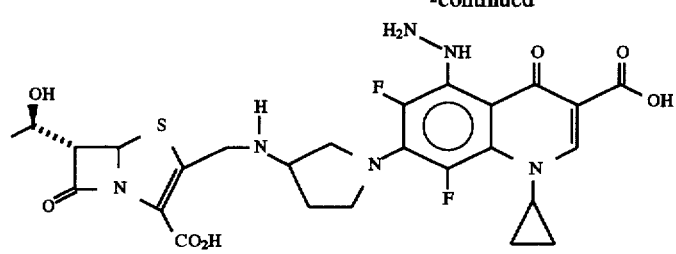
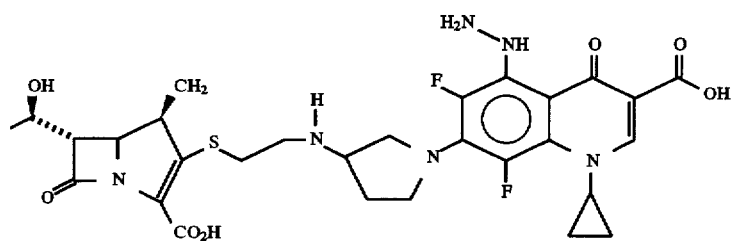
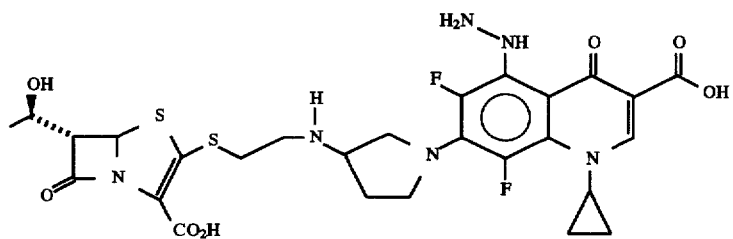
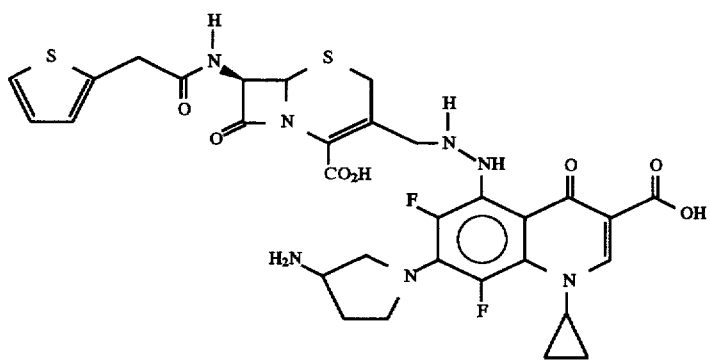
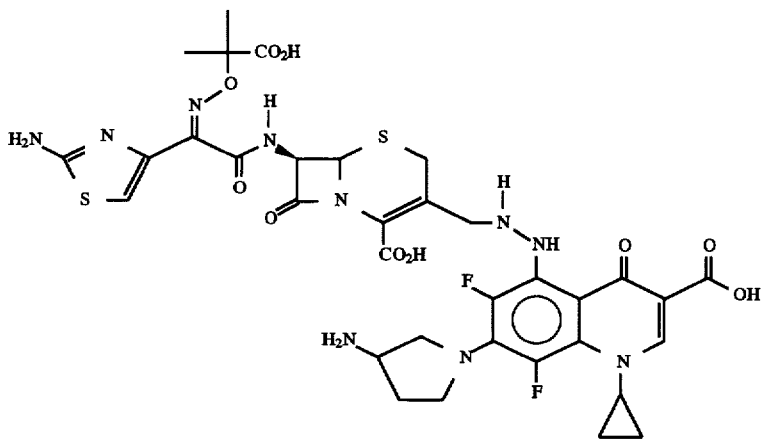

-continued
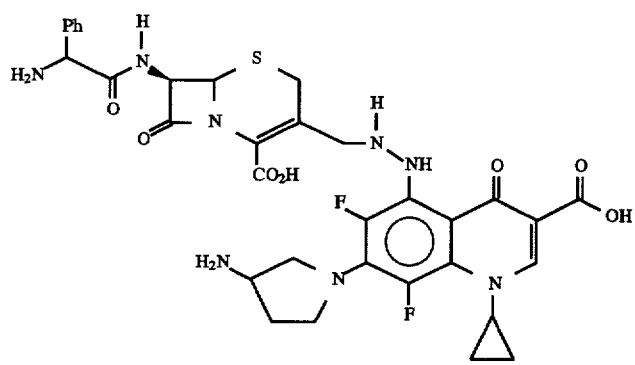
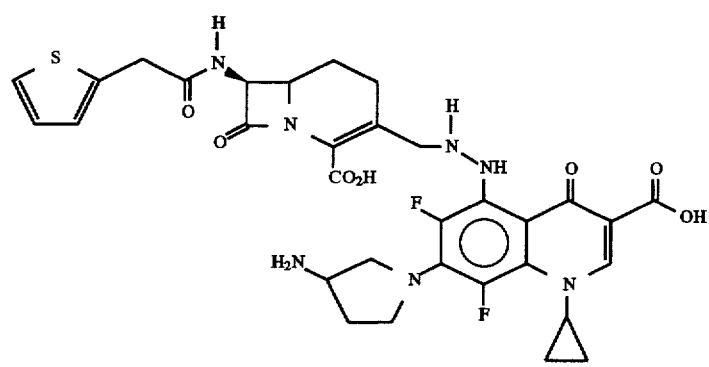
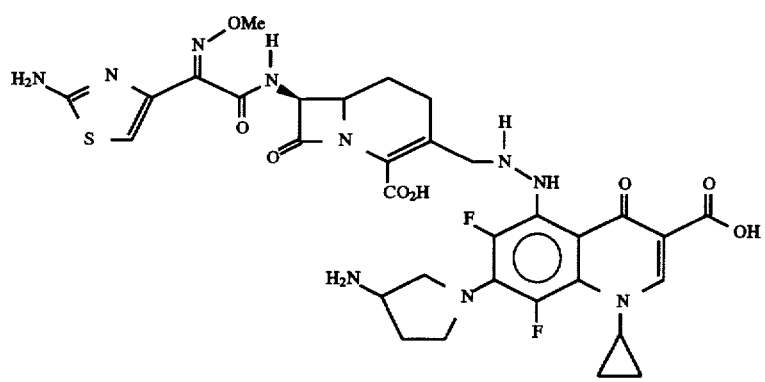
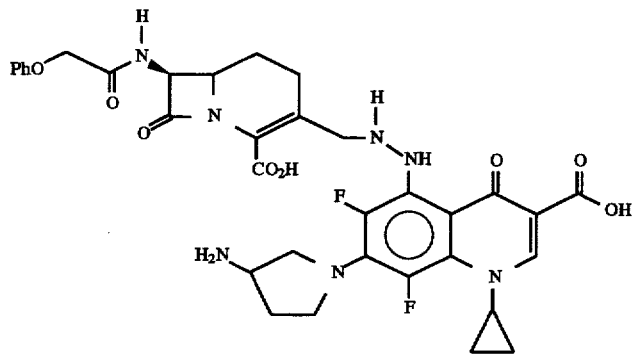

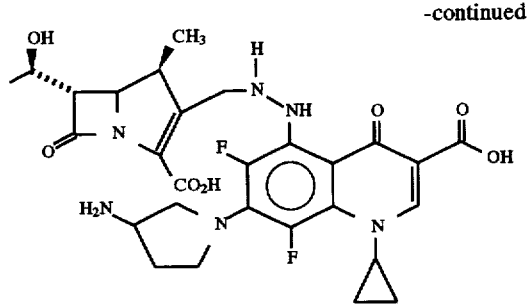

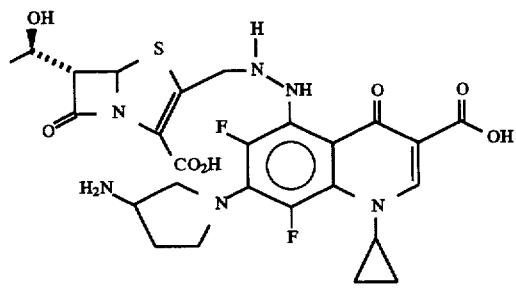

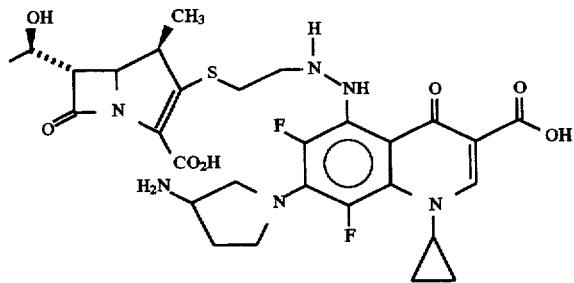

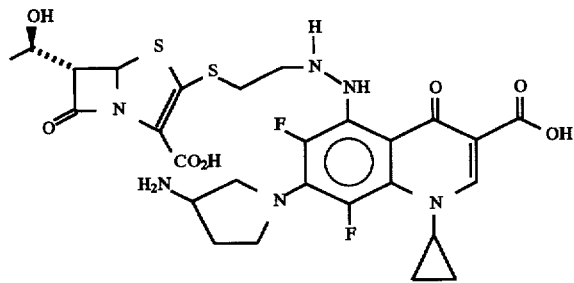

All publications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. A process for making a compound having a structure according to Formula (I)

$$\text{(I)}$$

wherein (A)

(1) $A^1$ is N or $C(R^7)$; where (a) $R^7$ is hydrogen, hydroxy, alkoxy, nitro, cyano, halogen, alkyl, or $-N(R^8)(R^9)$, and (b) $R^8$ and $R^9$ are, independently, $R^{8a}$; where $R^{8a}$ is hydrogen, alkyl, alkenyl, a carbocyclic ring, or a heterocyclic ring; or $R^8$ and $R^9$ together comprise a heterocyclic ring including the nitrogen to which they are bonded;

(2) $A^2$ is N or $C(R^2)$; where $R^2$ is hydrogen or halogen;

(3) $A^3$ is N or $C(R^5)$; where $R^5$ is hydrogen;

(4) $R^1$ is hydrogen, alkyl, a carbocyclic ring, a heterocyclic ring, alkoxy, hydroxy, alkenyl, arylalkyl, heteroalkyl, —$N(R^8)(R^9)$, or a lactam-containing moiety;

(5) $R^3$ is hydrogen, halogen, alkyl, a carbocyclic ring, a heterocyclic ring, or a lactam-containing moiety;

(6) $R^4$ is hydroxy; and (7) $R^6$ is hydrogen, halogen, nitro, hydrazino, alkoxyamino, —$N(R^8)(R^9)$, or a lactam-containing moiety;

except that if one of $R^1$, $R^3$, or $R^6$ is a lactam-containing moiety, then the other two are not a lactam-containing moiety;

(B) and (1) when $A^2$ is $C(R^2)$, $R^2$ and $R^3$ may together comprise —O—$(CH_2)n$—O—, where n is from 1 to 4;

(2) when $A^3$ is $C(R^5)$, $R^4$ and $R^5$ may together comprise a heterocyclic ring including the carbon atom to which $R^4$ and $R^5$ are bonded and the carbon atoms of Formula (I) to which said carbon atom(s) are bonded; and (3) when $A^1$ is $C(R^7)$, $R^3$ and $R^7$ may together comprise a heterocyclic ring including $A^1$ and the carbon atom to which $R^3$ is bonded;

or a protected form, salt, pharmaceutically-acceptable salt, biohydrolyzable ester, or solvate thereof; the process comprising reacting one or more organosilicon compounds with a compound having a structure according to Formula (II),

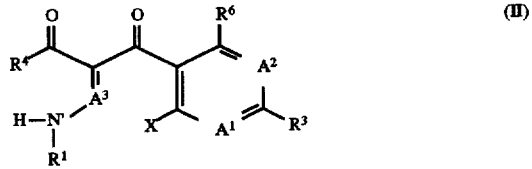

(II)

wherein (A)

(1) $A^1$ is N or $C(R^7)$; where (a) $R^7$ is hydrogen, hydroxy, alkoxy, nitro, cyano, halogen, alkyl, or —$N(R^8)(R^9)$, and (b) $R^8$ and $R^9$ are, independently, $R^{8a}$; where $R^{8a}$ is hydrogen, alkyl, alkenyl, a carbocyclic ring, or a heterocyclic ring; or $R^8$ and $R^9$ together comprise a heterocyclic ring including the nitrogen to which they are bonded;

(2) $A^2$ is N or $C(R^2)$; where $R^2$ is hydrogen or halogen;

(3) $A^3$ is N or $C(R^5)$; where $R^5$ is hydrogen;

(4) $R^1$ is hydrogen, alkyl, heteroalkyl, a carbocyclic ring, a heterocyclic ring, alkoxy, hydroxy, alkenyl, arylalkyl, —$N(R^8)(R^9)$, or a lactam-containing moiety;

(5) $R^3$ is hydrogen, halogen, alkyl, a carbocyclic ring, a heterocyclic ring, or a lactam-containing moiety;

(6) $R^4$ is hydroxy;

(7) $R^6$ is hydrogen, halogen, nitro, hydrazino, alkoxyamino, —$N(R^8)(R^9)$, or a lactam-containing moiety; and (8) X is a leaving group;

except that if one of $R^1$, $R^3$, or $R^6$ is a lactam-containing moiety, then the other two are not a lactam-containing moiety;

(B) and (1) when $A^2$ is $C(R^2)$, $R^2$ and $R^3$ may together comprise —O—$(CH_2)n$—O—, where n is from 1 to 4;

(2) when $A^3$ is $C(R^5)$, $R^4$ and $R^5$ may together comprise a heterocyclic ring including the carbon atoms to which $R^4$ and $R^5$ are bonded and the carbon atom of Formula (II) to which said carbon atom(s) are bonded; and (3) when $A^1$ is $C(R^7)$, $R^3$ and $R^7$ may together comprise a heterocyclic ring including A1 and the carbon atom to which $R^3$ is bonded;

or a protected form, salt, biohydrolyzable ester, or solvate thereof.

2. The process of claim 1, wherein the mole ratio of the organosilicon compound to the Formula (II) compound is from about 1:1 to about 14:1.

3. The process of claim 2, wherein the mole ratio of the organosilicon compound to the Formula (II) compound is from about 2:1 to about 6:1.

4. The process of claim 1, wherein the reaction is carried out at a temperature greater than about −15° C.

5. The process of claim 4, wherein the reaction is carried out at a temperature from about 25° C. to about 50° C.

6. The process of claim 1, wherein the reaction is carried out in an alkyl nitrile, halocarbon, or ether solvent, or a mixture thereof.

7. The process of claim 6, wherein the solvent is methylene chloride, tetrahydrofuran, or acetonitrile, or a mixture thereof.

8. The process of claim 1, wherein the reaction comprises adding the organosilicon compound to a mixture of the compound of Formula (II) in a solvent.

9. The process of claim 1, wherein the organosilicon compound is chlorotrimethylsilane, N,O-bis(trimethylsilyl)acetamide, N,O-bis(trimethylsilyl)trifluoroacetamide, bis(trimethylsilyl)urea, hexamethyldisilazane, N-methyl-N-trimethylsilytrifluoroacetamide, 1-trimethylsilylimidazole, or a mixture thereof.

10. The process of claim 1, wherein $A^1$ is $C(R^7)$, $A^2$ is $C(R^2)$, and $A^3$ is $C(R^5)$; or $A^1$ is nitrogen, $A^2$ is $C(R^2)$, and $A^3$ is $C(R^5)$.

11. The process of claim 10, wherein $R^1$ is alkyl, aryl, cycloalkyl, or alkylamino.

12. The process of claim 10, wherein $A^1$ is $C(R^7)$, $A^2$ is $C(R^2)$, and $A^3$ is $C(R^5)$.

13. The process of claim 12, wherein $R^7$ is hydrogen or halogen.

14. The process of claim 10, wherein $R^3$ is a heterocyclic ring.

15. The process of claim 14, wherein $R^3$ is a substituted or unsubstituted pyrrolidine or a substituted or unsubstituted piperazine.

16. The process of claim 1, wherein $R^1$, $R^6$ or $R^3$ is a lactam-containing moiety.

17. The process of claim 16, wherein $R^3$ is a lactam-containing moiety.

18. The process of claim 16, wherein $R^6$ is a lactam-containing moiety.

19. The process of claim 16, wherein the lactam-containing moiety is a carbapenem, a penera, a carbacephem, or a cephem.

20. A process for making a compound having a structure according to Formula (A)

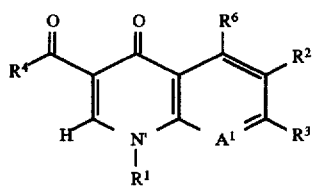

(A)

wherein (1) $A^1$ is N or $C(R^7)$; where
   (a) $R^7$ is hydrogen, hydroxy, alkoxy, nitro, cyano, halogen, alkyl, or —$N(R^8)(R^9)$, and
   (b) $R^8$ and $R^9$ are, independently, $R^{8a}$; where $R^{8a}$ is hydrogen, alkyl, alkenyl, a carbocyclic ring, or a heterocyclic ring; or $R^8$ and $R^9$ together comprise a heterocyclic ring including the nitrogen to which they are bonded;

(2) $R^1$ is hydrogen, alkyl, a carbocyclic ring, a heterocyclic ring, alkoxy, hydroxy, alkenyl, arylalkyl, or —$N(R^8)(R^9)$;

(3) $R^2$ is hydrogen or halogen;

(4) $R^3$ is hydrogen, halogen, alkyl, a carbocyclic ring, a heterocyclic ring, or a lactam-containing moiety;

(5) $R^4$ is hydroxy; and (6) $R^6$ is hydrogen, halogen, nitro, hydrazino, alkoxyamino, —$N(R^8)(R^9)$, or a lactam-containing moiety;

except that $R^3$ and $R^6$ cannot both be a lactam-containing moiety;

or a protected form, salt, pharmaceutically-acceptable salt, biohydrolyzable ester, or solvate thereof;

the process comprising reacting one or more oganosilicon compounds with a compound having a structure according to Formula (b),

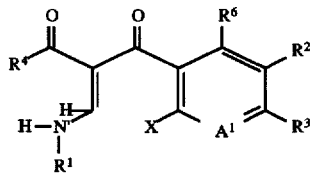

(b)

wherein (1) $A^1$ is N or $C(R^7)$; where
   (a) $R^7$ is hydrogen, hydroxy, alkoxy, nitro, cyano, halogen, alkyl, or —$N(R^8)(R^9)$, and
   (b) $R^8$ and $R^9$ are, independently, $R^{8a}$; where $R^{8a}$ is hydrogen, alkyl, alkenyl, a carbocyclic ring, or a heterocyclic ring; or $R^8$ and $R^9$ together comprise a heterocyclic ring including the nitrogen to which they are bonded;

(2) $R^1$ is hydrogen, alkyl, a carbocyclic ring, a heterocyclic ring, alkoxy, hydroxy, alkenyl, arylalkyl, or —$N(R^8)(R^9)$;

(3) $R^2$ is hydrogen or halogen;

(4) $R^3$ is hydrogen, halogen, alkyl, a carbocyclic ring, a heterocyclic ring, or a lactam-containing moiety;

(5) $R^4$ is hydroxy;

(6) $R^6$ is hydrogen, halogen, nitro, hydrazino, alkoxyamino, —$N(R^8)(R^9)$, or a lactam-containing moiety; and (7) X is a leaving group;

except that $R^3$ and $R^6$ cannot both be a lactam-containing moiety;

or a protected form, salt, biohydrolyzable ester, or solvate thereof.

21. The process of claim 20, wherein the reaction is carried out at a temperature greater than about $-15°$ C.

22. The process of claim 21, wherein the reaction is carried out at a temperature of from about $25°$ C. to about $50°$ C.

23. The process of claim 20, wherein $R^1$ is alkyl, aryl, cycloalkyl, or alkylamino; $R^7$ is hydrogen or halogen; and $R^3$ is a heterocyclic ring.

24. The process of claim 20, wherein $R^1$ is alkyl, aryl, cycloalkyl, or alkylamino; $R^7$ is hydrogen or halogen; and $R^3$ is a lactam-containing moiety.

25. The process of claim 1, wherein the compound of Formula (I) is 1-ethyl-6,7,8-trifluoro-1,4-dihydro-4-oxo-3-quinolinecarboxylic acid;

9-fluoro-2,3-dihydro-3-methyl-10-(4-methyl-1-piperazinyl)-7-oxo-7H-pyrido[1,2,3-de]-1,4-benzoxazine-6-carboxylic acid;

1-cyclopropyl-6-fluoro-1,4-dihydro-7-(4-methyl-1-piperazinyl)-4-oxo-3-quinolinecarboxylic acid;

1-cyclopropyl-6-fluoro-1,4-dihydro-7-(1-piperazinyl)-4-oxo-3-quinoline-carboxylic acid;

6,8-difluoro-1-(2-fluoroethyl)-1,4-dihydro-7-(4-methyl-1-piperazinyl)-4-oxo-3-quinolinecarboxylic acid;

1-cyclopropyl-6-fluoro-1,4-dihydro-7-(1-piperazinyl)-4-oxo-3-quinoline-carboxylic acid;

1-cyclopropyl-6,7-difluoro-1,4-dihydro-4-oxo-3-quinoline-carboxylic acid;

7-chloro-1-(2,4-difluorophenyl)-6-fluoro-1,4-dihydro-4-oxo-1,8-napthyridine-3-carboxylic acid;

1-(tert-butyl)-7-chloro-6-fluoro-1,4-dihydro-4-oxo-1,8-napthyridine-3-carboxylic acid, 1-Cyclopropyl-6-fluoro-1,4-dihydro-4-oxo-7-piperazinyl-quinoline-3-carboxylic acid;

1-cyclopropyl-6-fluoro-1,4-dihydro-4-oxo-7-piperazinyl-quinoline-3-carboxylic acid diphenylmethyl ester;

1-cyclopropyl-6-fluoro-1,4-dihydro-4-oxo-7-piperazinyl-quinoline-3-carboxylic acid t-butyl ester;

1-Cyclopropyl-6-fluoro-1,4-dihydro-4-oxo-7-piperazinyl-quinoline-3-carboxylic acid 2,2,2-trichloroethyl ester;

7-(3-Amino-1-pyrrolidinyl)-1-cyclopropyl-6,8-difluoro-1,4-dihydro-4-oxo-quinoline-3-carboxylic acid;

7-(3-Amino-1-pyrrolidinyl)-1-cyclopropyl-6,8-difluoro-1,4-dihydro-4-oxo-quinoline-3-carboxylic acid allyl ester;

7-(3-Amino-1-pyrrolidinyl)-1-cyclopropyl-6,8-difluoro-1,4-dihydro-4-oxo-quinoline-3-carboxylic acid allyl ester;

5-Amino-7-(3-amino-1-pyrrolidinyl)-1-cyclopropyl-6,8-difluoro-1,4-dihydro-4-oxo-quinoline-3-carboxylic acid allyl ester;

5-Amino-1-cyclopropyl-6,8-difluoro-1,4-dihydro-7-(2,6-dimethyl-4-piperazinyl)-4-oxo-quinoline-3-carboxylic acid;

7-(3-Amino-1-pyrrolidinyl)-1-(2,4-difluorophenyl)-6-fluoro-1,4-dihydro-4-oxo-1,8-naphthyridine-3-carboxylic acid allyl ester;

7-[3-(t-Butyloxycarbonyl)amino-1-pyrrolidinyl]-1-cyclopropyl-6,8-difluoro-1,4-dihydro-5-hydrazino-4-oxo-quinoline-3-carboxylic acid allyl ester;

[5R-[5a,6a]]-3-[[[4-(3-Carboxy-1-cyclopropyl-6-fluoro-1,4-dihydro-4-oxo-7-quinolinyl)-1-piperazinyl]

carbonyloxy]methyl]-6-[(R)-1-hydroxyethyl]-7-oxo-4-thia-1-azabicyclo[3.2.0]hept-2-ene-2-carboxylic Acid, Disodium Salt;

[5R-[4b,5a,6a]]-3-[[[4-(3-Carboxy-1-cyclopropyl-6-fluoro-1,4-dihydro-4-oxo-7-quinolinyl)-1-piperazinyl]carbonyloxy]methyl]-6-[(R)-1-hydroxyethyl]-4-methyl-7-oxo-1-azabicyclo[3.2.0]hept-2-ene-2-carboxylic Acid, Disodium Salt;

[5R-[5a,6a]]-3-[[[[4-(3-Carboxy-1-cyclopropyl-6,8-difluoro-1,4-dihydro-4-oxo-7-quinolinyl)-(S)-3-pyrrolidinyl]amino]-carbonyloxy]methyl]-6-[(R)-1-hydroxyethyl]-7-oxo-4-thia-1-azabicyclo[3.2.0]hept-2-ene-2-carboxylic Acid, Disodium Salt;

[5R-[4b,5a,6a]]-3-[[[[4-(3-Carboxy-1-cyclopropyl-6,8-difluoro-1,4-dihydro-4-oxo-7-quinolinyl)-(S)-3-pyrrolidinyl]amino]-carbonyloxy]methyl]-6-[(R)-1-hydroxyethyl]-4-methyl-7-oxo-1-azabicyclo[3.2.0]hept-2-ene-2-carboxylic Acid, Disodium Salt;

[5R-[5a,6a]]-3-[[[4-[3-Carboxy-1-(2,4-difluorophenyl)-6-fluoro-1,4-dihydro-4-oxo-1,8-naphthyridin-1-yl]-(S)-3-pyrrolidinyl]amino]-carbonyloxy]methyl]-6-[(R)-1-hydroxyethyl]-7-oxo-4-thia-1-azabicyclo[3.2.0]hept-2-ene-2-carboxylic Acid, Disodium Salt;

[5R-[4b,5a,6a]]-3-[[[[4-[3-Carboxy-1-(2,4-difluorophenyl)-6-fluoro-1,4-dihydro-4-oxo-1,8-naphthyridin-1-yl]-(S)-3-pyrrolidinyl]amino]-carbonyloxy]methyl]-6-[(R)-1-hydroxyethyl]-4-methyl-7-oxo-1-azabicyclo[3.2.0]hept-2-ene-2-carboxylic Acid, Disodium Salt;

[5R-[5a,6a]]-3-[[[4-(5-Amino-3-carboxy-1-cyclopropyl-6,8-difluoro-1,4-dihydro-4-oxo7-quinolinyl)-2,6-dimethyl-4-piperazinyl]carbonyloxy]methyl]-6-[(R)-1-hydroxyethyl]-7-oxo-4-thia-1-azabicyclo[3.2.0]hept-2-ene-2-carboxylic Acid, Disodium Salt;

[5R-[4b,5a,6a]]-3-[[[4-(5-Amino-3-carboxy-1-cyclopropyl-6,8-difluoro-1,4-dihydro-4-oxo-7-quinolinyl)-2,6-dimethyl-4-piperazinyl]carbonyloxy]methyl]-6-[(R)-1-hydroxyethyl]-4-methyl-7-oxo-1-azabicyclo[3.2.0]hept-2-ene-2-carboxylic Acid, Disodium Salt;

[5R-[5a,6a]]-3-[[[2-[7-((S)-3-Amino-1-pyrrolidinyl)-3-carboxy-1-cyclopropyl-6,8-difluoro-1,4-dihydro-4-oxo-5-quinolinyl]-1-hydrazino]-carbonyloxy]methyl]-6-[(R)-hydroxyethyl]-7-oxo-4-thia-1-azabicyclo[3.2.0]hept-2-ene-2-carboxylic Acid, Disodium Salt;

[5R-[4b,5a,6a]]-3-[[[2-[7-((S)-3-Amino-1-pyrrolidinyl)-3-carboxy-1-cyclo-propyl-6,8-difluoro-1,4-dihydro-4-oxo-5-quinolinyl]-1-hydrazino]-carbonyl-oxy]methyl]-6-[(R)-1-hydroxyethyl]-4-methyl-7-oxo-1-azabicyclo-[3.2.0]hept-2-ene-2-carboxylic Acid. Disodium Salt; [4R-[4a,5b,6b(R*)]]-3-[[[4-(3-Carboxy-1-cyclopropyl-6-fluoro-1,4-dihydro-4-oxo-7-quinolinyl)-1-piperazinyl]carbonyloxy]methyl]-6-(1-hydroxyethyl)-7-oxo-4-thia-1-azabicyclo[3.2.0]hept-2-ene-2-carboxylic Acid, Disodium salt;

[6R-[6a,7b]]-3-[[[4-(3-Carboxy-1-cyclopropyl-6-fluoro-1,4-dihydro-4-oxo-7-quinolinyl)-1-piperazinyl]carbonyloxy]methyl]-8-oxo-7-[(2-thienylacetyl)amino]-5-thia-1-azabicyclo[4.2.0]oct-2-ene-2-carboxylic Acid, Disodium Salt;

[6R-[6a,7b]]-3-[[[4-[3-Carboxy-1-(1,1-dimethylethyl)-6-fluoro-1,4-dihydro-4-oxo-1,8-napthyridin-7-yl]-1-piperazinyl]carbonyloxy]-methyl]-8-oxo-7-[(2-thienylacetyl)amino]-1-azabicyclo[4.2.0]oct-2-ene-2-carboxylic Acid, Disodium Salt;

[5R-[5a,6a(R*)]]-3-[[4-(3-Carboxy-1-cyclopropyl-6-fluoro-1,4-dihydro-4-oxo-7-quinolinyl)-1-piperazinyl]methyl]-6-(1-hydroxyethyl)-7-oxo-4-thia-1-azabicyclo[3.2.0]hept-2-ene-2-carboxylic Acid, Disodium Salt;

[4S-[3(R*),4a,5b,6b(S*)]]-3-[[[1-[3-Carboxy-1-(2,4-difluorophenyl)-6-fluoro-1,4-dihydro-4-oxo-1,8-napthyridin-7-yl]-3-pyrrolidinyl]amino]methyl]-6-(1-hydroxyethyl)4-methyl-7-oxo-1-azabicyclo-[3.2.0]hept-2-ene-2-carboxylic Acid, Disodium salt; or

[6R-[3(S*),6a,7b]]-3-[[[1-[3-Carboxy-1-(1,1-dimethylethyl)-6-fluoro-1,4-dihydro-4-oxo-1,8-napthyridin-7-yl]-3-pyrrolidinyl]amino]methyl]-8-oxo-7-[(2-thienylacetyl)amino]-5-thia-1-azabicyclo[4.2.0]oct-2-ene-2-carboxylic Acid.

* * * * *